US009951123B2

(12) United States Patent
Hasegawa et al.

(10) Patent No.: US 9,951,123 B2
(45) Date of Patent: Apr. 24, 2018

(54) ANTI-LPS O11 ANTIBODY

(71) Applicant: Daiichi Sankyo Company, Limited, Tokyo (JP)

(72) Inventors: Jun Hasegawa, Tokyo (JP); Kiyoshi Sugihara, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/025,703

(22) PCT Filed: Sep. 29, 2014

(86) PCT No.: PCT/JP2014/075866
§ 371 (c)(1),
(2) Date: Mar. 29, 2016

(87) PCT Pub. No.: WO2015/046505
PCT Pub. Date: Apr. 2, 2015

(65) Prior Publication Data
US 2016/0311892 A1    Oct. 27, 2016

(30) Foreign Application Priority Data
Sep. 30, 2013 (JP) ................. 2013-203297

(51) Int. Cl.
*A61K 39/395* (2006.01)
*C07K 16/12* (2006.01)
*A61K 31/436* (2006.01)
*A61K 31/43* (2006.01)
*A61K 31/496* (2006.01)
*C12N 15/09* (2006.01)
*A61K 39/40* (2006.01)
*A61K 45/06* (2006.01)
*A61K 39/00* (2006.01)

(52) U.S. Cl.
CPC ......... *C07K 16/1214* (2013.01); *A61K 31/43* (2013.01); *A61K 31/436* (2013.01); *A61K 31/496* (2013.01); *A61K 39/395* (2013.01); *A61K 39/40* (2013.01); *A61K 45/06* (2013.01); *C12N 15/09* (2013.01); *A61K 2039/505* (2013.01); *C07K 2317/21* (2013.01); *C07K 2317/24* (2013.01); *C07K 2317/33* (2013.01); *C07K 2317/54* (2013.01); *C07K 2317/55* (2013.01); *C07K 2317/565* (2013.01); *C07K 2317/622* (2013.01); *C07K 2317/76* (2013.01)

(58) Field of Classification Search
CPC .............................................. C07K 16/1214
See application file for complete search history.

(56) References Cited

U.S. PATENT DOCUMENTS

2011/0177087 A1    7/2011  Schreiber
2013/0004499 A1    1/2013  Tanaka et al.

FOREIGN PATENT DOCUMENTS

| EP | 0 441 395 B1 | 5/1995 |
|---|---|---|
| JP | 04-211393 | 8/1992 |
| JP | 2008-530988 | 8/2008 |
| JP | 2013-520159 | 6/2013 |
| WO | WO-2006/084758 A1 | 8/2006 |
| WO | WO-2011/102551 A1 | 8/2011 |

OTHER PUBLICATIONS

Office Action issued in Canadian Patent Application No. 2,925,897 dated Jan. 17, 2017.
Lam et al., "Production and Characterization of Monoclonal Antibodies against Serotype Strains of *Pseudomonas aeruginosa*", Infection and Immunity, American Society for Microbiology, US, vol. 55, No. 5, pp. 1051-1057, XP055358894, May 1, 1987, ISSN: 0019-9567.
Ivanov et al., "Relating the Physical of *Pseudomonas aeruginosa* Lipopolysaccharides to Virulence by Atomic Force Microscopy", Journal of Bacteriology, vol. 193, No. 5, pp. 1259-1266, Dec. 10, 2010, XP055358094, US, ISSN: 0021-9193.
Dean et al., "WbjA Adds Glucose to Complete the O-Antigen Trisaccharide Repeating Unit of the Lipopolysaccharide of *Pseudomonas aeruginosa* Serogroup O11", Journal of Bacteriology, vol. 184, No. 1, pp. 323-326, Jan. 1, 2002, US, XP055358164, ISSN: 0021-9193.
Lai et al., "Multi-valent human monoclonal antibody preparation against *Pseudomonas aeruginosa* derived from transgenic mice containing human immunoglobulin loci is protective against fatal pseudomonas sepsis caused by multiple serotypes", Vaccine, vol. 23, No. 25, pp. 3264-3271, May 1, 2005, XP055358847, Amsterdam, NL, ISSN: 0264-410X.
Pier et al., "Human Monoclonal Antibodies to *Pseudomonas aeruginosa* alginate That Protect against Infection by Both Mucoid and Nonmucoid Strains", The Journal of Immunology, The American Association of Immunologists, US. vol. 173, No. 9, pp. 5671-5678, Nov. 1, 2004, XP002529719, ISSN: 0022-1767.
Extended European Search Report dated Apr. 4, 2017 in Application No. 14849593.0.
Cholley et al, Most Multidrug-Resistant Pseudomonas aeruginosa Isolates from Hospitals in Eastern France Belong to a Few Clonal Types, Journal of Clinical Microbiology, Jul. 2011, p. 2578-2583, vol. 29, No. 7, American Society for Microbiology.
Collins et al, Opsonic and protective activity of five human IgM monoclonal antibodies reactive with lipopolysaccharide antigen of Pseudomonas aeruginosa, FEMS Microbiology Immunology, 1990, p. 263-268, ELSEVIER.
Fujitani et al, Pneumonia Due to Pseudomonas aeruginosa Part I: Epidemiology, Clinical Diagnosis, and Source, Recent Advances in Chest Medicine, 2011, p. 909-919, vol. 129, American College of Chest Physicians.
Glupczynski et al, Detection and characterization of class A extended-spectrum-B-lactamase-producing Pseudomonas aeruginosa isolates in Belgian hospitals, Journal of Antimicrobial Chemotherapy, Mar. 3, 2010, p. 866-871.

(Continued)

Primary Examiner — Albert M Navarro
(74) Attorney, Agent, or Firm — Foley & Lardner LLP

(57) ABSTRACT

The purpose of the present invention is to provide a substance having superior antibacterial activity against *Pseudomonas aeruginosa*, and a pharmaceutical composition for treatment and/or prophylaxis of pseudomonal infections. A pharmaceutical composition is provided, containing an antibody which specifically binds to the LPS O11 antigen of *Pseudomonas aeruginosa*, and which has superior antibacterial activity.

16 Claims, 25 Drawing Sheets

(56) References Cited

OTHER PUBLICATIONS

Hidron et al, Antimicrobial-Resistant Pathogens Associated With Healthcare-Associated Infections: Annual Summary of Data Reported to the National Healthcare Safety Network at the Centers for Disease Control and Prevention, 2006-2007, Infection Control and Hospital Epidemiology, Nov. 2008, p. 996-1011, vol. 29, No. 11, The Society for Healthcare Epidemiology of America, Atlanta, Georgia, USA.

Horn et al., Preclinical In Vitro and In Vivo Characterization of the Fully Human Monoclonal IgM Antibody KBPA101 Specific for Pseudomonas aeruginosa Serotype IATS-O11, Antimocrobial Agents and Chemotherapy., Jun. 2010, vol. 54, No. 6, pp. 2338-2344.

International Search Report and Written Opinion dated Dec. 22, 2014 in corresponding application No. PCT/JP2014/075866.

Kitao et al, Emergence of a novel multidrug-resistant Pseudomonas aeruginosa strain producing IMP-type metallo-B-lactamases and AAC(6')-Iae in Japan, International Journal of Antimicrobial Agents, 2012, p. 518-521, Elsevier.

Knirel et al, Conserved and variable structural features in lipopolysaccharide of Pseudomonas aeruginosa, Journal of Endotoxin Research, 2006, p. 324,335, vol. 12 No. 6.

Knirel, Yuriy A, Polysaccharide Antigens of Pseudomonas Aeruginosa, Critical Reviews in Micobiology, Sep. 25, 2008, p. 273-304, vol. 17, Issue 4.

Maatallah et al, Population Structure of Pseudomonas aeruginosa from Five Mediterranean Countries: Evidence for Frequent Recombination and Epidemic Occurrence of CC235, PLos ONE, 2011, p. 1-11, vol. 6, Issue 10.

Nemec et al, Multidrug-resistant epidemic clones among bloodstream isolates of Pseudomonas aeruginosa in the Czech Republic. Research in Microbiology, 2010, p. 234-242, ELSEVIER.

Pier et al, In Vitro and In Vivo Activity of Polyclonal and Monoclonal Human Immunoglobulins G, M, and A against Pseudomonas aeruginosa Lipopolysaccharide, Infection and Immunity, Jan. 1989, p. 174-179, vol. 57, No. 1, American Society for Microbiology.

Preston et al, Production and Characterization of a Set of Mouse-Human Chimeric Immunoglobulin G (IgG) Subclass and IgA Monoclonal Antibodies with Identical Variable Regions Specific for Pseudomonas aeruginosa Serogroup O6 Lipopolysaccharide, Infection and Immunity, Sep. 1998, p. 4137-4142, vol. 66, No. 9, American Society for Microbiology.

Sekiguchi et al, Outbreaks of Multidrug-Resistant Pseudomonas aeruginosa in Community Hospitals in Japan, Journal of Clinical Microbiology, Mar. 2007, p. 979-989, vol. 45, No. 3, American Society for Microbiology.

Fig. 1

SEQ ID NO: 4: AMINO ACID SEQUENCE OF No.76 LIGHT CHAIN VARIABLE REGION

MESQTLVFISILLWLYGADGNIVMTQSPKSMSMSVGERVTLSCKASENVGTSVSWYQEKPEQSPKLL
IFGASNRYTGVPDRFTGSGSATDFTLTISSVQAEDLADYHCGQSYSYPYTFGGRTKLEIKRA

SIGNAL SEQUENCE (1-20), VARIABLE REGION (21-129)

SEQ ID NO: 5: AMINO ACID SEQUENCE OF No.76 LIGHT CHAIN CDR1

KASENVGTSVS

SEQ ID NO: 6: AMINO ACID SEQUENCE OF No.76 LIGHT CHAIN CDR2

GASNRYT

SEQ ID NO: 7: AMINO ACID SEQUENCE OF No.76 LIGHT CHAIN CDR3

GQSYSYPYT

SEQ ID NO: 8: AMINO ACID SEQUENCE OF No.76 HEAVY CHAIN VARIABLE REGION

MGWSCIILFLVAAATGVHSQVQLQQPGAELVKPGASVNLSCKSSGYTFTNYWINWVKQRPGQGLEWI
GDIYPGTSTTNYNEKFKNKATLTVDTSSSTAYMQLSSLTSDDSAVYYCTRIYYDYDGYYFDYWGQGT
TLTVSS

SIGNAL SEQUENCE (1-19), VARIABLE REGION (20-140)

SEQ ID NO: 9: AMINO ACID SEQUENCE OF No.76 HEAVY CHAIN CDR1

NYWIN

SEQ ID NO: 10: AMINO ACID SEQUENCE OF No.76 HEAVY CHAIN CDR2

DIYPGTSTTNYNEKFKN

SEQ ID NO: 11: AMINO ACID SEQUENCE OF No.76 HEAVY CHAIN CDR13

IYYDYDGYYFDY

Fig. 2

SEQ ID NO: 12: AMINO ACID SEQUENCE OF #1G5 LIGHT CHAIN VARIABLE REGION

MESQTLVFISILLWLYGSDGNIVMTQSPKSMSMSVGERVTLSCKASENVGNSVSWYQQKAEQSPKPL
IYGASNRYTGVPDRFTGSGSATDFTLTISSVQAEDLADYHCGQSYSYPYTFGGGTKLEIKRA

SIGNAL SEQUENCE (1-20), VARIABLE REGION (21-129)

SEQ ID NO: 13: AMINO ACID SEQUENCE OF #1G5 LIGHT CHAIN CDR1

KASENVGNSVS

SEQ ID NO: 14: AMINO ACID SEQUENCE OF #1G5 LIGHT CHAIN CDR2

GASNRYT

SEQ ID NO: 15: AMINO ACID SEQUENCE OF #1G5 LIGHT CHAIN CDR3

GQSYSYPYT

SEQ ID NO: 16: AMINO ACID SEQUENCE OF #1G5 HEAVY CHAIN VARIABLE REGION

MGWSCIILFLVAAATGVHSQVQLQQPGAELVKPGASVKLSCKASGYTFTSYWINWVKQRPGQGLEWI
GNIYPGSSSINYNEKFKSKATLTVDTSSSTAYMQLSSLTSDDSAVYYCSRTIYNYGSSGYNYAMDYW
GQGTSVIVSS

SIGNAL SEQUENCE (1-19), VARIABLE REGION (20-144)

SEQ ID NO: 17: AMINO ACID SEQUENCE OF #1G5 HEAVY CHAIN CDR1

SYWIN

SEQ ID NO: 18: AMINO ACID SEQUENCE OF #1G5 HEAVY CHAIN CDR2

NIYPGSSSINYNEKFKS

SEQ ID NO: 19: AMINO ACID SEQUENCE OF #1G5 HEAVY CHAIN CDR3

TIYNYGSSGYNYAMDY

Fig. 3

SEQ ID NO: 20: AMINO ACID SEQUENCE OF #4C12 LIGHT CHAIN VARIABLE REGION

MESQTLVFISILLWLYGADGNIVMTQSPKSMSMSVGERVTLSCKASENVGVSVSWYQQKPEQSPKLL
IYGASNRCTGVPDRFTGSRSATDPTLTVSNVQAEDLADYHCGQSYSYPYTFGGGTRLEIKRA

SIGNAL SEQUENCE (1-20), VARIABLE REGION (21-129)

SEQ ID NO: 21: AMINO ACID SEQUENCE OF #4C12 LIGHT CHAIN CDR1

KASENVGVSVS

SEQ ID NO: 22: AMINO ACID SEQUENCE OF #4C12 LIGHT CHAIN CDR2

GASNRCT

SEQ ID NO: 23: AMINO ACID SEQUENCE OF #4C12 LIGHT CHAIN CDR3

GQSYSYPYT

SEQ ID NO: 24: AMINO ACID SEQUENCE OF #4C12 HEAVY CHAIN VARIABLE REGION

MGWSCIILFLVAAATGVQSQVQLQQPGAELVKPGASVKLSCKASGYTFTTYWINWMQQRPGQGLEWI
GNIYPGTRSSNYNEKFKNKATLTVDTSSSTAYMQLNSLTSDDSAVYYCTRVYYDHVGYYFDYWGQGT
TLTVSS

SIGNAL SEQUENCE (1-19), VARIABLE REGION (20-140)

SEQ ID NO: 25: AMINO ACID SEQUENCE OF #4C12 HEAVY CHAIN CDR1

TYWIN

SEQ ID NO: 26: AMINO ACID SEQUENCE OF #4C12 HEAVY CHAIN CDR2

NIYPGTRSSNYNEKFKN

SEQ ID NO: 27: AMINO ACID SEQUENCE OF #4C12 HEAVY CHAIN CDR3

VYYDHVGYYFDY

Fig. 9

SEQ ID NO: 56: NUCLEOTIDE SEQUENCE OF h#1G5-H1

```
atgaaacacctgtggttcttcctcctgctggtggcagctcccagatgggtgctgagccaggtgc
agctggtgcagtctggcgccgaagtgaagaaaccaggcgccagcgtgaaggtgtcctgcaaggc
cagcggctacaccttttaccagctactggatcaactgggtgcgccaggcccctggacagggcctg
gaatggatgggcaacatctaccccggcagcagcagcatcaactacaacgagaagttcaagagcc
gcgtgaccatcaccgccgacaccagcacaagcaccgcctacatggaactgagcagcctgcggag
cgaggacaccgccgtgtactactgcgccagaaccatctacaactacggcagctccggctacaat
tacgccatggactactggggccagggcaccctcgtgaccgtgagctcagcctccaccaagggcc
caagcgtcttccccctggcaccctcctccaagagcacctctgggggcacagcggccctgggctg
cctggtcaaggactacttccccgaacccgtgaccgtgagctggaactcaggcgccctgaccagc
ggcgtgcacaccttcccggctgtcctgcagtcctcaggactctactccctcagcagcgtggtga
ccgtgccctccagcagcttgggcacccagacctacatctgcaacgtgaatcacaagcccagcaa
caccaaggtggacaagagagttgagcccaaatcttgtgacaaaactcacacatgcccaccgtgc
ccagcacctgaactcctgggggggaccgtcagtcttcctcttccccccaaaacccaaggacacc
ctcatgatctcccggacccctgaggtcacatgcgtggtggtggacgtgagccacgaagaccctga
ggtcaagttcaactggtacgtggacggcgtggaggtgcataatgccaagacaaagccgcgggag
gagcagtacaacagcacgtaccgggtggtcagcgtcctcaccgtcctgcaccaggactggctga
atggcaaggagtacaagtgcaaggtctccaacaaagccctcccagcccccatcgagaaaaccat
ctccaaagccaaagggcagccccgggaaccacaggtgtacaccctgcccccatcccgggaggag
atgaccaagaaccaggtcagcctgacctgcctggtcaaaggcttctatcccagcgacatcgccg
tggagtgggagagcaatggccagccggagaacaactacaagaccacgcctcccgtgctggactc
cgacggctccttcttcctctacagcaagctcaccgtggacaagagcaggtggcagcaggggaac
gtcttctcatgctccgtgatgcatgaggctctgcacaaccactacacgcagaagagcctctccc
tgtctccgggcaaa
```

SIGNAL SEQUENCE (1-57), VARIABLE REGION (58-432), CONSTANT REGION (433-1422)

SEQ ID NO: 57: AMINO ACID SEQUENCE OF h#1G5-H1

```
MKHLWFFLLLVAAPRWVLSQVQLVQSGAEVKKPGASVKVSCKASGYTFTQYWINWVRQAPGQGL
EWMGNIYPGSSINYNEKFKSRVTITADTSTSTAYMELSSLRSEDTAVYYCARTIYNYGSSGYN
YAMDYWGQGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGN
VFSCSVMHEALHNHYTQKSLSLSPGK
```

SIGNAL SEQUENCE (1-19), VARIABLE REGION (20-144), CONSTANT REGION (145-474)

Fig. 10

SEQ ID NO: 58: NUCLEOTIDE SEQUENCE OF h#1G5-H2

```
atgaaacacctgtggttcttcctcctgctggtggcagctcccagatgggtgctgagccaggtgc
agctggtgcagtctggcgccgaagtgaagaaaccaggcgccagcgtgaaggtgtcctgcaaggc
cagcggctacaccttttaccagctactggatcaactgggtgcgccaggcccctggacagggcctg
gaatggatgggcaacatctaccccggcagcagcagcatcaactacaacgagaagttcaagagcc
gcgtgaccctgaccgtggacaccagcacaagcaccgcctacatggaactgagcagcctgcggag
cgaggacaccgccgtgtactactgcagccggaccatctacaactacggcagctccggctacaat
tacgccatggactactgggggcagggcaccctcgtgaccgtgagctcagcctccaccaagggcc
caagcgtcttccccctggcaccctcctccaagagcacctctgggggcacagcggccctgggctg
cctggtcaaggactacttccccgaaccggtgacggtgagctggaactcaggcgccctgaccagc
ggcgtgcacaccttcccggctgtcctgcagtcctcaggactctactccctcagcagcgtggtga
ccgtgccctccagcagcttgggcacccagacctacatctgcaacgtgaatcacaagcccagcaa
caccaaggtggacaagagagttgagcccaaatcttgtgacaaaactcacacatgcccaccctgc
ccagcacctgaactcctgggggggaccgtcagtcttcctcttccccccaaaacccaaggacaccc
tcatgatctcccggacccctgaggtcacatgcgtggtggtggacgtgagccacgaagaccctga
ggtcaagttcaactggtacgtggacggcgtggaggtgcataatgccaagacaaagccgcgggag
gagcagtacaacagcacgtaccgggtggtcagcgtcctcaccgtcctgcaccaggactggctga
atggcaaggagtacaagtgcaaggtctccaacaaagcccctcccagcccccatcgagaaaacat
ctccaaagccaaaggccagccccgggaaccacaggtgtacaccctgcccccatcccgggaggag
atgaccaagaaccaggtcagcctgacctgcctggtcaaaggcttctatcccagcgacatcgccg
tggagtgggagagcaatggccagccggagaacaactacaagaccacccctccgtgctggactc
cgacggctccttcttcctctacagcaagctcaccgtggacaagagcaggtggcagcaggggcaac
gtcttctcatgctccgtgatgcatgaggctctgcacaaccactacacccagaagagcctctccc
tgtctccgggcaaa
```

SIGNAL SEQUENCE (1-57), VARIABLE REGION (58-432), CONSTANT REGION (433-1422)

SEQ ID NO: 59: AMINO ACID SEQUENCE OF h#1G5-H2

```
MKHLWFFLLLVAAPRWVLSQVQLVQSGAEVKKPGASVKVSCKASGYTFTSYWINWVRQAPGQGL
EWMGNIYPGSSSINYNEKFKSRVTLTVDTSTSTAYMELSSLRSEDTAVYYCSRTIYNYGSSGYN
YAMDYWGQGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGN
VFSCSVMHEALHNHYTQKSLSLSPGK
```

SIGNAL SEQUENCE (1-19), VARIABLE REGION (20-144), CONSTANT REGION (145-474)

Fig. 11

SEQ ID NO: 60: NUCLEOTIDE SEQUENCE OF h#1G5-H3

```
atgaaacacctgtggttcttcctcctgctggtggcagctcccagatgggtgctgagccaggtgc
agctgcagcagcctggggctgagctgaaaaagccaggggcccagcgtgaaggtgtcctgcaaggc
cagcggctacacctttaccagctactggatcaactgggtgcgccaggcccctggacagggcctg
gaatggatgggcaacatctaccccggcagcagcagcatcaactacaacgagaagttcaagagcc
gggccaccctgaccgtggacaccagcaccaagcaccgcctacatggaactgagcagcctgaccag
cgaggacaccgccgtgtactactgcagccggaccatctacaactacggcagctccggctacaat
tacgccatggactactggggccagggcaccctcgtgaccgtgagctcagcctccaccaagggcc
caagcgtcttccccctggcaccctcctccaagagcacctctggcggcacagcggccctgggctg
cctggtcaaggactacttccccgaacccgtgaccgtgagctggaactcaggcgccctgaccagc
ggcgtgcacaccttcccggctgtcctacagtcctcaggactctactccctcagcagcgtggtga
ccgtgccctccagcagcttgggcacccagacctacatctgcaacgtgaatcacaagcccagcaa
caccaaggtggacaagagagttgagcccaaatcttgtgacaaaactcacacatgcccaccctgc
ccagcacctgaactcctggggggaccctcagtcttcctcttccccccaaaacccaaggacaccc
tcatgatctcccggacccctgaggtcacatgcgtggtggtggacgtgagccacgaagacccctga
ggtcaagttcaactggtacgtggacggcgtggaggtgcataatgccaagacaaagccgcgggag
gagcagtacaacagcacgtaccgggtggtcagcgtcctcaccgtcctgcaccaggactggctga
atggcaaggagtacaagtgcaaggtctccaacaaagcccctcccagcccccatcgagaaaaccat
ctccaaagccaaaggccagccccgggaaccacaggtgtacaccctgcccccatcccgggaggag
atgaccaagaaccaggtcagcctgacctgcctggtcaaaggcttctatcccagcgacatcgccg
tggagtgggagagcaatggccagccggagaacaactacaagaccacccctcccgtgctggactc
cgacggctccttcttcctctacagcaagctcaccgtggacaagagcaggtggcagcagggcaac
gtcttctcatgctccgtgatgcatgaggctctgcacaaccactacacccagaagagcctctccc
tgtctccgggcaaa
```

SIGNAL SEQUENCE (1-57), VARIABLE REGION (58-432), CONSTANT REGION (433-1422)

SEQ ID NO: 61: AMINO ACID SEQUENCE OF h#1G5-H3

```
MKHLWFFLLLVAAPRWVLSQVQLQQPGAEVKKPGASVKVSCKASGYTFTSYWINWVRQAPGQGL
EWMGNIYPGSSSINYNEKFKSRATLTVDTSTSTAYMELSSLTSEDTAVYYCSRTIYNYGSSGYN
YAMDYWGQGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGN
VFSCSVMHEALHNHYTQKSLSLSPGK
```

SIGNAL SEQUENCE (1-19), VARIABLE REGION (20-144), CONSTANT REGION (145-474)

Fig. 12

SEQ ID NO: 62: NUCLEOTIDE SEQUENCE OF h#1G5-H4

```
atgaaacacctgtggttcttcctcctgctggtggcagctcccagatgggtgctgagccaggtgc
agctgcagcagcctggcgccgagctgaaaaaacctggcgcctccgtgaaggtgtcctgcaaggc
cagcggctacacctttaccagctactggatcaactgggtgcgccaggcccctggacagggcctg
gaatggatcggcaacatctacccgcagcagcagcatcaactacaacgagaagttcaagagca
aggccaccctgaccgtggacaccagcagctccacagcctacatgcagctgtccagcctgaccag
cgacgacagcgccgtgtactactgcagccggaccatctacaactacggcagctccggctacaat
tacgccatggactactggggccagggcaccctcgtgaccgtgagctcagcctccaccaagggcc
caagcgtcttccccctggcaccctcctccaagagcacctctgggggcacagcggccctgggctg
cctggtcaaggactacttccccgaaccggtgacggtgagctggaactcaggcgccctgaccagc
ggcgtgcacaccttcccggctgtcctgcagtcctcaggactctactccctcagcagcgtggtga
ccgtgccctccagcagcttgggcacccagacctacatctgcaacgtgaatcacaagcccagcaa
caccaaggtggacaagagagttgagcccaaatcttgtgacaaaactcacacatgcccaccctgc
ccagcacctgaactcctggggggaccctcagtcttcctcttccccccaaaacccaaggacaccc
tcatgatctcccggacccctgaggtcacatgcgtggtggtggacgtgagccacgaagaccctga
ggtcaagttcaactggtacgtggacggcgtggaggtgcataatgccaagacaaagccgcgggag
gagcagtacaacagcacgtaccgggtggtcagcgtcctcaccgtcctgcaccaggactggctga
atggcaaggagtacaagtgcaaggtctccaacaaagccctcccagcccccatcgagaaaaccat
ctccaaagccaaaggccagccccgggaaccacaggtgtacaccctgcccccatcccgggaggag
atgaccaagaaccaggtcagcctgacctgcctggtcaaaggcttctatcccagcgacatcgccg
tggagtgggagagcaatgggcagccggagaacaactacaagaccaccctcccgtgctggactc
cgacggctccttcttcctctacagcaagctcaccgtggacaagagcaggtggcagcaggggaac
gtcttctcatgctccgtgatgcatgaggctctgcacaaccactacacccagaagagcctctccc
tgtctccgggcaaa
```

SIGNAL SEQUENCE (1-57), VARIABLE REGION (58-432), CONSTANT REGION (433-1422)

SEQ ID NO: 63: AMINO ACID SEQUENCE OF h#1G5-H4

```
MKHLWFFLLLVAAPRWVLSQVQLQQPGAELKKPGASVKVSCKASGYTFTSYWINWVRQAPGQGL
EWIGNIYPGSSSINYNEKFKSKATLTVDTSSSTAYMQLSSLTSDDSAVYYCSRTIYNYGSSGYN
YAMDYWGQGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGN
VFSCSVMHEALHNHYTQKSLSLSPGK
```

SIGNAL SEQUENCE (1-19), VARIABLE REGION (20-144), CONSTANT REGION (145-474)

Fig. 13

SEQ ID NO: 64: NUCLEOTIDE SEQUENCE OF h#1G5-H5

```
atgaaacacctgtggttcttcctcctgctggtggcagctcccagatgggtgctgagccaggtgc
agctgcagcagcctggggcggagctgaaaaaacctggggcctccgtgaaggtgtcctgcaaggc
cagcggctacaccttcaccagctactggatcaactgggtcaagcagcggccaggccagggcctg
gaatggatcggcaatatctaccccggcagcagcagcatcaactacaacgagaagttcaagagca
aggccaccctgaccgtggacaccagcagctccacagcctacatgcagctgtccagcctgaccag
cgacgacagcgccgtgtactactgcagccggaccatctacaactacggcagctccggctacaat
tacgccatggactactggggccaggccaccagcgtgatcgtgagctcagctccaccaagggcc
caagcgtcttcccctggcaccctcctccaagagcacctctggcggcacagccgccctgggctg
cctggtcaaggactacttccccgaaccgtgaccgtgagctggaactcaggcgccctgaccag
cggcgtgcacaccttccccgctgtcctgcagtcctcaggactctactccctcagcagcgtggtga
ccgtgccctccagcagcttgggcacccagacctacatctgcaacgtgaatcacaagcccagcaa
caccaaggtggacaagagagttgagcccaaatcttgtgacaaaactcacacatgcccaccctgc
ccagcacctgaactcctgggggggaccctcagtcttcctcttccccccaaaacccaaggacaccc
tcatgatctcccggacccctgaggtcacatgcgtggtggtggacgtgagccacgaagaccctga
ggtcaagttcaactggtacgtggacggcgtggaggtgcataatgccaagacaaagccgcggag
gagcagtacaacagcacgtaccgggtggtcagcgtcctcaccgtcctgcaccaggactggctga
atggcaaggagtacaagtgcaaggtctccaacaaagccctcccagcccccatcgagaaaaccat
ctccaaagccaaaggcagccccgggaaccacaggtgtacaccctgcccccatcccgggaggag
atgaccaagaaccaggtcagcctgacctgcctggtcaaaggcttctatcccagcgacatcgccg
tggagtgggagagcaatggccagccggagaacaactacaagaccacccctcccgtgctggactc
cgacggctccttcttcctctacagcaagctcaccgtggacaagagcaggtggcagcagggcaac
gtcttctcatgctccgtgatgcatgaggctctgcacaaccactacacccagaagagcctctccc
tgtctccgggcaaa
```

SIGNAL SEQUENCE (1-57), VARIABLE REGION (58-432), CONSTANT REGION (433-1422)

SEQ ID NO: 65: AMINO ACID SEQUENCE OF h#1G5-H5

```
MKHLWFFLLLVAAPRWVLSQVQLQQPGAELKKPGASVKVSCKASGYTFTSYWINWVKQRPGQGL
EWIGNIYPGSSSINYNEKFKSKATLTVDTSSSTAYMQLSSLTSDDSAVYYCSRTIYNYGSSGYN
YAMDYWGQGTSVIVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSCDKTHTCPPC
PAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGN
VFSCSVMHEALHNHYTQKSLSLSPGK
```

SIGNAL SEQUENCE (1-19), VARIABLE REGION (20-144), CONSTANT REGION (145-474)

Fig. 14

SEQ ID NO: 66: NUCLEOTIDE SEQUENCE OF h#1G5-L1 atggtgctgcagacccaggtgttcatctccctgctgctgtggatctccggcgcgtacggcgaca
tcgtgatgacccagagccctgacagcctggcgtgtctctgggagagagagccaccatcaactg
caaggccagcgagaacgtgggcaacagcgtgtcctggtatcagcagaagccaggccagccccc
aagctgctgatctacggcgccagcaacagatacaccggcgtgcccgatagattcagcggcagcg
gctctggcaccgacttcaccctgacaatcagctccctgcaggccgaggacgtggccgtgtacta
ctgtggccagagctacagctaccccctacaccttcggccagggcaccaaggtggaaatcaagcgt
acggtggccgcccctccgtgttcatcttcccccctccgacgagcagctgaagtccggcaccg
cctccgtggtgtgctgctgaataacttctaccccagagaggccaaggtgcagtggaaggtgga
caacgccctgcagtccggggaactcccaggagagcgtgaccgagcaggacagcaaggacagcacc
tacagcctgagcagcaccctgaccctgagcaaagccgactacgagaagcacaaggtgtacgcct
gcgaggtgacccaccagggcctgagctcccccgtcaccaagagcttcaacaggggggagtgt

SIGNAL SEQUENCE (1-60), VARIABLE REGION (61-387), CONSTANT

REGION (388-702)

SEQ ID NO: 67: AMINO ACID SEQUENCE OF h#1G5-L1

MVLQTQVFISLLLWISGAYGDIVMTQSPDSLAVSLGERATINCKASENVGNSVSWYQQKPGQPP
KLLIYGASNRYTGVPDRFSGSGSGTDFTLTISSLQAEDVAVYYCGQSYSYPYTFGQGTKVEIKR
TVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC

SIGNAL SEQUENCE (1-20), VARIABLE REGION (21-129), CONSTANT

REGION (130-234)

Fig. 15

SEQ ID NO: 68: NUCLEOTIDE SEQUENCE OF h#1G5-L2 atggtgctgcagacccaggtgttcatctccctgctgctgtggatctccggcgcgtacggcaaca
tgtgatgacccagagccccgacagcctggccgtgtctctgggagagagagccaccatcagctg
caaggccagcgagaacgtgggcaacagcgtgtcctggtatcagcagaagcccggccagagccct
aagcccctgatctacggcgccagcaacagatacaccggcgtgcccgatagattcagcggcagcg
gctctgccaccgacttcaccctgacaatcagctcccTgcaggccgaggacgtggccgtgtatca
ctgtggccagagctacagctacccctacaccttcggcggaggcaccaaggtggaaatcaagcgt
acggtggccgcccctccgtgttcatcttcccccctccgacgagcagctgaagtccggcaccg
cctccgtggtgtgcctgctgaataacttctaccccagagaggccaaggtgcagtggaaggtgga
caacgccctgcagtccgggaactcccaggagagcgtgaccgagcaggacagcaaggacagcacc
tacagcctgagcagcaccctgaccctgagcaaagccgactacgagaagcacaaggtgtacgcct
gcgaggtgacccaccagggcctgagctcccccgtcaccaagagcttcaacaggggggagtgt

SIGNAL SEQUENCE (1-60), VARIABLE REGION (61-387), CONSTANT REGION (388-702)

SEQ ID NO: 69: AMINO ACID SEQUENCE OF h#1G5-L2

MVLQTQVFISLLLWISGAYGNIVMTQSPDSLAVSLGERATISCKASENVGNSVSWYQQKPGQSP
KPLIYGASNRYTGVPDRFSGSGSATDFTLTISSLQAEDVAVYHCGQSYSYPYTFGGGTKVEIKR
TVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC

SIGNAL SEQUENCE (1-20), VARIABLE REGION (21-129), CONSTANT REGION (130-234)

Fig. 16

SEQ ID NO: 70: NUCLEOTIDE SEQUENCE OF h#1G5-L3

```
atggtgctgcagacccaggtgttcatctccctgctgctgtggatctccggcgcgtacggcaaca
tcgtgatgacccagagccccgacagcctggccgtgtctctgggagagagagccaccatcagctg
caaggccagcgagaacgtgggcaacagcgtgtcctggtatcagcagaagcccggccagagccct
aagcccctgatctacggcgccagcaacagatacaccggcgtgcccgatagattcagcggcagcg
gctctgccaccgacttcaccctgacaatcagctccctgcaggccgaggacgtggccgattatca
ctgcggccagtcctacagctaccccctacaccttaggcggaggcaccaaggtggaaatcaagcgt
acggtggccgccccctccgtgttcatcttcccccctccgacgagcagctgaagtccggcaccg
cctccgtggtgtgcctgctgaataacttctaccccagagaggccaaggtgcagtggaaggtgga
caacgccctgcagtccggggaactcccaggagagcgtgaccgagcaggacagcaaggacagcacc
tacagcctgagcagcaccctgaccctgagcaaagccgactacgagaagcacaaggtgtacgcct
gcgaggtgacccaccagggcctgagctccccgtcaccaagagcttcaacagggggggagtgt
```

SIGNAL SEQUENCE (1-60), VARIABLE REGION (61-387), CONSTANT REGION (388-702)

SEQ ID NO: 71: AMINO ACID SEQUENCE OF h#1G5-L3

```
MVLQTQVFISLLLWISGAYGNIVMTQSPDSLAVSLGERATISCKASENVGNSVSWYQQKPGQSP
KPLIYGASNRYTGVPDRFSGSGSATDFTLTISSLQAEDVADYHCGQSYSYPYTFGGGTKVEIKR
TVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC
```

SIGNAL SEQUENCE (1-20), VARIABLE REGION (21-129), CONSTANT REGION (130-234)

Fig. 17

SEQ ID NO: 72: NUCLEOTIDE SEQUENCE OF h#1G5-L4

```
atggtgctgcagacccaggtgttcatctcctgctgctgtggatctccggcgcgtacggcaaca
tcgtgatgacccagagccccgacagcatgagcatgagcgtgggcgagagagccacccctgagctg
caaggcctctgagaacgtgggcaacagcgtgtcctggtatcagcagaaggccgagcagagcccc
aagcccctgatctacggcgccagcaacagatacaccggcgtgcccgatagattcaccggcagcg
gcagcgccaccgacttcaccctgacaatcagctccctgcaggccgaggacctggccgattatca
ctgcggccagagctacagctaccccctacaccttggcggaggcaccaagctggaaatcaagcgt
acggtggccgcccctccgtgttcatcttcccccctccgacgagcagctgaagtccggcaccg
cctccgtggtgtgcctgctgaataacttctaccccagagaggccaaggtgcagtggaaggtgga
caacgccctgcagtccgggaactcccaggagagcgtgaccgagcaggacagcaaggacagcacc
tacagcctgagcagcaccctgaccctgagcaaagccgactacgagaagcacaaggtgtacgcct
gcgaggtgacccaccagggcctgagctcccccgtcaccaagagcttcaacaggggggagtgt
```

SIGNAL SEQUENCE (1-60), VARIABLE REGION (61-387), CONSTANT REGION (388-702)

SEQ ID NO: 73: AMINO ACID SEQUENCE OF h#1G5-L4

```
MVLQTQVFISLLLWISGAYGNIVMTQSPDSMSMSVGERATLSCKASENVGNSVSWYQQKAEQSP
KPLIYGASNRYTGVPDRFTGSGSATDFTLTISSLQAEDLADYHCGQSYSYPYTFGGGTKLEIKR
TVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC
```

SIGNAL SEQUENCE (1-20), VARIABLE REGION (21-129), CONSTANT REGION (130-234)

Fig. 18

SEQ ID NO: 74: NUCLEOTIDE SEQUENCE OF h#1G5-L5 atggtgctgcagacccaggtgttcatctccctgctgctgtggatctccggcgcgtacggcaaca
tcgtgatgacccagagccccgacagcatgagcatgagcgtgggcgagagagtgaccctgagctg
caaggccagcgagaacgtgggcaacagcgtgtcctggtatcagcagaaggccgagcagagcccc
aagcccctgatctacggcgccagcaacagatacaccggcgtgcccgatagattcaccggcagcg
gcagcgccaccgacttcaccctgacaatcagctccctgcaggccgaggacctggccgattatca
ctgcggccagagctacagctaccctacaccttttggcggaggcaccaagctggaaatcaagcgt
acggtggccgcccctccgtgttcatcttccccccctccgacgagcagctgaagtccggcaccg
cctccgtggtgtgcctgctgaataacttctaccccagagagggccaaggtgcagtggaaggtgga
caacgccctgcagtccgggaactcccaggagagcgtgaccgagcaggacagcaaggacagcacc
tacagcctgagcagcaccctgaccctgagcaaagccgactacgagaagcacaaggtgtacgcct
gcgaggtgacccaccagggcctgagctcccccgtcaccaagagcttcaacaggggggagtgt

SIGNAL SEQUENCE (1-60), VARIABLE REGION (61-387), CONSTANT

REGION (388-702)

SEQ ID NO: 75: AMINO ACID SEQUENCE OF h#1G5-L5

MVLQTQVFISLLLWISGAYGNIVMTQSPDSMSMSVGERVTLSCKASENVGNSVSWYQQKAEQSP
KPLIYGASNRYTGVPDRFTGSGSATDFTLTISSLQAEDLADYHCGQSYSYPYTFGGGTKLEIKR
TVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC

SIGNAL SEQUENCE (1-20), VARIABLE REGION (21-129), CONSTANT

REGION (130-234)

Fig. 19

SEQ ID NO: 76: NUCLEOTIDE SEQUENCE OF h#4C13K-H1 atgaaacacctgtggttcttcctcctgctggtggcagctccagatgggtgctgagccaggtgc
agctggtgcagtctggcgccgaagtgaagaaaccaggcgccagcgtgaaggtgtcctgcaaggc
cagcggctacaccttaccacctactggatcaactgggtgcgccaggcccctggacagggcctg
gaatggatgggcaacatctaccccggcaccagaagcagcaactacaacgagaagttcaagaacc
gcgtgaccatcaccgccgacaccagcaccagcacagcctacatggaactgagcagcctgcggag
cgaggacaccgccgtgtactactgcgccagagtgtactacgaccacgtgggctactactcgac
tactggggccagggcaccctcgtgacctgagcctcagcctccaccaagggcccaagcgtcttcc
ccctggcaccctcctccaagagcacctctggcggcacagccgcctgggctgcctggtcaagga
ctacttccccgaaccggtgaccgtgagctggaactcaggcgccctgaccagcggcgtgcacacc
ttccccgctgtcctgcagtcctcaggactctactccctcagcagcgtggtgaccgtgccctca
gcagcttgggcacccagacctacatctgcaacgtgaatcacaagcccagcaacaccaaggtgga
caagagagttgagcccaaatcttgtgacaaaactcacacatgcccaccctgcccagcacctgaa
ctcctggggggaccctcagtcttcctcttccccccaaaacccaaggacaccctcatgatctccc
ggacccctgaggtcacatgcgtggtggtggacgtgagccacgaagaccctgaggtcaagttcaa
ctggtacgtggacggcgtggaggtgcataatgccaagacaaagccgcgggaggagcagtacaac
agcacgtaccgggtggtcagcgtcctcaccgtcctgcaccaggactggctgaatggcaaggagt
acaagtgcaaggtctccaacaaagcccctcccagccccatcgagaaaaccatctccaaagccaa
aggccagccccgggaaccacaggtgtacaccctgcccccatcccgggaggagatgaccaagaac
caggtcagcctgacctgcctggtcaaaggcttctatcccagcgacatcgccgtggagtgggaga
gcaatggccagccggagaacaactacaagaccaccctcccgtgctggactccgacggctcctt
cttcctctacagcaagctcaccgtggacaagagcaggtggcagcagggcaacgtcttctcatgc
tccgtgatgcatgaggctctgcacaaccactacacccagaagagcctctccctgtctccggca
aa

SIGNAL SEQUENCE (1-57), VARIABLE REGION (58-420), CONSTANT

REGION (421-1410)

SEQ ID NO: 77: AMINO ACID SEQUENCE OF h#4C13K-H1

MKHLWFFLLLVAAPRWVLSQVQLVQSGAEVKKPGASVKVSCKASGYTFTTYWINWVRQAPGQGL
EWMGNIYPGTRSSNYNEKFKNRVTITADTSTSTAYMELSSLRSEDTAVYYCARVYYDHVGYYFD
YWGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK

SIGNAL SEQUENCE (1-19), VARIABLE REGION (20-140), CONSTANT

REGION (141-470)

Fig. 20

SEQ ID NO: 78: NUCLEOTIDE SEQUENCE OF h#4C13K-H2 atgaaacacctgtggttcttcctcctgctggtggcagctcccagatgggtgctgagccaggtgc
agctggtgcagtctggcgccgaagtgaagaaaccaggcgccagcgtgaaggtgtcctgcaaggc
cagcggctacaccttaccacctactggatcaactgggtgcgccaggcccctggacagggcctg
gaatggatgggcaacatctaccccggcaccagaagcagcaactacaacgagaagttcaagaacc
gcgtgaccctgaccgtggacacaagcaccagcacagcctacatggaactgagcagcctgcggag
cgaggacacggccgtgtactactgtaccggtgtactacgaccacgtgggctactacttcgac
tactggggccagggcaccctcgtgaccgtgagctcagcctccaccaagggcccaagcgtcttcc
cctggcacctcctccaagagcacctctggcggcacagccgccctgggctgcctggtcaagga
ctacttccccgaaccggtgaccgtgagctggaactcaggcgccctgaccagcggcgtgcacacc
ttccccgctgtcctgcagtcctcaggactctactccctcagcagcgtggtgaccgtgccctca
gcagcttgggcacccagacctacatctgcaacgtgaatcacaagcccagcaacaccaaggtgga
caagagagttgagcccaaatcttgtgacaaaactcacacatgcccaccctgcccagcacctgaa
ctcctggggggaccctcagtcttcctcttccccccaaaacccaaggacaccctcatgatctccc
ggacccctgaggtcacatgcgtggtggtggacgtgagccacgaagaccctgaggtcaagttcaa
ctggtacgtggacggcgtggaggtgcataatgccaagacaaagccgcgggaggagcagtacaac
agcacgtaccgggtggtcagcgtcctcaccgtcctgcaccaggactggctgaatggcaaggagt
acaagtgcaaggtctccaacaaagccctcccagcccccatcgagaaaaccatctccaaagccaa
aggccagccccgggaaccacaggtgtacaccctgccccatcccgggaggagatgaccaagaac
caggtcagcctgacctgcctggtcaaaggcttctatcccagcgacatcgccgtggagtgggaga
gcaatgggcagccggagaacaactacaagaccacccctcccgtgctggactccgacggctcctt
cttcctctacagcaagctcaccgtggacaagagcaggtggcagcaggcaacgtcttctcatgc
tccgtgatgcatgaggctctgcacaaccactacacccagaagagcctctccctgtctccgggca
aa

SIGNAL SEQUENCE (1-57), VARIABLE REGION (58-420), CONSTANT

REGION (421-1410)

SEQ ID NO: 79: AMINO ACID SEQUENCE OF h#4C13K-H2

MKHLWFFLLLVAAPRWVLSQVQLVQSGAEVKKPGASVKVSCKASGYTFTTYWINWVRQAPGQGL
EWMGNIYPGTRSSNYNEKFKNRVTLTVDTSTSTAYMELSSLRSEDTAVYYCTRVYYDHVGYYFD
YWGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK

SIGNAL SEQUENCE (1-19), VARIABLE REGION (20-140), CONSTANT

REGION (141-470)

Fig. 21

SEQ ID NO: 80: NUCLEOTIDE SEQUENCE OF h#4C13K-H3

```
atgaaacacctgtggttcttcctcctgctggtggcagctccagatgggtgctgagccaggtgc
agctgcagcagcctggcgccgaagtgaaaaagccaggcgccagcgtgaaggtgtcctgcaaggc
cagcggctacacctttaccacctactggatcaactggatgcagcagcggccaggccagggcctg
gaatggatgggcaatatctacccoggcaccagaagcagcaactacaacgagaagttcaagaacc
gggccaccctgaccgtggacaccagcacaagcacCgcCtacatggaactgagcagcctgaccag
cgaggacaccgccgtgtactactgcaccagagtgtactacgaccacgtgggctactacttcgac
tactggggccagggcaccctcgtgaccgtgagctcagcctccaccaagggcccaagcgtcttcc
cCctggcaccctcctccaagagcacctctgggggcacagcggccctgggctgcctggtcaagga
ctacttccccgaaccCgtgacCgtgagctggaactCaggcgCcctgaccagcggCgtgcaCaCc
ttccccgctgtcctgcagtcCtcaggactctactcCctcagcagcgtggtgaccgtgccctca
gcagcttgggcacccagacctacatctgcaacgtgaatcacaagcccagcaacaccaaggtgga
caagagagttgagcccaaatcttgtgacaaaactcacacatgcccaccctgcccagcacctgaa
ctcctgggggaccctcagtcttcctcttccccccaaaacccaaggacaccctcatgatctccc
ggacccctgaggtcacatgcgtggtggtggacgtgagccacgaagaccctgaggtcaagttcaa
Ctggtacgtggacggcgtggaggtgcataatgccaagacaaagccccgggaggagcagtacaac
agcacgtaccgggtggtcagcgtcctcaccgtcctgcaccaggactggctgaatggcaaggagt
acaagtgcaaggtctccaacaaagccctcccagccCccatcgagaaaaccatctccaaagccaa
aggCcagccCcgggaaccacaggtgtacaccctgcccccatcccgggaggagatgaccaagaac
caggtcagcctgacctgcctggtcaaaggcttctatcccagcgacatcgccgtggagtgggaga
gcaatgggcagccggagaacaactacaagaccacccctcccgtgctggactccgacggctcctt
cttcctctacagcaagctcaccgtggacaagagcaggtggcagcaggggaacgtcttctcatgc
tccgtgatgcatgaggctctgcacaaccactacacccagaagagcctctccctgtctccggca
aa
```

SIGNAL SEQUENCE (1-57), VARIABLE REGION (58-420), CONSTANT REGION (421-1410)

SEQ ID NO: 81: AMINO ACID SEQUENCE OF h#4C13K-H3

```
MEHLWFFLLLVAAPRWVLSQVQLQQPGAEVKKPGASVKVSCKASGYTFTTYWINWMQQRPGQGL
EWMGNIYPGTRSSNYNEKFKNRATLTVDTSTSTAYMELSSLTSEDTAVYYCTRVYYDHVGYYFD
YWGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK
```

SIGNAL SEQUENCE (1-19), VARIABLE REGION (20-140), CONSTANT REGION (141-470)

Fig. 22

SEQ ID NO: 82: NUCLEOTIDE SEQUENCE OF h#4C13K-H4

```
atgaaacacctgtggttcttcctcctgctggtggcagctcccagatgggtgctgagccaggtgc
agctgcagcagcctggggcggagctgaaaaaacctggggcctccgtgaaggtgtcctgcaaggc
cagcggctacacctttaccacctactggatcaactggatgcagcagcggccaggccagggcctg
gaatggatcggcaatatctaccccggcaccagaagcagcaactacaacgagaagttcaagaaca
aggccaccctgaccgtggacaccagcagctccaccgcctacatggaactgagcagcctgaccag
cgacgacagcgccgtgtactactgcaccagagtgtactacgaccacgtgggctactacttcgac
tactggggccagggcaccctcgtgaccgtgagctcagcctccaccaaggggccaagcgtcttcc
ccctggcaccctcctccaagagcacctctgggggcacagcggccctgggctgcctggtcaagga
ctacttccccgaaccggtgacggtgagctggaactcaggcgccctgaccagcggcgtgcacacc
ttccccgctgtcctgcagtcctcaggactctactccctcagcagcgtggtgaccgtgccctcca
gcagcttgggcacccagacctacatctgcaacgtgaatcacaagcccagcaacaccaaggtgga
caagagagttgagcccaaatcttgtgacaaaactcacacatgcccaccctgcccagcacctgaa
ctcctggggggaccgtcagtcttcctcttccccccaaaacccaaggacaccctcatgatctccc
ggacccctgaggtcacatgcgtggtggtggacgtgagccacgaagaccctgaggtcaagttcaa
ctggtacgtggacggcgtggaggtgcataatgccaagacaaagccgcgggaggagcagtacaac
agcacgtaccgggtggtcagcgtcctcaccgtcctgcaccaggactggctgaatggcaaggagt
acaagtgcaaggtctccaacaaagccctcccagcccccatcgagaaaaccatctccaaagccaa
aggccagccccgggaaccacaggtgtacaccctgcccccatcccgggaggagatgaccaagaac
caggtcagcctgacctgcctggtcaaaggcttctatcccagcgacatcgccgtggagtgggaga
gcaatggccagccggagaacaactacaagaccaccctcccgtgctggactccgacggctcctt
cttcctctacagcaagctcaccgtggacaagagcaggtggcagcagggcaacgtcttctcatgc
tccgtgatgcatgaggctctgcacaaccactacacccagaagagcctctccctgtctccgggca
aa
```

SIGNAL SEQUENCE (1-57), VARIABLE REGION (58-420), CONSTANT REGION (421-1410)

SEQ ID NO: 83: AMINO ACID SEQUENCE OF h#4C13K-H4

```
MKHLWFFLLLVAAPRWVLSQVQLQQPGAELKKPGASVKVSCKASGYTFTTYWINWMQQRPGQGL
EWIGNIYPGTRSSNYNEKFKNKATLTVDTSSSTAYMELSSLTSDDSAVYYCTRVYYDHVGYYFD
YWGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK
```

SIGNAL SEQUENCE (1-19), VARIABLE REGION (20-140), CONSTANT REGION (141-470)

Fig. 23

SEQ ID NO: 84: NUCLEOTIDE SEQUENCE OF h#4C13K-H5

```
atgaaacacctgtggttcttcctcctgctggtggcagctccagatgggtgctgagccaggtgc
agctgcagcagcctggcgccgagctgaaaaaacctggcgcctccgtgaaggtgtcctgcaaggc
cagcggctacacctttaccacctactggatcaactggatgcagcagcggccaggccagggcctg
gaatggatcggcaatatctaccccggcaccagaagcagcaactacaacgagaagttcaagaaca
aggccaccctgaccgtggacaccagcagctccacagcctacatgcagctgaactccctgaccag
cgacgacagcgccgtgtactactgcaccagagtgtactacgaccacgtgggctactacttcgac
tactggggccagggcaccctcgtgaccgtgagctcagcctccaccaagggcccaagcgtcttcc
ccctggcaccctcctccaagagcacctctgggggcacagccgccctgggctgcctggtcaagga
ctacttccccgaacccgtgaccgtgagctggaactcaggcgccctgaccagcggcgtgcacacc
ttccccgctgtcctgcagtcctcaggactctactccctcagcagcgtggtgaccgtgccctca
gcagcttgggcacccagacctacatctgcaacgtgaatcacaagcccagcaacaccaaggtgga
caagagagttgagcccaaatcttgtgacaaaactcacacatgcccaccctgcccagcacctgaa
ctcctgggggaccctcagtcttcctcttccccccaaaacccaaggacaccctcatgatctccc
ggacccctgaggtcacatgcgtggtggtggacgtgagccacgaagaccctgaggtcaagttcaa
ctggtacgtggacggcgtggaggtgcataatgccaagacaaagccgcgggaggagcagtacaac
agcacgtaccgggtggtcagcgtcctcaccgtcctgcaccaggactggctgaatggcaaggagt
acaagtgcaaggtctccaacaaagccctcccagcccccatcgagaaaaccatctccaaagccaa
aggccagccccgggaaccacaggtgtacaccctgcccccatcccgggaggagatgaccaagaac
caggtcagcctgacctgcctggtcaaaggcttctatcccagcgacatcgccgtggagtgggaga
gcaatggccagccggagaacaactacaagaccacccctcccgtgctggactccgacggctcctt
cttcctctacagcaagctcaccgtggacaagagcaggtggcagcagggcaacgtcttctcatgc
tccgtgatgcatgaggctctgcacaaccactacacccagaagagcctctccctgtctccgggca
aa
```

SIGNAL SEQUENCE (1-57), VARIABLE REGION (58-420), CONSTANT REGION (421-1410)

SEQ ID NO: 85: AMINO ACID SEQUENCE OF h#4C13K-H5

```
MKHLWFFLLVAAPRWVLSQVQLQQPGAELKKPGASVKVSCKASGYTFTTYWINWMQQRPGQGL
EWIGNIYPGTRSSNYNEKFKNKATLTVDTSSSTAYMQLNSLTSDDSAVYYCTRVYYDHVGYYFD
YWGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK
```

SIGNAL SEQUENCE (1-19), VARIABLE REGION (20-140), CONSTANT REGION (141-470)

Fig. 24

SEQ ID NO: 123: AMINO ACID SEQUENCE OF #4C13 LIGHT CHAIN CDR1

KASENVGVSVS

SEQ ID NO: 124: AMINO ACID SEQUENCE OF #4C13 LIGHT CHAIN CDR2

GASNRYT

SEQ ID NO: 125: AMINO ACID SEQUENCE OF #4C13 LIGHT CHAIN CDR3

GQSYSYPYT

SEQ ID NO: 86: AMINO ACID SEQUENCE OF #4C13 HEAVY CHAIN CDR1

TYWIN

SEQ ID NO: 87: AMINO ACID SEQUENCE OF #4C13 HEAVY CHAIN CDR2

NIYPGTRSSNYNEKFKN

SEQ ID NO: 88: AMINO ACID SEQUENCE OF #4C13 HEAVY CHAIN CDR3

VYYDHVGYYFDY

SEQUENCE LISTING

<160> NUMBER OF SEQ ID NOS: 125

<210> SEQ ID NO 1
<211> LENGTH: 6007
<212> TYPE: DNA
<213> ORGANISM: Artificial Sequence
<220> FEATURE:
<223> OTHER INFORMATION: Nucleotide coding of pJON mIgG2a

<400> SEQUENCE: 1

| | | | | | |
|---|---|---|---|---|---|
| tagttattaa | tagtaatcaa | ttacggggtc | attagttcat | agcccatata | tggagttccg | 60 |
| cgttacataa | cttacggtaa | atggcccgcc | tggctgaccg | cccaacgacc | cccgcccatt | 120 |
| gacgtcaata | atgacgtatg | ttcccatagt | aacgccaata | gggactttcc | attgacgtca | 180 |
| atgggtggag | tatttacggt | aaactgccca | cttggcagta | catcaagtgt | atcatatgcc | 240 |
| aagtacgccc | cctattgacg | tcaatgacgg | taaatggccc | gcctggcatt | atgcccagta | 300 |
| catgacctta | tgggactttc | ctacttggca | gtacatctac | gtattagtca | tcgctattac | 360 |
| catggtgatg | cggttttggc | agtacatcaa | tgggcgtgga | tagcggtttg | actcacgggg | 420 |
| atttccaagt | ctccacccca | ttgacgtcaa | tgggagtttg | ttttggcacc | aaaatcaacg | 480 |
| ggactttcca | aaatgtcgta | acaactccgc | cccattgacg | caaatgggcg | gtaggcgtgt | 540 |
| acggtgggag | gtctatataa | gcagagctgg | tttagtgaac | cgtcagatcc | gctagaattc | 600 |
| tgcagtcgac | ggtaccgcgg | gcccgggatc | ccccccccc | ccgatgggac | gtccacatat | 660 |
| acctgccgtt | cactattatt | tagtgaaatg | agatattatg | atattttctg | aattgtgatt | 720 |
| aaaaaggcaa | ctttatgccc | atgcaacaga | actataaaa | aatacagaga | atgaaaagaa | 780 |
| acagatagat | tttttagttc | tttaggcccg | tagtctgcaa | atccttttat | gattttctat | 840 |
| caaacaaaag | aggaaaatag | accagttgca | atccaaacga | gagtctaata | gaatgaggtc | 900 |
| gaaaagtaaa | tcgcgcgggt | ttgttactga | taaagcaggc | aagacctaaa | atgtgtaaag | 960 |
| ggcaaagtgt | atactttggc | gtcacccctt | acatatttta | ggtcttttt | tattgtgcgt | 1020 |
| aactaacttg | ccatcttcaa | acaggagggc | tggaagaagc | agaccgctaa | cacagtacat | 1080 |
| aaaaaaggag | acatgaacga | tgaacatcaa | aaagtttgca | aaacaagcaa | cagtattaac | 1140 |
| ctttactacc | gcactgctgg | caggaggcgc | aactcaagcg | tttgcgaaag | aaacgaacca | 1200 |
| aaagccatat | aaggaaacat | acggcatttc | ccatattaca | cgccatgata | tgctgcaaat | 1260 |
| ccctgaacag | caaaaaaatg | aaaaatatca | agttcctgag | ttcgattcgt | ccacaattaa | 1320 |
| aaatatctct | tctgcaaaag | gcctggacgt | ttgggacagc | tggccattac | aaaacgctga | 1380 |
| cggcactgtc | gcaaactatc | acggctacca | catcgtcttt | gcattagccg | agatcctaa | 1440 |
| aaatgcggat | gacacatcga | tttacatgtt | ctatcaaaaa | gtcggcgaaa | cttctattga | 1500 |
| cagctggaaa | aacgctggcc | gcgtctttaa | agacagcgac | aaattcgatg | caaatgattc | 1560 |
| tatcctaaaa | gaccaaacac | aagaatggtc | aggttcagcc | acatttacat | ctgacggaaa | 1620 |
| aatccgttta | ttctacactg | atttctccgg | taaacattac | ggcaaacaaa | cactgacaac | 1680 |
| tgcacaagtt | aacgtatcag | catcagacag | ctctttgaac | atcaacggtg | tagaggatta | 1740 |
| taaatcaatc | tttgacggtg | acggaaaaac | gtatcaaaat | gtacagcagt | tcatcgatga | 1800 |
| aggcaactac | agctcaggcg | acaaccatac | gctgagagat | cctcactacg | tagaagataa | 1860 |
| aggccacaaa | tacttagtat | ttgaagcaaa | cactggaact | gaagatggct | accaaggcga | 1920 |
| agaatctttg | tttaacaaag | catactatgg | caaaagcaca | tcattcttcc | gtcaagaaag | 1980 |
| tcaaaaactt | ctgcaaagcg | ataaaaaacg | cacggctgag | ttagcaaacg | gcgctctcgg | 2040 |

```
tatgattgag ctaaacgatg attacacact gaaaaaagtg atgaaaccgc tgattgcatc    2100
taacacagta acagatgaaa ttgaacgcgc gaacgtcttt aaaatgaacg gcaaatggta    2160
cctgttcact gactcccgcg gatcaaaaat gacgattgac ggcattacgt ctaacgatat    2220
ttacatgctt ggttatgttt ctaattcttt aactggccca tacaagccgc tgaacaaaac    2280
tggccttgtg ttaaaaatgg atcttgatcc taacgatgta acctttactt actcacactt    2340
cgctgtacct caagcgaaag gaaacaatgt cgtgattaca agctatatga caaacagagg    2400
attctacgca gacaaacaat caacgtttgc gcctagcttc ctgctgaaca tcaaaggcaa    2460
gaaaacatct gttgtcaaag acagcatcct gaacaagga caattaacag ttaacaaata    2520
aaaacgcaaa agaaaatgcc gatatcctat tggcattgac gtcaggtggc acttttcggg    2580
gaaatgtgcg cggaacccct atttgtttat ttttctaaat acattcaaat atgtatccgc    2640
tcatgagaca ataaccctga taaatgcttc aataatattg aaaaaggaag agtatgagta    2700
ttcaacattt ccgtgtcgcc cttattccct tttttgcggc attttgcctt cctgtttttg    2760
ctcacccaga aacgctggtg aaagtaaaag atgctgaaga tcagttgggt gcacgagtgg    2820
gttacatcga actggatctc aacagcggta agatccttga gagttttcgc cccgaagaac    2880
gttttccaat gatgagcact tttaaagttc tgctatgtgg cgcggtatta tcccgtattg    2940
acgccgggca agagcaactc ggtcgccgca tacactattc tcagaatgac ttggttgagt    3000
actcaccagt cacagaaaag catcttacgg atggcatgac agtaagagaa ttatgcagtg    3060
ctgccataac catgagtgat aacactgcgg ccaacttact tctgacaacg atcggaggac    3120
cgaaggagct aaccgctttt ttgcacaaca tgggggatca tgtaactcgc cttgatcgtt    3180
gggaaccgga gctgaatgaa gccataccaa acgacgagcg tgacaccacg atgcctgtag    3240
caatggcaac aacgttgcgc aaactattaa ctggcgaact acttactcta gcttcccggc    3300
aacaattaat agactggatg gaggcggata aagttgcagg accacttctg cgctcggccc    3360
ttccggctgg ctggtttatt gctgataaat ctggagccgg tgagcgtggg tctcgcggta    3420
tcattgcagc actggggcca gatggtaagc cctcccgtat cgtagttatc tacacgacgg    3480
ggagtcaggc aactatggat gaacgaaata gacagatcgc tgagataggt gcctcactga    3540
ttaagcattg gtaactgtca gaccaagttt actcatatat actttagatt gatttaaaac    3600 ttcatttta atttaaaagg atctaggtga agatccttt tgataatctc atgaccaaaa    3660
tcccttaacg tgagttttcg ttccactgag cgtcagaccc cgtagaaaag atcaaaggat    3720
cttcttgaga tcctttttt ctgcgcgtaa tctgctgctt gcaaacaaaa aaaccaccgc    3780
taccagcggt ggtttgtttg ccggatcaag agctaccaac tctttttccg aaggtaactg    3840
gcttcagcag agcgcagata ccaaatactg ttcttctagt gtagccgtag ttaggccacc    3900
acttcaagaa ctctgtagca ccgcctacat acctcgctct gctaatcctg ttaccagtgg    3960
ctgctgccag tggcgataag tcgtgtctta ccgggttgga ctcaagacga tagttaccgg    4020
ataaggcgca gcggtcgggc tgaacggggg gttcgtgcac acagcccagc ttggagcgaa    4080
cgacctacac cgaactgaga tacctacagc gtgagctatg agaaagcgcc acgcttcccg    4140
aagggagaaa ggcggacagg tatccggtaa gcggcagggt cggaacagga gagcgcacga    4200
gggagcttcc agggggaaac gcctggtatc tttatagtcc tgtcgggttt cgccacctct    4260
gacttgagcg tcgatttttg tgatgctcgt caggggggcg gagcctatgg aaaaacgcca    4320
gcaacgcggc ctttttacgg ttcctggccc atcacgtgcg catgcctggt caagggttat    4380
```

```
ttccctgagc cagtgacctt gacctggaac tctggatccc tgtccagtgg tgtgcacacc   4440
ttcccagctg tcctgcagtc tgacctctac accctcagca gctcagtgac tgtaacctcg   4500
agcacctggc ccagccagtc catcacctgc aatgtggccc acccggcaag cagcaccaag   4560
gtggacaaga aaattgagcc cagagggccc acaatcaagc cctgtcctcc atgcaaatgc   4620
ccagcaccta acctcttggg tggaccatcc gtcttcatct tccctccaaa gatcaaggat   4680
gtactcatga tctccctgag ccccatagtc acatgtgtgg tggtggatgt gagcgaggat   4740
gacccagatg tccagatcag ctggtttgtg aacaacgtgg aagtacacac agctcagaca   4800
caaacccata gagaggatta caacagtact ctccgggtgg tcagtgccct ccccatccag   4860
caccaggact ggatgagtgg caaggagttc aaatgcaagg tcaacaacaa agacctccca   4920
gcgcccatcg agagaaccat ctcaaaaccc aaagggtcag taagagctcc acaggtatat   4980
gtcttgcctc caccagaaga agagatgact aagaaacagg tcactctgac ctgcatggtc   5040
acagacttca tgcctgaaga catttacgtg gagtggacca acaacgggaa aacagagcta   5100
aactacaaga acactgaacc agtcctggac tctgatggtt cttacttcat gtacagcaag   5160
ctgagagtgg aaaagaagaa ctgggtggaa agaaatagct actcctgttc agtggtccac   5220
gagggtctgc acaatcacca cacgactaag agcttctccc ggactccggg taaatgatcc   5280
agcggccaag tcgacttggc cgcgactcta gatcataatc agccatacca catttgtaga   5340
ggttttactt gctttaaaaa acctcccaca cctccccctg aacctgaaac ataaaatgaa   5400
tgcaattgtt gttgttaact tgtttattgc agcttataat ggttacaaat aaagcaatag   5460
catcacaaat ttcacaaata aagcattttt ttcactgcat tctagttgtg gtttgtccaa   5520
actcatcaat gtatcttaag gcgtaaattg taagcgttaa tattttgtta aaattcgcgt   5580
taaatttttg ttaaatcagc tcatttttta accaataggc cgaaatcggc aaaatccctt   5640
ataaatcaaa agaatagacc gagatagggt tgagtgttgt tccagtttgg aacaagagtc   5700
cactattaaa gaacgtggac tccaacgtca aagggcgaaa aaccgtctat cagggcgatg   5760
gcccactacg tgaaccatca ccctaatcaa gttttttggg gtcgaggtgc cgtaaagcac   5820
taaatcggaa ccctaaaggg agcccccgat ttagagcttg acggggaaag ccggcgaacg   5880
tggcgagaaa ggaagggaag aaagcgaaag gagcgggcgc tagggcgctg gcaagtgtag   5940
cggtcacgct gcgcgtaacc accacacccg ccgcgcttaa tgcgccgcta cagggcgcgt   6000
cagatct                                                              6007
```

<210> SEQ ID NO 2
<211> LENGTH: 6004
<212> TYPE: DNA
<213> ORGANISM: Artificial Sequence
<220> FEATURE:
<223> OTHER INFORMATION: Nucleotide coding of pJON mIgG2a-hIgG1

<400> SEQUENCE: 2

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
```

```
atttccaagt ctccacccca ttgacgtcaa tgggagtttg ttttggcacc aaaatcaacg      480
ggactttcca aaatgtcgta acaactccgc cccattgacg caaatgggcg gtaggcgtgt      540
acggtgggag gtctatataa gcagagctgg tttagtgaac cgtcagatcc gctagaattc      600
tgcagtcgac ggtaccgcgg gcccgggatc cccccccccc ccgatgggac gtccacatat      660
acctgccgtt cactattatt tagtgaaatg agatattatg atattttctg aattgtgatt      720
aaaaaggcaa ctttatgccc atgcaacaga actataaaa aatacagaga atgaaaagaa       780
acagatagat tttttagttc tttaggcccg tagtctgcaa atccttttat gattttctat      840
caaacaaaat aggaaaatag accagttgca atccaaacga gagtctaata gaatgaggtc     900
gaaaagtaaa tcgcgcgggt ttgttactga taaagcaggc aagacctaaa atgtgtaaag     960
ggcaaagtgt atactttggc gtcaccccctt acatatttta ggtctttttt tattgtgcgt    1020
aactaacttg ccatcttcaa acaggagggc tggaagaagc agaccgctaa cacagtacat    1080
aaaaaaggag acatgaacga tgaacatcaa aaagtttgca aaacaagcaa cagtattaac    1140
ctttactacc gcactgctgg caggaggcgc aactcaagcg tttgcgaaag aaacgaacca    1200
aaagccatat aaggaaacat acggcatttc ccatattaca cgccatgata tgctgcaaat    1260
ccctgaacag caaaaaaatg aaaaatataa agttcctgag ttcgattcgt ccacaattaa    1320
aaatatctct tctgcaaaag gcctggacgt ttgggacagc tggccattac aaaacactga    1380
cggcactgtc gcaaactatc acggctacca catcgtcttt gcattagccg gagatcctaa    1440
aaatgcggat gacacatcga tttacatgtt ctatcaaaaa gtcggcgaaa cttctattga    1500
cagctggaaa aacgctggcc gcgtctttaa agacagcgac aaattcgatg caaatgattc    1560
tatcctaaaa gaccaaacac aagaatggtc aggttcagcc acatttacat ctgacggaaa    1620 aatccgtttta ttctacactg atttctccgg taaacattac ggcaaacaaa cactgacaac    1680
tgcacaagtt aacgtatcag catcagacag ctctttgaac atcaacggtg tagaggatta    1740
taaatcaatc tttgacggtg acggaaaaac gtatcaaaat gtacagcagt tcatcgatga    1800
aggcaactac agctcaggcg acaaccatac gctgagagat cctcactacg tagaagataa    1860
aggccacaaa tacttagtat ttgaagcaaa cactggaact gaagatggct accaaggcga    1920
agaatcttta tttaacaaag catactatgg caaaagcaca tcattcttcc gtcaagaaag    1980
tcaaaaactt ctgcaaagcg ataaaaaacg cacggctgag ttagcaaacg gcgctctcgg    2040
tatgattgag ctaaacgatg attacacact gaaaaaagtg atgaaaccgc tgattgcatc    2100
taacacagta acagatgaaa ttgaacgcgc gaacgtcttt aaaatgaacg gcaaatggta    2160
cctgttcact gactcccgcg gatcaaaaat gacgattgac ggcattacgt ctaacgatat    2220
ttacatgctt ggttatgttt ctaattcttt aactggccca tacaagccgc tgaacaaaac    2280
tggccttgtg ttaaaaatgg atcttgatcc taacgatgta acctttactt actcacactt    2340
cgctgtacct caagcgaaag gaacaatgt cgtgattaca agctatatga caaacagagg    2400
attctacgca gacaaacaat caacgtttgc gcctagcttc ctgctgaaca tcaaaggcaa    2460
gaaaacatct gttgtcaaag acagcatcct tgaacaagga caattaacag ttaacaaata    2520
aaaacgcaaa agaaaatgcc gatatcctat tggcattgat tcaggtggc acttttcggg    2580 gaaatgtgcg cggaaccct atttgtttat ttttctaaat acattcaaat atgtatccgc    2640
tcatgagaca ataaccctga taaatgcttc aataatattg aaaaaggaag agtatgagta    2700
ttcaacattt ccgtgtcgcc cttattccct tttttgcggc attttgcctt cctgttttg    2760
```

-continued

| | |
|---|---|
| ctcacccaga aacgctggtg aaagtaaaag atgctgaaga tcagttgggt gcacgagtgg | 2820 |
| gttacatcga actggatctc aacagcggta agatccttga gagttttcgc cccgaagaac | 2880 |
| gttttccaat gatgagcact tttaaagttc tgctatgtgg cgcggtatta tcccgtattg | 2940 |
| acgccgggca agagcaactc ggtcgccgca tacactattc tcagaatgac ttggttgagt | 3000 |
| actcaccagt cacagaaaag catcttacgg atggcatgac agtaagagaa ttatgcagtg | 3060 |
| ctgccataac catgagtgat aacactgcgg ccaacttact tctgacaacg atcgaggac | 3120 |
| cgaaggagct aaccgctttt tgcacaaca tgggggatca tgtaactcgc cttgatcgtt | 3180 |
| gggaaccgga gctgaatgaa gccataccaa acgacgagcg tgacaccacg atgcctgtag | 3240 |
| caatggcaac aacgttgcgc aaactattaa ctggcgaact acttactcta gcttcccggc | 3300 |
| aacaattaat agactggatg gaggcggata aagttgcagg accacttctg cgctcggccc | 3360 |
| ttccggctgg ctggtttatt gctgataaat ctggagccgg tgagcgtggg tctcgcggta | 3420 |
| tcattgcagc actggggcca gatggtaagc cctcccgtat cgtagttatc tacacgacgg | 3480 |
| ggagtcaggc aactatggat gaacgaaata gacagatcgc tgagataggt gcctcactga | 3540 |
| ttaagcattg gtaactgtca gaccaagttt actcatatat actttagatt gatttaaaac | 3600 |
| ttcatttta atttaaaagg atctaggtga agatccttt tgataatctc atgaccaaaa | 3660 |
| tcccttaacg tgagttttcg ttccactgag cgtcagaccc cgtagaaaag atcaaaggat | 3720 |
| cttcttgaga tcctttttt ctgcgcgtaa tctgctgctt gcaaacaaaa aaaccaccgc | 3780 |
| taccagcggt ggtttgtttg ccggatcaag agctaccaac tctttttccg aaggtaactg | 3840 |
| gcttcagcag agcgcagata ccaaatactg ttcttctagt gtagccgtag ttaggccacc | 3900 |
| acttcaagaa ctctgtagca ccgcctacat acctcgctct gctaatcctg ttaccagtgg | 3960 |
| ctgctgccag tggcgataag tcgtgtctta ccgggttgga ctcaagacga tagttaccgg | 4020 |
| ataaggcgca gcggtcgggc tgaacggggg gttcgtgcac acagcccagc ttggagcgaa | 4080 |
| cgacctacac cgaactgaga tacctacagc gtgagctatg agaaagcgcc acgcttcccg | 4140 |
| aagggagaaa ggcggacagg tatccggtaa gcggcagggt cggaacagga gagcgcacga | 4200 |
| gggagcttcc agggggaaac gcctggtatc tttatagtcc tgtcgggttt cgccacctct | 4260 |
| gacttgagcg tcgatttttg tgatgctcgt caggggggcg gagcctatgg aaaaacgcca | 4320 |
| gcaacgcggc cttttacgg ttcctggccc atcacgtgcg catgcctggt caagggttat | 4380 |
| ttccctgagc cagtgacctt gacctggaac tctggatccc tgtccagtgg tgtgcacacc | 4440 |
| ttcccagctg tcctgcagtc tgacctctac accctcagca gctcagtgac tgtaacctcg | 4500 |
| agcacctggc ccagccagtc catcacctgc aatgtggccc accggcaag cagcaccaag | 4560 |
| gtggacaaga aaattgagcc caaatcttgt gacaaaactc acacatgccc accgtgccca | 4620 |
| gcacctgaac tcctgggggg accgtcagtc ttcctcttcc ccccaaaacc caaggacacc | 4680 |
| ctcatgatct cccggacccc tgaggtcaca tgcgtggtgg tggacgtgag ccacgaagac | 4740 |
| cctgaggtca agttcaactg gtacgtggac ggcgtggagg tgcataatgc caagacaaag | 4800 |
| ccgcgggagg agcagtacaa cagcacgtac cgtgtggtca gcgtcctcac cgtcctgcac | 4860 |
| caggactggc tgaatggcaa ggagtacaag tgcaaggtct ccaacaaagc cctcccagcc | 4920 |
| cccatcgaga aaaccatctc caaagccaaa gggcagcccc gagaaccaca ggtgtacacc | 4980 |
| ctgcccccat cccgggatga gctgaccaag aaccaggtca gcctgacctg cctggtcaaa | 5040 |
| ggcttctatc ccagcgacat cgccgtggag tgggagagca atgggcagcc ggagaacaac | 5100 |
| tacaagacca cgcctcccgt gctggactcc gacggctcct tcttcctcta cagcaagctc | 5160 |

```
accgtggaca agagcaggtg gcagcagggg aacgtcttct catgctccgt gatgcatgag   5220
gctctgcaca accactacac gcagaagagc ctctccctgt ctccgggtaa atgatccagc   5280
ggccaagtcg acttggccgc gactctagat cataatcagc cataccacat ttgtagaggt   5340
tttacttgct ttaaaaaacc tcccacacct cccccctgaac ctgaaacata aaatgaatgc   5400
```
```
aattgttgtt gttaacttgt ttattgcagc ttataatggt tacaaataaa gcaatagcat   5460
cacaaatttc acaaataaag catttttttc actgcattct agttgtggtt tgtccaaact   5520
catcaatgta tcttaaggcg taaattgtaa gcgttaatat tttgttaaaa ttcgcgttaa   5580 attttttgtta aatcagctca ttttttaacc aataggccga atcggcaaaa tcccttata   5640 aatcaaaaga atagaccgag ataggggttga gtgttgttcc agtttggaac aagagtccac   5700
tattaaagaa cgtggactcc aacgtcaaag ggcgaaaaac cgtctatcag ggcgatggcc   5760
cactacgtga accatcaccc taatcaagtt ttttggggtc gaggtgccgt aaagcactaa   5820
atcggaaccc taaagggagc ccccgattta gagcttgacg gggaaagccg gcgaacgtgg   5880
cgagaaagga agggaagaaa gcgaaaggag cgggcgctag ggcgctggca agtgtagcgg   5940
tcacgctgcg cgtaaccacc acacccgccg cgcttaatgc gccgctacag ggcgcgtcag   6000
atct                                                                6004
```

<210> SEQ ID NO 3
<211> LENGTH: 5394
<212> TYPE: DNA
<213> ORGANISM: Artificial Sequence
<220> FEATURE:
<223> OTHER INFORMATION: Nucleotide coding of pJON mIgkappa

<400> SEQUENCE: 3

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagaattc    600
tgcagtcgac ggtaccgcgg gcccgggatc ccccccccc cgatgggcc aggaaccgta     660 aaaaggccgc gttgctggcg ttttttccata ggctccgccc cctgacgag catcacaaaa    720 atcgacgctc aagtcagagg tggcgaaacc cgacaggact ataaagatac caggcgtttc    780
cccctggaag ctccctcgtg cgctctcctg ttccgaccct gccgcttacc ggatacctgt    840
ccgcctttct cccttcggga agcgtggcgc tttctcatag ctcacgctgt aggtatctca    900
gttcggtgta ggtcgttcgc tccaagctgg gctgtgtgca cgaaccccc gttcagcccg     960 accgctgcgc cttatccggt aactatcgtc ttgagtccaa cccggtaaga cacgacttat    1020
cgccactggc agcagccact ggtaacagga ttagcagagc gaggtatgta ggcggtgcta   1080
cagagttctt gaagtggtgg cctaactacg gctacactag aagaacagta tttggtatct   1140
```

```
gcgctctgct gaagccagtt accttcggaa aaagagttgg tagctcttga tccggcaaac      1200
aaaccaccgc tggtagcggt ggttttttg tttgcaagca gcagattacg cgcagaaaaa       1260
aaggatctca agaagatcct ttgatctttt ctacggggtc tgacgctcag tggaacgaaa      1320
actcacgtta agggattttg gtcatgagat tatcaaaaag gatcttcacc tagatccttt      1380
taaattaaaa atgaagtttt aaatcaatct aaagtatata tgagtaaact tggtctgaca      1440
gttaccaatg cttaatcagt gaggcaccta tctcagcgat ctgtctattt cgttcatcca      1500
tagttgcctg actccccgtc gtgtagataa ctacgatacg ggagggctta ccatctggcc      1560
ccagtgctgc aatgataccg cgagacccac gctcaccggc tccagattta tcagcaataa      1620
accagccagc cggaagggcc gagcgcagaa gtggtcctgc aactttatcc gcctccatcc      1680
agtctattaa ttgttgccgg gaagctagag taagtagttc gccagttaat agtttgcgca      1740
acgttgttgc cattgctaca ggcatcgtgg tgtcacgctc gtcgtttggt atggcttcat      1800
tcagctccgg ttcccaacga tcaaggcgag ttacatgatc ccccatgttg tgcaaaaaag      1860
cggttagctc cttcggtcct ccgatcgttg tcagaagtaa gttggccgca gtgttatcac      1920
tcatggttat ggcagcactg cataattctc ttactgtcat gccatccgta agatgctttt      1980
ctgtgactgg tgagtactca accaagtcat tctgagaata gtgtatgcgg cgaccgagtt      2040
gctcttgccc ggcgtcaata cgggataata ccgcgccaca tagcagaact ttaaaagtgc      2100
tcatcattgg aaaacgttct cggggcgaaa actctcaag gatcttaccg ctgttgagat       2160
ccagttcgat gtaacccact cgtgcaccca actgatcttc agcatctttt actttcacca      2220
gcgtttctgg gtgagcaaaa acaggaaggc aaaatgccgc aaaaaaggga ataagggcga      2280
cacggaaatg ttgaatactc atactcttcc ttttcaata ttattgaagc atttatcagg       2340
gttattgtct catgagcgga tacatatttg aatgtattta gaaaaataaa caaatagggg      2400
ttccgcgcac atttccccga aaagtgccac ctgacgtcaa tgccataggg atatcggcat      2460
tttcttttgc gtttttattt gttaactgtt aattgtcctt gttcaaggat gctgtctttg      2520
acaacagatg ttttcttgcc tttgatgttc agcaggaagc taggcgcaaa cgttgattgt      2580
ttgtctgcgt agaatcctct gtttgtcata tagcttgtaa tcacgacatt gtttcctttc      2640
gcttgaggta cagcgaagtg tgagtaagta aaggttacat cgttaggatc aagatccatt      2700
tttaacacaa ggccagtttt gttcagcggc ttgtatgggc cagttaaaga attagaaaca      2760
taaccaagca tgtaaatatc gttagacgta atgccgtcaa tcgtcatttt tgatccgcgg      2820
gagtcagtga acaggtacca tttgccgttc attttaaaga cgttcgcgcg ttcaatttca      2880
tctgttactg tgttagatgc aatcagcggt ttcatcactt ttttcagtgt gtaatcatcg      2940
tttagctcaa tcataccgag agcgccgttt gctaactcag ccgtgcgttt tttatcgctt      3000
tgcagaagtt tttgactttc ttgacggaag aatgatgtgc ttttgccata gtatgctttg      3060
ttaaataaag attcttcgcc ttggtagcca tcttcagttc cagtgtttgc ttcaaatact      3120
aagtatttgt ggcctttatc ttctacgtag tgaggatctc tcagcgtatg gttgtcgcct      3180
gagctgtagt tgccttcatc gatgaactgc tgtacatttt gatacgtttt tccgtcaccg      3240
tcaaagattg atttataatc ctctacaccg ttgatgttca aagagctgtc tgatgctgat      3300
acgttaactt gtgcagttgt cagtgtttgt ttgccgtaat gtttaccgga gaaatcagtg      3360
tagaataaac ggattttcc gtcagatgta aatgtggctg aacctgacca ttcttgtgtt       3420 tggtcttta ggatagaatc atttgcatcg aatttgtcgc tgtctttaaa gacgcggcca       3480 gcgttttcc agctgtcaat agaagtttcg ccgacttttt gatagaacat gtaaatcgat       3540
```

```
gtgtcatccg catttttagg atctccggct aatgcaaaga cgatgtggta gccgtgatag    3600
tttgcgacag tgccgtcagc gttttgtaat ggccagctgt cccaaacgtc caggccttt    3660 gcagaagaga tatttttaat tgtggacgaa tcgaactcag gaacttgata ttttcattt    3720 ttttgctgtt cagggatttg cagcatatca tggcgtgtaa tatgggaaat gccgtatgtt    3780
tccttatatg gcttttggtt cgtttctttc gcaaacgctt gagttgcgcc tcctgccagc    3840
agtgcggtag taaaggttaa tactgttgct tgttttgcaa acttttttgat gttcatcgtt    3900 catgtctcct tttttatgta ctgtgttagc ggtctgcttc ttccagcccct cctgtttgaa    3960 gatggcaagt tagttacgca caataaaaaa agacctaaaa tatgtaaggg gtgacgccaa    4020
agtatacact ttgcccttta cacattttag gtcttgcctg ctttatcagt aacaaacccg    4080
cgcgatttac ttttcgacct cattctatta gactctcgtt tggattgcaa ctggtctatt    4140
ttcctctttt gtttgataga aaatcataaa aggatttgca gactacgggc ctaaagaact    4200
aaaaaatcta tctgtttctt ttcattctct gtattttta tagtttctgt tgcatgggca    4260
taaagttgcc ttttaatca caattcagaa aatatcataa tatctcatt cactaaataa    4320 tagtgaacgg caggtatatg tggacgtccc atcacgtgct gtatccatct tcccaccatc    4380
cagtgagcag ttaacatctg gaggtgcctc agtcgtgtgc ttcttgaaca acttctaccc    4440
caaagacatc aatgtcaagt ggaagattga tggcagtgaa cgacaaaatg gcgtcctgaa    4500
cagttggact gatcaggaca gcaaagacag cacctacagc atgagcagca ccctcacgtt    4560
gaccaaggac gagtatgaac gacataacag ctatacctgt gaggccactc acaagacatc    4620
aacttcaccc attgtcaaga gcttcaacag gaatgagtgt tagagacagc ggccaagtcg    4680
acttggccgc gactctagat cataatcagc cataccacat tgtagaggt tttacttgct    4740 ttaaaaaacc tcccacacct cccctgaac ctgaaacata aaatgaatgc aattgttgtt    4800
gttaacttgt ttattgcagc ttataatggt tacaaataaa gcaatagcat cacaaatttc    4860
acaaataaag cattttttc actgcattct agttgtggtt tgtccaaact catcaatgta    4920
tcttaaggcg taaattgtaa gcgttaatat tttgttaaaa ttcgcgttaa attttttgtta    4980 aatcagctca ttttttaacc aataggccga atcggcaaa atcccttata aatcaaaaga    5040
atagaccgag atagggttga gtgttgttcc agtttggaac aagagtccac tattaaagaa    5100
cgtggactcc aacgtcaaag ggcgaaaaac cgtctatcag ggcgatggcc cactacgtga    5160
accatcaccc taatcaagtt ttttggggtc gaggtgccgt aaagcactaa atcggaaccc    5220
taaagggagc ccccgattta gagcttgacg gggaaagccg gcgaacgtgg cgagaaagga    5280
agggaagaaa gcgaaaggag cgggcgctag ggcgctggca agtgtagcgg tcacgctgcg    5340
cgtaaccacc acacccgccg cgcttaatgc gccgctacag ggcgcgtcag atct    5394
```

<210> SEQ ID NO 4
<211> LENGTH: 129
<212> TYPE: PRT
<213> ORGANISM: Artificial Sequence
<220> FEATURE:
<223> OTHER INFORMATION: Light chain variable of No.76

<400> SEQUENCE: 4

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

```
Met Ser Val Gly Glu Arg Val Thr Leu Ser Cys Lys Ala Ser Glu Asn
 35                  40                  45

Val Gly Thr Ser Val Ser Trp Tyr Gln Glu Lys Pro Glu Gln Ser Pro
 50                  55                  60

Lys Leu Leu Ile Phe Gly Ala Ser Asn Arg Tyr Thr Gly Val Pro Asp
 65                  70                  75                  80

Arg Phe Thr Gly Ser Gly Ser Ala Thr Asp Phe Thr Leu Thr Ile Ser
             85                  90                  95

Ser Val Gln Ala Glu Asp Leu Ala Asp Tyr His Cys Gly Gln Ser Tyr
            100                 105                 110

Ser Tyr Pro Tyr Thr Phe Gly Gly Arg Thr Lys Leu Glu Ile Lys Arg
115                 120                 125

Ala

<210> SEQ ID NO 5
<211> LENGTH: 11
<212> TYPE: PRT
<213> ORGANISM: Artificial Sequence
<220> FEATURE:
<223> OTHER INFORMATION: CDRL1 of No.76

<400> SEQUENCE: 5

Lys Ala Ser Glu Asn Val Gly Thr Ser Val Ser
1               5                   10

<210> SEQ ID NO 6
<211> LENGTH: 7
<212> TYPE: PRT
<213> ORGANISM: Artificial Sequence
<220> FEATURE:
<223> OTHER INFORMATION: CDRL2 of No.76

<400> SEQUENCE: 6

Gly Ala Ser Asn Arg Tyr Thr
1               5

<210> SEQ ID NO 7
<211> LENGTH: 9
<212> TYPE: PRT
<213> ORGANISM: Artificial Sequence
<220> FEATURE:
<223> OTHER INFORMATION: CDRL3 of No.76

<400> SEQUENCE: 7

Gly Gln Ser Tyr Ser Tyr Pro Tyr Thr
1               5

<210> SEQ ID NO 8
<211> LENGTH: 140
<212> TYPE: PRT
<213> ORGANISM: Artificial Sequence
<220> FEATURE:
<223> OTHER INFORMATION: Heavy chain variable of No.76

<400> SEQUENCE: 8

Met Gly Trp Ser Cys Ile Ile Leu Phe Leu Val Ala Ala Ala Thr Gly
1               5                   10                  15

Val His Ser Gln Val Gln Leu Gln Gln Pro Gly Ala Glu Leu Val Lys
             20                  25                  30

Pro Gly Ala Ser Val Asn Leu Ser Cys Lys Ser Ser Gly Tyr Thr Phe
         35                  40                  45

Thr Asn Tyr Trp Ile Asn Trp Val Lys Gln Arg Pro Gly Gln Gly Leu
```

```
                   50                  55                  60
Glu Trp Ile Gly Asp Ile Tyr Pro Gly Thr Ser Thr Asn Tyr Asn
 65                  70                  75                  80

Glu Lys Phe Lys Asn Lys Ala Thr Leu Thr Val Asp Thr Ser Ser
                 85                  90                  95

Thr Ala Tyr Met Gln Leu Ser Ser Leu Thr Ser Asp Asp Ser Ala Val
            100                 105                 110

Tyr Tyr Cys Thr Arg Ile Tyr Tyr Asp Tyr Asp Gly Tyr Tyr Phe Asp
        115                 120                 125

Tyr Trp Gly Gln Gly Thr Thr Leu Thr Val Ser Ser
    130                 135                 140

<210> SEQ ID NO 9
<211> LENGTH: 5
<212> TYPE: PRT
<213> ORGANISM: Artificial Sequence
<220> FEATURE:
<223> OTHER INFORMATION: CDRH1 of No.76

<400> SEQUENCE: 9

Asn Tyr Trp Ile Asn
1               5

<210> SEQ ID NO 10
<211> LENGTH: 17
<212> TYPE: PRT
<213> ORGANISM: Artificial Sequence
<220> FEATURE:
<223> OTHER INFORMATION: CDRH2 of No.76

<400> SEQUENCE: 10

Asp Ile Tyr Pro Gly Thr Ser Thr Thr Asn Tyr Asn Glu Lys Phe Lys
1               5                   10                  15

Asn

<210> SEQ ID NO 11
<211> LENGTH: 12
<212> TYPE: PRT
<213> ORGANISM: Artificial Sequence
<220> FEATURE:
<223> OTHER INFORMATION: CDRH3 of No.76

<400> SEQUENCE: 11

Ile Tyr Tyr Asp Tyr Asp Gly Tyr Tyr Phe Asp Tyr
1               5                   10

<210> SEQ ID NO 12
<211> LENGTH: 129
<212> TYPE: PRT
<213> ORGANISM: Artificial Sequence
<220> FEATURE:
<223> OTHER INFORMATION: Light chain variable of #1G5

<400> SEQUENCE: 12

Met Glu Ser Gln Thr Leu Val Phe Ile Ser Ile Leu Leu Trp Leu Tyr
1               5                   10                  15

Gly Ser Asp Gly Asn Ile Val Met Thr Gln Ser Pro Lys Ser Met Ser
            20                  25                  30

Met Ser Val Gly Glu Arg Val Thr Leu Ser Cys Lys Ala Ser Glu Asn
        35                  40                  45

Val Gly Asn Ser Val Ser Trp Tyr Gln Gln Lys Ala Glu Gln Ser Pro
    50                  55                  60
```

Lys Pro Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Ser Tyr
            100                 105                 110

Ser Tyr Pro Tyr Thr Phe Gly Gly Thr Lys Leu Glu Ile Lys Arg
        115                 120                 125

Ala

<210> SEQ ID NO 13
<211> LENGTH: 11
<212> TYPE: PRT
<213> ORGANISM: Artificial Sequence
<220> FEATURE:
<223> OTHER INFORMATION: CDRL1 of #1G5

<400> SEQUENCE: 13

Lys Ala Ser Glu Asn Val Gly Asn Ser Val Ser
1               5                   10

<210> SEQ ID NO 14
<211> LENGTH: 7
<212> TYPE: PRT
<213> ORGANISM: Artificial Sequence
<220> FEATURE:
<223> OTHER INFORMATION: CDRL2 of #1G5

<400> SEQUENCE: 14

Gly Ala Ser Asn Arg Tyr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: CDRL3 of #1G5

<400> SEQUENCE: 15

Gly Gln Ser Tyr Ser Tyr Pro Tyr Thr
1               5

<210> SEQ ID NO 16
<211> LENGTH: 144
<212> TYPE: PRT
<213> ORGANISM: Artificial Sequence
<220> FEATURE:
<223> OTHER INFORMATION: Heavy chain variable of #1G5

<400> SEQUENCE: 16

Met Gly Trp Ser Cys Ile Ile Leu Phe Leu Val Ala Ala Ala Thr Gly
1               5                   10                  15

Val His Ser Gln Val Gln Leu Gln Gln Pro Gly Ala Glu Leu Val Lys
                20                  25                  30

Pro Gly Ala Ser Val Lys Leu Ser Cys Lys Ala Ser Gly Tyr Thr Phe
            35                  40                  45

Thr Ser Tyr Trp Ile Asn Trp Val Lys Gln Arg Pro Gly Gln Gly Leu
        50                  55                  60

Glu Trp Ile Gly Asn Ile Tyr Pro Gly Ser Ser Ile Asn Tyr Asn
65                  70                  75                  80

```
Glu Lys Phe Lys Ser Lys Ala Thr Leu Thr Val Asp Thr Ser Ser
                85                  90                  95

Thr Ala Tyr Met Gln Leu Ser Ser Leu Thr Ser Asp Asp Ser Ala Val
            100                 105                 110

Tyr Tyr Cys Ser Arg Thr Ile Tyr Asn Tyr Gly Ser Ser Gly Tyr Asn
        115                 120                 125

Tyr Ala Met Asp Tyr Trp Gly Gln Gly Thr Val Ile Val Ser Ser
    130                 135                 140

<210> SEQ ID NO 17
<211> LENGTH: 5
<212> TYPE: PRT
<213> ORGANISM: Artificial Sequence
<220> FEATURE:
<223> OTHER INFORMATION: CDRH1 of #1G5

<400> SEQUENCE: 17

Ser Tyr Trp Ile Asn
1               5

<210> SEQ ID NO 18
<211> LENGTH: 17
<212> TYPE: PRT
<213> ORGANISM: Artificial Sequence
<220> FEATURE:
<223> OTHER INFORMATION: CDRH2 of #1G5

<400> SEQUENCE: 18

Asn Ile Tyr Pro Gly Ser Ser Ser Ile Asn Tyr Asn Glu Lys Phe Lys
1               5                   10                  15

Ser

<210> SEQ ID NO 19
<211> LENGTH: 16
<212> TYPE: PRT
<213> ORGANISM: Artificial Sequence
<220> FEATURE:
<223> OTHER INFORMATION: CDRH3 of #1G5

<400> SEQUENCE: 19

Thr Ile Tyr Asn Tyr Gly Ser Ser Gly Tyr Asn Tyr Ala Met Asp Tyr
1               5                   10                  15

<210> SEQ ID NO 20
<211> LENGTH: 129
<212> TYPE: PRT
<213> ORGANISM: Artificial Sequence
<220> FEATURE:
<223> OTHER INFORMATION: Light chain variable of #4C12

<400> SEQUENCE: 20

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Ser Cys Lys Ala Ser Glu Asn
        35                  40                  45

Val Gly Val Ser Val Ser Trp Tyr Gln Gln Lys Pro Glu Gln Ser Pro
    50                  55                  60

Lys Leu Leu Ile Tyr Gly Ala Ser Asn Arg Cys Thr Gly Val Pro Asp
65                  70                  75                  80

Arg Phe Thr Gly Ser Arg Ser Ala Thr Asp Phe Thr Leu Thr Val Ser
```

```
                    85                  90                  95
Asn Val Gln Ala Glu Asp Leu Ala Asp Tyr His Cys Gly Gln Ser Tyr
                100                 105                 110

Ser Tyr Pro Tyr Thr Phe Gly Gly Gly Thr Arg Leu Glu Ile Lys Arg
        115                 120                 125

Ala

<210> SEQ ID NO 21
<211> LENGTH: 11
<212> TYPE: PRT
<213> ORGANISM: Artificial Sequence
<220> FEATURE:
<223> OTHER INFORMATION: CDRL1 of #4C12

<400> SEQUENCE: 21

Lys Ala Ser Glu Asn Val Gly Val Ser Val Ser
1               5                   10

<210> SEQ ID NO 22
<211> LENGTH: 7
<212> TYPE: PRT
<213> ORGANISM: Artificial Sequence
<220> FEATURE:
<223> OTHER INFORMATION: CDRL2 of #4C12

<400> SEQUENCE: 22

Gly Ala Ser Asn Arg Cys Thr
1               5

<210> SEQ ID NO 23
<211> LENGTH: 9
<212> TYPE: PRT
<213> ORGANISM: Artificial Sequence
<220> FEATURE:
<223> OTHER INFORMATION: CDRL3 of #4C12

<400> SEQUENCE: 23

Gly Gln Ser Tyr Ser Tyr Pro Tyr Thr
1               5

<210> SEQ ID NO 24
<211> LENGTH: 140
<212> TYPE: PRT
<213> ORGANISM: Artificial Sequence
<220> FEATURE:
<223> OTHER INFORMATION: Heavy chain variable of #4C12

<400> SEQUENCE: 24

Met Gly Trp Ser Cys Ile Ile Leu Phe Leu Val Ala Ala Thr Gly
1               5                   10                  15

Val Gln Ser Gln Val Gln Leu Gln Gln Pro Gly Ala Glu Leu Val Lys
                20                  25                  30

Pro Gly Ala Ser Val Lys Leu Ser Cys Lys Ala Ser Gly Tyr Thr Phe
            35                  40                  45

Thr Thr Tyr Trp Ile Asn Trp Met Gln Gln Arg Pro Gly Gln Gly Leu
    50                  55                  60

Glu Trp Ile Gly Asn Ile Tyr Pro Gly Thr Arg Ser Ser Asn Tyr Asn
65                  70                  75                  80

Glu Lys Phe Lys Asn Lys Ala Thr Leu Thr Val Asp Thr Ser Ser Ser
                85                  90                  95

Thr Ala Tyr Met Gln Leu Asn Ser Leu Thr Ser Asp Asp Ser Ala Val
                100                 105                 110
```

```
Tyr Tyr Cys Thr Arg Val Tyr Tyr Asp His Val Gly Tyr Tyr Phe Asp
        115                 120                 125

Tyr Trp Gly Gln Gly Thr Thr Leu Thr Val Ser Ser
    130                 135                 140

<210> SEQ ID NO 25
<211> LENGTH: 5
<212> TYPE: PRT
<213> ORGANISM: Artificial Sequence
<220> FEATURE:
<223> OTHER INFORMATION: CDRH1 of #4C12

<400> SEQUENCE: 25

Thr Tyr Trp Ile Asn
1               5

<210> SEQ ID NO 26
<211> LENGTH: 17
<212> TYPE: PRT
<213> ORGANISM: Artificial Sequence
<220> FEATURE:
<223> OTHER INFORMATION: CDRH2 of #4C12

<400> SEQUENCE: 26

Asn Ile Tyr Pro Gly Thr Arg Ser Ser Asn Tyr Asn Glu Lys Phe Lys
1               5                   10                  15
Asn

<210> SEQ ID NO 27
<211> LENGTH: 12
<212> TYPE: PRT
<213> ORGANISM: Artificial Sequence
<220> FEATURE:
<223> OTHER INFORMATION: CDRH3 of #4C12

<400> SEQUENCE: 27

Val Tyr Tyr Asp His Val Gly Tyr Tyr Phe Asp Tyr
1               5                   10

<210> SEQ ID NO 28
<211> LENGTH: 449
<212> TYPE: DNA
<213> ORGANISM: Artificial Sequence
<220> FEATURE:
<223> OTHER INFORMATION: Nuc of signal and constant of light chain

<400> SEQUENCE: 28
gcctccggac tctagagcca ccatggtgct gcagacccag gtgttcatct ccctgctgct      60
gtggatctcc ggcgcgtacg gcgatatcgt gatgattaaa cgtacggtgg ccgcccccte     120 cgtgttcatc ttccccccct ccgacgagca gctgaagtcc ggcaccgcct ccgtggtgtg     180
cctgctgaat aacttctacc ccagagaggc caaggtgcag tggaaggtgg acaacgccct     240
gcagtccggg aactcccagg agagcgtgac cgagcaggac agcaaggaca gcacctacag     300
cctgagcagc accctgaccc tgagcaaagc cgactacgag aagcacaagg tgtacgcctg     360
cgaggtgacc caccagggcc tgagctcccc cgtcaccaag agcttcaaca gggggggagtg    420 ttagggggccc gtttaaacgg gggaggcta                                      449

<210> SEQ ID NO 29
<211> LENGTH: 1132
<212> TYPE: DNA
<213> ORGANISM: Artificial Sequence
```

<220> FEATURE:
<223> OTHER INFORMATION: Nuc of signal and constant of IgG1 chain

<400> SEQUENCE: 29

```
gcctccggac tctagagcca ccatgaaaca cctgtggttc ttcctcctgc tggtggcagc      60
tcccagatgg gtgctgagcc aggtgcaatt gtgcaggcgg ttagctcagc ctccaccaag     120
ggcccaagcg tcttccccct ggcaccctcc tccaagagca cctctggcgg cacagccgcc     180
ctgggctgcc tggtcaagga ctacttcccc gaacccgtga ccgtgagctg gaactcaggc     240
gccctgacca gcggcgtgca caccttcccc gctgtcctgc agtcctcagg actctactcc     300
ctcagcagcg tggtgaccgt gccctccagc agcttgggca cccagaccta catctgcaac     360
gtgaatcaca agcccagcaa caccaaggtg gacaagagag ttgagcccaa atcttgtgac     420
aaaactcaca catgcccacc ctgcccagca cctgaactcc tggggggacc ctcagtcttc     480
ctcttccccc caaaacccaa ggacaccctc atgatctccc ggacccctga ggtcacatgc     540
gtggtggtgg acgtgagcca cgaagaccct gaggtcaagt tcaactggta cgtggacggc     600
gtggaggtgc ataatgccaa gacaaagccc cgggaggagc agtacaacag cacgtaccgg     660
gtggtcagcg tcctcaccgt cctgcaccag gactggctga atggcaagga gtacaagtgc     720
aaggtctcca acaaagccct cccagccccc atcgagaaaa ccatctccaa agccaaaggc     780
cagccccggg aaccacaggt gtacaccctg cccccatccc gggaggagat gaccaagaac     840
caggtcagcc tgacctgcct ggtcaaaggc ttctatccca gcgacatcgc cgtggagtgg     900
gagagcaatg ccagcccga gaacaactac aagaccaccc ctcccgtgct ggactccgac     960
ggctccttct tcctctacag caagctcacc gtggacaaga gcaggtggca gcagggcaac    1020
gtcttctcat gctccgtgat gcatgaggct ctgcacaacc actacaccca gaagagcctc    1080
tccctgtctc ccggcaaatg agatatcggg cccgtttaaa cggggaggc ta             1132
```

<210> SEQ ID NO 30
<211> LENGTH: 702
<212> TYPE: DNA
<213> ORGANISM: Artificial Sequence
<220> FEATURE:
<223> OTHER INFORMATION: Nucleotide coding light chain of chimeric No.76
<220> FEATURE:
<221> NAME/KEY: CDS
<222> LOCATION: (1)..(702)

<400> SEQUENCE: 30

```
atg gtg ctg cag acc cag gtg ttc atc tcc ctg ctg ctg tgg atc tcc       48
Met Val Leu Gln Thr Gln Val Phe Ile Ser Leu Leu Leu Trp Ile Ser
1               5                   10                  15 ggc gcg tac ggc aac att gta atg acc caa tct ccc aaa tcc atg tcc       96
Gly Ala Tyr Gly Asn Ile Val Met Thr Gln Ser Pro Lys Ser Met Ser
            20                  25                  30 atg tca gta gga gag agg gtc acc ttg agc tgc aag gcc agt gag aat      144
Met Ser Val Gly Glu Arg Val Thr Leu Ser Cys Lys Ala Ser Glu Asn
        35                  40                  45 gtg ggt act tct gta tcc tgg tat caa gag aaa cca gag cag tct cct      192
Val Gly Thr Ser Val Ser Trp Tyr Gln Glu Lys Pro Glu Gln Ser Pro
    50                  55                  60 aaa ctg ctg ata ttc ggg gca tcc aac cgc tac act ggg gtc ccc gat      240
Lys Leu Leu Ile Phe Gly Ala Ser Asn Arg Tyr Thr Gly Val Pro Asp
65                  70                  75                  80 cgc ttc aca ggc agt gga tct gca aca gat ttc act ctg acc atc agc      288
Arg Phe Thr Gly Ser Gly Ser Ala Thr Asp Phe Thr Leu Thr Ile Ser
                85                  90                  95
```

```
agt gtg cag gct gaa gac ctt gca gat tat cac tgt gga cag agt tac       336
Ser Val Gln Ala Glu Asp Leu Ala Asp Tyr His Cys Gly Gln Ser Tyr
    100                 105                 110 agt tat ccg tac acg ttc gga ggg agg acc aag ctg gaa ata aaa cgg       384
Ser Tyr Pro Tyr Thr Phe Gly Gly Arg Thr Lys Leu Glu Ile Lys Arg
115                 120                 125 gct gtg gcc gcc ccc tcc gtg ttc atc ttc ccc ccc tcc gac gag cag       432
Ala Val Ala Ala Pro Ser Val Phe Ile Phe Pro Pro Ser Asp Glu Gln
130                 135                 140 ctg aag tcc ggc acc gcc tcc gtg gtg tgc ctg ctg aat aac ttc tac       480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc       528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc       576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag       624
Tyr Ser Leu Ser Ser Thr Leu Thr Leu Ser Lys Ala Asp Tyr Glu Lys
195                 200                 205 cac aag gtg tac gcc tgc gag gtg acc cac cag ggc ctg agc tcc ccc       672
His Lys Val Tyr Ala Cys Glu Val Thr His Gln Gly Leu Ser Ser Pro
210                 215                 220 gtc acc aag agc ttc aac agg ggg gag tgt                               702
Val Thr Lys Ser Phe Asn Arg Gly Glu Cys
225                 230

<210> SEQ ID NO 31
<211> LENGTH: 234
<212> TYPE: PRT
<213> ORGANISM: Artificial Sequence
<220> FEATURE:
<223> OTHER INFORMATION: Synthetic Construct

<400> SEQUENCE: 31

Met Val Leu Gln Thr Gln Val Phe Ile Ser Leu Leu Leu Trp Ile Ser
1               5                   10                  15

Gly Ala Tyr Gly Asn Ile Val Met Thr Gln Ser Pro Lys Ser Met Ser
            20                  25                  30

Met Ser Val Gly Glu Arg Val Thr Leu Ser Cys Lys Ala Ser Glu Asn
35                  40                  45

Val Gly Thr Ser Val Ser Trp Tyr Gln Glu Lys Pro Glu Gln Ser Pro
50                  55                  60

Lys Leu Leu Ile Phe Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Ser Tyr
            100                 105                 110

Ser Tyr Pro Tyr Thr Phe Gly Gly Arg Thr Lys Leu Glu Ile Lys Arg
115                 120                 125

Ala Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175
```

Gly Asn Ser Gln Glu Ser Val Thr Glu Gln Asp Ser Lys Asp Ser Thr
        180                 185                 190

Tyr Ser Leu Ser Ser Thr Leu Thr Leu Ser Lys Ala Asp Tyr Glu Lys
195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 32
<211> LENGTH: 1410
<212> TYPE: DNA
<213> ORGANISM: Artificial Sequence
<220> FEATURE:
<223> OTHER INFORMATION: Nucleotide coding heavy chain of chimeric No.76
<220> FEATURE:
<221> NAME/KEY: CDS
<222> LOCATION: (1)..(1410)

<400> SEQUENCE: 32

| | | |
|---|---|---|
| atg aaa cac ctg tgg ttc ttc ctc ctg ctg gtg gca gct ccc aga tgg<br>Met Lys His Leu Trp Phe Phe Leu Leu Leu Val Ala Ala Pro Arg Trp<br>1               5                   10                  15 | 48 |
| gtg ctg agc cag gtc caa ctg cag cag cct ggt gct gag ctt gtg aag<br>Val Leu Ser Gln Val Gln Leu Gln Gln Pro Gly Ala Glu Leu Val Lys<br>            20                  25                  30 | 96 |
| cct ggg gcc tca gtg aat ctg tcc tgc aag tct tct ggc tac act ttc<br>Pro Gly Ala Ser Val Asn Leu Ser Cys Lys Ser Ser Gly Tyr Thr Phe<br>        35                  40                  45 | 144 |
| acc aac tac tgg ata aac tgg gtg aag cag agg cct gga caa ggc ctt<br>Thr Asn Tyr Trp Ile Asn Trp Val Lys Gln Arg Pro Gly Gln Gly Leu<br>    50                  55                  60 | 192 |
| gag tgg att gga gat att tat cct ggt act agt act aac tac aat<br>Glu Trp Ile Gly Asp Ile Tyr Pro Gly Thr Ser Thr Asn Tyr Asn<br>65                  70                  75                  80 | 240 |
| gag aag ttc aag aac aag gcc aca ctg act gta gac aca tcc tcc agc<br>Glu Lys Phe Lys Asn Lys Ala Thr Leu Thr Val Asp Thr Ser Ser Ser<br>                85                  90                  95 | 288 |
| aca gcc tac atg cag ctc agc agc ctg aca tct gac gac tct gcg gtc<br>Thr Ala Tyr Met Gln Leu Ser Ser Leu Thr Ser Asp Asp Ser Ala Val<br>            100                 105                 110 | 336 |
| tat tat tgt aca aga atc tac tat gat tac gac ggg tac tac ttt gac<br>Tyr Tyr Cys Thr Arg Ile Tyr Tyr Asp Tyr Asp Gly Tyr Tyr Phe Asp<br>        115                 120                 125 | 384 |
| tac tgg ggc caa ggc acc act ctc aca gtc agc tca gcc tcc acc aag<br>Tyr Trp Gly Gln Gly Thr Thr Leu Thr Val Ser Ser Ala Ser Thr Lys<br>    130                 135                 140 | 432 |
| ggc cca agc gtc ttc ccc ctg gca ccc tcc tcc aag agc acc tct ggc<br>Gly Pro Ser Val Phe Pro Leu Ala Pro Ser Ser Lys Ser Thr Ser Gly<br>145                 150                 155                 160 | 480 |
| ggc aca gcc gcc ctg ggc tgc ctg gtc aag gac tac ttc ccc gaa ccc<br>Gly Thr Ala Ala Leu Gly Cys Leu Val Lys Asp Tyr Phe Pro Glu Pro<br>                165                 170                 175 | 528 |
| gtg acc gtg agc tgg aac tca ggc gcc ctg acc agc ggc gtg cac acc<br>Val Thr Val Ser Trp Asn Ser Gly Ala Leu Thr Ser Gly Val His Thr<br>            180                 185                 190 | 576 |
| ttc ccc gct gtc ctg cag tcc tca gga ctc tac tcc ctc agc agc gtg<br>Phe Pro Ala Val Leu Gln Ser Ser Gly Leu Tyr Ser Leu Ser Ser Val<br>        195                 200                 205 | 624 |
| gtg acc gtg ccc tcc agc agc ttg ggc acc cag acc tac atc tgc aac<br> | 672 |

```
Val Thr Val Pro Ser Ser Leu Gly Thr Gln Thr Tyr Ile Cys Asn
    210                 215                 220 gtg aat cac aag ccc agc aac acc aag gtg gac aag aga gtt gag ccc      720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa      768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac      816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
    290                 295                 300 gtg gag gtg cat aat gcc aag aca aag ccc cgg gag gag cag tac aac      960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac     1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc     1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag     1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc     1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc     1392
Ser Val Met His Glu Ala Leu His Asn His Tyr Thr Gln Lys Ser Leu
    450                 455                 460 tcc ctg tct ccc ggc aaa                                             1410
Ser Leu Ser Pro Gly Lys
465                 470

<210> SEQ ID NO 33
<211> LENGTH: 470
<212> TYPE: PRT
<213> ORGANISM: Artificial Sequence
<220> FEATURE:
<223> OTHER INFORMATION: Synthetic Construct

<400> SEQUENCE: 33

Met Lys His Leu Trp Phe Phe Leu Leu Leu Val Ala Ala Pro Arg Trp
1               5                   10                  15
```

```
Val Leu Ser Gln Val Gln Leu Gln Gln Pro Gly Ala Glu Leu Val Lys
             20                  25                  30
Pro Gly Ala Ser Val Asn Leu Ser Cys Lys Ser Ser Gly Tyr Thr Phe
             35                  40                  45
Thr Asn Tyr Trp Ile Asn Trp Val Lys Gln Arg Pro Gly Gln Gly Leu
 50                  55                  60
Glu Trp Ile Gly Asp Ile Tyr Pro Gly Thr Ser Thr Thr Asn Tyr Asn
 65                  70                  75                  80
Glu Lys Phe Lys Asn Lys Ala Thr Leu Thr Val Asp Thr Ser Ser Ser
             85                  90                  95
Thr Ala Tyr Met Gln Leu Ser Ser Leu Thr Ser Asp Asp Ser Ala Val
            100                 105                 110
Tyr Tyr Cys Thr Arg Ile Tyr Tyr Asp Tyr Asp Gly Tyr Tyr Phe Asp
            115                 120                 125
Tyr Trp Gly Gln Gly Thr Thr Leu Thr Val Ser Ser Ala Ser Thr Lys
130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
            165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
            195                 200                 205
Val Thr Val Pro Ser Ser Ser Leu Gly Thr Gln Thr Tyr Ile Cys Asn
            210                 215                 220
Val Asn His Lys Pro Ser Asn Thr Lys Val Asp Lys Arg Val Glu Pro
225                 230                 235                 240
Lys Ser Cys Asp Lys Thr His Thr Cys Pro Pro Cys Pro Ala Pro Glu
            245                 250                 255
Leu Leu Gly Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
            275                 280                 285
Val Ser His Glu Asp Pro Glu Val Lys Phe Asn Trp Tyr Val Asp Gly
290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
            325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
            355                 360                 365
Pro Gln Val Tyr Thr Leu Pro Pro Ser Arg Glu Glu Met Thr Lys Asn
            370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
            405                 410                 415
Thr Pro Pro Val Leu Asp Ser Asp Gly Ser Phe Phe Leu Tyr Ser Lys
            420                 425                 430
```

```
Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 34
<211> LENGTH: 752
<212> TYPE: DNA
<213> ORGANISM: Artificial Sequence
<220> FEATURE:
<223> OTHER INFORMATION: Nucleotide coding light chain of chimeric #1G5
<220> FEATURE:
<221> NAME/KEY: CDS
<222> LOCATION: (26)..(727)

<400> SEQUENCE: 34
ccagcctccg gactctagag ccacc atg gtg ctg cag acc cag gtg ttc atc          52
                            Met Val Leu Gln Thr Gln Val Phe Ile
                              1               5 agc ctg ctg ctg tgg atc agc ggc gcc tac ggc aac atc gtg atg acc         100
Ser Leu Leu Leu Trp Ile Ser Gly Ala Tyr Gly Asn Ile Val Met Thr
 10              15                  20                  25 cag agc ccc aag agc atg agc atg tcc gtg ggc gag aga gtg acc ctg         148
Gln Ser Pro Lys Ser Met Ser Met Ser Val Gly Glu Arg Val Thr Leu
                 30                  35                  40 agc tgc aag gcc agc gag aac gtg ggc aac agc gtg tcc tgg tat cag         196
Ser Cys Lys Ala Ser Glu Asn Val Gly Asn Ser Val Ser Trp Tyr Gln
             45                  50                  55 cag aag gcc gag cag tcc ccc aag ccc ctg atc tac ggc gcc agc aac         244
Gln Lys Ala Glu Gln Ser Pro Lys Pro Leu Ile Tyr Gly Ala Ser Asn
         60                  65                  70 aga tac acc ggc gtg ccc gat aga ttc acc ggc agc ggc agc gcc acc         292
Arg Tyr Thr Gly Val Pro Asp Arg Phe Thr Gly Ser Gly Ser Ala Thr
     75                  80                  85 gac ttc acc ctg aca atc agc agc gtg cag gcc gag gac ctg gcc gat         340
Asp Phe Thr Leu Thr Ile Ser Ser Val Gln Ala Glu Asp Leu Ala Asp
 90                  95                 100                 105 tat cac tgc ggc cag agc tac agc tac ccc tac acc ttt ggc gga ggc         388
Tyr His Cys Gly Gln Ser Tyr Ser Tyr Pro Tyr Thr Phe Gly Gly Gly
                110                 115                 120 acc aag ctg gaa atc aag cgg gct gtg gcc gct ccc tcc gtg ttc atc         436
Thr Lys Leu Glu Ile Lys Arg Ala Val Ala Ala Pro Ser Val Phe Ile
            125                 130                 135 ttt cca ccc agc gac gag cag ctg aag tcc ggc aca gct agc gtc gtg         484
Phe Pro Pro Ser Asp Glu Gln Leu Lys Ser Gly Thr Ala Ser Val Val
        140                 145                 150 tgc ctg ctg aac aac ttc tac ccc cgc gag gcc aag gtg cag tgg aag         532
Cys Leu Leu Asn Asn Phe Tyr Pro Arg Glu Ala Lys Val Gln Trp Lys
    155                 160                 165 gtg gac aat gcc ctg cag agc ggc aac tcc cag gaa agc gtg acc gag         580
Val Asp Asn Ala Leu Gln Ser Gly Asn Ser Gln Glu Ser Val Thr Glu
170                 175                 180                 185 cag gac agc aag gac tcc acc tac agc ctg agc agc acc ctg acc ctg         628
Gln Asp Ser Lys Asp Ser Thr Tyr Ser Leu Ser Ser Thr Leu Thr Leu
                190                 195                 200 tcc aag gcc gac tac gag aag cac aag gtg tac gcc tgc gaa gtg acc         676
Ser Lys Ala Asp Tyr Glu Lys His Lys Val Tyr Ala Cys Glu Val Thr
            205                 210                 215 cac cag ggc ctg tct agc ccc gtg acc aag agc ttc aac cgg ggc gag         724
His Gln Gly Leu Ser Ser Pro Val Thr Lys Ser Phe Asn Arg Gly Glu
```

```
His Gln Gly Leu Ser Ser Pro Val Thr Lys Ser Phe Asn Arg Gly Glu
            220                 225                 230 tgt tgagtttaaa cggggggaggc taact                                      752
Cys

<210> SEQ ID NO 35
<211> LENGTH: 234
<212> TYPE: PRT
<213> ORGANISM: Artificial Sequence
<220> FEATURE:
<223> OTHER INFORMATION: Synthetic Construct

<400> SEQUENCE: 35

Met Val Leu Gln Thr Gln Val Phe Ile Ser Leu Leu Leu Trp Ile Ser
1               5                   10                  15

Gly Ala Tyr Gly Asn Ile Val Met Thr Gln Ser Pro Lys Ser Met Ser
            20                  25                  30

Met Ser Val Gly Glu Arg Val Thr Leu Ser Cys Lys Ala Ser Glu Asn
        35                  40                  45

Val Gly Asn Ser Val Ser Trp Tyr Gln Gln Lys Ala Glu Gln Ser Pro
    50                  55                  60

Lys Pro Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Ser Tyr
            100                 105                 110

Ser Tyr Pro Tyr Thr Phe Gly Gly Gly Thr Lys Leu Glu Ile Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 36
<211> LENGTH: 1422
<212> TYPE: DNA
<213> ORGANISM: Artificial Sequence
<220> FEATURE:
<223> OTHER INFORMATION: Nucleotide coding heavy chain of chimeric #1G5
<220> FEATURE:
<221> NAME/KEY: CDS
<222> LOCATION: (1)..(1422)

<400> SEQUENCE: 36 atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15 gtg ctg agc cag gtg cag ctg cag cag cct ggc gcc gaa ctc gtg aaa    96
```

-continued

|  |  |
|---|---|
| Val Leu Ser Gln Val Gln Leu Gln Gln Pro Gly Ala Glu Leu Val Lys<br>20              25                  30 | |
| cct ggc gcc tct gtg aag ctg agc tgc aag gcc agc ggc tac acc ttc<br>Pro Gly Ala Ser Val Lys Leu Ser Cys Lys Ala Ser Gly Tyr Thr Phe<br>35                  40                  45 | 144 |
| acc agc tac tgg atc aac tgg gtc aag cag cgg cca ggc cag ggc ctg<br>Thr Ser Tyr Trp Ile Asn Trp Val Lys Gln Arg Pro Gly Gln Gly Leu<br>50                  55                  60 | 192 |
| gaa tgg atc ggc aat atc tac ccc ggc agc agc atc aac tac aac<br>Glu Trp Ile Gly Asn Ile Tyr Pro Gly Ser Ser Ile Asn Tyr Asn<br>65              70                  75              80 | 240 |
| gag aag ttc aag agc aag gcc acc ctg acc gtg gac acc agc agc tcc<br>Glu Lys Phe Lys Ser Lys Ala Thr Leu Thr Val Asp Thr Ser Ser Ser<br>85                  90                  95 | 288 |
| aca gcc tac atg cag ctg tcc agc ctg acc agc gac gac agc gcc gtg<br>Thr Ala Tyr Met Gln Leu Ser Ser Leu Thr Ser Asp Asp Ser Ala Val<br>100                 105                 110 | 336 |
| tac tac tgc agc cgg acc atc tac aac tac ggc agc tcc ggc tac aat<br>Tyr Tyr Cys Ser Arg Thr Ile Tyr Asn Tyr Gly Ser Ser Gly Tyr Asn<br>115                 120                 125 | 384 |
| tac gcc atg gac tac tgg ggc cag ggc acc agc gtg atc gtc agc tca<br>Tyr Ala Met Asp Tyr Trp Gly Gln Gly Thr Ser Val Ile Val Ser Ser<br>130                 135                 140 | 432 |
| gcc tcc acc aag ggc cca agc gtc ttc ccc ctg gca ccc tcc tcc aag<br>Ala Ser Thr Lys Gly Pro Ser Val Phe Pro Leu Ala Pro Ser Ser Lys<br>145                 150                 155                 160 | 480 |
| agc acc tct ggc ggc aca gcc gcc ctg ggc tgc ctg gtc aag gac tac<br>Ser Thr Ser Gly Gly Thr Ala Ala Leu Gly Cys Leu Val Lys Asp Tyr<br>165                 170                 175 | 528 |
| ttc ccc gaa ccc gtg acc gtg agc tgg aac tca ggc gcc ctg acc agc<br>Phe Pro Glu Pro Val Thr Val Ser Trp Asn Ser Gly Ala Leu Thr Ser<br>180                 185                 190 | 576 |
| ggc gtg cac acc ttc ccc gct gtc ctg cag tcc tca gga ctc tac tcc<br>Gly Val His Thr Phe Pro Ala Val Leu Gln Ser Ser Gly Leu Tyr Ser<br>195                 200                 205 | 624 |
| ctc agc agc gtg gtg acc gtg ccc tcc agc agc ttg ggc acc cag acc<br>Leu Ser Ser Val Val Thr Val Pro Ser Ser Ser Leu Gly Thr Gln Thr<br>210                 215                 220 | 672 |
| tac atc tgc aac gtg aat cac aag ccc agc aac acc aag gtg gac aag<br>Tyr Ile Cys Asn Val Asn His Lys Pro Ser Asn Thr Lys Val Asp Lys<br>225                 230                 235                 240 | 720 |
| aga gtt gag ccc aaa tct tgt gac aaa act cac aca tgc cca ccc tgc<br>Arg Val Glu Pro Lys Ser Cys Asp Lys Thr His Thr Cys Pro Pro Cys<br>245                 250                 255 | 768 |
| cca gca cct gaa ctc ctg ggg gga ccc tca gtc ttc ctc ttc ccc cca<br>Pro Ala Pro Glu Leu Leu Gly Gly Pro Ser Val Phe Leu Phe Pro Pro<br>260                 265                 270 | 816 |
| aaa ccc aag gac acc ctc atg atc tcc cgg acc cct gag gtc aca tgc<br>Lys Pro Lys Asp Thr Leu Met Ile Ser Arg Thr Pro Glu Val Thr Cys<br>275                 280                 285 | 864 |
| gtg gtg gtg gac gtg agc cac gaa gac cct gag gtc aag ttc aac tgg<br>Val Val Val Asp Val Ser His Glu Asp Pro Glu Val Lys Phe Asn Trp<br>290                 295                 300 | 912 |
| tac gtg gac ggc gtg gag gtg cat aat gcc aag aca aag ccc cgg gag<br>Tyr Val Asp Gly Val Glu Val His Asn Ala Lys Thr Lys Pro Arg Glu<br>305                 310                 315                 320 | 960 |
| gag cag tac aac agc acg tac cgg gtg gtc agc gtc ctc acc gtc ctg<br>Glu Gln Tyr Asn Ser Thr Tyr Arg Val Val Ser Val Leu Thr Val Leu<br>325                 330                 335 | 1008 |

```
cac cag gac tgg ctg aat ggc aag gag tac aag tgc aag gtc tcc aac      1056
His Gln Asp Trp Leu Asn Gly Lys Glu Tyr Lys Cys Lys Val Ser Asn
            340                 345                 350 aaa gcc ctc cca gcc ccc atc gag aaa acc atc tcc aaa gcc aaa ggc      1104
Lys Ala Leu Pro Ala Pro Ile Glu Lys Thr Ile Ser Lys Ala Lys Gly
        355                 360                 365 cag ccc cgg gaa cca cag gtg tac acc ctg ccc cca tcc cgg gag gag      1152
Gln Pro Arg Glu Pro Gln Val Tyr Thr Leu Pro Pro Ser Arg Glu Glu
370                 375                 380 atg acc aag aac cag gtc agc ctg acc tgc ctg gtc aaa ggc ttc tat      1200
Met Thr Lys Asn Gln Val Ser Leu Thr Cys Leu Val Lys Gly Phe Tyr
385                 390                 395                 400 ccc agc gac atc gcc gtg gag tgg gag agc aat ggc cag ccc gag aac      1248
Pro Ser Asp Ile Ala Val Glu Trp Glu Ser Asn Gly Gln Pro Glu Asn
                405                 410                 415 aac tac aag acc acc cct ccc gtg ctg gac tcc gac ggc tcc ttc ttc      1296
Asn Tyr Lys Thr Thr Pro Pro Val Leu Asp Ser Asp Gly Ser Phe Phe
            420                 425                 430 ctc tac agc aag ctc acc gtg gac aag agc agg tgg cag cag ggc aac      1344
Leu Tyr Ser Lys Leu Thr Val Asp Lys Ser Arg Trp Gln Gln Gly Asn
        435                 440                 445 gtc ttc tca tgc tcc gtg atg cat gag gct ctg cac aac cac tac acc      1392
Val Phe Ser Cys Ser Val Met His Glu Ala Leu His Asn His Tyr Thr
450                 455                 460 cag aag agc ctc tcc ctg tct ccc ggc aaa                              1422
Gln Lys Ser Leu Ser Leu Ser Pro Gly Lys
465                 470

<210> SEQ ID NO 37
<211> LENGTH: 474
<212> TYPE: PRT
<213> ORGANISM: Artificial Sequence
<220> FEATURE:
<223> OTHER INFORMATION: Synthetic Construct

<400> SEQUENCE: 37

Met Lys His Leu Trp Phe Phe Leu Leu Leu Val Ala Ala Pro Arg Trp
1               5                   10                  15

Val Leu Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Gly Ser Ser Ile Asn Tyr Asn
65                  70                  75                  80

Glu Lys Phe Lys Ser Lys Ala Thr Leu Thr Val Asp Thr Ser Ser Ser
                85                  90                  95

Thr Ala Tyr Met Gln Leu Ser Ser Leu Thr Ser Asp Asp Ser Ala Val
            100                 105                 110

Tyr Tyr Cys Ser Arg Thr Ile Tyr Asn Tyr Gly Ser Ser Gly Tyr Asn
        115                 120                 125

Tyr Ala Met Asp Tyr Trp Gly Gln Gly Thr Ser Val Ile Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175
```

```
Phe Pro Glu Pro Val Thr Val Ser Trp Asn Ser Gly Ala Leu Thr Ser
            180                 185                 190

Gly Val His Thr Phe Pro Ala Val Leu Gln Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 38
<211> LENGTH: 752
<212> TYPE: DNA
<213> ORGANISM: Artificial Sequence
<220> FEATURE:
<223> OTHER INFORMATION: Nucleotide coding light chain of chimeric #4C13
<220> FEATURE:
<221> NAME/KEY: CDS
<222> LOCATION: (26)..(727)

<400> SEQUENCE: 38
ccagcctccg gactctagag ccacc atg gtg ctg cag acc cag gtg ttc atc      52
                            Met Val Leu Gln Thr Gln Val Phe Ile
                            1               5 agc ctg ctg ctg tgg atc agc ggc gcc tac ggc aac atc gtg atg acc    100
Ser Leu Leu Leu Trp Ile Ser Gly Ala Tyr Gly Asn Ile Val Met Thr
10              15                  20                  25 cag agc ccc aag agc atg agc atg tcc gtg ggc gag aga gtg acc ctg    148
```

```
Gln Ser Pro Lys Ser Met Ser Met Ser Val Gly Glu Arg Val Thr Leu
                30              35                  40 agc tgc aag gcc agc gag aac gtg ggc gtg tcc gtg tcc tgg tat cag       196
Ser Cys Lys Ala Ser Glu Asn Val Gly Val Ser Val Ser Trp Tyr Gln
            45                  50                  55 cag aag ccc gag cag tcc ccc aag ctg ctg atc tac ggc gcc agc aac       244
Gln Lys Pro Glu Gln Ser Pro Lys Leu Leu Ile Tyr Gly Ala Ser Asn
        60                  65                  70 aga tac acc ggc gtg ccc gat cgg ttc acc ggc tct aga agc gcc acc       292
Arg Tyr Thr Gly Val Pro Asp Arg Phe Thr Gly Ser Arg Ser Ala Thr
    75                  80                  85 gac ttc acc ctg acc gtg tcc aat gtg cag gcc gag gac ctg gcc gat       340
Asp Phe Thr Leu Thr Val Ser Asn Val Gln Ala Glu Asp Leu Ala Asp
90                  95                  100                 105 tac cac tgt ggc cag agc tac agc tac ccc tac acc ttc ggc gga ggc       388
Tyr His Cys Gly Gln Ser Tyr Ser Tyr Pro Tyr Thr Phe Gly Gly Gly
                110                 115                 120 acc cgg ctg gaa atc aag aga gct gtg gcc gct ccc tcc gtg ttc atc       436
Thr Arg Leu Glu Ile Lys Arg Ala Val Ala Ala Pro Ser Val Phe Ile
            125                 130                 135 ttc cca cct agc gac gag cag ctg aag tcc ggc aca gcc tct gtc gtg       484
Phe Pro Pro Ser Asp Glu Gln Leu Lys Ser Gly Thr Ala Ser Val Val
        140                 145                 150 tgc ctg ctg aac aac ttc tac ccc cgc gag gcc aag gtg cag tgg aag       532
Cys Leu Leu Asn Asn Phe Tyr Pro Arg Glu Ala Lys Val Gln Trp Lys
    155                 160                 165 gtg gac aat gcc ctg cag agc ggc aac agc cag gaa agc gtg acc gag       580
Val Asp Asn Ala Leu Gln Ser Gly Asn Ser Gln Glu Ser Val Thr Glu
170                 175                 180                 185 cag gac agc aag gac tcc acc tac agc ctg agc agc acc ctg aca ctg       628
Gln Asp Ser Lys Asp Ser Thr Tyr Ser Leu Ser Ser Thr Leu Thr Leu
                190                 195                 200 agc aag gcc gac tac gag aag cac aag gtg tac gcc tgc gaa gtg acc       676
Ser Lys Ala Asp Tyr Glu Lys His Lys Val Tyr Ala Cys Glu Val Thr
            205                 210                 215 cac cag ggc ctg tct agc ccc gtg acc aag agc ttc aac cgg ggc gag       724
His Gln Gly Leu Ser Ser Pro Val Thr Lys Ser Phe Asn Arg Gly Glu
        220                 225                 230 tgt tgagtttaaa cggggaggc taact                                        752
Cys

<210> SEQ ID NO 39
<211> LENGTH: 234
<212> TYPE: PRT
<213> ORGANISM: Artificial Sequence
<220> FEATURE:
<223> OTHER INFORMATION: Synthetic Construct

<400> SEQUENCE: 39

Met Val Leu Gln Thr Gln Val Phe Ile Ser Leu Leu Trp Ile Ser
1               5                   10                  15

Gly Ala Tyr Gly Asn Ile Val Met Thr Gln Ser Pro Lys Ser Met Ser
                20                  25                  30

Met Ser Val Gly Glu Arg Val Thr Leu Ser Cys Lys Ala Ser Glu Asn
            35                  40                  45

Val Gly Val Ser Val Ser Trp Tyr Gln Gln Lys Pro Glu Gln Ser Pro
        50                  55                  60

Lys Leu Leu Ile Tyr Gly Ala Ser Asn Arg Tyr Thr Gly Val Pro Asp
65                  70                  75                  80
```

```
Arg Phe Thr Gly Ser Arg Ser Ala Thr Asp Phe Thr Leu Thr Val Ser
                85                  90                  95
Asn Val Gln Ala Glu Asp Leu Ala Asp Tyr His Cys Gly Gln Ser Tyr
            100                 105                 110
Ser Tyr Pro Tyr Thr Phe Gly Gly Gly Thr Arg Leu Glu Ile Lys Arg
        115                 120                 125
Ala Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230

<210> SEQ ID NO 40
<211> LENGTH: 1410
<212> TYPE: DNA
<213> ORGANISM: Artificial Sequence
<220> FEATURE:
<223> OTHER INFORMATION: Nucleotide coding heavy chain of chimeric #4C13
<220> FEATURE:
<221> NAME/KEY: CDS
<222> LOCATION: (1)..(1410)

<400> SEQUENCE: 40 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg cag cag cct ggc gcc gaa ctc gtg aaa      96
Val Leu Ser Gln Val Gln Leu Gln Gln Pro Gly Ala Glu Leu Val Lys
            20                  25                  30 cct ggc gcc tct gtg aag ctg agc tgc aag gcc agc ggc tac acc ttc     144
Pro Gly Ala Ser Val Lys Leu Ser Cys Lys Ala Ser Gly Tyr Thr Phe
        35                  40                  45 acc acc tac tgg atc aac tgg atg cag cag cgg cca ggc cag ggc ctg     192
Thr Thr Tyr Trp Ile Asn Trp Met Gln Gln Arg Pro Gly Gln Gly Leu
    50                  55                  60 gaa tgg atc ggc aat atc tac ccc ggc acc aga agc agc aac tac aac     240
Glu Trp Ile Gly Asn Ile Tyr Pro Gly Thr Arg Ser Ser Asn Tyr Asn
65                  70                  75                  80 gag aag ttc aag aac aag gcc acc ctg acc gtg gac acc agc agc tcc     288
Glu Lys Phe Lys Asn Lys Ala Thr Leu Thr Val Asp Thr Ser Ser Ser
                85                  90                  95 aca gcc tac atg cag ctg aac tcc ctg acc agc gac gac agc gcc gtg     336
Thr Ala Tyr Met Gln Leu Asn Ser Leu Thr Ser Asp Asp Ser Ala Val
            100                 105                 110 tac tac tgc acc aga gtg tac tac gac cac gtg ggc tac tac ttc gac     384
Tyr Tyr Cys Thr Arg Val Tyr Tyr Asp His Val Gly Tyr Tyr Phe Asp
        115                 120                 125 tac tgg ggc cag ggc aca aca ctg acc gtc agc tca gcc tcc acc aag     432
Tyr Trp Gly Gln Gly Thr Thr Leu Thr Val Ser Ser Ala Ser Thr Lys
    130                 135                 140
```

```
                                                              -continued ggc cca agc gtc ttc ccc ctg gca ccc tcc tcc aag agc acc tct ggc       480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc       528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc       576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg       624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac       672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc       720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa       768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac       816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac       864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc       912
Val Ser His Glu Asp Pro Glu Val Lys Phe Asn Trp Tyr Val Asp Gly
    290                 295                 300 gtg gag gtg cat aat gcc aag aca aag ccc cgg gag gag cag tac aac       960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg      1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca      1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa      1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac      1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc      1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc      1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag      1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc      1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc      1392
Ser Val Met His Glu Ala Leu His Asn His Tyr Thr Gln Lys Ser Leu
    450                 455                 460
```

```
                                                            tcc ctg tct ccc ggc aaa                                      1410
                                                            Ser Leu Ser Pro Gly Lys
                                                            465             470

<210> SEQ ID NO 41
<211> LENGTH: 470
<212> TYPE: PRT
<213> ORGANISM: Artificial Sequence
<220> FEATURE:
<223> OTHER INFORMATION: Synthetic Construct

<400> SEQUENCE: 41

Met Lys His Leu Trp Phe Phe Leu Leu Val Ala Ala Pro Arg Trp
1               5                   10                  15

Val Leu Ser Gln Val Gln Leu Gln Gln Pro Gly Ala Glu Leu Val Lys
                20                  25                  30

Pro Gly Ala Ser Val Lys Leu Ser Cys Lys Ala Ser Gly Tyr Thr Phe
            35                  40                  45

Thr Thr Tyr Trp Ile Asn Trp Met Gln Gln Arg Pro Gly Gln Gly Leu
    50                  55                  60

Glu Trp Ile Gly Asn Ile Tyr Pro Gly Thr Arg Ser Ser Asn Tyr Asn
65                  70                  75                  80

Glu Lys Phe Lys Asn Lys Ala Thr Leu Thr Val Asp Thr Ser Ser Ser
                85                  90                  95

Thr Ala Tyr Met Gln Leu Asn Ser Leu Thr Ser Asp Asp Ser Ala Val
            100                 105                 110

Tyr Tyr Cys Thr Arg Val Tyr Tyr Asp His Val Gly Tyr Tyr Phe Asp
        115                 120                 125

Tyr Trp Gly Gln Gly Thr Thr Leu Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
```

```
                         340               345               350
Ala Pro Ile Glu Lys Thr Ile Ser Lys Ala Lys Gly Gln Pro Arg Glu
            355                 360                 365
Pro Gln Val Tyr Thr Leu Pro Pro Ser Arg Glu Glu Met Thr Lys Asn
        370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
Ser Leu Ser Pro Gly Lys
465                 470

<210> SEQ ID NO 42
<211> LENGTH: 708
<212> TYPE: DNA
<213> ORGANISM: Artificial Sequence
<220> FEATURE:
<223> OTHER INFORMATION: Nucleotide coding light chain of Meiji1640
<220> FEATURE:
<221> NAME/KEY: CDS
<222> LOCATION: (1)..(708)

<400> SEQUENCE: 42 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc gac atc cag atg acc cag agc ccc agc agc ctg agc      96
Gly Ala Tyr Gly Asp Ile Gln Met Thr Gln Ser Pro Ser Ser Leu Ser
                20                  25                  30 gcc agc gtg ggc gac aga gtg acc atc acc tgt cgg gcc agc cag agc     144
Ala Ser Val Gly Asp Arg Val Thr Ile Thr Cys Arg Ala Ser Gln Ser
            35                  40                  45 atc ggc aag tac ctg aac tgg tat cag cag aag ccc ggc aag gcc ccc     192
Ile Gly Lys Tyr Leu Asn Trp Tyr Gln Gln Lys Pro Gly Lys Ala Pro
        50                  55                  60 aag ctg ctg atc tac gcc gcc agc aac ctg cag agc ggc gtg ccc agc     240
Lys Leu Leu Ile Tyr Ala Ala Ser Asn Leu Gln Ser Gly Val Pro Ser
65                  70                  75                  80 aga ttt ggc ggc agc ggc tcc ggc acc gac ttc acc ctg acc atc agc     288
Arg Phe Gly Gly Ser Gly Ser Gly Thr Asp Phe Thr Leu Thr Ile Ser
                85                  90                  95 agc ctg cag ccc gag gac tgc gcc acc tac tac tgc cag cag agc ttc     336
Ser Leu Gln Pro Glu Asp Cys Ala Thr Tyr Tyr Cys Gln Gln Ser Phe
                100                 105                 110 acc gcc cct cag aag tac acc ttc ggc cag ggc acc aag ctg gaa atc     384
Thr Ala Pro Gln Lys Tyr Thr Phe Gly Gln Gly Thr Lys Leu Glu Ile
            115                 120                 125 aag cgt acg gtg gcc gcc ccc tcc gtg ttc atc ttc ccc ccc tcc gac     432
Lys Arg Thr Val Ala Ala Pro Ser Val Phe Ile Phe Pro Pro Ser Asp
        130                 135                 140 gag cag ctg aag tcc ggc acc gcc tcc gtg gtg tgc ctg ctg aat aac     480
Glu Gln Leu Lys Ser Gly Thr Ala Ser Val Val Cys Leu Leu Asn Asn
145                 150                 155                 160
```

```
ttc tac ccc aga gag gcc aag gtg cag tgg aag gtg gac aac gcc ctg      528
Phe Tyr Pro Arg Glu Ala Lys Val Gln Trp Lys Val Asp Asn Ala Leu
            165                 170                 175 cag tcc ggg aac tcc cag gag agc gtg acc gag cag gac agc aag gac      576
Gln Ser Gly Asn Ser Gln Glu Ser Val Thr Glu Gln Asp Ser Lys Asp
        180                 185                 190 agc acc tac agc ctg agc agc acc ctg acc ctg agc aaa gcc gac tac      624
Ser Thr Tyr Ser Leu Ser Ser Thr Leu Thr Leu Ser Lys Ala Asp Tyr
    195                 200                 205 gag aag cac aag gtg tac gcc tgc gag gtg acc cac cag ggc ctg agc      672
Glu Lys His Lys Val Tyr Ala Cys Glu Val Thr His Gln Gly Leu Ser
210                 215                 220 tcc ccc gtc acc aag agc ttc aac agg ggg gag tgt                      708
Ser Pro Val Thr Lys Ser Phe Asn Arg Gly Glu Cys
225                 230                 235
```

<210> SEQ ID NO 43
<211> LENGTH: 236
<212> TYPE: PRT
<213> ORGANISM: Artificial Sequence
<220> FEATURE:
<223> OTHER INFORMATION: Synthetic Construct

<400> SEQUENCE: 43

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Ser
        35                  40                  45

Ile Gly Lys Tyr Leu Asn Trp Tyr Gln Gln Lys Pro Gly Lys Ala Pro
    50                  55                  60

Lys Leu Leu Ile Tyr Ala Ala Ser Asn Leu Gln Ser Gly Val Pro Ser
65                  70                  75                  80

Arg Phe Gly Gly Ser Gly Ser Gly Thr Asp Phe Thr Leu Thr Ile Ser
                85                  90                  95

Ser Leu Gln Pro Glu Asp Cys Ala Thr Tyr Tyr Cys Gln Gln Ser Phe
            100                 105                 110

Thr Ala Pro Gln Lys Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 44
<211> LENGTH: 1431
<212> TYPE: DNA

```
<213> ORGANISM: Artificial Sequence
<220> FEATURE:
<223> OTHER INFORMATION: Nucleotide coding heavy chain of Meiji1640
<220> FEATURE:
<221> NAME/KEY: CDS
<222> LOCATION: (1)..(1431)

<400> SEQUENCE: 44 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc gag gtg cag ctg gtg gaa agc ggc gga gga ctg gtg cag      96
Val Leu Ser Glu Val Gln Leu Val Glu Ser Gly Gly Gly Leu Val Gln
            20                  25                  30 cct ggc ggc agc ctg aga ctg tct tgc gcc gcc agc ggc ttc acc atc     144
Pro Gly Gly Ser Leu Arg Leu Ser Cys Ala Ala Ser Gly Phe Thr Ile
        35                  40                  45 ccc ttc aga aag tac tgg ctg cac tgg gtc cgc cag gcc cct ggc aag     192
Pro Phe Arg Lys Tyr Trp Leu His Trp Val Arg Gln Ala Pro Gly Lys
    50                  55                  60 gga ctc gtg tgg gtg tcc ctg atc atc ggc gac ggc agc agc acc aac     240
Gly Leu Val Trp Val Ser Leu Ile Ile Gly Asp Gly Ser Ser Thr Asn
65                  70                  75                  80 tac gcc gac agc gtg aag ggc cgg ttc acc atc agc cgg gac aac gac     288
Tyr Ala Asp Ser Val Lys Gly Arg Phe Thr Ile Ser Arg Asp Asn Asp
                85                  90                  95 aag aac acc ctg tac ctg cag atg aac agc ctg cgg gtg gaa gat acc     336
Lys Asn Thr Leu Tyr Leu Gln Met Asn Ser Leu Arg Val Glu Asp Thr
            100                 105                 110 gcc gtg tac tac tgc gcc agg gac ctg ggc gag cgg acc ggc gat aat     384
Ala Val Tyr Tyr Cys Ala Arg Asp Leu Gly Glu Arg Thr Gly Asp Asn
        115                 120                 125 tgg cac agc ctg ggc ccc gac tac tgg ggc cag ggc aca ctg gtc acc     432
Trp His Ser Leu Gly Pro Asp Tyr Trp Gly Gln Gly Thr Leu Val Thr
    130                 135                 140 gtc agc tca gcc tcc acc aag ggc cca agc gtc ttc ccc ctg gca ccc     480
Val Ser Ser Ala Ser Thr Lys Gly Pro Ser Val Phe Pro Leu Ala Pro
145                 150                 155                 160 tcc tcc aag agc acc tct ggc ggc aca gcc gcc ctg ggc tgc ctg gtc     528
Ser Ser Lys Ser Thr Ser Gly Gly Thr Ala Ala Leu Gly Cys Leu Val
                165                 170                 175 aag gac tac ttc ccc gaa ccc gtg acc gtg agc tgg aac tca ggc gcc     576
Lys Asp Tyr Phe Pro Glu Pro Val Thr Val Ser Trp Asn Ser Gly Ala
            180                 185                 190 ctg acc agc ggc gtg cac acc ttc ccc gct gtc ctg cag tcc tca gga     624
Leu Thr Ser Gly Val His Thr Phe Pro Ala Val Leu Gln Ser Ser Gly
        195                 200                 205 ctc tac tcc ctc agc agc gtg gtg acc gtg ccc tcc agc agc ttg ggc     672
Leu Tyr Ser Leu Ser Ser Val Val Thr Val Pro Ser Ser Ser Leu Gly
    210                 215                 220 acc cag acc tac atc tgc aac gtg aat cac aag ccc agc aac acc aag     720
Thr Gln Thr Tyr Ile Cys Asn Val Asn His Lys Pro Ser Asn Thr Lys
225                 230                 235                 240 gtg gac aag aga gtt gag ccc aaa tct tgt gac aaa act cac aca tgc     768
Val Asp Lys Arg Val Glu Pro Lys Ser Cys Asp Lys Thr His Thr Cys
                245                 250                 255 cca ccc tgc cca gca cct gaa ctc ctg ggg gga ccc tca gtc ttc ctc     816
Pro Pro Cys Pro Ala Pro Glu Leu Leu Gly Gly Pro Ser Val Phe Leu
            260                 265                 270 ttc ccc cca aaa ccc aag gac acc ctc atg atc tcc cgg acc cct gag     864
Phe Pro Pro Lys Pro Lys Asp Thr Leu Met Ile Ser Arg Thr Pro Glu
```

```
                275                 280                 285
gtc aca tgc gtg gtg gtg gac gtg agc cac gaa gac cct gag gtc aag      912
Val Thr Cys Val Val Val Asp Val Ser His Glu Asp Pro Glu Val Lys
    290                 295                 300 ttc aac tgg tac gtg gac ggc gtg gag gtg cat aat gcc aag aca aag      960
Phe Asn Trp Tyr Val Asp Gly Val Glu Val His Asn Ala Lys Thr Lys
305                 310                 315                 320 ccc cgg gag gag cag tac aac agc acg tac cgg gtg gtc agc gtc ctc     1008
Pro Arg Glu Glu Gln Tyr Asn Ser Thr Tyr Arg Val Val Ser Val Leu
                325                 330                 335 acc gtc ctg cac cag gac tgg ctg aat ggc aag gag tac aag tgc aag     1056
Thr Val Leu His Gln Asp Trp Leu Asn Gly Lys Glu Tyr Lys Cys Lys
            340                 345                 350 gtc tcc aac aaa gcc ctc cca gcc ccc atc gag aaa acc atc tcc aaa     1104
Val Ser Asn Lys Ala Leu Pro Ala Pro Ile Glu Lys Thr Ile Ser Lys
        355                 360                 365 gcc aaa ggc cag ccc cgg gaa cca cag gtg tac acc ctg ccc cca tcc     1152
Ala Lys Gly Gln Pro Arg Glu Pro Gln Val Tyr Thr Leu Pro Pro Ser
    370                 375                 380 cgg gag gag atg acc aag aac cag gtc agc ctg acc tgc ctg gtc aaa     1200
Arg Glu Glu Met Thr Lys Asn Gln Val Ser Leu Thr Cys Leu Val Lys
385                 390                 395                 400 ggc ttc tat ccc agc gac atc gcc gtg gag tgg gag agc aat ggc cag     1248
Gly Phe Tyr Pro Ser Asp Ile Ala Val Glu Trp Glu Ser Asn Gly Gln
                405                 410                 415 ccc gag aac aac tac aag acc acc cct ccc gtg ctg gac tcc gac ggc     1296
Pro Glu Asn Asn Tyr Lys Thr Thr Pro Pro Val Leu Asp Ser Asp Gly
            420                 425                 430 tcc ttc ttc ctc tac agc aag ctc acc gtg gac aag agc agg tgg cag     1344
Ser Phe Phe Leu Tyr Ser Lys Leu Thr Val Asp Lys Ser Arg Trp Gln
        435                 440                 445 cag ggc aac gtc ttc tca tgc tcc gtg atg cat gag gct ctg cac aac     1392
Gln Gly Asn Val Phe Ser Cys Ser Val Met His Glu Ala Leu His Asn
    450                 455                 460 cac tac acc cag aag agc ctc tcc ctg tct ccc ggc aaa                 1431
His Tyr Thr Gln Lys Ser Leu Ser Leu Ser Pro Gly Lys
465                 470                 475

<210> SEQ ID NO 45
<211> LENGTH: 477
<212> TYPE: PRT
<213> ORGANISM: Artificial Sequence
<220> FEATURE:
<223> OTHER INFORMATION: Synthetic Construct

<400> SEQUENCE: 45

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Ile
        35                  40                  45

Pro Phe Arg Lys Tyr Trp Leu His Trp Val Arg Gln Ala Pro Gly Lys
    50                  55                  60

Gly Leu Val Trp Val Ser Leu Ile Ile Gly Asp Gly Ser Ser Thr Asn
65                  70                  75                  80

Tyr Ala Asp Ser Val Lys Gly Arg Phe Thr Ile Ser Arg Asp Asn Asp
                85                  90                  95

Lys Asn Thr Leu Tyr Leu Gln Met Asn Ser Leu Arg Val Glu Asp Thr
```

```
                100             105             110
Ala Val Tyr Tyr Cys Ala Arg Asp Leu Gly Glu Arg Thr Gly Asp Asn
            115             120             125

Trp His Ser Leu Gly Pro Asp Tyr Trp Gly Gln Gly Thr Leu Val Thr
            130             135             140

Val Ser Ser Ala Ser Thr Lys Gly Pro Ser Val Phe Pro Leu Ala Pro
145             150             155             160

Ser Ser Lys Ser Thr Ser Gly Gly Thr Ala Ala Leu Gly Cys Leu Val
            165             170             175

Lys Asp Tyr Phe Pro Glu Pro Val Thr Val Ser Trp Asn Ser Gly Ala
            180             185             190

Leu Thr Ser Gly Val His Thr Phe Pro Ala Val Leu Gln Ser Ser Gly
            195             200             205

Leu Tyr Ser Leu Ser Ser Val Val Thr Val Pro Ser Ser Ser Leu Gly
            210             215             220

Thr Gln Thr Tyr Ile Cys Asn Val Asn His Lys Pro Ser Asn Thr Lys
225             230             235             240

Val Asp Lys Arg Val Glu Pro Lys Ser Cys Asp Lys Thr His Thr Cys
            245             250             255

Pro Pro Cys Pro Ala Pro Glu Leu Leu Gly Gly Pro Ser Val Phe Leu
            260             265             270

Phe Pro Pro Lys Pro Lys Asp Thr Leu Met Ile Ser Arg Thr Pro Glu
            275             280             285

Val Thr Cys Val Val Val Asp Val Ser His Glu Asp Pro Glu Val Lys
            290             295             300

Phe Asn Trp Tyr Val Asp Gly Val Glu Val His Asn Ala Lys Thr Lys
305             310             315             320

Pro Arg Glu Glu Gln Tyr Asn Ser Thr Tyr Arg Val Val Ser Val Leu
            325             330             335

Thr Val Leu His Gln Asp Trp Leu Asn Gly Lys Glu Tyr Lys Cys Lys
            340             345             350

Val Ser Asn Lys Ala Leu Pro Ala Pro Ile Glu Lys Thr Ile Ser Lys
            355             360             365

Ala Lys Gly Gln Pro Arg Glu Pro Gln Val Tyr Thr Leu Pro Pro Ser
            370             375             380

Arg Glu Glu Met Thr Lys Asn Gln Val Ser Leu Thr Cys Leu Val Lys
385             390             395             400

Gly Phe Tyr Pro Ser Asp Ile Ala Val Glu Trp Glu Ser Asn Gly Gln
            405             410             415

Pro Glu Asn Asn Tyr Lys Thr Thr Pro Pro Val Leu Asp Ser Asp Gly
            420             425             430

Ser Phe Phe Leu Tyr Ser Lys Leu Thr Val Asp Lys Ser Arg Trp Gln
            435             440             445

Gln Gly Asn Val Phe Ser Cys Ser Val Met His Glu Ala Leu His Asn
            450             455             460

His Tyr Thr Gln Lys Ser Leu Ser Leu Ser Pro Gly Lys
465             470             475

<210> SEQ ID NO 46
<211> LENGTH: 702
<212> TYPE: DNA
<213> ORGANISM: Artificial Sequence
<220> FEATURE:
<223> OTHER INFORMATION: Nucleotide coding light chain of Meiji1656
<220> FEATURE:
```

<221> NAME/KEY: CDS
<222> LOCATION: (1)..(702)

<400> SEQUENCE: 46

```
atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc gac atc cag ctg acc cag agc ccc agc ttc ctg agc      96
Gly Ala Tyr Gly Asp Ile Gln Leu Thr Gln Ser Pro Ser Phe Leu Ser
            20                  25                  30 acc agc gtg ggc gac aga gtg acc atc acc tgt cgg gcc agc cag ggc     144
Thr Ser Val Gly Asp Arg Val Thr Ile Thr Cys Arg Ala Ser Gln Gly
        35                  40                  45 atc agc aac tac ctg gcc tgg tat cag cag aag ccc ggc acc gcc ccc     192
Ile Ser Asn Tyr Leu Ala Trp Tyr Gln Gln Lys Pro Gly Thr Ala Pro
    50                  55                  60 aag ctg ctg atc tac agc gcc agc acc ctg cag agc ggc gtg ccc agc     240
Lys Leu Leu Ile Tyr Ser Ala Ser Thr Leu Gln Ser Gly Val Pro Ser
65                  70                  75                  80 aga ttt tct ggc agc ggc agc ggc acc gag ttc acc ctg acc atc agc     288
Arg Phe Ser Gly Ser Gly Ser Gly Thr Glu Phe Thr Leu Thr Ile Ser
                85                  90                  95 agc ctg cag ccc gag gac ttc gcc acc tac tac tgc cag cac ctg aaa     336
Ser Leu Gln Pro Glu Asp Phe Ala Thr Tyr Tyr Cys Gln His Leu Lys
            100                 105                 110 acc agc ctg gtc acc ttc ggc cag ggc acc cgg ctg gaa atg aag cgt     384
Thr Ser Leu Val Thr Phe Gly Gln Gly Thr Arg Leu Glu Met Lys Arg
        115                 120                 125 acg gtg gcc gcc ccc tcc gtg ttc atc ttc ccc ccc tcc gac gag cag     432
Thr Val Ala Ala Pro Ser Val Phe Ile Phe Pro Pro Ser Asp Glu Gln
    130                 135                 140 ctg aag tcc ggc acc gcc tcc gtg gtg tgc ctg ctg aat aac ttc tac     480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc     528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc     576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag     624
Tyr Ser Leu Ser Ser Thr Leu Thr Leu Ser Lys Ala Asp Tyr Glu Lys
        195                 200                 205 cac aag gtg tac gcc tgc gag gtg acc cac cag ggc ctg agc tcc ccc     672
His Lys Val Tyr Ala Cys Glu Val Thr His Gln Gly Leu Ser Ser Pro
    210                 215                 220 gtc acc aag agc ttc aac agg ggg gag tgt                             702
Val Thr Lys Ser Phe Asn Arg Gly Glu Cys
225                 230
```

<210> SEQ ID NO 47
<211> LENGTH: 234
<212> TYPE: PRT
<213> ORGANISM: Artificial Sequence
<220> FEATURE:
<223> OTHER INFORMATION: Synthetic Construct

<400> SEQUENCE: 47

```
Met Val Leu Gln Thr Gln Val Phe Ile Ser Leu Leu Leu Trp Ile Ser
1               5                   10                  15

Gly Ala Tyr Gly Asp Ile Gln Leu Thr Gln Ser Pro Ser Phe Leu Ser
```

```
                    20                  25                  30
Thr Ser Val Gly Asp Arg Val Thr Ile Thr Cys Arg Ala Ser Gln Gly
            35                  40                  45
Ile Ser Asn Tyr Leu Ala Trp Tyr Gln Gln Lys Pro Gly Thr Ala Pro
        50                  55                  60
Lys Leu Leu Ile Tyr Ser Ala Ser Thr Leu Gln Ser Gly Val Pro Ser
 65                  70                  75                  80
Arg Phe Ser Gly Ser Gly Ser Gly Thr Glu Phe Thr Leu Thr Ile Ser
                    85                  90                  95
Ser Leu Gln Pro Glu Asp Phe Ala Thr Tyr Tyr Cys Gln His Leu Lys
            100                 105                 110
Thr Ser Leu Val Thr Phe Gly Gln Gly Thr Arg Leu Glu Met Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230

<210> SEQ ID NO 48
<211> LENGTH: 1440
<212> TYPE: DNA
<213> ORGANISM: Artificial Sequence
<220> FEATURE:
<223> OTHER INFORMATION: Nucleotide coding heavy chain of Meiji1656
<220> FEATURE:
<221> NAME/KEY: CDS
<222> LOCATION: (1)..(1440)

<400> SEQUENCE: 48 atg aaa cac ctg tgg ttc ttc ctc ctg ctg gtg gca gct ccc aga tgg        48
Met Lys His Leu Trp Phe Phe Leu Leu Leu Val Ala Ala Pro Arg Trp
 1               5                  10                  15 gtg ctg agc gag gtg cag ctg gtg gaa agc ggc gga gga ctg gtg cag        96
Val Leu Ser Glu Val Gln Leu Val Glu Ser Gly Gly Gly Leu Val Gln
                20                  25                  30 cct ggc ggc agc ctg aga ctg agc tgc agc gcc agc ggc ttc acc gac       144
Pro Gly Gly Ser Leu Arg Leu Ser Cys Ser Ala Ser Gly Phe Thr Asp
            35                  40                  45 agc cgg ttc acc ttc cgg aac tac tgg atg cac tgg gtc cga cag gct       192
Ser Arg Phe Thr Phe Arg Asn Tyr Trp Met His Trp Val Arg Gln Ala
        50                  55                  60 cca ggc aag ggc ctc gtg tgg gtg tcc aga atc aac ggc gac ggc gga       240
Pro Gly Lys Gly Leu Val Trp Val Ser Arg Ile Asn Gly Asp Gly Gly
 65                  70                  75                  80 ggc acc gtg tac agc gac agc gtg aag ggc aga ttc acc atc agc cgg       288
Gly Thr Val Tyr Ser Asp Ser Val Lys Gly Arg Phe Thr Ile Ser Arg
                85                  90                  95 gac aac gcc cgg aac atc gtg tac ctg cag atg gac agc ctg cgg gcc       336
```

```
                Asp Asn Ala Arg Asn Ile Val Tyr Leu Gln Met Asp Ser Leu Arg Ala
                                100                 105                 110 gag gac acc gcc gtg tac tac tgc gtg cgc gag ttc ggc ctg ttc gac           384
Glu Asp Thr Ala Val Tyr Tyr Cys Val Arg Glu Phe Gly Leu Phe Asp
            115                 120                 125 agc ggc aca tgg tac agc ggc ggc ttc gac tac tgg ggc cag ggc acc           432
Ser Gly Thr Trp Tyr Ser Gly Gly Phe Asp Tyr Trp Gly Gln Gly Thr
130                 135                 140 ctg gtc acc gtc agc tca gcc tcc acc aag ggc cca agc gtc ttc ccc           480
Leu Val Thr Val Ser Ser Ala Ser Thr Lys Gly Pro Ser Val Phe Pro
145                 150                 155                 160 ctg gca ccc tcc tcc aag agc acc tct ggc ggc aca gcc gcc ctg ggc           528
Leu Ala Pro Ser Ser Lys Ser Thr Ser Gly Gly Thr Ala Ala Leu Gly
                165                 170                 175 tgc ctg gtc aag gac tac ttc ccc gaa ccc gtg acc gtg agc tgg aac           576
Cys Leu Val Lys Asp Tyr Phe Pro Glu Pro Val Thr Val Ser Trp Asn
                180                 185                 190 tca ggc gcc ctg acc agc ggc gtg cac acc ttc ccc gct gtc ctg cag           624
Ser Gly Ala Leu Thr Ser Gly Val His Thr Phe Pro Ala Val Leu Gln
                195                 200                 205 tcc tca gga ctc tac tcc ctc agc agc gtg gtg acc gtg ccc tcc agc           672
Ser Ser Gly Leu Tyr Ser Leu Ser Ser Val Val Thr Val Pro Ser Ser
210                 215                 220 agc ttg ggc acc cag acc tac atc tgc aac gtg aat cac aag ccc agc           720
Ser Leu Gly Thr Gln Thr Tyr Ile Cys Asn Val Asn His Lys Pro Ser
225                 230                 235                 240 aac acc aag gtg gac aag aga gtt gag ccc aaa tct tgt gac aaa act           768
Asn Thr Lys Val Asp Lys Arg Val Glu Pro Lys Ser Cys Asp Lys Thr
                245                 250                 255 cac aca tgc cca ccc tgc cca gca cct gaa ctc ctg ggg gga ccc tca           816
His Thr Cys Pro Pro Cys Pro Ala Pro Glu Leu Leu Gly Gly Pro Ser
                260                 265                 270 gtc ttc ctc ttc ccc cca aaa ccc aag gac acc ctc atg atc tcc cgg           864
Val Phe Leu Phe Pro Pro Lys Pro Lys Asp Thr Leu Met Ile Ser Arg
                275                 280                 285 acc cct gag gtc aca tgc gtg gtg gtg gac gtg agc cac gaa gac cct           912
Thr Pro Glu Val Thr Cys Val Val Val Asp Val Ser His Glu Asp Pro
290                 295                 300 gag gtc aag ttc aac tgg tac gtg gac ggc gtg gag gtg cat aat gcc           960
Glu Val Lys Phe Asn Trp Tyr Val Asp Gly Val Glu Val His Asn Ala
305                 310                 315                 320 aag aca aag ccc cgg gag gag cag tac aac agc acg tac cgg gtg gtc          1008
Lys Thr Lys Pro Arg Glu Glu Gln Tyr Asn Ser Thr Tyr Arg Val Val
                325                 330                 335 agc gtc ctc acc gtc ctg cac cag gac tgg ctg aat ggc aag gag tac          1056
Ser Val Leu Thr Val Leu His Gln Asp Trp Leu Asn Gly Lys Glu Tyr
                340                 345                 350 aag tgc aag gtc tcc aac aaa gcc ctc cca gcc ccc atc gag aaa acc          1104
Lys Cys Lys Val Ser Asn Lys Ala Leu Pro Ala Pro Ile Glu Lys Thr
                355                 360                 365 atc tcc aaa gcc aaa ggc cag ccc cgg gaa cca cag gtg tac acc ctg          1152
Ile Ser Lys Ala Lys Gly Gln Pro Arg Glu Pro Gln Val Tyr Thr Leu
370                 375                 380 ccc cca tcc cgg gag gag atg acc aag aac cag gtc agc ctg acc tgc          1200
Pro Pro Ser Arg Glu Glu Met Thr Lys Asn Gln Val Ser Leu Thr Cys
385                 390                 395                 400 ctg gtc aaa ggc ttc tat ccc agc gac atc gcc gtg gag tgg gag agc          1248
Leu Val Lys Gly Phe Tyr Pro Ser Asp Ile Ala Val Glu Trp Glu Ser
                405                 410                 415
```

| aat | ggc | cag | ccc | gag | aac | aac | tac | aag | acc | acc | cct | ccc | gtg | ctg | gac | 1296 |
| Asn | Gly | Gln | Pro | Glu | Asn | Asn | Tyr | Lys | Thr | Thr | Pro | Pro | Val | Leu | Asp | |
| | | | 420 | | | | 425 | | | | | 430 | | | | |

| tcc | gac | ggc | tcc | ttc | ttc | ctc | tac | agc | aag | ctc | acc | gtg | gac | aag | agc | 1344 |
| Ser | Asp | Gly | Ser | Phe | Phe | Leu | Tyr | Ser | Lys | Leu | Thr | Val | Asp | Lys | Ser | |
| | | 435 | | | | | 440 | | | | | 445 | | | | |

| agg | tgg | cag | cag | ggc | aac | gtc | ttc | tca | tgc | tcc | gtg | atg | cat | gag | gct | 1392 |
| Arg | Trp | Gln | Gln | Gly | Asn | Val | Phe | Ser | Cys | Ser | Val | Met | His | Glu | Ala | |
| | | 450 | | | | | 455 | | | | | 460 | | | | |

| ctg | cac | aac | cac | tac | acc | cag | aag | agc | ctc | tcc | ctg | tct | ccc | ggc | aaa | 1440 |
| Leu | His | Asn | His | Tyr | Thr | Gln | Lys | Ser | Leu | Ser | Leu | Ser | Pro | Gly | Lys | |
| 465 | | | | 470 | | | | | 475 | | | | | 480 | | |

<210> SEQ ID NO 49
<211> LENGTH: 480
<212> TYPE: PRT
<213> ORGANISM: Artificial Sequence
<220> FEATURE:
<223> OTHER INFORMATION: Synthetic Construct

<400> SEQUENCE: 49

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ser Ala Ser Gly Phe Thr Asp
        35                  40                  45

Ser Arg Phe Thr Phe Arg Asn Tyr Trp Met His Trp Val Arg Gln Ala
    50                  55                  60

Pro Gly Lys Gly Leu Val Trp Val Ser Arg Ile Asn Gly Asp Gly Gly
65                  70                  75                  80

Gly Thr Val Tyr Ser Asp Ser Val Lys Gly Arg Phe Thr Ile Ser Arg
                85                  90                  95

Asp Asn Ala Arg Asn Ile Val Tyr Leu Gln Met Asp Ser Leu Arg Ala
            100                 105                 110

Glu Asp Thr Ala Val Tyr Tyr Cys Val Arg Glu Phe Gly Leu Phe Asp
        115                 120                 125

Ser Gly Thr Trp Tyr Ser Gly Gly Phe Asp Tyr Trp Gly Gln Gly Thr
    130                 135                 140

Leu Val Thr Val Ser Ser Ala Ser Thr Lys Gly Pro Ser Val Phe Pro
145                 150                 155                 160

Leu Ala Pro Ser Ser Lys Ser Thr Ser Gly Gly Thr Ala Ala Leu Gly
                165                 170                 175

Cys Leu Val Lys Asp Tyr Phe Pro Glu Pro Val Thr Val Ser Trp Asn
            180                 185                 190

Ser Gly Ala Leu Thr Ser Gly Val His Thr Phe Pro Ala Val Leu Gln
        195                 200                 205

Ser Ser Gly Leu Tyr Ser Leu Ser Ser Val Val Thr Val Pro Ser Ser
    210                 215                 220

Ser Leu Gly Thr Gln Thr Tyr Ile Cys Asn Val Asn His Lys Pro Ser
225                 230                 235                 240

Asn Thr Lys Val Asp Lys Arg Val Glu Pro Lys Ser Cys Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

```
Thr Pro Glu Val Thr Cys Val Val Asp Val Ser His Glu Asp Pro
    290             295                 300
Glu Val Lys Phe Asn Trp Tyr Val Asp Gly Val Glu Val His Asn Ala
305                 310                 315                 320
Lys Thr Lys Pro Arg Glu Glu Gln Tyr Asn Ser Thr Tyr Arg Val Val
                325                 330                 335
Ser Val Leu Thr Val Leu His Gln Asp Trp Leu Asn Gly Lys Glu Tyr
            340                 345                 350
Lys Cys Lys Val Ser Asn Lys Ala Leu Pro Ala Pro Ile Glu Lys Thr
        355                 360                 365
Ile Ser Lys Ala Lys Gly Gln Pro Arg Glu Pro Gln Val Tyr Thr Leu
    370                 375                 380
Pro Pro Ser Arg Glu Glu Met Thr Lys Asn Gln Val Ser Leu Thr Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
            420                 425                 430
Ser Asp Gly Ser Phe Phe Leu Tyr Ser Lys Leu Thr Val Asp Lys Ser
        435                 440                 445
Arg Trp Gln Gln Gly Asn Val Phe Ser Cys Ser Val Met His Glu Ala
    450                 455                 460
Leu His Asn His Tyr Thr Gln Lys Ser Leu Ser Leu Ser Pro Gly Lys
465                 470                 475                 480

<210> SEQ ID NO 50
<211> LENGTH: 717
<212> TYPE: DNA
<213> ORGANISM: Artificial Sequence
<220> FEATURE:
<223> OTHER INFORMATION: Nucleotide coding light chain of mouse IgG2b
      type chimeric 1BO11

<400> SEQUENCE: 50
atgagcgtgc tgacccaggt gcttgccctg cttctgcttt ggctgaccgg cgctcggtgt        60
gacgtggtga tgacccagag ccctctgtcc cttcctgtga ccctgggcca gcctgccagc       120
atctcctgtc ggagctccca gagccttgtg tactccgacg gcaacaccta cctgaactgg       180
ttccagcaga gacctggcca gagccctcgg agacttatct acaaggtgtc caaccgggac       240
agcggagtgc ctgacagatt ctccggcagc ggatccggca ccgacttcac cctgaagatc       300
agccgggtgg aggctgagga cgtgggagtg tactactgta tgcagggcac ccactggcct       360
cttaccttcg gcggaggcac caaggtggag atcaagagag ccgacgctgc ccctaccgtg       420
tccatcttcc ctcctagctc cgagcagctt accagcggcg gcgcctccgt ggtgtgtttc       480
ctgaacaact ctaccctaa ggacatcaac gtgctttgga agatcgacgg cagcgagaga       540
caaaacggcg tgctgaactc ctggaccgac caggacagca aggactccac ctacagcatg       600
tccagcaccc ttaccctgac caaggacgag tacgagcggc acaactccta cacctgtgag       660
gctacccaca agaccagcac ctcccctatc gtgaagagct caacagaaa cgagtgt          717

<210> SEQ ID NO 51
<211> LENGTH: 717
<212> TYPE: DNA
<213> ORGANISM: Artificial Sequence
<220> FEATURE:
<223> OTHER INFORMATION: Nucleotide coding light chain of human IgG1
``` type 1B011
<220> FEATURE:
<221> NAME/KEY: CDS
<222> LOCATION: (1)..(717)

<400> SEQUENCE: 51

```
atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc gac gtg gtg atg acc cag agc cct ctg tcc ctt cct      96
Gly Ala Tyr Gly Asp Val Val Met Thr Gln Ser Pro Leu Ser Leu Pro
            20                  25                  30 gtg acc ctg ggc cag cct gcc agc atc tcc tgt cgg agc tcc cag agc     144
Val Thr Leu Gly Gln Pro Ala Ser Ile Ser Cys Arg Ser Ser Gln Ser
        35                  40                  45 ctt gtg tac tcc gac ggc aac acc tac ctg aac tgg ttc cag cag aga     192
Leu Val Tyr Ser Asp Gly Asn Thr Tyr Leu Asn Trp Phe Gln Gln Arg
    50                  55                  60 cct ggc cag agc cct cgg aga ctt atc tac aag gtg tcc aac cgg gac     240
Pro Gly Gln Ser Pro Arg Arg Leu Ile Tyr Lys Val Ser Asn Arg Asp
65                  70                  75                  80 agc gga gtg cct gac aga ttc tcc ggc agc gga tcc ggc acc gac ttc     288
Ser Gly Val Pro Asp Arg Phe Ser Gly Ser Gly Ser Gly Thr Asp Phe
                85                  90                  95 acc ctg aag atc agc cgg gtg gag gct gag gac gtg gga gtg tac tac     336
Thr Leu Lys Ile Ser Arg Val Glu Ala Glu Asp Val Gly Val Tyr Tyr
            100                 105                 110 tgt atg cag ggc acc cac tgg cct ctt acc ttc ggc gga ggc acc aag     384
Cys Met Gln Gly Thr His Trp Pro Leu Thr Phe Gly Gly Gly Thr Lys
        115                 120                 125 gtg gag atc aag cgt acg gtg gcc gcc ccc tcc gtg ttc atc ttc ccc     432
Val Glu Ile Lys Arg Thr Val Ala Ala Pro Ser Val Phe Ile Phe Pro
    130                 135                 140 ccc tcc gac gag cag ctg aag tcc ggc acc gcc tcc gtg gtg tgc ctg     480
Pro Ser Asp Glu Gln Leu Lys Ser Gly Thr Ala Ser Val Val Cys Leu
145                 150                 155                 160 ctg aat aac ttc tac ccc aga gag gcc aag gtg cag tgg aag gtg gac     528
Leu Asn Asn Phe Tyr Pro Arg Glu Ala Lys Val Gln Trp Lys Val Asp
                165                 170                 175 aac gcc ctg cag tcc ggg aac tcc cag gag agc gtg acc gag cag gac     576
Asn Ala Leu Gln Ser Gly Asn Ser Gln Glu Ser Val Thr Glu Gln Asp
            180                 185                 190 agc aag gac agc acc tac agc ctg agc agc acc ctg acc ctg agc aaa     624
Ser Lys Asp Ser Thr Tyr Ser Leu Ser Ser Thr Leu Thr Leu Ser Lys
        195                 200                 205 gcc gac tac gag aag cac aag gtg tac gcc tgc gag gtg acc cac cag     672
Ala Asp Tyr Glu Lys His Lys Val Tyr Ala Cys Glu Val Thr His Gln
    210                 215                 220 ggc ctg agc tcc ccc gtc acc aag agc ttc aac agg ggg gag tgt         717
Gly Leu Ser Ser Pro Val Thr Lys Ser Phe Asn Arg Gly Glu Cys
225                 230                 235
```

<210> SEQ ID NO 52
<211> LENGTH: 239
<212> TYPE: PRT
<213> ORGANISM: Artificial Sequence
<220> FEATURE:
<223> OTHER INFORMATION: Synthetic Construct

<400> SEQUENCE: 52

```
Met Val Leu Gln Thr Gln Val Phe Ile Ser Leu Leu Leu Trp Ile Ser
1               5                   10                  15
```

Gly Ala Tyr Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val Tyr Ser Asp Gly Asn Thr Tyr Leu Asn Trp Phe Gln Gln Arg
 50                  55                  60

Pro Gly Gln Ser Pro Arg Arg Leu Ile Tyr Lys Val Ser Asn Arg Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Gly Thr His Trp Pro Leu Thr Phe Gly Gly Gly Thr Lys
        115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 53
<211> LENGTH: 1413
<212> TYPE: DNA
<213> ORGANISM: Artificial Sequence
<220> FEATURE:
<223> OTHER INFORMATION: Nucleotide coding heavy chain of mouse IgG2b
      type chimeric 1B011

<400> SEQUENCE: 53
atggccgtgc tgggccttct gttctgtctt gtgaccttcc cttcctgtgt gctgagcgag    60
gagcaagtgg tggagagcgg cggcggattc gtgcagcctg gcggctccct gcggctttcc    120
tgtgccgctt ccggattcac cttcagccct tactggatgc actgggtgag acaagcccct    180
ggcaagggcc tggtgtgggt gtcccggatc aacagcgacg gatccaccta ctacgctgac    240
agcgtgaagg gccggttcac catctccaga gacaacgccc ggaacaccct ttacctgcag    300
atgaacagcc ttagagctga ggacaccgcc gtgtactact gtgctcggga cagatactac    360
ggccctgaga tgtggggaca aggcaccatg gtgaccgtga gctcagccaa gaccacccct    420
cctagcgtgt accctctggc tcctggctgt ggcgacacca ccggctccag cgtgaccctt    480
ggctgtctgg tgaagggcta cttccctgag tccgtaccg tgacctggaa cagcggctcc    540
cttagctcca gcgtgcacac cttccctgcc ctgcttcagt ccggcctgta caccatgagc    600
tccagcgtga ccgtgccttc cagcacctgg ccttcccaga ccgtgacctg tagcgtggct    660
caccctgcct ccagcaccac cgtggacaag aagcttgagc cttccggccc tatcagcacc    720
atcaaccctt gtcctccttg taaggagtgt cacaagtgtc ctgctcctaa cctggagggc    780

```
ggcccttccg tgttcatctt ccctcctaac atcaaggacg tgcttatgat cagcctgacc    840
cctaaggtga cctgtgtggt ggtggacgtg tccgaggacc ccctgacgt gcagatcagc    900 tggttcgtga caacgtgga ggtgcacacc gcccagaccc agaccaccg ggaggactac    960 aactccacca tcagagtggt gagcacccttcctatccagc accaggactg gatgtccggc    1020
aaggagttca gtgtaaggt gaacaacaag gacctgccta gccctatcga gcggaccatc    1080
tccaagatca agggccttgt gcgggctcct caggtgtaca tcctgcctcc tcctgccgag    1140
cagctttcca gaaaggacgt gtccctgacc tgtcttgtgg tgggcttcaa ccctggcgac    1200
atcagcgtgg agtggacctc caacggccac accgaggaga actacaagga caccgctcct    1260
gtgctggaca gcgacggctc ctacttcatc tacagcaagc ttaacatgaa gacctccaag    1320
tgggagaaga ccgacagctt ctcctgtaac gtgcggcacg agggcctgaa gaactactac    1380
cttaagaaga ccatcagcag atcccctggc aag                                1413

<210> SEQ ID NO 54
<211> LENGTH: 1395
<212> TYPE: DNA
<213> ORGANISM: Artificial Sequence
<220> FEATURE:
<223> OTHER INFORMATION: Nucleotide coding heavy chain of human IgG1
      type 1B011
<220> FEATURE:
<221> NAME/KEY: CDS
<222> LOCATION: (1)..(1395)

<400> SEQUENCE: 54 atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15 gtg ctg agc gag gag caa gtg gtg gag agc ggc ggc gga ttc gtg cag    96
Val Leu Ser Glu Glu Gln Val Val Glu Ser Gly Gly Gly Phe Val Gln
            20                  25                  30 cct ggc ggc tcc ctg cgg ctt tcc tgt gcc gct tcc gga ttc acc ttc    144
Pro Gly Gly Ser Leu Arg Leu Ser Cys Ala Ala Ser Gly Phe Thr Phe
        35                  40                  45 agc cct tac tgg atg cac tgg gtg aga caa gcc cct ggc aag ggc ctg    192
Ser Pro Tyr Trp Met His Trp Val Arg Gln Ala Pro Gly Lys Gly Leu
    50                  55                  60 gtg tgg gtg tcc cgg atc aac agc gac gga tcc acc tac tac gct gac    240
Val Trp Val Ser Arg Ile Asn Ser Asp Gly Ser Thr Tyr Tyr Ala Asp
65                  70                  75                  80 agc gtg aag ggc cgg ttc acc atc tcc aga gac aac gcc cgg aac acc    288
Ser Val Lys Gly Arg Phe Thr Ile Ser Arg Asp Asn Ala Arg Asn Thr
                85                  90                  95 ctt tac ctg cag atg aac agc ctt aga gct gag gac acc gcc gtg tac    336
Leu Tyr Leu Gln Met Asn Ser Leu Arg Ala Glu Asp Thr Ala Val Tyr
            100                 105                 110 tac tgt gct cgg gac aga tac tac ggc cct gag atg tgg gga caa ggc    384
Tyr Cys Ala Arg Asp Arg Tyr Tyr Gly Pro Glu Met Trp Gly Gln Gly
        115                 120                 125 acc atg gtg acc gtg agc tca gcc tcc acc aag ggc cca agc gtc ttc    432
Thr Met Val Thr Val Ser Ser Ala Ser Thr Lys Gly Pro Ser Val Phe
    130                 135                 140 ccc ctg gca ccc tcc tcc aag agc acc tct ggc ggc aca gcc gcc ctg    480
Pro Leu Ala Pro Ser Ser Lys Ser Thr Ser Gly Gly Thr Ala Ala Leu
145                 150                 155                 160 ggc tgc ctg gtc aag gac tac ttc ccc gaa ccc gtg acc gtg agc tgg    528
Gly Cys Leu Val Lys Asp Tyr Phe Pro Glu Pro Val Thr Val Ser Trp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 165 |     |     |     |     | 170 |     |     |     |     | 175 |     |     |      |
| aac | tca | ggc | gcc | ctg | acc | agc | ggc | gtg | cac | acc | ttc | ccc | gct | gtc | ctg | 576  |
| Asn | Ser | Gly | Ala | Leu | Thr | Ser | Gly | Val | His | Thr | Phe | Pro | Ala | Val | Leu |      |
|     |     |     | 180 |     |     |     |     | 185 |     |     |     |     | 190 |     |     |      |
| cag | tcc | tca | gga | ctc | tac | tcc | ctc | agc | agc | gtg | gtg | acc | gtg | ccc | tcc | 624  |
| Gln | Ser | Ser | Gly | Leu | Tyr | Ser | Leu | Ser | Ser | Val | Val | Thr | Val | Pro | Ser |      |
|     |     | 195 |     |     |     |     | 200 |     |     |     |     | 205 |     |     |     |      |
| agc | agc | ttg | ggc | acc | cag | acc | tac | atc | tgc | aac | gtg | aat | cac | aag | ccc | 672  |
| Ser | Ser | Leu | Gly | Thr | Gln | Thr | Tyr | Ile | Cys | Asn | Val | Asn | His | Lys | Pro |      |
|     | 210 |     |     |     |     | 215 |     |     |     |     | 220 |     |     |     |     |      |
| agc | aac | acc | aag | gtg | gac | aag | aga | gtt | gag | ccc | aaa | tct | tgt | gac | aaa | 720  |
| Ser | Asn | Thr | Lys | Val | Asp | Lys | Arg | Val | Glu | Pro | Lys | Ser | Cys | Asp | Lys |      |
| 225 |     |     |     |     | 230 |     |     |     |     | 235 |     |     |     |     | 240 |      |
| act | cac | aca | tgc | cca | ccc | tgc | cca | gca | cct | gaa | ctc | ctg | ggg | gga | ccc | 768  |
| Thr | His | Thr | Cys | Pro | Pro | Cys | Pro | Ala | Pro | Glu | Leu | Leu | Gly | Gly | Pro |      |
|     |     |     |     | 245 |     |     |     |     | 250 |     |     |     |     | 255 |     |      |
| tca | gtc | ttc | ctc | ttc | ccc | cca | aaa | ccc | aag | gac | acc | ctc | atg | atc | tcc | 816  |
| Ser | Val | Phe | Leu | Phe | Pro | Pro | Lys | Pro | Lys | Asp | Thr | Leu | Met | Ile | Ser |      |
|     |     |     | 260 |     |     |     |     | 265 |     |     |     |     | 270 |     |     |      |
| cgg | acc | cct | gag | gtc | aca | tgc | gtg | gtg | gtg | gac | gtg | agc | cac | gaa | gac | 864  |
| Arg | Thr | Pro | Glu | Val | Thr | Cys | Val | Val | Val | Asp | Val | Ser | His | Glu | Asp |      |
|     |     | 275 |     |     |     |     | 280 |     |     |     |     | 285 |     |     |     |      |
| cct | gag | gtc | aag | ttc | aac | tgg | tac | gtg | gac | ggc | gtg | gag | gtg | cat | aat | 912  |
| Pro | Glu | Val | Lys | Phe | Asn | Trp | Tyr | Val | Asp | Gly | Val | Glu | Val | His | Asn |      |
|     | 290 |     |     |     |     | 295 |     |     |     |     | 300 |     |     |     |     |      |
| gcc | aag | aca | aag | ccc | cgg | gag | gag | cag | tac | aac | agc | acg | tac | cgg | gtg | 960  |
| Ala | Lys | Thr | Lys | Pro | Arg | Glu | Glu | Gln | Tyr | Asn | Ser | Thr | Tyr | Arg | Val |      |
| 305 |     |     |     |     | 310 |     |     |     |     | 315 |     |     |     |     | 320 |      |
| gtc | agc | gtc | ctc | acc | gtc | ctg | cac | cag | gac | tgg | ctg | aat | ggc | aag | gag | 1008 |
| Val | Ser | Val | Leu | Thr | Val | Leu | His | Gln | Asp | Trp | Leu | Asn | Gly | Lys | Glu |      |
|     |     |     |     | 325 |     |     |     |     | 330 |     |     |     |     | 335 |     |      |
| tac | aag | tgc | aag | gtc | tcc | aac | aaa | gcc | ctc | cca | gcc | ccc | atc | gag | aaa | 1056 |
| Tyr | Lys | Cys | Lys | Val | Ser | Asn | Lys | Ala | Leu | Pro | Ala | Pro | Ile | Glu | Lys |      |
|     |     |     | 340 |     |     |     |     | 345 |     |     |     |     | 350 |     |     |      |
| acc | atc | tcc | aaa | gcc | aaa | ggc | cag | ccc | cgg | gaa | cca | cag | gtg | tac | acc | 1104 |
| Thr | Ile | Ser | Lys | Ala | Lys | Gly | Gln | Pro | Arg | Glu | Pro | Gln | Val | Tyr | Thr |      |
|     |     | 355 |     |     |     |     | 360 |     |     |     |     | 365 |     |     |     |      |
| ctg | ccc | cca | tcc | cgg | gag | gag | atg | acc | aag | aac | cag | gtc | agc | ctg | acc | 1152 |
| Leu | Pro | Pro | Ser | Arg | Glu | Glu | Met | Thr | Lys | Asn | Gln | Val | Ser | Leu | Thr |      |
|     | 370 |     |     |     |     | 375 |     |     |     |     | 380 |     |     |     |     |      |
| tgc | ctg | gtc | aaa | ggc | ttc | tat | ccc | agc | gac | atc | gcc | gtg | gag | tgg | gag | 1200 |
| Cys | Leu | Val | Lys | Gly | Phe | Tyr | Pro | Ser | Asp | Ile | Ala | Val | Glu | Trp | Glu |      |
| 385 |     |     |     |     | 390 |     |     |     |     | 395 |     |     |     |     | 400 |      |
| agc | aat | ggc | cag | ccc | gag | aac | aac | tac | aag | acc | acc | cct | ccc | gtg | ctg | 1248 |
| Ser | Asn | Gly | Gln | Pro | Glu | Asn | Asn | Tyr | Lys | Thr | Thr | Pro | Pro | Val | Leu |      |
|     |     |     |     | 405 |     |     |     |     | 410 |     |     |     |     | 415 |     |      |
| gac | tcc | gac | ggc | tcc | ttc | ttc | ctc | tac | agc | aag | ctc | acc | gtg | gac | aag | 1296 |
| Asp | Ser | Asp | Gly | Ser | Phe | Phe | Leu | Tyr | Ser | Lys | Leu | Thr | Val | Asp | Lys |      |
|     |     |     | 420 |     |     |     |     | 425 |     |     |     |     | 430 |     |     |      |
| agc | agg | tgg | cag | cag | ggc | aac | gtc | ttc | tca | tgc | tcc | gtg | atg | cat | gag | 1344 |
| Ser | Arg | Trp | Gln | Gln | Gly | Asn | Val | Phe | Ser | Cys | Ser | Val | Met | His | Glu |      |
|     |     | 435 |     |     |     |     | 440 |     |     |     |     | 445 |     |     |     |      |
| gct | ctg | cac | aac | cac | tac | acc | cag | aag | agc | ctc | tcc | ctg | tct | ccc | ggc | 1392 |
| Ala | Leu | His | Asn | His | Tyr | Thr | Gln | Lys | Ser | Leu | Ser | Leu | Ser | Pro | Gly |      |
|     | 450 |     |     |     |     | 455 |     |     |     |     | 460 |     |     |     |     |      |
| aaa |     |     |     |     |     |     |     |     |     |     |     |     |     |     |     | 1395 |
| Lys |     |     |     |     |     |     |     |     |     |     |     |     |     |     |     |      |
| 465 |     |     |     |     |     |     |     |     |     |     |     |     |     |     |     |      |

```
<210> SEQ ID NO 55
<211> LENGTH: 465
<212> TYPE: PRT
<213> ORGANISM: Artificial Sequence
<220> FEATURE:
<223> OTHER INFORMATION: Synthetic Construct

<400> SEQUENCE: 55

Met Lys His Leu Trp Phe Phe Leu Leu Leu Val Ala Ala Pro Arg Trp
1               5                   10                  15

Val Leu Ser Glu Glu Gln Val Val Ser Gly Gly Gly Phe Val Gln
            20                  25                  30

Pro Gly Gly Ser Leu Arg Leu Ser Cys Ala Ala Ser Gly Phe Thr Phe
        35                  40                  45

Ser Pro Tyr Trp Met His Trp Val Arg Gln Ala Pro Gly Lys Gly Leu
    50                  55                  60

Val Trp Val Ser Arg Ile Asn Ser Asp Gly Ser Thr Tyr Tyr Ala Asp
65                  70                  75                  80

Ser Val Lys Gly Arg Phe Thr Ile Ser Arg Asp Asn Ala Arg Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Arg Tyr Tyr Gly Pro Glu Met Trp Gly Gln Gly
        115                 120                 125

Thr Met Val Thr Val Ser Ser Ala Ser Thr Lys Gly Pro Ser Val Phe
130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
```

```
                     370                 375                 380
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 56
<211> LENGTH: 1422
<212> TYPE: DNA
<213> ORGANISM: Artificial Sequence
<220> FEATURE:
<223> OTHER INFORMATION: Nucleotide coding of h#1G5-H1
<220> FEATURE:
<221> NAME/KEY: CDS
<222> LOCATION: (1)..(1422)

<400> SEQUENCE: 56 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
            20                  25                  30 cca ggc gcc agc gtg aag gtg tcc tgc aag gcc agc ggc tac acc ttt     144
Pro Gly Ala Ser Val Lys Val Ser Cys Lys Ala Ser Gly Tyr Thr Phe
        35                  40                  45 acc agc tac tgg atc aac tgg gtg cgc cag gcc cct gga cag ggc ctg     192
Thr Ser Tyr Trp Ile Asn Trp Val Arg Gln Ala Pro Gly Gln Gly Leu
    50                  55                  60 gaa tgg atg ggc aac atc tac ccc ggc agc agc agc atc aac tac aac     240
Glu Trp Met Gly Asn Ile Tyr Pro Gly Ser Ser Ser Ile Asn Tyr Asn
65                  70                  75                  80 gag aag ttc aag agc cgc gtg acc atc acc gcc gac acc agc aca agc     288
Glu Lys Phe Lys Ser Arg Val Thr Ile Thr Ala Asp Thr Ser Thr Ser
                85                  90                  95 acc gcc tac atg gaa ctg agc agc ctg cgg agc gag gac acc gcc gtg     336
Thr Ala Tyr Met Glu Leu Ser Ser Leu Arg Ser Glu Asp Thr Ala Val
            100                 105                 110 tac tac tgc gcc cgg acc atc tac aac tac ggc agc tcc ggc tac aat     384
Tyr Tyr Cys Ala Arg Thr Ile Tyr Asn Tyr Gly Ser Ser Gly Tyr Asn
        115                 120                 125 tac gcc atg gac tac tgg ggc cag ggc acc ctc gtg acc gtg agc tca     432
Tyr Ala Met Asp Tyr Trp Gly Gln Gly Thr Leu Val Thr Val Ser Ser
    130                 135                 140 gcc tcc acc aag ggc cca agc gtc ttc ccc ctg gca ccc tcc tcc aag     480
Ala Ser Thr Lys Gly Pro Ser Val Phe Pro Leu Ala Pro Ser Ser Lys
145                 150                 155                 160 agc acc tct ggc ggc aca gcc gcc ctg ggc tgc ctg gtc aag gac tac     528
Ser Thr Ser Gly Gly Thr Ala Ala Leu Gly Cys Leu Val Lys Asp Tyr
                165                 170                 175 ttc ccc gaa ccc gtg acc gtg agc tgg aac tca ggc gcc ctg acc agc     576
Phe Pro Glu Pro Val Thr Val Ser Trp Asn Ser Gly Ala Leu Thr Ser
```

|   |   |   |   |   |   |   |   |   |   |   |   |   |   |   |   |   |
|---|---|---|---|---|---|---|---|---|---|---|---|---|---|---|---|---|
|   |   |   | 180 |   |   |   |   | 185 |   |   |   |   | 190 |   |   |   |
| ggc | gtg | cac | acc | ttc | ccc | gct | gtc | ctg | cag | tcc | tca | gga | ctc | tac | tcc | 624 |
| Gly | Val | His | Thr | Phe | Pro | Ala | Val | Leu | Gln | Ser | Ser | Gly | Leu | Tyr | Ser |   |
|   |   | 195 |   |   |   |   | 200 |   |   |   |   | 205 |   |   |   |   |
| ctc | agc | agc | gtg | gtg | acc | gtg | ccc | tcc | agc | agc | ttg | ggc | acc | cag | acc | 672 |
| Leu | Ser | Ser | Val | Val | Thr | Val | Pro | Ser | Ser | Ser | Leu | Gly | Thr | Gln | Thr |   |
|   | 210 |   |   |   |   | 215 |   |   |   |   | 220 |   |   |   |   |   |
| tac | atc | tgc | aac | gtg | aat | cac | aag | ccc | agc | aac | acc | aag | gtg | gac | aag | 720 |
| Tyr | Ile | Cys | Asn | Val | Asn | His | Lys | Pro | Ser | Asn | Thr | Lys | Val | Asp | Lys |   |
| 225 |   |   |   |   | 230 |   |   |   |   | 235 |   |   |   |   | 240 |   |
| aga | gtt | gag | ccc | aaa | tct | tgt | gac | aaa | act | cac | aca | tgc | cca | ccc | tgc | 768 |
| Arg | Val | Glu | Pro | Lys | Ser | Cys | Asp | Lys | Thr | His | Thr | Cys | Pro | Pro | Cys |   |
|   |   |   |   | 245 |   |   |   |   | 250 |   |   |   |   | 255 |   |   |
| cca | gca | cct | gaa | ctc | ctg | ggg | gga | ccc | tca | gtc | ttc | ctc | ttc | ccc | cca | 816 |
| Pro | Ala | Pro | Glu | Leu | Leu | Gly | Gly | Pro | Ser | Val | Phe | Leu | Phe | Pro | Pro |   |
|   |   | 260 |   |   |   |   | 265 |   |   |   |   | 270 |   |   |   |   |
| aaa | ccc | aag | gac | acc | ctc | atg | atc | tcc | cgg | acc | cct | gag | gtc | aca | tgc | 864 |
| Lys | Pro | Lys | Asp | Thr | Leu | Met | Ile | Ser | Arg | Thr | Pro | Glu | Val | Thr | Cys |   |
|   | 275 |   |   |   |   | 280 |   |   |   |   | 285 |   |   |   |   |   |
| gtg | gtg | gtg | gac | gtg | agc | cac | gaa | gac | cct | gag | gtc | aag | ttc | aac | tgg | 912 |
| Val | Val | Val | Asp | Val | Ser | His | Glu | Asp | Pro | Glu | Val | Lys | Phe | Asn | Trp |   |
| 290 |   |   |   |   | 295 |   |   |   |   | 300 |   |   |   |   |   |   |
| tac | gtg | gac | ggc | gtg | gag | gtg | cat | aat | gcc | aag | aca | aag | ccc | cgg | gag | 960 |
| Tyr | Val | Asp | Gly | Val | Glu | Val | His | Asn | Ala | Lys | Thr | Lys | Pro | Arg | Glu |   |
| 305 |   |   |   |   | 310 |   |   |   |   | 315 |   |   |   |   | 320 |   |
| gag | cag | tac | aac | agc | acg | tac | cgg | gtg | gtc | agc | gtc | ctc | acc | gtc | ctg | 1008 |
| Glu | Gln | Tyr | Asn | Ser | Thr | Tyr | Arg | Val | Val | Ser | Val | Leu | Thr | Val | Leu |   |
|   |   |   | 325 |   |   |   |   | 330 |   |   |   |   | 335 |   |   |   |
| cac | cag | gac | tgg | ctg | aat | ggc | aag | gag | tac | aag | tgc | aag | gtc | tcc | aac | 1056 |
| His | Gln | Asp | Trp | Leu | Asn | Gly | Lys | Glu | Tyr | Lys | Cys | Lys | Val | Ser | Asn |   |
|   |   | 340 |   |   |   |   | 345 |   |   |   |   | 350 |   |   |   |   |
| aaa | gcc | ctc | cca | gcc | ccc | atc | gag | aaa | acc | atc | tcc | aaa | gcc | aaa | ggc | 1104 |
| Lys | Ala | Leu | Pro | Ala | Pro | Ile | Glu | Lys | Thr | Ile | Ser | Lys | Ala | Lys | Gly |   |
|   | 355 |   |   |   |   | 360 |   |   |   |   | 365 |   |   |   |   |   |
| cag | ccc | cgg | gaa | cca | cag | gtg | tac | acc | ctg | ccc | cca | tcc | cgg | gag | gag | 1152 |
| Gln | Pro | Arg | Glu | Pro | Gln | Val | Tyr | Thr | Leu | Pro | Pro | Ser | Arg | Glu | Glu |   |
| 370 |   |   |   |   | 375 |   |   |   |   | 380 |   |   |   |   |   |   |
| atg | acc | aag | aac | cag | gtc | agc | ctg | acc | tgc | ctg | gtc | aaa | ggc | ttc | tat | 1200 |
| Met | Thr | Lys | Asn | Gln | Val | Ser | Leu | Thr | Cys | Leu | Val | Lys | Gly | Phe | Tyr |   |
| 385 |   |   |   |   | 390 |   |   |   |   | 395 |   |   |   |   | 400 |   |
| ccc | agc | gac | atc | gcc | gtg | gag | tgg | gag | agc | aat | ggc | cag | ccc | gag | aac | 1248 |
| Pro | Ser | Asp | Ile | Ala | Val | Glu | Trp | Glu | Ser | Asn | Gly | Gln | Pro | Glu | Asn |   |
|   |   |   |   | 405 |   |   |   |   | 410 |   |   |   |   | 415 |   |   |
| aac | tac | aag | acc | acc | cct | ccc | gtg | ctg | gac | tcc | gac | ggc | tcc | ttc | ttc | 1296 |
| Asn | Tyr | Lys | Thr | Thr | Pro | Pro | Val | Leu | Asp | Ser | Asp | Gly | Ser | Phe | Phe |   |
|   |   | 420 |   |   |   |   | 425 |   |   |   |   | 430 |   |   |   |   |
| ctc | tac | agc | aag | ctc | acc | gtg | gac | aag | agc | agg | tgg | cag | cag | ggc | aac | 1344 |
| Leu | Tyr | Ser | Lys | Leu | Thr | Val | Asp | Lys | Ser | Arg | Trp | Gln | Gln | Gly | Asn |   |
|   | 435 |   |   |   |   | 440 |   |   |   |   | 445 |   |   |   |   |   |
| gtc | ttc | tca | tgc | tcc | gtg | atg | cat | gag | gct | ctg | cac | aac | cac | tac | acc | 1392 |
| Val | Phe | Ser | Cys | Ser | Val | Met | His | Glu | Ala | Leu | His | Asn | His | Tyr | Thr |   |
| 450 |   |   |   |   | 455 |   |   |   |   | 460 |   |   |   |   |   |   |
| cag | aag | agc | ctc | tcc | ctg | tct | ccc | ggc | aaa |   |   |   |   |   |   | 1422 |
| Gln | Lys | Ser | Leu | Ser | Leu | Ser | Pro | Gly | Lys |   |   |   |   |   |   |   |
| 465 |   |   |   | 470 |   |   |   |   |   |   |   |   |   |   |   |   |

<210> SEQ ID NO 57
<211> LENGTH: 474
<212> TYPE: PRT
<213> ORGANISM: Artificial Sequence
<220> FEATURE:
<223> OTHER INFORMATION: Synthetic Construct

<400> SEQUENCE: 57

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Ile Asn Trp Val Arg Gln Ala Pro Gly Gln Gly Leu
    50                  55                  60

Glu Trp Met Gly Asn Ile Tyr Pro Gly Ser Ser Ile Asn Tyr Asn
65                  70                  75                  80

Glu Lys Phe Lys Ser Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Thr Ile Tyr Asn Tyr Gly Ser Ser Gly Tyr Asn
        115                 120                 125

Tyr Ala Met Asp Tyr Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400
```

```
Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
            450                 455                 460

Gln Lys Ser Leu Ser Leu Ser Pro Gly Lys
465                 470

<210> SEQ ID NO 58
<211> LENGTH: 1422
<212> TYPE: DNA
<213> ORGANISM: Artificial Sequence
<220> FEATURE:
<223> OTHER INFORMATION: Nucleotide coding of h#1G5-H2
<220> FEATURE:
<221> NAME/KEY: CDS
<222> LOCATION: (1)..(1422)

<400> SEQUENCE: 58 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa      96
Val Leu Ser Gln Val Gln Leu Val Gln Ser Gly Ala Glu Val Lys Lys
                20                  25                  30 cca ggc gcc agc gtg aag gtg tcc tgc aag gcc agc ggc tac acc ttt     144
Pro Gly Ala Ser Val Lys Val Ser Cys Lys Ala Ser Gly Tyr Thr Phe
            35                  40                  45 acc agc tac tgg atc aac tgg gtg cgc cag gcc cct gga cag ggc ctg     192
Thr Ser Tyr Trp Ile Asn Trp Val Arg Gln Ala Pro Gly Gln Gly Leu
        50                  55                  60 gaa tgg atg ggc aac atc tac ccc ggc agc agc agc atc aac tac aac     240
Glu Trp Met Gly Asn Ile Tyr Pro Gly Ser Ser Ser Ile Asn Tyr Asn
65                  70                  75                  80 gag aag ttc aag agc cgc gtg acc ctg acc gtg gac acc agc aca agc     288
Glu Lys Phe Lys Ser Arg Val Thr Leu Thr Val Asp Thr Ser Thr Ser
                85                  90                  95 acc gcc tac atg gaa ctg agc agc ctg cgg agc gag gac acc gcc gtg     336
Thr Ala Tyr Met Glu Leu Ser Ser Leu Arg Ser Glu Asp Thr Ala Val
            100                 105                 110 tac tac tgc agc cgg acc atc tac aac tac ggc agc tcc ggc tac aat     384
Tyr Tyr Cys Ser Arg Thr Ile Tyr Asn Tyr Gly Ser Ser Gly Tyr Asn
        115                 120                 125 tac gcc atg gac tac tgg ggc cag ggc acc ctc gtg acc gtg agc tca     432
Tyr Ala Met Asp Tyr Trp Gly Gln Gly Thr Leu Val Thr Val Ser Ser
    130                 135                 140 gcc tcc acc aag ggc cca agc gtc ttc ccc ctg gca ccc tcc tcc aag     480
Ala Ser Thr Lys Gly Pro Ser Val Phe Pro Leu Ala Pro Ser Ser Lys
145                 150                 155                 160 agc acc tct ggc ggc aca gcc gcc ctg ggc tgc ctg gtc aag gac tac     528
Ser Thr Ser Gly Gly Thr Ala Ala Leu Gly Cys Leu Val Lys Asp Tyr
                165                 170                 175 ttc ccc gaa ccc gtg acc gtg agc tgg aac tca ggc gcc ctg acc agc     576
Phe Pro Glu Pro Val Thr Val Ser Trp Asn Ser Gly Ala Leu Thr Ser
            180                 185                 190 ggc gtg cac acc ttc ccc gct gtc ctg cag tcc tca gga ctc tac tcc     624
Gly Val His Thr Phe Pro Ala Val Leu Gln Ser Ser Gly Leu Tyr Ser
```

|  |  |  |  |  |  |  |  |  |  |  |  |  |  |  |  |
|---|---|---|---|---|---|---|---|---|---|---|---|---|---|---|---|
| | | | 195 | | | | 200 | | | | 205 | | | | |
| ctc | agc | agc | gtg | gtg | acc | gtg | ccc | tcc | agc | agc | ttg | ggc | acc | cag | acc | 672 |
| Leu | Ser | Ser | Val | Val | Thr | Val | Pro | Ser | Ser | Ser | Leu | Gly | Thr | Gln | Thr |
| | | 210 | | | | | 215 | | | | | 220 | | | |
| tac | atc | tgc | aac | gtg | aat | cac | aag | ccc | agc | aac | acc | aag | gtg | gac | aag | 720 |
| Tyr | Ile | Cys | Asn | Val | Asn | His | Lys | Pro | Ser | Asn | Thr | Lys | Val | Asp | Lys |
| 225 | | | | | 230 | | | | | 235 | | | | | 240 |
| aga | gtt | gag | ccc | aaa | tct | tgt | gac | aaa | act | cac | aca | tgc | cca | ccc | tgc | 768 |
| Arg | Val | Glu | Pro | Lys | Ser | Cys | Asp | Lys | Thr | His | Thr | Cys | Pro | Pro | Cys |
| | | | | 245 | | | | | 250 | | | | | 255 | |
| cca | gca | cct | gaa | ctc | ctg | ggg | gga | ccc | tca | gtc | ttc | ctc | ttc | ccc | cca | 816 |
| Pro | Ala | Pro | Glu | Leu | Leu | Gly | Gly | Pro | Ser | Val | Phe | Leu | Phe | Pro | Pro |
| | | 260 | | | | | 265 | | | | | 270 | | | |
| aaa | ccc | aag | gac | acc | ctc | atg | atc | tcc | cgg | acc | cct | gag | gtc | aca | tgc | 864 |
| Lys | Pro | Lys | Asp | Thr | Leu | Met | Ile | Ser | Arg | Thr | Pro | Glu | Val | Thr | Cys |
| | | | | 275 | | | | | 280 | | | | | 285 | |
| gtg | gtg | gtg | gac | gtg | agc | cac | gaa | gac | cct | gag | gtc | aag | ttc | aac | tgg | 912 |
| Val | Val | Val | Asp | Val | Ser | His | Glu | Asp | Pro | Glu | Val | Lys | Phe | Asn | Trp |
| | | 290 | | | | | 295 | | | | | 300 | | | |
| tac | gtg | gac | ggc | gtg | gag | gtg | cat | aat | gcc | aag | aca | aag | ccc | cgg | gag | 960 |
| Tyr | Val | Asp | Gly | Val | Glu | Val | His | Asn | Ala | Lys | Thr | Lys | Pro | Arg | Glu |
| 305 | | | | | 310 | | | | | 315 | | | | | 320 |
| gag | cag | tac | aac | agc | acg | tac | cgg | gtg | gtc | agc | gtc | ctc | acc | gtc | ctg | 1008 |
| Glu | Gln | Tyr | Asn | Ser | Thr | Tyr | Arg | Val | Val | Ser | Val | Leu | Thr | Val | Leu |
| | | | | 325 | | | | | 330 | | | | | 335 | |
| cac | cag | gac | tgg | ctg | aat | ggc | aag | gag | tac | aag | tgc | aag | gtc | tcc | aac | 1056 |
| His | Gln | Asp | Trp | Leu | Asn | Gly | Lys | Glu | Tyr | Lys | Cys | Lys | Val | Ser | Asn |
| | | | 340 | | | | | 345 | | | | | 350 | | |
| aaa | gcc | ctc | cca | gcc | ccc | atc | gag | aaa | acc | atc | tcc | aaa | gcc | aaa | ggc | 1104 |
| Lys | Ala | Leu | Pro | Ala | Pro | Ile | Glu | Lys | Thr | Ile | Ser | Lys | Ala | Lys | Gly |
| | | 355 | | | | | 360 | | | | | 365 | | | |
| cag | ccc | cgg | gaa | cca | cag | gtg | tac | acc | ctg | ccc | cca | tcc | cgg | gag | gag | 1152 |
| Gln | Pro | Arg | Glu | Pro | Gln | Val | Tyr | Thr | Leu | Pro | Pro | Ser | Arg | Glu | Glu |
| 370 | | | | | 375 | | | | | 380 | | | | | |
| atg | acc | aag | aac | cag | gtc | agc | ctg | acc | tgc | ctg | gtc | aaa | ggc | ttc | tat | 1200 |
| Met | Thr | Lys | Asn | Gln | Val | Ser | Leu | Thr | Cys | Leu | Val | Lys | Gly | Phe | Tyr |
| 385 | | | | | 390 | | | | | 395 | | | | | 400 |
| ccc | agc | gac | atc | gcc | gtg | gag | tgg | gag | agc | aat | ggc | cag | ccc | gag | aac | 1248 |
| Pro | Ser | Asp | Ile | Ala | Val | Glu | Trp | Glu | Ser | Asn | Gly | Gln | Pro | Glu | Asn |
| | | | | 405 | | | | | 410 | | | | | 415 | |
| aac | tac | aag | acc | acc | cct | ccc | gtg | ctg | gac | tcc | gac | ggc | tcc | ttc | ttc | 1296 |
| Asn | Tyr | Lys | Thr | Thr | Pro | Pro | Val | Leu | Asp | Ser | Asp | Gly | Ser | Phe | Phe |
| | | | 420 | | | | | 425 | | | | | 430 | | |
| ctc | tac | agc | aag | ctc | acc | gtg | gac | aag | agc | agg | tgg | cag | cag | ggc | aac | 1344 |
| Leu | Tyr | Ser | Lys | Leu | Thr | Val | Asp | Lys | Ser | Arg | Trp | Gln | Gln | Gly | Asn |
| | | 435 | | | | | 440 | | | | | 445 | | | |
| gtc | ttc | tca | tgc | tcc | gtg | atg | cat | gag | gct | ctg | cac | aac | cac | tac | acc | 1392 |
| Val | Phe | Ser | Cys | Ser | Val | Met | His | Glu | Ala | Leu | His | Asn | His | Tyr | Thr |
| 450 | | | | | 455 | | | | | 460 | | | | | |
| cag | aag | agc | ctc | tcc | ctg | tct | ccc | ggc | aaa | | | | | | | 1422 |
| Gln | Lys | Ser | Leu | Ser | Leu | Ser | Pro | Gly | Lys |
| 465 | | | | | 470 | | | | | |

<210> SEQ ID NO 59
<211> LENGTH: 474
<212> TYPE: PRT
<213> ORGANISM: Artificial Sequence
<220> FEATURE:
<223> OTHER INFORMATION: Synthetic Construct

<400> SEQUENCE: 59

```
Met Lys His Leu Trp Phe Phe Leu Leu Leu Val Ala Ala Pro Arg Trp
1               5                   10                  15
Val Leu Ser Gln Val Gln Leu Val Gln Ser Gly Ala Glu Val Lys Lys
            20                  25                  30
Pro Gly Ala Ser Val Lys Val Ser Cys Lys Ala Ser Gly Tyr Thr Phe
        35                  40                  45
Thr Ser Tyr Trp Ile Asn Trp Val Arg Gln Ala Pro Gly Gln Gly Leu
    50                  55                  60
Glu Trp Met Gly Asn Ile Tyr Pro Gly Ser Ser Ile Asn Tyr Asn
65              70                  75                  80
Glu Lys Phe Lys Ser Arg Val Thr Leu Thr Val Asp Thr Ser Thr Ser
                85                  90                  95
Thr Ala Tyr Met Glu Leu Ser Ser Leu Arg Ser Glu Asp Thr Ala Val
            100                 105                 110
Tyr Tyr Cys Ser Arg Thr Ile Tyr Asn Tyr Gly Ser Ser Gly Tyr Asn
        115                 120                 125
Tyr Ala Met Asp Tyr Trp Gly Gln Gly Thr Leu Val Thr Val Ser Ser
    130                 135                 140
Ala Ser Thr Lys Gly Pro Ser Val Phe Pro Leu Ala Pro Ser Ser Lys
145                 150                 155                 160
Ser Thr Ser Gly Gly Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
            180                 185                 190
Gly Val His Thr Phe Pro Ala Val Leu Gln Ser Ser Gly Leu Tyr Ser
        195                 200                 205
Leu Ser Ser Val Val Thr Val Pro Ser Ser Ser Leu Gly Thr Gln Thr
    210                 215                 220
Tyr Ile Cys Asn Val Asn His Lys Pro Ser Asn Thr Lys Val Asp Lys
225                 230                 235                 240
Arg Val Glu Pro Lys Ser Cys Asp Lys Thr His Thr Cys Pro Pro Cys
                245                 250                 255
Pro Ala Pro Glu Leu Leu Gly Gly Pro Ser Val Phe Leu Phe Pro Pro
            260                 265                 270
Lys Pro Lys Asp Thr Leu Met Ile Ser Arg Thr Pro Glu Val Thr Cys
        275                 280                 285
Val Val Val Asp Val Ser His Glu Asp Pro Glu Val Lys Phe Asn Trp
    290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
                325                 330                 335
His Gln Asp Trp Leu Asn Gly Lys Glu Tyr Lys Cys Lys Val Ser Asn
            340                 345                 350
Lys Ala Leu Pro Ala Pro Ile Glu Lys Thr Ile Ser Lys Ala Lys Gly
        355                 360                 365
Gln Pro Arg Glu Pro Gln Val Tyr Thr Leu Pro Pro Ser Arg Glu Glu
    370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
```

```
Asn Tyr Lys Thr Thr Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 60
<211> LENGTH: 1422
<212> TYPE: DNA
<213> ORGANISM: Artificial Sequence
<220> FEATURE:
<223> OTHER INFORMATION: Nucleotide coding of h#1G5-H3
<220> FEATURE:
<221> NAME/KEY: CDS
<222> LOCATION: (1)..(1422)

<400> SEQUENCE: 60 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg cag cag cct ggc gcc gaa gtg aaa aag      96
Val Leu Ser Gln Val Gln Leu Gln Gln Pro Gly Ala Glu Val Lys Lys
            20                  25                  30 cca ggc gcc agc gtg aag gtg tcc tgc aag gcc agc ggc tac acc ttt     144
Pro Gly Ala Ser Val Lys Val Ser Cys Lys Ala Ser Gly Tyr Thr Phe
        35                  40                  45 acc agc tac tgg atc aac tgg gtg cgc cag gcc cct gga cag ggc ctg     192
Thr Ser Tyr Trp Ile Asn Trp Val Arg Gln Ala Pro Gly Gln Gly Leu
    50                  55                  60 gaa tgg atg ggc aac atc tac ccc ggc agc agc agc atc aac tac aac     240
Glu Trp Met Gly Asn Ile Tyr Pro Gly Ser Ser Ser Ile Asn Tyr Asn
65                  70                  75                  80 gag aag ttc aag agc cgg gcc acc ctg acc gtg gac acc agc aca agc     288
Glu Lys Phe Lys Ser Arg Ala Thr Leu Thr Val Asp Thr Ser Thr Ser
                85                  90                  95 acc gcc tac atg gaa ctg agc agc ctg acc agc gag gac acc gcc gtg     336
Thr Ala Tyr Met Glu Leu Ser Ser Leu Thr Ser Glu Asp Thr Ala Val
            100                 105                 110 tac tac tgc agc cgg acc atc tac aac tac ggc agc tcc ggc tac aat     384
Tyr Tyr Cys Ser Arg Thr Ile Tyr Asn Tyr Gly Ser Ser Gly Tyr Asn
        115                 120                 125 tac gcc atg gac tac tgg ggc cag ggc acc ctc gtg acc gtg agc tca     432
Tyr Ala Met Asp Tyr Trp Gly Gln Gly Thr Leu Val Thr Val Ser Ser
    130                 135                 140 gcc tcc acc aag ggc cca agc gtc ttc ccc ctg gca ccc tcc tcc aag     480
Ala Ser Thr Lys Gly Pro Ser Val Phe Pro Leu Ala Pro Ser Ser Lys
145                 150                 155                 160 agc acc tct ggc ggc aca gcc gcc ctg ggc tgc ctg gtc aag gac tac     528
Ser Thr Ser Gly Gly Thr Ala Ala Leu Gly Cys Leu Val Lys Asp Tyr
                165                 170                 175 ttc ccc gaa ccc gtg acc gtg agc tgg aac tca ggc gcc ctg acc agc     576
Phe Pro Glu Pro Val Thr Val Ser Trp Asn Ser Gly Ala Leu Thr Ser
            180                 185                 190 ggc gtg cac acc ttc ccc gct gtc ctg cag tcc tca gga ctc tac tcc     624
Gly Val His Thr Phe Pro Ala Val Leu Gln Ser Ser Gly Leu Tyr Ser
        195                 200                 205 ctc agc agc gtg gtg acc gtg ccc tcc agc agc ttg ggc acc cag acc     672
Leu Ser Ser Val Val Thr Val Pro Ser Ser Ser Leu Gly Thr Gln Thr
```

| | | | | | | | | | | | | | | | |
|---|---|---|---|---|---|---|---|---|---|---|---|---|---|---|---|
| | | 210 | | | | 215 | | | | | 220 | | | | |

```
tac atc tgc aac gtg aat cac aag ccc agc aac acc aag gtg gac aag         720
Tyr Ile Cys Asn Val Asn His Lys Pro Ser Asn Thr Lys Val Asp Lys
225                 230                 235                 240 aga gtt gag ccc aaa tct tgt gac aaa act cac aca tgc cca ccc tgc         768
Arg Val Glu Pro Lys Ser Cys Asp Lys Thr His Thr Cys Pro Pro Cys
                245                 250                 255 cca gca cct gaa ctc ctg ggg gga ccc tca gtc ttc ctc ttc ccc cca         816
Pro Ala Pro Glu Leu Leu Gly Gly Pro Ser Val Phe Leu Phe Pro Pro
            260                 265                 270 aaa ccc aag gac acc ctc atg atc tcc cgg acc cct gag gtc aca tgc         864
Lys Pro Lys Asp Thr Leu Met Ile Ser Arg Thr Pro Glu Val Thr Cys
        275                 280                 285 gtg gtg gtg gac gtg agc cac gaa gac cct gag gtc aag ttc aac tgg         912
Val Val Val Asp Val Ser His Glu Asp Pro Glu Val Lys Phe Asn Trp
    290                 295                 300 tac gtg gac ggc gtg gag gtg cat aat gcc aag aca aag ccc cgg gag         960
Tyr Val Asp Gly Val Glu Val His Asn Ala Lys Thr Lys Pro Arg Glu
305                 310                 315                 320 gag cag tac aac agc acg tac cgg gtg gtc agc gtc ctc acc gtc ctg        1008
Glu Gln Tyr Asn Ser Thr Tyr Arg Val Val Ser Val Leu Thr Val Leu
                325                 330                 335 cac cag gac tgg ctg aat ggc aag gag tac aag tgc aag gtc tcc aac        1056
His Gln Asp Trp Leu Asn Gly Lys Glu Tyr Lys Cys Lys Val Ser Asn
            340                 345                 350 aaa gcc ctc cca gcc ccc atc gag aaa acc atc tcc aaa gcc aaa ggc        1104
Lys Ala Leu Pro Ala Pro Ile Glu Lys Thr Ile Ser Lys Ala Lys Gly
        355                 360                 365 cag ccc cgg gaa cca cag gtg tac acc ctg ccc cca tcc cgg gag gag        1152
Gln Pro Arg Glu Pro Gln Val Tyr Thr Leu Pro Pro Ser Arg Glu Glu
    370                 375                 380 atg acc aag aac cag gtc agc ctg acc tgc ctg gtc aaa ggc ttc tat        1200
Met Thr Lys Asn Gln Val Ser Leu Thr Cys Leu Val Lys Gly Phe Tyr
385                 390                 395                 400 ccc agc gac atc gcc gtg gag tgg gag agc aat ggc cag ccc gag aac        1248
Pro Ser Asp Ile Ala Val Glu Trp Glu Ser Asn Gly Gln Pro Glu Asn
                405                 410                 415 aac tac aag acc acc cct ccc gtg ctg gac tcc gac ggc tcc ttc ttc        1296
Asn Tyr Lys Thr Thr Pro Pro Val Leu Asp Ser Asp Gly Ser Phe Phe
            420                 425                 430 ctc tac agc aag ctc acc gtg gac aag agc agg tgg cag cag ggc aac        1344
Leu Tyr Ser Lys Leu Thr Val Asp Lys Ser Arg Trp Gln Gln Gly Asn
        435                 440                 445 gtc ttc tca tgc tcc gtg atg cat gag gct ctg cac aac cac tac acc        1392
Val Phe Ser Cys Ser Val Met His Glu Ala Leu His Asn His Tyr Thr
    450                 455                 460 cag aag agc ctc tcc ctg tct ccc ggc aaa                                1422
Gln Lys Ser Leu Ser Leu Ser Pro Gly Lys
465                 470

<210> SEQ ID NO 61
<211> LENGTH: 474
<212> TYPE: PRT
<213> ORGANISM: Artificial Sequence
<220> FEATURE:
<223> OTHER INFORMATION: Synthetic Construct

<400> SEQUENCE: 61

Met Lys His Leu Trp Phe Phe Leu Leu Leu Val Ala Ala Pro Arg Trp
1               5                   10                  15
```

-continued

```
Val Leu Ser Gln Val Gln Leu Gln Gln Pro Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Trp Ile Asn Trp Val Arg Gln Ala Pro Gly Gln Gly Leu
     50                  55                  60

Glu Trp Met Gly Asn Ile Tyr Pro Gly Ser Ser Ile Asn Tyr Asn
65                  70                  75                  80

Glu Lys Phe Lys Ser Arg Ala Thr Leu Thr Val Asp Thr Ser Thr Ser
                 85                  90                  95

Thr Ala Tyr Met Glu Leu Ser Ser Leu Thr Ser Glu Asp Thr Ala Val
            100                 105                 110

Tyr Tyr Cys Ser Arg Thr Ile Tyr Asn Tyr Gly Ser Ser Gly Tyr Asn
        115                 120                 125

Tyr Ala Met Asp Tyr Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
```

```
                435                 440                 445
Val Phe Ser Cys Ser Val Met His Glu Ala Leu His Asn His Tyr Thr
        450                 455                 460

Gln Lys Ser Leu Ser Leu Ser Pro Gly Lys
465                 470

<210> SEQ ID NO 62
<211> LENGTH: 1422
<212> TYPE: DNA
<213> ORGANISM: Artificial Sequence
<220> FEATURE:
<223> OTHER INFORMATION: Nucleotide coding of h#1G5-H4
<220> FEATURE:
<221> NAME/KEY: CDS
<222> LOCATION: (1)..(1422)

<400> SEQUENCE: 62 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                  10                  15 gtg ctg agc cag gtg cag ctg cag cag cct ggc gcc gag ctg aaa aaa      96
Val Leu Ser Gln Val Gln Leu Gln Gln Pro Gly Ala Glu Leu Lys Lys
            20                  25                  30 cct ggc gcc tcc gtg aag gtg tcc tgc aag gcc agc ggc tac acc ttt     144
Pro Gly Ala Ser Val Lys Val Ser Cys Lys Ala Ser Gly Tyr Thr Phe
        35                  40                  45 acc agc tac tgg atc aac tgg gtg cgc cag gcc cct gga cag ggc ctg     192
Thr Ser Tyr Trp Ile Asn Trp Val Arg Gln Ala Pro Gly Gln Gly Leu
    50                  55                  60 gaa tgg atc ggc aac atc tac ccc ggc agc agc agc atc aac tac aac     240
Glu Trp Ile Gly Asn Ile Tyr Pro Gly Ser Ser Ser Ile Asn Tyr Asn
65                  70                  75                  80 gag aag ttc aag agc aag gcc acc ctg acc gtg gac acc agc agc tcc     288
Glu Lys Phe Lys Ser Lys Ala Thr Leu Thr Val Asp Thr Ser Ser Ser
                85                  90                  95 aca gcc tac atg cag ctg tcc agc ctg acc agc gac gac agc gcc gtg     336
Thr Ala Tyr Met Gln Leu Ser Ser Leu Thr Ser Asp Asp Ser Ala Val
            100                 105                 110 tac tac tgc agc cgg acc atc tac aac tac ggc agc tcc ggc tac aat     384
Tyr Tyr Cys Ser Arg Thr Ile Tyr Asn Tyr Gly Ser Ser Gly Tyr Asn
        115                 120                 125 tac gcc atg gac tac tgg ggc cag ggc acc ctc gtg acc gtg agc tca     432
Tyr Ala Met Asp Tyr Trp Gly Gln Gly Thr Leu Val Thr Val Ser Ser
    130                 135                 140 gcc tcc acc aag ggc cca agc gtc ttc ccc ctg gca ccc tcc tcc aag     480
Ala Ser Thr Lys Gly Pro Ser Val Phe Pro Leu Ala Pro Ser Ser Lys
145                 150                 155                 160 agc acc tct ggc ggc aca gcc gcc ctg ggc tgc ctg gtc aag gac tac     528
Ser Thr Ser Gly Gly Thr Ala Ala Leu Gly Cys Leu Val Lys Asp Tyr
                165                 170                 175 ttc ccc gaa ccc gtg acc gtg agc tgg aac tca ggc gcc ctg acc agc     576
Phe Pro Glu Pro Val Thr Val Ser Trp Asn Ser Gly Ala Leu Thr Ser
            180                 185                 190 ggc gtg cac acc ttc ccc gct gtc ctg cag tcc tca gga ctc tac tcc     624
Gly Val His Thr Phe Pro Ala Val Leu Gln Ser Ser Gly Leu Tyr Ser
        195                 200                 205 ctc agc agc gtg gtg acc gtg ccc tcc agc agc ttg ggc acc cag acc     672
Leu Ser Ser Val Val Thr Val Pro Ser Ser Ser Leu Gly Thr Gln Thr
    210                 215                 220 tac atc tgc aac gtg aat cac aag ccc agc aac acc aag gtg gac aag     720
Tyr Ile Cys Asn Val Asn His Lys Pro Ser Asn Thr Lys Val Asp Lys
```

```
                225                 230                 235                 240
aga gtt gag ccc aaa tct tgt gac aaa act cac aca tgc cca ccc tgc       768
Arg Val Glu Pro Lys Ser Cys Asp Lys Thr His Thr Cys Pro Pro Cys
                245                 250                 255 cca gca cct gaa ctc ctg ggg gga ccc tca gtc ttc ctc ttc ccc cca       816
Pro Ala Pro Glu Leu Leu Gly Gly Pro Ser Val Phe Leu Phe Pro Pro
            260                 265                 270 aaa ccc aag gac acc ctc atg atc tcc cgg acc cct gag gtc aca tgc       864
Lys Pro Lys Asp Thr Leu Met Ile Ser Arg Thr Pro Glu Val Thr Cys
        275                 280                 285 gtg gtg gtg gac gtg agc cac gaa gac cct gag gtc aag ttc aac tgg       912
Val Val Val Asp Val Ser His Glu Asp Pro Glu Val Lys Phe Asn Trp
    290                 295                 300 tac gtg gac ggc gtg gag gtg cat aat gcc aag aca aag ccc cgg gag       960
Tyr Val Asp Gly Val Glu Val His Asn Ala Lys Thr Lys Pro Arg Glu
305                 310                 315                 320 gag cag tac aac agc acg tac cgg gtg gtc agc gtc ctc acc gtc ctg       1008
Glu Gln Tyr Asn Ser Thr Tyr Arg Val Val Ser Val Leu Thr Val Leu
                325                 330                 335 cac cag gac tgg ctg aat ggc aag gag tac aag tgc aag gtc tcc aac       1056
His Gln Asp Trp Leu Asn Gly Lys Glu Tyr Lys Cys Lys Val Ser Asn
            340                 345                 350 aaa gcc ctc cca gcc ccc atc gag aaa acc atc tcc aaa gcc aaa ggc       1104
Lys Ala Leu Pro Ala Pro Ile Glu Lys Thr Ile Ser Lys Ala Lys Gly
        355                 360                 365 cag ccc cgg gaa cca cag gtg tac acc ctg ccc cca tcc cgg gag gag       1152
Gln Pro Arg Glu Pro Gln Val Tyr Thr Leu Pro Pro Ser Arg Glu Glu
    370                 375                 380 atg acc aag aac cag gtc agc ctg acc tgc ctg gtc aaa ggc ttc tat       1200
Met Thr Lys Asn Gln Val Ser Leu Thr Cys Leu Val Lys Gly Phe Tyr
385                 390                 395                 400 ccc agc gac atc gcc gtg gag tgg gag agc aat ggc cag ccc gag aac       1248
Pro Ser Asp Ile Ala Val Glu Trp Glu Ser Asn Gly Gln Pro Glu Asn
                405                 410                 415 aac tac aag acc acc cct ccc gtg ctg gac tcc gac ggc tcc ttc ttc       1296
Asn Tyr Lys Thr Thr Pro Pro Val Leu Asp Ser Asp Gly Ser Phe Phe
            420                 425                 430 ctc tac agc aag ctc acc gtg gac aag agc agg tgg cag cag ggc aac       1344
Leu Tyr Ser Lys Leu Thr Val Asp Lys Ser Arg Trp Gln Gln Gly Asn
        435                 440                 445 gtc ttc tca tgc tcc gtg atg cat gag gct ctg cac aac cac tac acc       1392
Val Phe Ser Cys Ser Val Met His Glu Ala Leu His Asn His Tyr Thr
    450                 455                 460 cag aag agc ctc tcc ctg tct ccc ggc aaa                               1422
Gln Lys Ser Leu Ser Leu Ser Pro Gly Lys
465                 470

<210> SEQ ID NO 63
<211> LENGTH: 474
<212> TYPE: PRT
<213> ORGANISM: Artificial Sequence
<220> FEATURE:
<223> OTHER INFORMATION: Synthetic Construct

<400> SEQUENCE: 63

Met Lys His Leu Trp Phe Phe Leu Leu Leu Val Ala Ala Pro Arg Trp
1               5                   10                  15

Val Leu Ser Gln Val Gln Leu Gln Gln Pro Gly Ala Glu Leu Lys Lys
            20                  25                  30

Pro Gly Ala Ser Val Lys Val Ser Cys Lys Ala Ser Gly Tyr Thr Phe
```

```
            35                  40                  45
Thr Ser Tyr Trp Ile Asn Trp Val Arg Gln Ala Pro Gly Gln Gly Leu
 50                  55                  60

Glu Trp Ile Gly Asn Ile Tyr Pro Gly Ser Ser Ile Asn Tyr Asn
 65                  70                  75                  80

Glu Lys Phe Lys Ser Lys Ala Thr Leu Thr Val Asp Thr Ser Ser
                 85                  90                  95

Thr Ala Tyr Met Gln Leu Ser Ser Leu Thr Ser Asp Asp Ser Ala Val
                100                 105                 110

Tyr Tyr Cys Ser Arg Thr Ile Tyr Asn Tyr Gly Ser Ser Gly Tyr Asn
                115                 120                 125

Tyr Ala Met Asp Tyr Trp Gly Gln Gly Thr Leu Val Thr Val Ser Ser
130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
                180                 185                 190

Gly Val His Thr Phe Pro Ala Val Leu Gln Ser Ser Gly Leu Tyr Ser
                195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
                355                 360                 365

Gln Pro Arg Glu Pro Gln Val Tyr Thr Leu Pro Pro Ser Arg Glu Glu
                370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                        405                 410                 415

Asn Tyr Lys Thr Thr Pro Pro Val Leu Asp Ser Asp Gly Ser Phe Phe
                420                 425                 430

Leu Tyr Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
                450                 455                 460
```

```
Gln Lys Ser Leu Ser Leu Ser Pro Gly Lys
465                 470
```

<210> SEQ ID NO 64
<211> LENGTH: 1422
<212> TYPE: DNA
<213> ORGANISM: Artificial Sequence
<220> FEATURE:
<223> OTHER INFORMATION: Nucleotide coding of h#1G5-H5
<220> FEATURE:
<221> NAME/KEY: CDS
<222> LOCATION: (1)..(1422)

<400> SEQUENCE: 64

```
atg aaa cac ctg tgg ttc ttc ctc ctg ctg gtg gca gct ccc aga tgg        48
Met Lys His Leu Trp Phe Phe Leu Leu Leu Val Ala Ala Pro Arg Trp
1               5                   10                  15 gtg ctg agc cag gtg cag ctg cag cag cct ggc gcc gag ctg aaa aaa        96
Val Leu Ser Gln Val Gln Leu Gln Gln Pro Gly Ala Glu Leu Lys Lys
            20                  25                  30 cct ggc gcc tcc gtg aag gtg tcc tgc aag gcc agc ggc tac acc ttt       144
Pro Gly Ala Ser Val Lys Val Ser Cys Lys Ala Ser Gly Tyr Thr Phe
        35                  40                  45 acc agc tac tgg atc aac tgg gtc aag cag cgg cca ggc cag ggc ctg       192
Thr Ser Tyr Trp Ile Asn Trp Val Lys Gln Arg Pro Gly Gln Gly Leu
    50                  55                  60 gaa tgg atc ggc aat atc tac ccc ggc agc agc agc atc aac tac aac       240
Glu Trp Ile Gly Asn Ile Tyr Pro Gly Ser Ser Ser Ile Asn Tyr Asn
65                  70                  75                  80 gag aag ttc aag agc aag gcc acc ctg acc gtg gac acc agc agc tcc       288
Glu Lys Phe Lys Ser Lys Ala Thr Leu Thr Val Asp Thr Ser Ser Ser
                85                  90                  95 aca gcc tac atg cag ctg tcc agc ctg acc agc gac gac agc gcc gtg       336
Thr Ala Tyr Met Gln Leu Ser Ser Leu Thr Ser Asp Asp Ser Ala Val
            100                 105                 110 tac tac tgc agc cgg acc atc tac aac tac ggc agc tcc ggc tac aat       384
Tyr Tyr Cys Ser Arg Thr Ile Tyr Asn Tyr Gly Ser Ser Gly Tyr Asn
        115                 120                 125 tac gcc atg gac tac tgg ggc cag ggc acc agc gtg atc gtg agc tca       432
Tyr Ala Met Asp Tyr Trp Gly Gln Gly Thr Ser Val Ile Val Ser Ser
    130                 135                 140 gcc tcc acc aag ggc cca agc gtc ttc ccc ctg gca ccc tcc tcc aag       480
Ala Ser Thr Lys Gly Pro Ser Val Phe Pro Leu Ala Pro Ser Ser Lys
145                 150                 155                 160 agc acc tct ggc ggc aca gcc gcc ctg ggc tgc ctg gtc aag gac tac       528
Ser Thr Ser Gly Gly Thr Ala Ala Leu Gly Cys Leu Val Lys Asp Tyr
                165                 170                 175 ttc ccc gaa ccc gtg acc gtg agc tgg aac tca ggc gcc ctg acc agc       576
Phe Pro Glu Pro Val Thr Val Ser Trp Asn Ser Gly Ala Leu Thr Ser
            180                 185                 190 ggc gtg cac acc ttc ccc gct gtc ctg cag tcc tca gga ctc tac tcc       624
Gly Val His Thr Phe Pro Ala Val Leu Gln Ser Ser Gly Leu Tyr Ser
        195                 200                 205 ctc agc agc gtg gtg acc gtg ccc tcc agc agc ttg ggc acc cag acc       672
Leu Ser Ser Val Val Thr Val Pro Ser Ser Ser Leu Gly Thr Gln Thr
    210                 215                 220 tac atc tgc aac gtg aat cac aag ccc agc aac acc aag gtg gac aag       720
Tyr Ile Cys Asn Val Asn His Lys Pro Ser Asn Thr Lys Val Asp Lys
225                 230                 235                 240 aga gtt gag ccc aaa tct tgt gac aaa act cac aca tgc cca ccc tgc       768
Arg Val Glu Pro Lys Ser Cys Asp Lys Thr His Thr Cys Pro Pro Cys
```

```
                      245                 250                 255
cca gca cct gaa ctc ctg ggg gga ccc tca gtc ttc ctc ttc ccc cca        816
Pro Ala Pro Glu Leu Leu Gly Gly Pro Ser Val Phe Leu Phe Pro Pro
            260                 265                 270 aaa ccc aag gac acc ctc atg atc tcc cgg acc cct gag gtc aca tgc        864
Lys Pro Lys Asp Thr Leu Met Ile Ser Arg Thr Pro Glu Val Thr Cys
        275                 280                 285 gtg gtg gtg gac gtg agc cac gaa gac cct gag gtc aag ttc aac tgg        912
Val Val Val Asp Val Ser His Glu Asp Pro Glu Val Lys Phe Asn Trp
    290                 295                 300 tac gtg gac ggc gtg gag gtg cat aat gcc aag aca aag ccc cgg gag        960
Tyr Val Asp Gly Val Glu Val His Asn Ala Lys Thr Lys Pro Arg Glu
305                 310                 315                 320 gag cag tac aac agc acg tac cgg gtg gtc agc gtc ctc acc gtc ctg       1008
Glu Gln Tyr Asn Ser Thr Tyr Arg Val Val Ser Val Leu Thr Val Leu
                325                 330                 335 cac cag gac tgg ctg aat ggc aag gag tac aag tgc aag gtc tcc aac       1056
His Gln Asp Trp Leu Asn Gly Lys Glu Tyr Lys Cys Lys Val Ser Asn
            340                 345                 350 aaa gcc ctc cca gcc ccc atc gag aaa acc atc tcc aaa gcc aaa ggc       1104
Lys Ala Leu Pro Ala Pro Ile Glu Lys Thr Ile Ser Lys Ala Lys Gly
        355                 360                 365 cag ccc cgg gaa cca cag gtg tac acc ctg ccc cca tcc cgg gag gag       1152
Gln Pro Arg Glu Pro Gln Val Tyr Thr Leu Pro Pro Ser Arg Glu Glu
    370                 375                 380 atg acc aag aac cag gtc agc ctg acc tgc ctg gtc aaa ggc ttc tat       1200
Met Thr Lys Asn Gln Val Ser Leu Thr Cys Leu Val Lys Gly Phe Tyr
385                 390                 395                 400 ccc agc gac atc gcc gtg gag tgg gag agc aat ggc cag ccc gag aac       1248
Pro Ser Asp Ile Ala Val Glu Trp Glu Ser Asn Gly Gln Pro Glu Asn
                405                 410                 415 aac tac aag acc acc cct ccc gtg ctg gac tcc gac ggc tcc ttc ttc       1296
Asn Tyr Lys Thr Thr Pro Pro Val Leu Asp Ser Asp Gly Ser Phe Phe
            420                 425                 430 ctc tac agc aag ctc acc gtg gac aag agc agg tgg cag cag ggc aac       1344
Leu Tyr Ser Lys Leu Thr Val Asp Lys Ser Arg Trp Gln Gln Gly Asn
        435                 440                 445 gtc ttc tca tgc tcc gtg atg cat gag gct ctg cac aac cac tac acc       1392
Val Phe Ser Cys Ser Val Met His Glu Ala Leu His Asn His Tyr Thr
    450                 455                 460 cag aag agc ctc tcc ctg tct ccc ggc aaa                               1422
Gln Lys Ser Leu Ser Leu Ser Pro Gly Lys
465                 470

<210> SEQ ID NO 65
<211> LENGTH: 474
<212> TYPE: PRT
<213> ORGANISM: Artificial Sequence
<220> FEATURE:
<223> OTHER INFORMATION: Synthetic Construct

<400> SEQUENCE: 65

Met Lys His Leu Trp Phe Phe Leu Leu Leu Val Ala Ala Pro Arg Trp
1               5                   10                  15

Val Leu Ser Gln Val Gln Leu Gln Gln Pro Gly Ala Glu Leu Lys Lys
            20                  25                  30

Pro Gly Ala Ser Val Lys Val Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60
```

Glu Trp Ile Gly Asn Ile Tyr Pro Gly Ser Ser Ile Asn Tyr Asn
65                  70                  75                  80

Glu Lys Phe Lys Ser Lys Ala Thr Leu Thr Val Asp Thr Ser Ser
            85                  90                  95

Thr Ala Tyr Met Gln Leu Ser Ser Leu Thr Ser Asp Asp Ser Ala Val
            100                 105                 110

Tyr Tyr Cys Ser Arg Thr Ile Tyr Asn Tyr Gly Ser Ser Gly Tyr Asn
            115                 120                 125

Tyr Ala Met Asp Tyr Trp Gly Gln Gly Thr Ser Val Ile Val Ser Ser
130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
        370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 66
<211> LENGTH: 702
<212> TYPE: DNA
<213> ORGANISM: Artificial Sequence
<220> FEATURE:
<223> OTHER INFORMATION: Nucleotide coding of h#1G5-L1
<220> FEATURE:
<221> NAME/KEY: CDS
<222> LOCATION: (1)..(702)

<400> SEQUENCE: 66

```
atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc gac atc gtg atg acc cag agc cct gac agc ctg gcc      96
Gly Ala Tyr Gly Asp Ile Val Met Thr Gln Ser Pro Asp Ser Leu Ala
            20                  25                  30 gtg tct ctg gga gag aga gcc acc atc aac tgc aag gcc agc gag aac     144
Val Ser Leu Gly Glu Arg Ala Thr Ile Asn Cys Lys Ala Ser Glu Asn
        35                  40                  45 gtg ggc aac agc gtg tcc tgg tat cag cag aag ccc ggc cag ccc ccc     192
Val Gly Asn Ser Val Ser Trp Tyr Gln Gln Lys Pro Gly Gln Pro Pro
    50                  55                  60 aag ctg ctg atc tac ggc gcc agc aac aga tac acc ggc gtg ccc gat     240
Lys Leu Leu Ile Tyr Gly Ala Ser Asn Arg Tyr Thr Gly Val Pro Asp
65                  70                  75                  80 aga ttc agc ggc agc ggc tct ggc acc gac ttc acc ctg aca atc agc     288
Arg Phe Ser Gly Ser Gly Ser Gly Thr Asp Phe Thr Leu Thr Ile Ser
                85                  90                  95 tcc ctg cag gcc gag gac gtg gcc gtg tac tac tgt ggc cag agc tac     336
Ser Leu Gln Ala Glu Asp Val Ala Val Tyr Tyr Cys Gly Gln Ser Tyr
            100                 105                 110 agc tac ccc tac acc ttc ggc cag ggc acc aag gtg gaa atc aag cgt     384
Ser Tyr Pro Tyr Thr Phe Gly Gln Gly Thr Lys Val Glu Ile Lys Arg
        115                 120                 125 acg gtg gcc gcc ccc tcc gtg ttc atc ttc ccc ccc tcc gac gag cag     432
Thr Val Ala Ala Pro Ser Val Phe Ile Phe Pro Pro Ser Asp Glu Gln
    130                 135                 140 ctg aag tcc ggc acc gcc tcc gtg gtg tgc ctg ctg aat aac ttc tac     480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc     528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc     576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag     624
Tyr Ser Leu Ser Ser Thr Leu Thr Leu Ser Lys Ala Asp Tyr Glu Lys
        195                 200                 205 cac aag gtg tac gcc tgc gag gtg acc cac cag ggc ctg agc tcc ccc     672
His Lys Val Tyr Ala Cys Glu Val Thr His Gln Gly Leu Ser Ser Pro
    210                 215                 220 gtc acc aag agc ttc aac agg ggg gag tgt                             702
Val Thr Lys Ser Phe Asn Arg Gly Glu Cys
225                 230
```

<210> SEQ ID NO 67
<211> LENGTH: 234
<212> TYPE: PRT
<213> ORGANISM: Artificial Sequence
<220> FEATURE:

<223> OTHER INFORMATION: Synthetic Construct

<400> SEQUENCE: 67

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ala Ser Glu Asn
        35                  40                  45

Val Gly Asn Ser Val Ser Trp Tyr Gln Gln Lys Pro Gly Gln Pro Pro
    50                  55                  60

Lys Leu Leu Ile Tyr Gly Ala Ser Asn Arg Tyr Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Tyr Cys Gly Gln Ser Tyr
            100                 105                 110

Ser Tyr Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 68
<211> LENGTH: 702
<212> TYPE: DNA
<213> ORGANISM: Artificial Sequence
<220> FEATURE:
<223> OTHER INFORMATION: Nucleotide coding of h#1G5-L2
<220> FEATURE:
<221> NAME/KEY: CDS
<222> LOCATION: (1)..(702)

<400> SEQUENCE: 68

```
atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc aac atc gtg atg acc cag agc ccc gac agc ctg gcc      96
Gly Ala Tyr Gly Asn Ile Val Met Thr Gln Ser Pro Asp Ser Leu Ala
            20                  25                  30 gtg tct ctg gga gag aga gcc acc atc agc tgc aag gcc agc gag aac     144
Val Ser Leu Gly Glu Arg Ala Thr Ile Ser Cys Lys Ala Ser Glu Asn
        35                  40                  45 gtg ggc aac agc gtg tcc tgg tat cag cag aag ccc ggc cag agc cct     192
Val Gly Asn Ser Val Ser Trp Tyr Gln Gln Lys Pro Gly Gln Ser Pro
    50                  55                  60 aag ccc ctg atc tac ggc gcc agc aac aga tac acc ggc gtg ccc gat     240
```

```
Lys Pro Leu Ile Tyr Gly Ala Ser Asn Arg Tyr Thr Gly Val Pro Asp
 65                 70                  75                  80 aga ttc agc ggc agc ggc tct gcc acc gac ttc acc ctg aca atc agc      288
Arg Phe Ser Gly Ser Gly Ser Ala Thr Asp Phe Thr Leu Thr Ile Ser
                    85                  90                  95 tcc ctg cag gcc gag gac gtg gcc gtg tat cac tgt ggc cag agc tac      336
Ser Leu Gln Ala Glu Asp Val Ala Val Tyr His Cys Gly Gln Ser Tyr
                100                 105                 110 agc tac ccc tac acc ttc ggc gga ggc acc aag gtg gaa atc aag cgt      384
Ser Tyr Pro Tyr Thr Phe Gly Gly Gly Thr Lys Val Glu Ile Lys Arg
            115                 120                 125 acg gtg gcc gcc ccc tcc gtg ttc atc ttc ccc ccc tcc gac gag cag      432
Thr Val Ala Ala Pro Ser Val Phe Ile Phe Pro Pro Ser Asp Glu Gln
130                 135                 140 ctg aag tcc ggc acc gcc tcc gtg gtg tgc ctg ctg aat aac ttc tac      480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc      528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc      576
Gly Asn Ser Gln Glu Ser Val Thr Glu Gln Asp Ser Lys Asp Ser Thr
                180                 185                 190 tac agc ctg agc agc acc ctg acc ctg agc aaa gcc gac tac gag aag      624
Tyr Ser Leu Ser Ser Thr Leu Thr Leu Ser Lys Ala Asp Tyr Glu Lys
            195                 200                 205 cac aag gtg tac gcc tgc gag gtg acc cac cag ggc ctg agc tcc ccc      672
His Lys Val Tyr Ala Cys Glu Val Thr His Gln Gly Leu Ser Ser Pro
210                 215                 220 gtc acc aag agc ttc aac agg ggg gag tgt                              702
Val Thr Lys Ser Phe Asn Arg Gly Glu Cys
225                 230
```

<210> SEQ ID NO 69
<211> LENGTH: 234
<212> TYPE: PRT
<213> ORGANISM: Artificial Sequence
<220> FEATURE:
<223> OTHER INFORMATION: Synthetic Construct

<400> SEQUENCE: 69

```
Met Val Leu Gln Thr Gln Val Phe Ile Ser Leu Leu Leu Trp Ile Ser
  1               5                  10                  15

Gly Ala Tyr Gly Asn Ile Val Met Thr Gln Ser Pro Asp Ser Leu Ala
                 20                  25                  30

Val Ser Leu Gly Glu Arg Ala Thr Ile Ser Cys Lys Ala Ser Glu Asn
             35                  40                  45

Val Gly Asn Ser Val Ser Trp Tyr Gln Gln Lys Pro Gly Gln Ser Pro
 50                  55                  60

Lys Pro Leu Ile Tyr Gly Ala Ser Asn Arg Tyr Thr Gly Val Pro Asp
 65                  70                  75                  80

Arg Phe Ser Gly Ser Gly Ser Ala Thr Asp Phe Thr Leu Thr Ile Ser
                 85                  90                  95

Ser Leu Gln Ala Glu Asp Val Ala Val Tyr His Cys Gly Gln Ser Tyr
            100                 105                 110

Ser Tyr Pro Tyr Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
130                 135                 140
```

```
Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 70
<211> LENGTH: 702
<212> TYPE: DNA
<213> ORGANISM: Artificial Sequence
<220> FEATURE:
<223> OTHER INFORMATION: Nucleotide coding of h#1G5-L3
<220> FEATURE:
<221> NAME/KEY: CDS
<222> LOCATION: (1)..(702)

<400> SEQUENCE: 70 atg gtg ctg cag acc cag gtg ttc atc tcc ctg ctg ctg tgg atc tcc       48
Met Val Leu Gln Thr Gln Val Phe Ile Ser Leu Leu Leu Trp Ile Ser
1               5                   10                  15 ggc gcg tac ggc aac atc gtg atg acc cag agc ccc gac agc ctg gcc       96
Gly Ala Tyr Gly Asn Ile Val Met Thr Gln Ser Pro Asp Ser Leu Ala
                20                  25                  30 gtg tct ctg gga gag aga gcc acc atc agc tgc aag gcc agc gag aac      144
Val Ser Leu Gly Glu Arg Ala Thr Ile Ser Cys Lys Ala Ser Glu Asn
            35                  40                  45 gtg ggc aac agc gtg tcc tgg tat cag cag aag ccc ggc cag agc cct      192
Val Gly Asn Ser Val Ser Trp Tyr Gln Gln Lys Pro Gly Gln Ser Pro
        50                  55                  60 aag ccc ctg atc tac ggc gcc agc aac aga tac acc ggc gtg ccc gat      240
Lys Pro Leu Ile Tyr Gly Ala Ser Asn Arg Tyr Thr Gly Val Pro Asp
65                  70                  75                  80 aga ttc agc ggc agc ggc tct gcc acc gac ttc acc ctg aca atc agc      288
Arg Phe Ser Gly Ser Gly Ser Ala Thr Asp Phe Thr Leu Thr Ile Ser
                85                  90                  95 tcc ctg cag gcc gag gac gtg gcc gat tat cac tgc ggc cag tcc tac      336
Ser Leu Gln Ala Glu Asp Val Ala Asp Tyr His Cys Gly Gln Ser Tyr
                100                 105                 110 agc tac ccc tac acc ttt ggc gga ggc acc aag gtg gaa atc aag cgt      384
Ser Tyr Pro Tyr Thr Phe Gly Gly Gly Thr Lys Val Glu Ile Lys Arg
            115                 120                 125 acg gtg gcc gcc ccc tcc gtg ttc atc ttc ccc ccc tcc gac gag cag      432
Thr Val Ala Ala Pro Ser Val Phe Ile Phe Pro Pro Ser Asp Glu Gln
        130                 135                 140 ctg aag tcc ggc acc gcc tcc gtg gtg tgc ctg ctg aat aac ttc tac      480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc      528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc      576
Gly Asn Ser Gln Glu Ser Val Thr Glu Gln Asp Ser Lys Asp Ser Thr
            180                 185                 190
```

```
tac agc ctg agc agc acc ctg acc ctg agc aaa gcc gac tac gag aag      624
Tyr Ser Leu Ser Ser Thr Leu Thr Leu Ser Lys Ala Asp Tyr Glu Lys
        195                 200                 205 cac aag gtg tac gcc tgc gag gtg acc cac cag ggc ctg agc tcc ccc      672
His Lys Val Tyr Ala Cys Glu Val Thr His Gln Gly Leu Ser Ser Pro
    210                 215                 220 gtc acc aag agc ttc aac agg ggg gag tgt                              702
Val Thr Lys Ser Phe Asn Arg Gly Glu Cys
225                 230
```

<210> SEQ ID NO 71
<211> LENGTH: 234
<212> TYPE: PRT
<213> ORGANISM: Artificial Sequence
<220> FEATURE:
<223> OTHER INFORMATION: Synthetic Construct

<400> SEQUENCE: 71

```
Met Val Leu Gln Thr Gln Val Phe Ile Ser Leu Leu Trp Ile Ser
1               5                   10                  15

Gly Ala Tyr Gly Asn Ile Val Met Thr Gln Ser Pro Asp Ser Leu Ala
            20                  25                  30

Val Ser Leu Gly Glu Arg Ala Thr Ile Ser Cys Lys Ala Ser Glu Asn
        35                  40                  45

Val Gly Asn Ser Val Ser Trp Tyr Gln Gln Lys Pro Gly Gln Ser Pro
    50                  55                  60

Lys Pro Leu Ile Tyr Gly Ala Ser Asn Arg Tyr Thr Gly Val Pro Asp
65                  70                  75                  80

Arg Phe Ser Gly Ser Gly Ser Ala Thr Asp Phe Thr Leu Thr Ile Ser
                85                  90                  95

Ser Leu Gln Ala Glu Asp Val Ala Asp Tyr His Cys Gly Gln Ser Tyr
            100                 105                 110

Ser Tyr Pro Tyr Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 72
<211> LENGTH: 702
<212> TYPE: DNA
<213> ORGANISM: Artificial Sequence
<220> FEATURE:
<223> OTHER INFORMATION: Nucleotide coding of h#1G5-L4
<220> FEATURE:
<221> NAME/KEY: CDS
<222> LOCATION: (1)..(702)

```
<400> SEQUENCE: 72 atg gtg ctg cag acc cag gtg ttc atc tcc ctg ctg tgg atc tcc        48
Met Val Leu Gln Thr Gln Val Phe Ile Ser Leu Leu Trp Ile Ser
1               5                   10                  15 ggc gcg tac ggc aac atc gtg atg acc cag agc ccc gac agc atg agc    96
Gly Ala Tyr Gly Asn Ile Val Met Thr Gln Ser Pro Asp Ser Met Ser
            20                  25                  30 atg agc gtg ggc gag aga gcc acc ctg agc tgc aag gcc tct gag aac    144
Met Ser Val Gly Glu Arg Ala Thr Leu Ser Cys Lys Ala Ser Glu Asn
        35                  40                  45 gtg ggc aac agc gtg tcc tgg tat cag cag aag gcc gag cag agc ccc    192
Val Gly Asn Ser Val Ser Trp Tyr Gln Gln Lys Ala Glu Gln Ser Pro
    50                  55                  60 aag ccc ctg atc tac ggc gcc agc aac aga tac acc ggc gtg ccc gat    240
Lys Pro Leu Ile Tyr Gly Ala Ser Asn Arg Tyr Thr Gly Val Pro Asp
65                  70                  75                  80 aga ttc acc ggc agc ggc agc gcc acc gac ttc acc ctg aca atc agc    288
Arg Phe Thr Gly Ser Gly Ser Ala Thr Asp Phe Thr Leu Thr Ile Ser
                85                  90                  95 tcc ctg cag gcc gag gac ctg gcc gat tat cac tgc ggc cag agc tac    336
Ser Leu Gln Ala Glu Asp Leu Ala Asp Tyr His Cys Gly Gln Ser Tyr
            100                 105                 110 agc tac ccc tac acc ttt ggc gga ggc acc aag ctg gaa atc aag cgt    384
Ser Tyr Pro Tyr Thr Phe Gly Gly Gly Thr Lys Leu Glu Ile Lys Arg
        115                 120                 125 acg gtg gcc gcc ccc tcc gtg ttc atc ttc ccc ccc tcc gac gag cag    432
Thr Val Ala Ala Pro Ser Val Phe Ile Phe Pro Pro Ser Asp Glu Gln
    130                 135                 140 ctg aag tcc ggc acc gcc tcc gtg gtg tgc ctg ctg aat aac ttc tac    480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc    528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc    576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag    624
Tyr Ser Leu Ser Ser Thr Leu Thr Leu Ser Lys Ala Asp Tyr Glu Lys
        195                 200                 205 cac aag gtg tac gcc tgc gag gtg acc cac cag ggc ctg agc tcc ccc    672
His Lys Val Tyr Ala Cys Glu Val Thr His Gln Gly Leu Ser Ser Pro
    210                 215                 220 gtc acc aag agc ttc aac agg ggg gag tgt                            702
Val Thr Lys Ser Phe Asn Arg Gly Glu Cys
225                 230

<210> SEQ ID NO 73
<211> LENGTH: 234
<212> TYPE: PRT
<213> ORGANISM: Artificial Sequence
<220> FEATURE:
<223> OTHER INFORMATION: Synthetic Construct

<400> SEQUENCE: 73

Met Val Leu Gln Thr Gln Val Phe Ile Ser Leu Leu Trp Ile Ser
1               5                   10                  15

Gly Ala Tyr Gly Asn Ile Val Met Thr Gln Ser Pro Asp Ser Met Ser
            20                  25                  30

Met Ser Val Gly Glu Arg Ala Thr Leu Ser Cys Lys Ala Ser Glu Asn
```

```
                    35                  40                  45
Val Gly Asn Ser Val Ser Trp Tyr Gln Gln Lys Ala Glu Gln Ser Pro
 50                  55                  60

Lys Pro Leu Ile Tyr Gly Ala Ser Asn Arg Tyr Thr Gly Val Pro Asp
 65                  70                  75                  80

Arg Phe Thr Gly Ser Gly Ser Ala Thr Asp Phe Thr Leu Thr Ile Ser
                 85                  90                  95

Ser Leu Gln Ala Glu Asp Leu Ala Asp Tyr His Cys Gly Gln Ser Tyr
                100                 105                 110

Ser Tyr Pro Tyr Thr Phe Gly Gly Thr Lys Leu Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 74
<211> LENGTH: 702
<212> TYPE: DNA
<213> ORGANISM: Artificial Sequence
<220> FEATURE:
<223> OTHER INFORMATION: Nucleotide coding of h#1G5-L5
<220> FEATURE:
<221> NAME/KEY: CDS
<222> LOCATION: (1)..(702)

<400> SEQUENCE: 74 atg gtg ctg cag acc cag gtg ttc atc tcc ctg ctg ctg tgg atc tcc       48
Met Val Leu Gln Thr Gln Val Phe Ile Ser Leu Leu Leu Trp Ile Ser
 1               5                  10                  15 ggc gcg tac ggc aac atc gtg atg acc cag agc ccc gac agc atg agc       96
Gly Ala Tyr Gly Asn Ile Val Met Thr Gln Ser Pro Asp Ser Met Ser
                20                  25                  30 atg agc gtg ggc gag aga gtg acc ctg agc tgc aag gcc agc gag aac      144
Met Ser Val Gly Glu Arg Val Thr Leu Ser Cys Lys Ala Ser Glu Asn
         35                  40                  45 gtg ggc aac agc gtg tcc tgg tat cag cag aag gcc gag cag agc ccc      192
Val Gly Asn Ser Val Ser Trp Tyr Gln Gln Lys Ala Glu Gln Ser Pro
 50                  55                  60 aag ccc ctg atc tac ggc gcc agc aac aga tac acc ggc gtg ccc gat      240
Lys Pro Leu Ile Tyr Gly Ala Ser Asn Arg Tyr Thr Gly Val Pro Asp
 65                  70                  75                  80 aga ttc acc ggc agc ggc agc gcc acc gac ttc acc ctg aca atc agc      288
Arg Phe Thr Gly Ser Gly Ser Ala Thr Asp Phe Thr Leu Thr Ile Ser
                 85                  90                  95 tcc ctg cag gcc gag gac ctg gcc gat tat cac tgc ggc cag agc tac      336
Ser Leu Gln Ala Glu Asp Leu Ala Asp Tyr His Cys Gly Gln Ser Tyr
                100                 105                 110
```

```
agc tac ccc tac acc ttt ggc gga ggc acc aag ctg gaa atc aag cgt      384
Ser Tyr Pro Tyr Thr Phe Gly Gly Gly Thr Lys Leu Glu Ile Lys Arg
        115                 120                 125 acg gtg gcc gcc ccc tcc gtg ttc atc ttc ccc ccc tcc gac gag cag      432
Thr Val Ala Ala Pro Ser Val Phe Ile Phe Pro Pro Ser Asp Glu Gln
    130                 135                 140 ctg aag tcc ggc acc gcc tcc gtg gtg tgc ctg ctg aat aac ttc tac      480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc      528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc      576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag      624
Tyr Ser Leu Ser Ser Thr Leu Thr Leu Ser Lys Ala Asp Tyr Glu Lys
        195                 200                 205 cac aag gtg tac gcc tgc gag gtg acc cac cag ggc ctg agc tcc ccc      672
His Lys Val Tyr Ala Cys Glu Val Thr His Gln Gly Leu Ser Ser Pro
    210                 215                 220 gtc acc aag agc ttc aac agg ggg gag tgt                              702
Val Thr Lys Ser Phe Asn Arg Gly Glu Cys
225                 230

<210> SEQ ID NO 75
<211> LENGTH: 234
<212> TYPE: PRT
<213> ORGANISM: Artificial Sequence
<220> FEATURE:
<223> OTHER INFORMATION: Synthetic Construct

<400> SEQUENCE: 75

Met Val Leu Gln Thr Gln Val Phe Ile Ser Leu Leu Leu Trp Ile Ser
1               5                   10                  15

Gly Ala Tyr Gly Asn Ile Val Met Thr Gln Ser Pro Asp Ser Met Ser
            20                  25                  30

Met Ser Val Gly Glu Arg Val Thr Leu Ser Cys Lys Ala Ser Glu Asn
        35                  40                  45

Val Gly Asn Ser Val Ser Trp Tyr Gln Gln Lys Ala Glu Gln Ser Pro
    50                  55                  60

Lys Pro Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Leu Gln Ala Glu Asp Leu Ala Asp Tyr His Cys Gly Gln Ser Tyr
            100                 105                 110

Ser Tyr Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
```

```
                    195             200                 205
His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 76
<211> LENGTH: 1410
<212> TYPE: DNA
<213> ORGANISM: Artificial Sequence
<220> FEATURE:
<223> OTHER INFORMATION: Nucleotide coding of h#4C13K-H1
<220> FEATURE:
<221> NAME/KEY: CDS
<222> LOCATION: (1)..(1410)

<400> SEQUENCE: 76 atg aaa cac ctg tgg ttc ttc ctc ctg ctg gtg gca gct ccc aga tgg     48
Met Lys His Leu Trp Phe Phe Leu Leu Leu Val Ala Ala Pro Arg Trp
1               5                   10                  15 gtg ctg agc cag gtg cag ctg gtg cag tct ggc gcc gaa gtg aag aaa     96
Val Leu Ser Gln Val Gln Leu Val Gln Ser Gly Ala Glu Val Lys Lys
            20                  25                  30 cca ggc gcc agc gtg aag gtg tcc tgc aag gcc agc ggc tac acc ttt    144
Pro Gly Ala Ser Val Lys Val Ser Cys Lys Ala Ser Gly Tyr Thr Phe
        35                  40                  45 acc acc tac tgg atc aac tgg gtg cgc cag gcc cct gga cag ggc ctg    192
Thr Thr Tyr Trp Ile Asn Trp Val Arg Gln Ala Pro Gly Gln Gly Leu
    50                  55                  60 gaa tgg atg ggc aac atc tac ccc ggc acc aga agc agc aac tac aac    240
Glu Trp Met Gly Asn Ile Tyr Pro Gly Thr Arg Ser Ser Asn Tyr Asn
65                  70                  75                  80 gag aag ttc aag aac cgc gtg acc atc acc gcc gac acc agc acc agc    288
Glu Lys Phe Lys Asn Arg Val Thr Ile Thr Ala Asp Thr Ser Thr Ser
                85                  90                  95 aca gcc tac atg gaa ctg agc agc ctg cgg agc gag gac acc gcc gtg    336
Thr Ala Tyr Met Glu Leu Ser Ser Leu Arg Ser Glu Asp Thr Ala Val
            100                 105                 110 tac tac tgc gcc aga gtg tac tac gac cac gtg ggc tac tac ttc gac    384
Tyr Tyr Cys Ala Arg Val Tyr Tyr Asp His Val Gly Tyr Tyr Phe Asp
        115                 120                 125 tac tgg ggc cag ggc acc ctc gtg acc gtg agc tca gcc tcc acc aag    432
Tyr Trp Gly Gln Gly Thr Leu Val Thr Val Ser Ser Ala Ser Thr Lys
    130                 135                 140 ggc cca agc gtc ttc ccc ctg gca ccc tcc tcc aag agc acc tct ggc    480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc    528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc    576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg    624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac    672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc    720
Val Asn His Lys Pro Ser Asn Thr Lys Val Asp Lys Arg Val Glu Pro
225                 230                 235                 240
```

```
                225                 230                 235                 240
aaa tct tgt gac aaa act cac aca tgc cca ccc tgc cca gca cct gaa        768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac        816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac        864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc        912
Val Ser His Glu Asp Pro Glu Val Lys Phe Asn Trp Tyr Val Asp Gly
    290                 295                 300 gtg gag gtg cat aat gcc aag aca aag ccc cgg gag gag cag tac aac        960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg       1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca       1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa       1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac       1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc       1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc       1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag       1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc       1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc       1392
Ser Val Met His Glu Ala Leu His Asn His Tyr Thr Gln Lys Ser Leu
    450                 455                 460 tcc ctg tct ccc ggc aaa                                                1410
Ser Leu Ser Pro Gly Lys
465                 470

<210> SEQ ID NO 77
<211> LENGTH: 470
<212> TYPE: PRT
<213> ORGANISM: Artificial Sequence
<220> FEATURE:
<223> OTHER INFORMATION: Synthetic Construct

<400> SEQUENCE: 77

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
```

-continued

```
            35                  40                  45
Thr Thr Tyr Trp Ile Asn Trp Val Arg Gln Ala Pro Gly Gln Gly Leu
 50                  55                  60
Glu Trp Met Gly Asn Ile Tyr Pro Gly Thr Arg Ser Ser Asn Tyr Asn
 65                  70                  75                  80
Glu Lys Phe Lys Asn Arg Val Thr Ile Thr Ala Asp Thr Ser Thr Ser
                 85                  90                  95
Thr Ala Tyr Met Glu Leu Ser Ser Leu Arg Ser Glu Asp Thr Ala Val
            100                 105                 110
Tyr Tyr Cys Ala Arg Val Tyr Tyr Asp His Val Gly Tyr Tyr Phe Asp
        115                 120                 125
Tyr Trp Gly Gln Gly Thr Leu Val Thr Val Ser Ser Ala Ser Thr Lys
    130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
        195                 200                 205
Val Thr Val Pro Ser Ser Leu Gly Thr Gln Thr Tyr Ile Cys Asn
    210                 215                 220
Val Asn His Lys Pro Ser Asn Thr Lys Val Asp Lys Arg Val Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
        275                 280                 285
Val Ser His Glu Asp Pro Glu Val Lys Phe Asn Trp Tyr Val Asp Gly
    290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
        355                 360                 365
Pro Gln Val Tyr Thr Leu Pro Pro Ser Arg Glu Glu Met Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
```

```
<210> SEQ ID NO 78
<211> LENGTH: 1410
<212> TYPE: DNA
<213> ORGANISM: Artificial Sequence
<220> FEATURE:
<223> OTHER INFORMATION: Nucleotide coding of h#4C13K-H2
<220> FEATURE:
<221> NAME/KEY: CDS
<222> LOCATION: (1)..(1410)

<400> SEQUENCE: 78
```

| | | | | | | | | | | | | | | | | |
|---|---|---|---|---|---|---|---|---|---|---|---|---|---|---|---|---|
| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtg | ctg | agc | cag | gtg | cag | ctg | gtg | cag | tct | ggc | gcc | gaa | gtg | aag | aaa | 96 |
| Val | Leu | Ser | Gln | Val | Gln | Leu | Val | Gln | Ser | Gly | Ala | Glu | Val | Lys | Lys | |
| | | | 20 | | | | | 25 | | | | | 30 | | | |

| | | | | | | | | | | | | | | | | |
|---|---|---|---|---|---|---|---|---|---|---|---|---|---|---|---|---|
| cca | ggc | gcc | agc | gtg | aag | gtg | tcc | tgc | aag | gcc | agc | ggc | tac | acc | ttt | 144 |
| Pro | Gly | Ala | Ser | Val | Lys | Val | Ser | Cys | Lys | Ala | Ser | Gly | Tyr | Thr | Phe | |
| | | | 35 | | | | | 40 | | | | | 45 | | | |

| | | | | | | | | | | | | | | | | |
|---|---|---|---|---|---|---|---|---|---|---|---|---|---|---|---|---|
| acc | acc | tac | tgg | atc | aac | tgg | gtg | cgc | cag | gcc | cct | gga | cag | ggc | ctg | 192 |
| Thr | Thr | Tyr | Trp | Ile | Asn | Trp | Val | Arg | Gln | Ala | Pro | Gly | Gln | Gly | Leu | |
| 50 | | | | | 55 | | | | | 60 | | | | | | |

| | | | | | | | | | | | | | | | | |
|---|---|---|---|---|---|---|---|---|---|---|---|---|---|---|---|---|
| gaa | tgg | atg | ggc | aac | atc | tac | ccc | ggc | acc | aga | agc | agc | aac | tac | aac | 240 |
| Glu | Trp | Met | Gly | Asn | Ile | Tyr | Pro | Gly | Thr | Arg | Ser | Ser | Asn | Tyr | Asn | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gag | aag | ttc | aag | aac | cgc | gtg | acc | ctg | acc | gtg | gac | acc | agc | acc | agc | 288 |
| Glu | Lys | Phe | Lys | Asn | Arg | Val | Thr | Leu | Thr | Val | Asp | Thr | Ser | Thr | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | gcc | tac | atg | gaa | ctg | agc | agc | ctg | cgg | agc | gag | gac | acc | gcc | gtg | 336 |
| Thr | Ala | Tyr | Met | Glu | Leu | Ser | Ser | Leu | Arg | Ser | Glu | Asp | Thr | Ala | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| tac | tac | tgt | acc | cgg | gtg | tac | tac | gac | cac | gtg | ggc | tac | tac | ttc | gac | 384 |
| Tyr | Tyr | Cys | Thr | Arg | Val | Tyr | Tyr | Asp | His | Val | Gly | Tyr | Tyr | Phe | Asp | |
| | | 115 | | | | | 120 | | | | | 125 | | | | |

| | | | | | | | | | | | | | | | | |
|---|---|---|---|---|---|---|---|---|---|---|---|---|---|---|---|---|
| tac | tgg | ggc | cag | ggc | acc | ctc | gtg | acc | gtg | agc | tca | gcc | tcc | acc | aag | 432 |
| Tyr | Trp | Gly | Gln | Gly | Thr | Leu | Val | Thr | Val | Ser | Ser | Ala | Ser | Thr | Lys | |
| 130 | | | | | 135 | | | | | 140 | | | | | | |

| | | | | | | | | | | | | | | | | |
|---|---|---|---|---|---|---|---|---|---|---|---|---|---|---|---|---|
| ggc | cca | agc | gtc | ttc | ccc | ctg | gca | ccc | tcc | tcc | aag | agc | acc | tct | ggc | 480 |
| Gly | Pro | Ser | Val | Phe | Pro | Leu | Ala | Pro | Ser | Ser | Lys | Ser | Thr | Ser | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggc | aca | gcc | gcc | ctg | ggc | tgc | ctg | gtc | aag | gac | tac | ttc | ccc | gaa | ccc | 528 |
| Gly | Thr | Ala | Ala | Leu | Gly | Cys | Leu | Val | Lys | Asp | Tyr | Phe | Pro | Glu | Pro | |
| | | | | 165 | | | | | 170 | | | | | 175 | | |

| | | | | | | | | | | | | | | | | |
|---|---|---|---|---|---|---|---|---|---|---|---|---|---|---|---|---|
| gtg | acc | gtg | agc | tgg | aac | tca | ggc | gcc | ctg | acc | agc | ggc | gtg | cac | acc | 576 |
| Val | Thr | Val | Ser | Trp | Asn | Ser | Gly | Ala | Leu | Thr | Ser | Gly | Val | His | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| ttc | ccc | gct | gtc | ctg | cag | tcc | tca | gga | ctc | tac | tcc | ctc | agc | agc | gtg | 624 |
| Phe | Pro | Ala | Val | Leu | Gln | Ser | Ser | Gly | Leu | Tyr | Ser | Leu | Ser | Ser | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| gtg | acc | gtg | ccc | tcc | agc | agc | ttg | ggc | acc | cag | acc | tac | atc | tgc | aac | 672 |
| Val | Thr | Val | Pro | Ser | Ser | Ser | Leu | Gly | Thr | Gln | Thr | Tyr | Ile | Cys | Asn | |
| | | 210 | | | | | 215 | | | | | 220 | | | | |

| | | | | | | | | | | | | | | | | |
|---|---|---|---|---|---|---|---|---|---|---|---|---|---|---|---|---|
| gtg | aat | cac | aag | ccc | agc | aac | acc | aag | gtg | gac | aag | aga | gtt | gag | ccc | 720 |
| Val | Asn | His | Lys | Pro | Ser | Asn | Thr | Lys | Val | Asp | Lys | Arg | Val | Glu | Pro | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aaa | tct | tgt | gac | aaa | act | cac | aca | tgc | cca | ccc | tgc | cca | gca | cct | gaa | 768 |
| Lys | Ser | Cys | Asp | Lys | Thr | His | Thr | Cys | Pro | Pro | Cys | Pro | Ala | Pro | Glu | |

```
ctc ctg ggg gga ccc tca gtc ttc ctc ttc ccc cca aaa ccc aag gac      816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
290                 295                 300 gtg gag gtg cat aat gcc aag aca aag ccc cgg gag gag cag tac aac      960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg     1008
Ser Thr Tyr Arg Val Val Ser Val Leu Thr Val Leu His Gln Asp Trp
            325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
        340                 345                 350 gcc ccc atc gag aaa acc atc tcc aaa gcc aaa ggc cag ccc cgg gaa     1104
Ala Pro Ile Glu Lys Thr Ile Ser Lys Ala Lys Gly Gln Pro Arg Glu
    355                 360                 365 cca cag gtg tac acc ctg ccc cca tcc cgg gag gag atg acc aag aac     1152
Pro Gln Val Tyr Thr Leu Pro Pro Ser Arg Glu Glu Met Thr Lys Asn
370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc     1248
Ala Val Glu Trp Glu Ser Asn Gly Gln Pro Glu Asn Asn Tyr Lys Thr
            405                 410                 415 acc cct ccc gtg ctg gac tcc gac ggc tcc ttc ttc ctc tac agc aag     1296
Thr Pro Pro Val Leu Asp Ser Asp Gly Ser Phe Phe Leu Tyr Ser Lys
        420                 425                 430 ctc acc gtg gac aag agc agg tgg cag cag ggc aac gtc ttc tca tgc     1344
Leu Thr Val Asp Lys Ser Arg Trp Gln Gln Gly Asn Val Phe Ser Cys
    435                 440                 445 tcc gtg atg cat gag gct ctg cac aac cac tac acc cag aag agc ctc     1392
Ser Val Met His Glu Ala Leu His Asn His Tyr Thr Gln Lys Ser Leu
450                 455                 460 tcc ctg tct ccc ggc aaa                                             1410
Ser Leu Ser Pro Gly Lys
465                 470

<210> SEQ ID NO 79
<211> LENGTH: 470
<212> TYPE: PRT
<213> ORGANISM: Artificial Sequence
<220> FEATURE:
<223> OTHER INFORMATION: Synthetic Construct

<400> SEQUENCE: 79

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Thr Tyr Trp Ile Asn Trp Val Arg Gln Ala Pro Gly Gln Gly Leu
    50                  55                  60
```

-continued

```
Glu Trp Met Gly Asn Ile Tyr Pro Gly Thr Arg Ser Ser Asn Tyr Asn
 65                  70                  75                  80

Glu Lys Phe Lys Asn Arg Val Thr Leu Thr Val Asp Thr Ser Thr Ser
                 85                  90                  95

Thr Ala Tyr Met Glu Leu Ser Ser Leu Arg Ser Glu Asp Thr Ala Val
            100                 105                 110

Tyr Tyr Cys Thr Arg Val Tyr Tyr Asp His Val Gly Tyr Tyr Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

<210> SEQ ID NO 80
<211> LENGTH: 1410
<212> TYPE: DNA
<213> ORGANISM: Artificial Sequence
<220> FEATURE:
<223> OTHER INFORMATION: Nucleotide coding of h#4C13K-H3
<220> FEATURE:
<221> NAME/KEY: CDS
<222> LOCATION: (1)..(1410)

<400> SEQUENCE: 80

```
atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg cag cag cct ggc gcc gaa gtg aaa aag      96
Val Leu Ser Gln Val Gln Leu Gln Gln Pro Gly Ala Glu Val Lys Lys
                20                  25                  30 cca ggc gcc agc gtg aag gtg tcc tgc aag gcc agc ggc tac acc ttt     144
Pro Gly Ala Ser Val Lys Val Ser Cys Lys Ala Ser Gly Tyr Thr Phe
            35                  40                  45 acc acc tac tgg atc aac tgg atg cag cag cgg cca ggc cag ggc ctg     192
Thr Thr Tyr Trp Ile Asn Trp Met Gln Gln Arg Pro Gly Gln Gly Leu
        50                  55                  60 gaa tgg atg ggc aat atc tac ccc ggc acc aga agc agc aac tac aac     240
Glu Trp Met Gly Asn Ile Tyr Pro Gly Thr Arg Ser Ser Asn Tyr Asn
65                  70                  75                  80 gag aag ttc aag aac cgg gcc acc ctg acc gtg gac acc agc aca agc     288
Glu Lys Phe Lys Asn Arg Ala Thr Leu Thr Val Asp Thr Ser Thr Ser
                85                  90                  95 acc gcc tac atg gaa ctg agc agc ctg acc agc gag gac acc gcc gtg     336
Thr Ala Tyr Met Glu Leu Ser Ser Leu Thr Ser Glu Asp Thr Ala Val
            100                 105                 110 tac tac tgc acc aga gtg tac tac gac cac gtg ggc tac tac ttc gac     384
Tyr Tyr Cys Thr Arg Val Tyr Tyr Asp His Val Gly Tyr Tyr Phe Asp
        115                 120                 125 tac tgg ggc cag ggc acc ctc gtg acc gtg agc tca gcc tcc acc aag     432
Tyr Trp Gly Gln Gly Thr Leu Val Thr Val Ser Ser Ala Ser Thr Lys
130                 135                 140 ggc cca agc gtc ttc ccc ctg gca ccc tcc tcc aag agc acc tct ggc     480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc     528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc     576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg     624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac     672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc     720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa     768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac     816
Leu Leu Gly Gly Pro Ser Val Phe Leu Phe Pro Pro Lys Pro Lys Asp
```

```
acc ctc atg atc tcc cgg acc cct gag gtc aca tgc gtg gtg gtg gac      864
Thr Leu Met Ile Ser Arg Thr Pro Glu Val Thr Cys Val Val Val Asp
            275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
        290                 295                 300 gtg gag gtg cat aat gcc aag aca aag ccc cgg gag gag cag tac aac      960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac     1152
Pro Gln Val Tyr Thr Leu Pro Pro Ser Arg Glu Glu Met Thr Lys Asn
370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
                385                 390                 395                 400 gcc gtg gag tgg gag agc aat ggc cag ccc gag aac aac tac aag acc     1248
Ala Val Glu Trp Glu Ser Asn Gly Gln Pro Glu Asn Asn Tyr Lys Thr
            405                 410                 415 acc cct ccc gtg ctg gac tcc gac ggc tcc ttc ttc ctc tac agc aag     1296
Thr Pro Pro Val Leu Asp Ser Asp Gly Ser Phe Phe Leu Tyr Ser Lys
        420                 425                 430 ctc acc gtg gac aag agc agg tgg cag cag ggc aac gtc ttc tca tgc     1344
Leu Thr Val Asp Lys Ser Arg Trp Gln Gln Gly Asn Val Phe Ser Cys
                435                 440                 445 tcc gtg atg cat gag gct ctg cac aac cac tac acc cag aag agc ctc     1392
Ser Val Met His Glu Ala Leu His Asn His Tyr Thr Gln Lys Ser Leu
450                 455                 460 tcc ctg tct ccc ggc aaa                                             1410
Ser Leu Ser Pro Gly Lys
465                 470

<210> SEQ ID NO 81
<211> LENGTH: 470
<212> TYPE: PRT
<213> ORGANISM: Artificial Sequence
<220> FEATURE:
<223> OTHER INFORMATION: Synthetic Construct

<400> SEQUENCE: 81

Met Lys His Leu Trp Phe Phe Leu Leu Leu Val Ala Ala Pro Arg Trp
1               5                   10                  15

Val Leu Ser Gln Val Gln Leu Gln Gln Pro Gly Ala Glu Val Lys Lys
            20                  25                  30

Pro Gly Ala Ser Val Lys Val Ser Cys Lys Ala Ser Gly Tyr Thr Phe
        35                  40                  45

Thr Thr Tyr Trp Ile Asn Trp Met Gln Gln Arg Pro Gly Gln Gly Leu
    50                  55                  60

Glu Trp Met Gly Asn Ile Tyr Pro Gly Thr Arg Ser Ser Asn Tyr Asn
65                  70                  75                  80
```

Glu Lys Phe Lys Asn Arg Ala Thr Leu Thr Val Asp Thr Ser Thr Ser
             85                  90                  95

Thr Ala Tyr Met Glu Leu Ser Ser Leu Thr Ser Glu Asp Thr Ala Val
            100                 105                 110

Tyr Tyr Cys Thr Arg Val Tyr Tyr Asp His Val Gly Tyr Tyr Phe Asp
            115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
            210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 82
<211> LENGTH: 1410
<212> TYPE: DNA

<213> ORGANISM: Artificial Sequence
<220> FEATURE:
<223> OTHER INFORMATION: Nucleotide coding of h#4C13K-H4
<220> FEATURE:
<221> NAME/KEY: CDS
<222> LOCATION: (1)..(1410)

<400> SEQUENCE: 82

```
atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc cag gtg cag ctg cag cag cct ggc gcc gag ctg aaa aaa      96
Val Leu Ser Gln Val Gln Leu Gln Gln Pro Gly Ala Glu Leu Lys Lys
            20                  25                  30 cct ggc gcc tcc gtg aag gtg tcc tgc aag gcc agc ggc tac acc ttt     144
Pro Gly Ala Ser Val Lys Val Ser Cys Lys Ala Ser Gly Tyr Thr Phe
        35                  40                  45 acc acc tac tgg atc aac tgg atg cag cag cgg cca ggc cag ggc ctg     192
Thr Thr Tyr Trp Ile Asn Trp Met Gln Gln Arg Pro Gly Gln Gly Leu
    50                  55                  60 gaa tgg atc ggc aat atc tac ccc ggc acc aga agc agc aac tac aac     240
Glu Trp Ile Gly Asn Ile Tyr Pro Gly Thr Arg Ser Ser Asn Tyr Asn
65                  70                  75                  80 gag aag ttc aag aac aag gcc acc ctg acc gtg gac acc agc agc tcc     288
Glu Lys Phe Lys Asn Lys Ala Thr Leu Thr Val Asp Thr Ser Ser Ser
                85                  90                  95 acc gcc tac atg gaa ctg agc agc ctg acc agc gac gac agc gcc gtg     336
Thr Ala Tyr Met Glu Leu Ser Ser Leu Thr Ser Asp Asp Ser Ala Val
            100                 105                 110 tac tac tgc acc aga gtg tac tac gac cac gtg ggc tac tac ttc gac     384
Tyr Tyr Cys Thr Arg Val Tyr Tyr Asp His Val Gly Tyr Tyr Phe Asp
        115                 120                 125 tac tgg ggc cag ggc acc ctc gtg acc gtg agc tca gcc tcc acc aag     432
Tyr Trp Gly Gln Gly Thr Leu Val Thr Val Ser Ser Ala Ser Thr Lys
    130                 135                 140 ggc cca agc gtc ttc ccc ctg gca ccc tcc tcc aag agc acc tct ggc     480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc     528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc     576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg     624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac     672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc     720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa     768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac     816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac     864
Thr Leu Met Ile Ser Arg Thr Pro Glu Val Thr Cys Val Val Val Asp
```

```
                    275                 280                 285
gtg agc cac gaa gac cct gag gtc aag ttc aac tgg tac gtg gac ggc    912
Val Ser His Glu Asp Pro Glu Val Lys Phe Asn Trp Tyr Val Asp Gly
290                 295                 300 gtg gag gtg cat aat gcc aag aca aag ccc cgg gag gag cag tac aac    960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg   1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca   1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa   1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac   1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc   1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc   1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag   1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc   1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc   1392
Ser Val Met His Glu Ala Leu His Asn His Tyr Thr Gln Lys Ser Leu
    450                 455                 460 tcc ctg tct ccc ggc aaa                                           1410
Ser Leu Ser Pro Gly Lys
465                 470

<210> SEQ ID NO 83
<211> LENGTH: 470
<212> TYPE: PRT
<213> ORGANISM: Artificial Sequence
<220> FEATURE:
<223> OTHER INFORMATION: Synthetic Construct

<400> SEQUENCE: 83

Met Lys His Leu Trp Phe Phe Leu Leu Leu Val Ala Ala Pro Arg Trp
1               5                   10                  15

Val Leu Ser Gln Val Gln Leu Gln Gln Pro Gly Ala Glu Leu Lys Lys
            20                  25                  30

Pro Gly Ala Ser Val Lys Val Ser Cys Lys Ala Ser Gly Tyr Thr Phe
        35                  40                  45

Thr Thr Tyr Trp Ile Asn Trp Met Gln Gln Arg Pro Gly Gln Gly Leu
    50                  55                  60

Glu Trp Ile Gly Asn Ile Tyr Pro Gly Thr Arg Ser Ser Asn Tyr Asn
65                  70                  75                  80

Glu Lys Phe Lys Asn Lys Ala Thr Leu Thr Val Asp Thr Ser Ser Ser
                85                  90                  95

Thr Ala Tyr Met Glu Leu Ser Ser Leu Thr Ser Asp Asp Ser Ala Val
```

```
                100             105              110
Tyr Tyr Cys Thr Arg Val Tyr Tyr Asp His Val Gly Tyr Tyr Phe Asp
            115             120             125

Tyr Trp Gly Gln Gly Thr Leu Val Thr Val Ser Ser Ala Ser Thr Lys
130             135             140

Gly Pro Ser Val Phe Pro Leu Ala Pro Ser Ser Lys Ser Thr Ser Gly
145             150             155             160

Gly Thr Ala Ala Leu Gly Cys Leu Val Lys Asp Tyr Phe Pro Glu Pro
            165             170             175

Val Thr Val Ser Trp Asn Ser Gly Ala Leu Thr Ser Gly Val His Thr
            180             185             190

Phe Pro Ala Val Leu Gln Ser Ser Gly Leu Tyr Ser Leu Ser Ser Val
            195             200             205

Val Thr Val Pro Ser Ser Leu Gly Thr Gln Thr Tyr Ile Cys Asn
            210             215             220

Val Asn His Lys Pro Ser Asn Thr Lys Val Asp Lys Arg Val Glu Pro
225             230             235             240

Lys Ser Cys Asp Lys Thr His Thr Cys Pro Pro Cys Pro Ala Pro Glu
            245             250             255

Leu Leu Gly Gly Pro Ser Val Phe Leu Phe Pro Pro Lys Pro Lys Asp
            260             265             270

Thr Leu Met Ile Ser Arg Thr Pro Glu Val Thr Cys Val Val Val Asp
            275             280             285

Val Ser His Glu Asp Pro Glu Val Lys Phe Asn Trp Tyr Val Asp Gly
            290             295             300

Val Glu Val His Asn Ala Lys Thr Lys Pro Arg Glu Glu Gln Tyr Asn
305             310             315             320

Ser Thr Tyr Arg Val Val Ser Val Leu Thr Val Leu His Gln Asp Trp
            325             330             335

Leu Asn Gly Lys Glu Tyr Lys Cys Lys Val Ser Asn Lys Ala Leu Pro
            340             345             350

Ala Pro Ile Glu Lys Thr Ile Ser Lys Ala Lys Gly Gln Pro Arg Glu
            355             360             365

Pro Gln Val Tyr Thr Leu Pro Pro Ser Arg Glu Glu Met Thr Lys Asn
            370             375             380

Gln Val Ser Leu Thr Cys Leu Val Lys Gly Phe Tyr Pro Ser Asp Ile
385             390             395             400

Ala Val Glu Trp Glu Ser Asn Gly Gln Pro Glu Asn Asn Tyr Lys Thr
            405             410             415

Thr Pro Pro Val Leu Asp Ser Asp Gly Ser Phe Phe Leu Tyr Ser Lys
            420             425             430

Leu Thr Val Asp Lys Ser Arg Trp Gln Gln Gly Asn Val Phe Ser Cys
            435             440             445

Ser Val Met His Glu Ala Leu His Asn His Tyr Thr Gln Lys Ser Leu
            450             455             460

Ser Leu Ser Pro Gly Lys
465             470

<210> SEQ ID NO 84
<211> LENGTH: 1410
<212> TYPE: DNA
<213> ORGANISM: Artificial Sequence
<220> FEATURE:
<223> OTHER INFORMATION: Nucleotide coding of h#4C13K-H5
<220> FEATURE:
```

<221> NAME/KEY: CDS
<222> LOCATION: (1)..(1410)

<400> SEQUENCE: 84

| | | | | | | | | | | | | | | | | |
|---|---|---|---|---|---|---|---|---|---|---|---|---|---|---|---|---|
| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |

| gtg | ctg | agc | cag | gtg | cag | ctg | cag | cag | cct | ggc | gcc | gag | ctg | aaa | aaa | 96 |
|---|---|---|---|---|---|---|---|---|---|---|---|---|---|---|---|---|
| Val | Leu | Ser | Gln | Val | Gln | Leu | Gln | Gln | Pro | Gly | Ala | Glu | Leu | Lys | Lys | |
| | | | 20 | | | | | 25 | | | | | 30 | | | |

| cct | ggc | gcc | tcc | gtg | aag | gtg | tcc | tgc | aag | gcc | agc | ggc | tac | acc | ttt | 144 |
|---|---|---|---|---|---|---|---|---|---|---|---|---|---|---|---|---|
| Pro | Gly | Ala | Ser | Val | Lys | Val | Ser | Cys | Lys | Ala | Ser | Gly | Tyr | Thr | Phe | |
| | | 35 | | | | | 40 | | | | | 45 | | | | |

| acc | acc | tac | tgg | atc | aac | tgg | atg | cag | cag | cgg | cca | ggc | cag | ggc | ctg | 192 |
|---|---|---|---|---|---|---|---|---|---|---|---|---|---|---|---|---|
| Thr | Thr | Tyr | Trp | Ile | Asn | Trp | Met | Gln | Gln | Arg | Pro | Gly | Gln | Gly | Leu | |
| | 50 | | | | | 55 | | | | | 60 | | | | | |

| gaa | tgg | atc | ggc | aat | atc | tac | ccc | ggc | acc | aga | agc | agc | aac | tac | aac | 240 |
|---|---|---|---|---|---|---|---|---|---|---|---|---|---|---|---|---|
| Glu | Trp | Ile | Gly | Asn | Ile | Tyr | Pro | Gly | Thr | Arg | Ser | Ser | Asn | Tyr | Asn | |
| 65 | | | | | 70 | | | | | 75 | | | | | 80 | |

| gag | aag | ttc | aag | aac | aag | gcc | acc | ctg | acc | gtg | gac | acc | agc | agc | tcc | 288 |
|---|---|---|---|---|---|---|---|---|---|---|---|---|---|---|---|---|
| Glu | Lys | Phe | Lys | Asn | Lys | Ala | Thr | Leu | Thr | Val | Asp | Thr | Ser | Ser | Ser | |
| | | | | 85 | | | | | 90 | | | | | 95 | | |

| aca | gcc | tac | atg | cag | ctg | aac | tcc | ctg | acc | agc | gac | gac | agc | gcc | gtg | 336 |
|---|---|---|---|---|---|---|---|---|---|---|---|---|---|---|---|---|
| Thr | Ala | Tyr | Met | Gln | Leu | Asn | Ser | Leu | Thr | Ser | Asp | Asp | Ser | Ala | Val | |
| | | | 100 | | | | | 105 | | | | | 110 | | | |

| tac | tac | tgc | acc | aga | gtg | tac | tac | gac | cac | gtg | ggc | tac | tac | ttc | gac | 384 |
|---|---|---|---|---|---|---|---|---|---|---|---|---|---|---|---|---|
| Tyr | Tyr | Cys | Thr | Arg | Val | Tyr | Tyr | Asp | His | Val | Gly | Tyr | Tyr | Phe | Asp | |
| | | 115 | | | | | 120 | | | | | 125 | | | | |

| tac | tgg | ggc | cag | ggc | acc | ctc | gtg | acc | gtg | agc | tca | gcc | tcc | acc | aag | 432 |
|---|---|---|---|---|---|---|---|---|---|---|---|---|---|---|---|---|
| Tyr | Trp | Gly | Gln | Gly | Thr | Leu | Val | Thr | Val | Ser | Ser | Ala | Ser | Thr | Lys | |
| | 130 | | | | | 135 | | | | | 140 | | | | | |

| ggc | cca | agc | gtc | ttc | ccc | ctg | gca | ccc | tcc | tcc | aag | agc | acc | tct | ggc | 480 |
|---|---|---|---|---|---|---|---|---|---|---|---|---|---|---|---|---|
| Gly | Pro | Ser | Val | Phe | Pro | Leu | Ala | Pro | Ser | Ser | Lys | Ser | Thr | Ser | Gly | |
| 145 | | | | | 150 | | | | | 155 | | | | | 160 | |

| ggc | aca | gcc | gcc | ctg | ggc | tgc | ctg | gtc | aag | gac | tac | ttc | ccc | gaa | ccc | 528 |
|---|---|---|---|---|---|---|---|---|---|---|---|---|---|---|---|---|
| Gly | Thr | Ala | Ala | Leu | Gly | Cys | Leu | Val | Lys | Asp | Tyr | Phe | Pro | Glu | Pro | |
| | | | 165 | | | | | 170 | | | | | 175 | | | |

| gtg | acc | gtg | agc | tgg | aac | tca | ggc | gcc | ctg | acc | agc | ggc | gtg | cac | acc | 576 |
|---|---|---|---|---|---|---|---|---|---|---|---|---|---|---|---|---|
| Val | Thr | Val | Ser | Trp | Asn | Ser | Gly | Ala | Leu | Thr | Ser | Gly | Val | His | Thr | |
| | | | 180 | | | | | 185 | | | | | 190 | | | |

| ttc | ccc | gct | gtc | ctg | cag | tcc | tca | gga | ctc | tac | tcc | ctc | agc | agc | gtg | 624 |
|---|---|---|---|---|---|---|---|---|---|---|---|---|---|---|---|---|
| Phe | Pro | Ala | Val | Leu | Gln | Ser | Ser | Gly | Leu | Tyr | Ser | Leu | Ser | Ser | Val | |
| | | 195 | | | | | 200 | | | | | 205 | | | | |

| gtg | acc | gtg | ccc | tcc | agc | agc | ttg | ggc | acc | cag | acc | tac | atc | tgc | aac | 672 |
|---|---|---|---|---|---|---|---|---|---|---|---|---|---|---|---|---|
| Val | Thr | Val | Pro | Ser | Ser | Ser | Leu | Gly | Thr | Gln | Thr | Tyr | Ile | Cys | Asn | |
| | 210 | | | | | 215 | | | | | 220 | | | | | |

| gtg | aat | cac | aag | ccc | agc | aac | acc | aag | gtg | gac | aag | aga | gtt | gag | ccc | 720 |
|---|---|---|---|---|---|---|---|---|---|---|---|---|---|---|---|---|
| Val | Asn | His | Lys | Pro | Ser | Asn | Thr | Lys | Val | Asp | Lys | Arg | Val | Glu | Pro | |
| 225 | | | | | 230 | | | | | 235 | | | | | 240 | |

| aaa | tct | tgt | gac | aaa | act | cac | aca | tgc | cca | ccc | tgc | cca | gca | cct | gaa | 768 |
|---|---|---|---|---|---|---|---|---|---|---|---|---|---|---|---|---|
| Lys | Ser | Cys | Asp | Lys | Thr | His | Thr | Cys | Pro | Pro | Cys | Pro | Ala | Pro | Glu | |
| | | | | 245 | | | | | 250 | | | | | 255 | | |

| ctc | ctg | ggg | gga | ccc | tca | gtc | ttc | ctc | ttc | ccc | cca | aaa | ccc | aag | gac | 816 |
|---|---|---|---|---|---|---|---|---|---|---|---|---|---|---|---|---|
| Leu | Leu | Gly | Gly | Pro | Ser | Val | Phe | Leu | Phe | Pro | Pro | Lys | Pro | Lys | Asp | |
| | | | 260 | | | | | 265 | | | | | 270 | | | |

| acc | ctc | atg | atc | tcc | cgg | acc | cct | gag | gtc | aca | tgc | gtg | gtg | gtg | gac | 864 |
|---|---|---|---|---|---|---|---|---|---|---|---|---|---|---|---|---|
| Thr | Leu | Met | Ile | Ser | Arg | Thr | Pro | Glu | Val | Thr | Cys | Val | Val | Val | Asp | |
| | | | 275 | | | | | 280 | | | | | 285 | | | |

| gtg | agc | cac | gaa | gac | cct | gag | gtc | aag | ttc | aac | tgg | tac | gtg | gac | ggc | 912 |
|---|---|---|---|---|---|---|---|---|---|---|---|---|---|---|---|---|
| Val | Ser | His | Glu | Asp | Pro | Glu | Val | Lys | Phe | Asn | Trp | Tyr | Val | Asp | Gly | |

```
gtg gag gtg cat aat gcc aag aca aag ccc cgg gag gag cag tac aac      960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac     1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc     1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag     1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc     1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc     1392
Ser Val Met His Glu Ala Leu His Asn His Tyr Thr Gln Lys Ser Leu
    450                 455                 460 tcc ctg tct ccc ggc aaa                                             1410
Ser Leu Ser Pro Gly Lys
465                 470

<210> SEQ ID NO 85
<211> LENGTH: 470
<212> TYPE: PRT
<213> ORGANISM: Artificial Sequence
<220> FEATURE:
<223> OTHER INFORMATION: Synthetic Construct

<400> SEQUENCE: 85

Met Lys His Leu Trp Phe Phe Leu Leu Leu Val Ala Ala Pro Arg Trp
1               5                   10                  15

Val Leu Ser Gln Val Gln Leu Gln Gln Pro Gly Ala Glu Leu Lys Lys
            20                  25                  30

Pro Gly Ala Ser Val Lys Val Ser Cys Lys Ala Ser Gly Tyr Thr Phe
        35                  40                  45

Thr Thr Tyr Trp Ile Asn Trp Met Gln Gln Arg Pro Gly Gln Gly Leu
    50                  55                  60

Glu Trp Ile Gly Asn Ile Tyr Pro Gly Thr Arg Ser Ser Asn Tyr Asn
65                  70                  75                  80

Glu Lys Phe Lys Asn Lys Ala Thr Leu Thr Val Asp Thr Ser Ser Ser
                85                  90                  95

Thr Ala Tyr Met Gln Leu Asn Ser Leu Thr Ser Asp Asp Ser Ala Val
            100                 105                 110

Tyr Tyr Cys Thr Arg Val Tyr Tyr Asp His Val Gly Tyr Tyr Phe Asp
        115                 120                 125
```

Tyr Trp Gly Gln Gly Thr Leu Val Thr Val Ser Ser Ala Ser Thr Lys
                130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
                210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
                290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
                370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460

Ser Leu Ser Pro Gly Lys
465                 470

<210> SEQ ID NO 86
<211> LENGTH: 5
<212> TYPE: PRT
<213> ORGANISM: Artificial Sequence
<220> FEATURE:
<223> OTHER INFORMATION: CDRH1 of #4C13

<400> SEQUENCE: 86

Thr Tyr Trp Ile Asn
1               5

<210> SEQ ID NO 87
<211> LENGTH: 17
<212> TYPE: PRT
<213> ORGANISM: Artificial Sequence
<220> FEATURE:
<223> OTHER INFORMATION: CDRH2 of #4C13

<400> SEQUENCE: 87

Asn Ile Tyr Pro Gly Thr Arg Ser Ser Asn Tyr Asn Glu Lys Phe Lys
1               5                   10                  15
Asn

<210> SEQ ID NO 88
<211> LENGTH: 12
<212> TYPE: PRT
<213> ORGANISM: Artificial Sequence
<220> FEATURE:
<223> OTHER INFORMATION: CDRH3 of #4C13

<400> SEQUENCE: 88

Val Tyr Tyr Asp His Val Gly Tyr Tyr Phe Asp Tyr
1               5                   10

<210> SEQ ID NO 89
<211> LENGTH: 35
<212> TYPE: DNA
<213> ORGANISM: Artificial Sequence
<220> FEATURE:
<223> OTHER INFORMATION: AP3dC-S
<220> FEATURE:
<221> NAME/KEY: misc_feature
<222> LOCATION: (35)..(35)
<223> OTHER INFORMATION: n is a, c, g, or t

<400> SEQUENCE: 89
cggtaccgcg ggcccgggat ccccccccccc cccdn                       35

<210> SEQ ID NO 90
<211> LENGTH: 23
<212> TYPE: DNA
<213> ORGANISM: Artificial Sequence
<220> FEATURE:
<223> OTHER INFORMATION: mIggamma RT1 1111-AS

<400> SEQUENCE: 90
accytgcatt tgaactcctt gcc                                     23

<210> SEQ ID NO 91
<211> LENGTH: 25
<212> TYPE: DNA
<213> ORGANISM: Artificial Sequence
<220> FEATURE:
<223> OTHER INFORMATION: mIgkappa 1st 589-AS

<400> SEQUENCE: 91
actgccatca atcttccact tgaca                                   25

<210> SEQ ID NO 92
<211> LENGTH: 38
<212> TYPE: DNA
<213> ORGANISM: Artificial Sequence
<220> FEATURE:
<223> OTHER INFORMATION: MCS-AP3-S

<400> SEQUENCE: 92
cttcgaattc tgcagtcgac ggtaccgcgg gcccggga         38

<210> SEQ ID NO 93
<211> LENGTH: 23
<212> TYPE: DNA
<213> ORGANISM: Artificial Sequence
<220> FEATURE:
<223> OTHER INFORMATION: mIggamma 3rd 656T-AS

<400> SEQUENCE: 93
ctggacaggg atccagagtt cca         23

<210> SEQ ID NO 94
<211> LENGTH: 25
<212> TYPE: DNA
<213> ORGANISM: Artificial Sequence
<220> FEATURE:
<223> OTHER INFORMATION: mIgkappa 3rd 525-AS

<400> SEQUENCE: 94
actgaggcac ctccagatgt taact         25

<210> SEQ ID NO 95
<211> LENGTH: 26
<212> TYPE: DNA
<213> ORGANISM: Artificial Sequence
<220> FEATURE:
<223> OTHER INFORMATION: mIgG joint PCR-S

<400> SEQUENCE: 95
gcctggtcaa gggctatttc cctgag         26

<210> SEQ ID NO 96
<211> LENGTH: 24
<212> TYPE: DNA
<213> ORGANISM: Artificial Sequence
<220> FEATURE:
<223> OTHER INFORMATION: polyG-AS

<400> SEQUENCE: 96
gggggggggg ggggggatc ccgg         24

<210> SEQ ID NO 97
<211> LENGTH: 26
<212> TYPE: DNA
<213> ORGANISM: Artificial Sequence
<220> FEATURE:
<223> OTHER INFORMATION: mIgkappa joint PCR-S

<400> SEQUENCE: 97
ctgtatccat cttcccacca tccagt         26

<210> SEQ ID NO 98
<211> LENGTH: 27
<212> TYPE: DNA
<213> ORGANISM: Artificial Sequence
<220> FEATURE:
<223> OTHER INFORMATION: miniCMV f1-S

<400> SEQUENCE: 98
agagaaaccg tctatcaggg cgatggc         27

<210> SEQ ID NO 99
<211> LENGTH: 27
<212> TYPE: DNA
<213> ORGANISM: Artificial Sequence
<220> FEATURE:
<223> OTHER INFORMATION: miniCMV f1-AS

<400> SEQUENCE: 99
agagaccctt tgacgttgga gtccacg                                27

<210> SEQ ID NO 100
<211> LENGTH: 24
<212> TYPE: DNA
<213> ORGANISM: Artificial Sequence
<220> FEATURE:
<223> OTHER INFORMATION: mIgG sequence

<400> SEQUENCE: 100
acaccgctgg acagggatcc agag                                   24

<210> SEQ ID NO 101
<211> LENGTH: 24
<212> TYPE: DNA
<213> ORGANISM: Artificial Sequence
<220> FEATURE:
<223> OTHER INFORMATION: mIgkappa sequence

<400> SEQUENCE: 101
gtagaagttg ttcaagaagc acac                                   24

<210> SEQ ID NO 102
<211> LENGTH: 30
<212> TYPE: DNA
<213> ORGANISM: Artificial Sequence
<220> FEATURE:
<223> OTHER INFORMATION: 3.3-F1

<400> SEQUENCE: 102
tataccgtcg acctctagct agagcttggc                             30

<210> SEQ ID NO 103
<211> LENGTH: 30
<212> TYPE: DNA
<213> ORGANISM: Artificial Sequence
<220> FEATURE:
<223> OTHER INFORMATION: 3.3-R1

<400> SEQUENCE: 103
gctatggcag ggcctgccgc cccgacgttg                             30

<210> SEQ ID NO 104
<211> LENGTH: 47
<212> TYPE: DNA
<213> ORGANISM: Artificial Sequence
<220> FEATURE:
<223> OTHER INFORMATION: 76L-F

<400> SEQUENCE: 104
atctccggcg cgtacggcaa cattgtaatg acccaatctc ccaaatc          47

<210> SEQ ID NO 105
<211> LENGTH: 45
<212> TYPE: DNA
<213> ORGANISM: Artificial Sequence
<220> FEATURE:
<223> OTHER INFORMATION: 76L-R

<400> SEQUENCE: 105 ggaggggggcg gccacagccc gtttttatttc cagcttggtc ctccc          45

<210> SEQ ID NO 106
<211> LENGTH: 47
<212> TYPE: DNA
<213> ORGANISM: Artificial Sequence
<220> FEATURE:
<223> OTHER INFORMATION: 76H-F

<400> SEQUENCE: 106
ccagatgggt gctgagccag gtccaactgc agcagcctgg tgctgag         47

<210> SEQ ID NO 107
<211> LENGTH: 46
<212> TYPE: DNA
<213> ORGANISM: Artificial Sequence
<220> FEATURE:
<223> OTHER INFORMATION: 76H-R

<400> SEQUENCE: 107
cttggtggag gctgagctga ctgtgagagt ggtgccttgg ccccag          46

<210> SEQ ID NO 108
<211> LENGTH: 25
<212> TYPE: DNA
<213> ORGANISM: Artificial Sequence
<220> FEATURE:
<223> OTHER INFORMATION: CM-inf-F

<400> SEQUENCE: 108
ccagcctccg gactctagag ccacc                                 25

<210> SEQ ID NO 109
<211> LENGTH: 24
<212> TYPE: DNA
<213> ORGANISM: Artificial Sequence
<220> FEATURE:
<223> OTHER INFORMATION: CM-inf-R

<400> SEQUENCE: 109
agttagcctc ccccgtttaa actc                                  24

<210> SEQ ID NO 110
<211> LENGTH: 22
<212> TYPE: DNA
<213> ORGANISM: Artificial Sequence
<220> FEATURE:
<223> OTHER INFORMATION: EG-Inf-F

<400> SEQUENCE: 110
agctcccaga tgggtgctga gc                                    22

<210> SEQ ID NO 111
<211> LENGTH: 22
<212> TYPE: DNA
<213> ORGANISM: Artificial Sequence
<220> FEATURE:
<223> OTHER INFORMATION: EG1-Inf-R

<400> SEQUENCE: 111
gggcccttgg tggaggctga gc                                    22

<210> SEQ ID NO 112
<211> LENGTH: 24
<212> TYPE: DNA
<213> ORGANISM: Artificial Sequence
<220> FEATURE:
<223> OTHER INFORMATION: CM-LKF

```
<400> SEQUENCE: 112
ctgtggatct ccggcgcgta cggc                                          24

<210> SEQ ID NO 113
<211> LENGTH: 21
<212> TYPE: DNA
<213> ORGANISM: Artificial Sequence
<220> FEATURE:
<223> OTHER INFORMATION: KCL-Inf-R

<400> SEQUENCE: 113 ggaggggggcg gccaccgtac g                                            21

<210> SEQ ID NO 114
<211> LENGTH: 48
<212> TYPE: DNA
<213> ORGANISM: Artificial Sequence
<220> FEATURE:
<223> OTHER INFORMATION: h1B0-LF

<400> SEQUENCE: 114
atctccggcg cgtacggcga cgtggtgatg acccagagcc ctctgtcc                48

<210> SEQ ID NO 115
<211> LENGTH: 44
<212> TYPE: DNA
<213> ORGANISM: Artificial Sequence
<220> FEATURE:
<223> OTHER INFORMATION: h1B0-LR

<400> SEQUENCE: 115
gggcggccac cgtacgcttg atctccacct tggtgcctcc gccg                    44

<210> SEQ ID NO 116
<211> LENGTH: 40
<212> TYPE: DNA
<213> ORGANISM: Artificial Sequence
<220> FEATURE:
<223> OTHER INFORMATION: h1B0-HF

<400> SEQUENCE: 116
ccagatgggt gctgagcgag gagcaagtgg tggagagcgg                         40

<210> SEQ ID NO 117
<211> LENGTH: 41
<212> TYPE: DNA
<213> ORGANISM: Artificial Sequence
<220> FEATURE:
<223> OTHER INFORMATION: h1B0-HR

<400> SEQUENCE: 117
cttggtggag gctgagctca cggtcaccat ggtgccttgt c                       41

<210> SEQ ID NO 118
<211> LENGTH: 752
<212> TYPE: DNA
<213> ORGANISM: Artificial Sequence
<220> FEATURE:
<223> OTHER INFORMATION: Nucleotide coding light chain of No.76 mIgG2a
<220> FEATURE:
<221> NAME/KEY: CDS
<222> LOCATION: (26)..(727)

<400> SEQUENCE: 118
ccagcctccg gactctagag ccacc atg gtg ctg cag acc cag gtg ttc atc     52
```

|     |     |     |     |     |     |     |     | Met<br>1 | Val | Leu | Gln | Thr<br>5 | Gln | Val | Phe | Ile |     |
| --- | --- | --- | --- | --- | --- | --- | --- | --- | --- | --- | --- | --- | --- | --- | --- | --- | --- |
| agc | ctg | ctg | ctg | tgg | atc | agc | ggc | gcc | tac | ggc | aac | atc | gtg | atg | acc |     | 100 |
| Ser<br>10 | Leu | Leu | Leu | Trp | Ile<br>15 | Ser | Gly | Ala | Tyr | Gly<br>20 | Asn | Ile | Val | Met | Thr<br>25 |     |     |
| cag | agc | ccc | aag | agc | atg | agc | atg | tcc | gtg | ggc | gag | aga | gtg | acc | ctg |     | 148 |
| Gln | Ser | Pro | Lys | Ser<br>30 | Met | Ser | Met | Ser | Val<br>35 | Gly | Glu | Arg | Val | Thr<br>40 | Leu |     |     |
| agc | tgc | aag | gcc | agc | gag | aac | gtg | ggc | aca | agc | gtg | tcc | tgg | tat | cag |     | 196 |
| Ser | Cys | Lys | Ala<br>45 | Ser | Glu | Asn | Val | Gly<br>50 | Thr | Ser | Val | Ser | Trp<br>55 | Tyr | Gln |     |     |
| gaa | aag | ccc | gag | cag | tcc | ccc | aag | ctg | ctg | atc | ttc | ggc | gcc | agc | aac |     | 244 |
| Glu | Lys | Pro<br>60 | Glu | Gln | Ser | Pro | Lys<br>65 | Leu | Leu | Ile | Phe | Gly<br>70 | Ala | Ser | Asn |     |     |
| aga | tac | acc | ggc | gtg | ccc | gat | aga | ttc | acc | ggc | agc | ggc | agc | gcc | acc |     | 292 |
| Arg | Tyr<br>75 | Thr | Gly | Val | Pro | Asp<br>80 | Arg | Phe | Thr | Gly | Ser<br>85 | Gly | Ser | Ala | Thr |     |     |
| gac | ttc | acc | ctg | aca | atc | agc | agc | gtg | cag | gcc | gag | gac | ctg | gcc | gat |     | 340 |
| Asp<br>90 | Phe | Thr | Leu | Thr | Ile<br>95 | Ser | Ser | Val | Gln | Ala<br>100 | Glu | Asp | Leu | Ala | Asp<br>105 |     |     |
| tat | cac | tgc | ggc | cag | agc | tac | agc | tac | ccc | tac | acc | ttt | ggc | ggc | agg |     | 388 |
| Tyr | His | Cys | Gly | Gln | Ser<br>110 | Tyr | Ser | Tyr | Pro | Tyr<br>115 | Thr | Phe | Gly | Gly | Arg<br>120 |     |     |
| acc | aag | ctg | gaa | atc | aag | cgg | gcc | gat | gcc | gcc | cct | acc | gtg | tcc | atc |     | 436 |
| Thr | Lys | Leu | Glu | Ile<br>125 | Lys | Arg | Ala | Asp | Ala<br>130 | Ala | Pro | Thr | Val | Ser<br>135 | Ile |     |     |
| ttt | cca | ccc | agc | agc | gag | cag | ctg | aca | agc | ggc | gga | gct | agc | gtc | gtg |     | 484 |
| Phe | Pro | Pro<br>140 | Ser | Ser | Glu | Gln | Leu<br>145 | Thr | Ser | Gly | Gly | Ala<br>150 | Ser | Val | Val |     |     |
| tgc | ttc | ctg | aac | aac | ttc | tac | ccc | aag | gac | atc | aac | gtg | aag | tgg | aag |     | 532 |
| Cys | Phe | Leu<br>155 | Asn | Asn | Phe | Tyr | Pro<br>160 | Lys | Asp | Ile | Asn | Val<br>165 | Lys | Trp | Lys |     |     |
| atc | gac | ggc | agc | gag | cgg | cag | aac | ggc | gtg | ctg | aat | agc | tgg | acc | gac |     | 580 |
| Ile | Asp<br>170 | Gly | Ser | Glu | Arg | Gln<br>175 | Asn | Gly | Val | Leu | Asn<br>180 | Ser | Trp | Thr | Asp<br>185 |     |     |
| cag | gac | agc | aag | gac | tcc | acc | tac | agc | atg | tcc | agc | acc | ctg | acc | ctg |     | 628 |
| Gln | Asp | Ser | Lys | Asp<br>190 | Ser | Thr | Tyr | Ser | Met<br>195 | Ser | Ser | Thr | Leu | Thr<br>200 | Leu |     |     |
| acc | aag | gac | gag | tac | gag | cgg | cac | aac | agc | tac | aca | tgc | gag | gcc | acc |     | 676 |
| Thr | Lys | Asp | Glu | Tyr<br>205 | Glu | Arg | His | Asn | Ser<br>210 | Tyr | Thr | Cys | Glu | Ala<br>215 | Thr |     |     |
| cac | aag | acc | agc | acc | agc | ccc | atc | gtg | aag | tcc | ttc | aac | cgg | aac | gag |     | 724 |
| His | Lys | Thr | Ser<br>220 | Thr | Ser | Pro | Ile | Val<br>225 | Lys | Ser | Phe | Asn | Arg<br>230 | Asn | Glu |     |     |
| tgc | tgagtttaaa cggggggaggc taact |     |     |     |     |     |     |     |     |     |     |     |     |     |     |     | 752 |
| Cys |     |     |     |     |     |     |     |     |     |     |     |     |     |     |     |     |     |

<210> SEQ ID NO 119
<211> LENGTH: 234
<212> TYPE: PRT
<213> ORGANISM: Artificial Sequence
<220> FEATURE:
<223> OTHER INFORMATION: Synthetic Construct

<400> SEQUENCE: 119

Met Val Leu Gln Thr Gln Val Phe Ile Ser Leu Leu Leu Trp Ile Ser
1               5                   10                  15

Gly Ala Tyr Gly Asn Ile Val Met Thr Gln Ser Pro Lys Ser Met Ser
            20                  25                  30

Met Ser Val Gly Glu Arg Val Thr Leu Ser Cys Lys Ala Ser Glu Asn

```
                35                  40                  45
Val Gly Thr Ser Val Ser Trp Tyr Gln Glu Lys Pro Glu Gln Ser Pro
 50                  55                  60
Lys Leu Leu Ile Phe Gly Ala Ser Asn Arg Tyr Thr Gly Val Pro Asp
 65                  70                  75                  80
Arg Phe Thr Gly Ser Gly Ser Ala Thr Asp Phe Thr Leu Thr Ile Ser
                 85                  90                  95
Ser Val Gln Ala Glu Asp Leu Ala Asp Tyr His Cys Gly Gln Ser Tyr
                100                 105                 110
Ser Tyr Pro Tyr Thr Phe Gly Gly Arg Thr Lys Leu Glu Ile Lys Arg
                115                 120                 125
Ala Asp Ala Ala Pro Thr Val Ser Ile Phe Pro Pro Ser Ser Glu Gln
130                 135                 140
Leu Thr Ser Gly Gly Ala Ser Val Val Cys Phe Leu Asn Asn Phe Tyr
145                 150                 155                 160
Pro Lys Asp Ile Asn Val Lys Trp Lys Ile Asp Gly Ser Glu Arg Gln
                165                 170                 175
Asn Gly Val Leu Asn Ser Trp Thr Asp Gln Asp Ser Lys Asp Ser Thr
                180                 185                 190
Tyr Ser Met Ser Ser Thr Leu Thr Leu Thr Lys Asp Glu Tyr Glu Arg
                195                 200                 205
His Asn Ser Tyr Thr Cys Glu Ala Thr His Lys Thr Ser Thr Ser Pro
                210                 215                 220
Ile Val Lys Ser Phe Asn Arg Asn Glu Cys
225                 230

<210> SEQ ID NO 120
<211> LENGTH: 1460
<212> TYPE: DNA
<213> ORGANISM: Artificial Sequence
<220> FEATURE:
<223> OTHER INFORMATION: Nucleotide coding heavy chain of No.76 mIgG2a
<220> FEATURE:
<221> NAME/KEY: CDS
<222> LOCATION: (26)..(1435)

<400> SEQUENCE: 120
ccagcctccg gactctagag ccacc atg aag cac ctg tgg ttc ttt ctg ctg      52
                            Met Lys His Leu Trp Phe Phe Leu Leu
                              1               5 ctg gtg gcc gct ccc aga tgg gtg ctg tct cag gtg cag ctg cag cag    100
Leu Val Ala Ala Pro Arg Trp Val Leu Ser Gln Val Gln Leu Gln Gln
 10                  15                  20                  25 cct ggc gcc gag ctc gtg aaa cct ggc gcc tct gtg aac ctg agc tgc    148
Pro Gly Ala Glu Leu Val Lys Pro Gly Ala Ser Val Asn Leu Ser Cys
                 30                  35                  40 aag agc agc ggc tac acc ttc acc aac tac tgg atc aac tgg gtc aag    196
Lys Ser Ser Gly Tyr Thr Phe Thr Asn Tyr Trp Ile Asn Trp Val Lys
             45                  50                  55 cag cgg cca ggc cag ggc ctg gaa tgg atc ggc gat atc tac ccc ggc    244
Gln Arg Pro Gly Gln Gly Leu Glu Trp Ile Gly Asp Ile Tyr Pro Gly
         60                  65                  70 acc agc acc acc aat tac aac gag aag ttc aag aac aag gcc acc ctg    292
Thr Ser Thr Thr Asn Tyr Asn Glu Lys Phe Lys Asn Lys Ala Thr Leu
     75                  80                  85 acc gtg gac acc agc tcc agc aca gcc tac atg cag ctg tcc agc ctg    340
Thr Val Asp Thr Ser Ser Ser Thr Ala Tyr Met Gln Leu Ser Ser Leu
 90                  95                 100                 105
```

-continued

| | | |
|---|---|---|
| acc agc gac gac agc gcc gtg tac tac tgc acc cgg atc tac tac gac<br>Thr Ser Asp Asp Ser Ala Val Tyr Tyr Cys Thr Arg Ile Tyr Tyr Asp<br>          110                 115                 120 | 388 |
| tac gac ggc tac tac ttc gac tac tgg ggc cag ggc aca acc ctg aca<br>Tyr Asp Gly Tyr Tyr Phe Asp Tyr Trp Gly Gln Gly Thr Thr Leu Thr<br>              125                 130                 135 | 436 |
| gtg tcc agc gcc aag acc acc gcc cct agc gtg tac cct ctg gct cct<br>Val Ser Ser Ala Lys Thr Thr Ala Pro Ser Val Tyr Pro Leu Ala Pro<br>          140                 145                 150 | 484 |
| gtg tgt ggc gat acc acc ggc agc tct gtg aca ctg ggc tgc ctc gtg<br>Val Cys Gly Asp Thr Thr Gly Ser Ser Val Thr Leu Gly Cys Leu Val<br>          155                 160                 165 | 532 |
| aag ggc tac ttc ccc gag cct gtg acc ctg aca tgg aac agc ggc agc<br>Lys Gly Tyr Phe Pro Glu Pro Val Thr Leu Thr Trp Asn Ser Gly Ser<br>170                 175                 180                 185 | 580 |
| ctg tct agc ggc gtg cac acc ttt cca gcc gtg ctg cag agc gac ctg<br>Leu Ser Ser Gly Val His Thr Phe Pro Ala Val Leu Gln Ser Asp Leu<br>              190                 195                 200 | 628 |
| tac acc ctg agc agc agc gtg acc gtg acc tcc agc acc tgg ccc agc<br>Tyr Thr Leu Ser Ser Ser Val Thr Val Thr Ser Ser Thr Trp Pro Ser<br>          205                 210                 215 | 676 |
| cag agc atc acc tgt aac gtg gcc cac cct gcc agc agc acc aag gtg<br>Gln Ser Ile Thr Cys Asn Val Ala His Pro Ala Ser Ser Thr Lys Val<br>          220                 225                 230 | 724 |
| gac aag aag atc gag ccc aga ggc ccc acc atc aag cct tgc ccc cct<br>Asp Lys Lys Ile Glu Pro Arg Gly Pro Thr Ile Lys Pro Cys Pro Pro<br>          235                 240                 245 | 772 |
| tgc aaa tgc cct gcc ccc aat ctg ctg ggc gga ccc agc gtg ttc atc<br>Cys Lys Cys Pro Ala Pro Asn Leu Leu Gly Gly Pro Ser Val Phe Ile<br>250                 255                 260                 265 | 820 |
| ttc cca ccc aag atc aag gac gtg ctg atg atc agc ctg agc ccc atc<br>Phe Pro Pro Lys Ile Lys Asp Val Leu Met Ile Ser Leu Ser Pro Ile<br>              270                 275                 280 | 868 |
| gtg acc tgc gtg gtg gtg gac gtg tcc gag gac gac ccc gat gtg cag<br>Val Thr Cys Val Val Val Asp Val Ser Glu Asp Asp Pro Asp Val Gln<br>          285                 290                 295 | 916 |
| atc agt tgg ttc gtg aac aac gtg gaa gtg cac acc gcc cag acc cag<br>Ile Ser Trp Phe Val Asn Asn Val Glu Val His Thr Ala Gln Thr Gln<br>          300                 305                 310 | 964 |
| aca cac aga gag gac tac aac agc acc ctg aga gtg gtg tcc gcc ctg<br>Thr His Arg Glu Asp Tyr Asn Ser Thr Leu Arg Val Val Ser Ala Leu<br>          315                 320                 325 | 1012 |
| ccc atc cag cac cag gat tgg atg agc ggc aaa gaa ttc aag tgc aaa<br>Pro Ile Gln His Gln Asp Trp Met Ser Gly Lys Glu Phe Lys Cys Lys<br>330                 335                 340                 345 | 1060 |
| gtg aac aac aag gac ctg cca gcc ccc atc gag cgg acc atc tct aag<br>Val Asn Asn Lys Asp Leu Pro Ala Pro Ile Glu Arg Thr Ile Ser Lys<br>              350                 355                 360 | 1108 |
| cct aag ggc agc gtg cgg gct ccc cag gtg tac gtg ctg cct cct cca<br>Pro Lys Gly Ser Val Arg Ala Pro Gln Val Tyr Val Leu Pro Pro Pro<br>          365                 370                 375 | 1156 |
| gag gaa gag atg acc aag aaa caa gtg aca ctg acc tgt atg gtc acc<br>Glu Glu Glu Met Thr Lys Lys Gln Val Thr Leu Thr Cys Met Val Thr<br>          380                 385                 390 | 1204 |
| gac ttc atg ccc gag gac atc tac gtg gaa tgg acc aac aac ggc aag<br>Asp Phe Met Pro Glu Asp Ile Tyr Val Glu Trp Thr Asn Asn Gly Lys<br>          395                 400                 405 | 1252 |
| acc gag ctg aac tac aag aac acc gag ccc gtg ctg gac tcc gat ggc<br>Thr Glu Leu Asn Tyr Lys Asn Thr Glu Pro Val Leu Asp Ser Asp Gly<br>410                 415                 420                 425 | 1300 |

```
agc tac ttc atg tac agc aag ctg cgg gtg gaa aag aaa aac tgg gtg      1348
Ser Tyr Phe Met Tyr Ser Lys Leu Arg Val Glu Lys Lys Asn Trp Val
                430                 435                 440 gaa cgg aac agc tac agc tgc tcc gtg gtg cac gag ggc ctg cac aat      1396
Glu Arg Asn Ser Tyr Ser Cys Ser Val Val His Glu Gly Leu His Asn
            445                 450                 455 cac cac acc aca aag agc ttc agc cgg acc ccc ggc aaa tgagtttaaa       1445
His His Thr Thr Lys Ser Phe Ser Arg Thr Pro Gly Lys
        460                 465                 470 cgggggaggc taact                                                     1460
```

<210> SEQ ID NO 121
<211> LENGTH: 470
<212> TYPE: PRT
<213> ORGANISM: Artificial Sequence
<220> FEATURE:
<223> OTHER INFORMATION: Synthetic Construct

<400> SEQUENCE: 121

```
Met Lys His Leu Trp Phe Phe Leu Leu Leu Val Ala Ala Pro Arg Trp
1               5                   10                  15

Val Leu Ser Gln Val Gln Leu Gln Gln Pro Gly Ala Glu Leu Val Lys
            20                  25                  30

Pro Gly Ala Ser Val Asn Leu Ser Cys Lys Ser Ser Gly Tyr Thr Phe
        35                  40                  45

Thr Asn Tyr Trp Ile Asn Trp Val Lys Gln Arg Pro Gly Gln Gly Leu
    50                  55                  60

Glu Trp Ile Gly Asp Ile Tyr Pro Gly Thr Ser Thr Asn Tyr Asn
65                  70                  75                  80

Glu Lys Phe Lys Asn Lys Ala Thr Leu Thr Val Asp Thr Ser Ser Ser
                85                  90                  95

Thr Ala Tyr Met Gln Leu Ser Ser Leu Thr Ser Asp Asp Ser Ala Val
            100                 105                 110

Tyr Tyr Cys Thr Arg Ile Tyr Tyr Asp Tyr Asp Gly Tyr Tyr Phe Asp
        115                 120                 125

Tyr Trp Gly Gln Gly Thr Thr Leu Thr Val Ser Ser Ala Lys Thr Thr
    130                 135                 140

Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Thr Ser Ser Thr Trp Pro Ser Gln Ser Ile Thr Cys Asn Val
    210                 215                 220

Ala His Pro Ala Ser Ser Thr Lys Val Asp Lys Lys Ile Glu Pro Arg
225                 230                 235                 240

Gly Pro Thr Ile Lys Pro Cys Pro Pro Cys Lys Cys Pro Ala Pro Asn
                245                 250                 255

Leu Leu Gly Gly Pro Ser Val Phe Ile Phe Pro Pro Lys Ile Lys Asp
            260                 265                 270

Val Leu Met Ile Ser Leu Ser Pro Ile Val Thr Cys Val Val Val Asp
        275                 280                 285
```

-continued

```
Val Ser Glu Asp Asp Pro Asp Val Gln Ile Ser Trp Phe Val Asn Asn
    290                 295                 300

Val Glu Val His Thr Ala Gln Thr Gln Thr His Arg Glu Asp Tyr Asn
305                 310                 315                 320

Ser Thr Leu Arg Val Val Ser Ala Leu Pro Ile Gln His Gln Asp Trp
                325                 330                 335

Met Ser Gly Lys Glu Phe Lys Cys Lys Val Asn Asn Lys Asp Leu Pro
            340                 345                 350

Ala Pro Ile Glu Arg Thr Ile Ser Lys Pro Lys Gly Ser Val Arg Ala
        355                 360                 365

Pro Gln Val Tyr Val Leu Pro Pro Glu Glu Glu Met Thr Lys Lys
    370                 375                 380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                405                 410                 415

Thr Glu Pro Val Leu Asp Ser Asp Gly Ser Tyr Phe Met Tyr Ser Lys
            420                 425                 430

Leu Arg Val Glu Lys Lys Asn Trp Val Glu Arg Asn Ser Tyr Ser Cys
        435                 440                 445

Ser Val Val His Glu Gly Leu His Asn His His Thr Thr Lys Ser Phe
    450                 455                 460

Ser Arg Thr Pro Gly Lys
465                 470

<210> SEQ ID NO 122
<211> LENGTH: 42
<212> TYPE: DNA
<213> ORGANISM: Artificial Sequence
<220> FEATURE:
<223> OTHER INFORMATION: H-R

<400> SEQUENCE: 122
cttggtggag gctgagctca cggtcacgag ggtgccctgg cc                          42

<210> SEQ ID NO 123
<211> LENGTH: 11
<212> TYPE: PRT
<213> ORGANISM: Artificial Sequence
<220> FEATURE:
<223> OTHER INFORMATION: CDRL1 of #4C13

<400> SEQUENCE: 123

Lys Ala Ser Glu Asn Val Gly Val Ser Val Ser
1               5                   10

<210> SEQ ID NO 124
<211> LENGTH: 7
<212> TYPE: PRT
<213> ORGANISM: Artificial Sequence
<220> FEATURE:
<223> OTHER INFORMATION: CDRL2 of #4C13

<400> SEQUENCE: 124

Gly Ala Ser Asn Arg Tyr Thr
1               5

<210> SEQ ID NO 125
<211> LENGTH: 9
<212> TYPE: PRT
<213> ORGANISM: Artificial Sequence
```

```
<220> FEATURE:
<223> OTHER INFORMATION: CDRL3 of #4C13

<400> SEQUENCE: 125

Gly Gln Ser Tyr Ser Tyr Pro Tyr Thr
1               5
```

ANTI-LPS O11 ANTIBODY

TECHNICAL FIELD

The present invention relates to a substance useful as a therapeutic and/or prophylactic agent for pseudomonal infection, and to a method for the treatment and/or prophylaxis of pseudomonal infection.

BACKGROUND ART

*Pseudomonas aeruginosa* is a species of typical resident microbiota which exists in the natural environment, and is well known as a pathogen causing opportunistic infections in immune-compromised humans. In addition, *Pseudomonas aeruginosa* is one of the species that are most problematic from the high isolation rate and mortality rate in healthcare-associated infections. It has been reported that the isolation rate for *Pseudomonas aeruginosa* is the sixth highest out of all healthcare-associated pathogenic infections and the second highest for patients having pneumonia derived from tracheal intubation, and the mortality rate due to *Pseudomonas aeruginosa* is 27.6-47.9% in bloodstream infections and 42.1-87% in tracheal intubation (Non-Patent Literatures 1 to 3). Further, since *Pseudomonas aeruginosa* originally had a high resistance to disinfectants and antibiotics and there are many strains that have acquired drug resistance, it is often difficult to treat the pseudomonal infections. Antimicrobial agents for *Pseudomonas aeruginosa* include carbapenems, cephems, penicillins, quinolones, and the like, and the resistance rate against these antimicrobial agents is a high rate such as 25.3%, 11.2%, 17.5%, and 30.7%, respectively (Non-Patent Literature 1). There is therefore a demand for a new anti-*pseudomonas aeruginosa* drug which is also effective against multidrug-resistant *Pseudomonas aeruginosa*, especially since there are almost no antimicrobial agents effective against multidrug-resistant bacteria showing a resistance to the above antimicrobial agents.

*Pseudomonas aeruginosa* is a gram-negative bacterium having a lipopolysaccharide (LPS) on the surface layer, and a sugar chain structure called O antigen outside of this LPS. The O-antigen has antigenicity and because of its diversity, it has been used as a classification method for bacterial strains (Non-Patent Literatures 4 and 5). In general 20 species of the LPS O antigen serotype of *Pseudomonas aeruginosa* are known, and in recent years, it has been reported that the strains having O11 antigen (O11 strains) occupy a high ratio in the multidrug-resistant *Pseudomonas aeruginosa*. In Japan there are reports that the isolation rates of O11 stains in the multidrug-resistant *Pseudomonas aeruginosa* were 99% or about 60%, and in Europe such as France, Belgium, and Czech Republic, there are also reports that a number of multidrug-resistant *Pseudomonas aeruginosa* strains were O11 strains (Non-Patent Literatures 6 to 11).

Antibodies are known to provide long-term protection against infection in vivo. Many antibodies against the LPS O antigens of *Pseudomonas aeruginosa* have been reported to exhibit a therapeutic efficacy by their opsonophagocytic killing activities on infections in an animal infectionmodel (Non-Patent Literatures 12 to 14). From this, such antibodies against the LPS O11 antigens of *Pseudomonas aeruginosa* are expected to be a new drug against multidrug-resistant *Pseudomonas aeruginosa*, and there are already some reports on anti-LPS O11 antibodies (Patent Literatures 1 and 2).

The present invention relates to a therapeutic and diagnostic antibody that targets the *Pseudomonas aeruginosa* O11 strain. The therapeutic and diagnostic antibody is desired to have a high activity, and its opsonophagocytic killing activity is important. Further, antibodies are known to have high antigen specificity, and those having a high coverage ratio capable of broadly covering the O11 strains are desired as a therapeutic and diagnostic antibodies. Since the present antibodies are antibodies to the LPS O11 antigens and show a stronger opsonophagocytic killing activity and a higher coverage ratio compared to conventional antibodies, they are more useful.

CITATION LIST

Patent Literature

Patent Literature 1: WO 2006/084758
Patent Literature 2: WO 2011/102551

Non-Patent Literature

Non-Patent Literature 1: Infect. Control Hosp. Epidemiol., 29, 996-1011 (2008)
Non-Patent Literature 2: DATAMONITOR, DMHC2281, Nosocomial infections (2007)
Non-Patent Literature 3: Chest, 139, 909-919 (2011)
Non-Patent Literature 4: Crit. Rev. Microbiol., 17, 273-304 (1990)
Non-Patent Literature 5: J. Endotoxin Res., 12, 324-335 (2006)
Non-Patent Literature 6: J. Clin. Microbiol., 45, 979-989 (2007)
Non-Patent Literature 7: Inter. J. Antimicrob. Agents, 39, 518-521 (2012)
Non-Patent Literature 8: J. Clin. Microbiol., 49, 2578-2583 (2011)
Non-Patent Literature 9: J. Antimicrob. Chemother., 65, 866-871 (2010)
Non-Patent Literature 10: Research in Microbiology, 161, 234-242 (2010)
Non-Patent Literature 11: PLoS ONE, 6, e25617 (2011)
Non-Patent Literature 12: Infect. Immun., 57, 174-179 (1989)
Non-Patent Literature 13: FEMS Microbiol. Immunol., 2, 263-268 (1990)
Non-Patent Literature 14: Infect. Immun., 66, 4137-4142 (1998)

SUMMARY OF THE INVENTION

Technical Problem

The purpose of the present invention is to provide a substance having superior antimicrobial activity against *Pseudomonas aeruginosa*, and to provide a therapeutic and/or prophylactic agent for pseudomonal infection.

Solution to the Problem

The present inventors made intensive studies in order to solve the above problem and as a result, they have succeeded in obtaining a novel antibody which specifically binds to the LPS O11 antigen of *Pseudomonas aeruginosa* and which has therapeutic and/or prophylactic effects on pseudomonal infection. The present invention has been completed based on these findings.

That is, the present invention encompasses the following inventions.

(1) An antibody, or an antigen-binding fragment thereof, that recognizes LPS of *Pseudomonas aeruginosa*, binds to O11 antigen and does not bind to O1, O2, O3, O4, O5, O6, O7, O8, O9, O10, O13, O14, O15, O16, O17, O18, O19, O20 antigens, and O antigen-deficient strain, and has a coverage ratio of 85% or more for the O11 clinical isolates.

(2) The antibody or an antigen-binding fragment thereof according to (1), wherein the coverage ratio for the O11 clinical isolates is 95% or more.

(3) An antibody, or an antigen-binding fragment thereof, that recognizes LPS of *Pseudomonas aeruginosa*, binds to the O11 antigen, and does not bind to O1, O2, O3, O4, O5, O6, O7, O8, O9, O10, O13, O14, O15, O16, O17, O18, O19, O20 antigens and O antigen-deficient strain, and exhibits 50% minimum growth inhibitory concentration of opsonophagocytic killing activity against *Pseudomonas aeruginosa* which is identified by ATCC 29260 is 12 ng/mL or less.

(4) The antibody or an antigen-binding fragment thereof according to (3), wherein the 50% minimum growth inhibitory concentration of opsonophagocytic killing activity against *Pseudomonas aeruginosa* identified by ATCC 29260 is 4.1 ng/mL or less.

(5) An antibody, or an antigen-binding fragment thereof, characterized in that it cross-competes with at least one of the antibodies selected from the group consisting of an antibody containing a heavy chain variable region sequence comprising amino acid residues 20 to 140 of the amino acid sequence shown in SEQ ID NO: 8 and a light chain variable region sequence comprising amino acid residues 21 to 129 of the amino acid sequence shown in SEQ ID NO: 4; an antibody containing a heavy chain variable region sequence comprising amino acid residues 20 to 144 of the amino acid sequence shown in SEQ ID NO: 16 and a light chain variable region sequence comprising amino acid residues 21 to 129 of the amino acid sequence shown in SEQ ID NO: 12; and an antibody containing a heavy chain variable region sequence comprising amino acid residues 20 to 140 of the amino acid sequence shown in SEQ ID NO: 24 and a light chain variable region sequence comprising 21 to 129 amino acid residues of the amino acid sequence shown in SEQ ID NO: 12.

(6) The antibody or an antigen-binding fragment thereof according to (5), characterized in that it binds to an epitope to which at least one antibody binds, wherein the antibody is selected from the group consisting of an antibody containing a heavy chain variable region sequence comprising amino acid residues 20 to 140 of the amino acid sequence shown in SEQ ID NO: 8 and a light chain variable region sequence comprising amino acid residues 21 to 129 of the amino acid sequence shown in SEQ ID NO: 4; an antibody containing a heavy chain variable region sequence comprising amino acid residues 20 to 144 of the amino acid sequence shown in SEQ ID NO: 16 and a light chain variable region sequence comprising amino acid residues 21 to 129 of the amino acid sequence shown in SEQ ID NO: 12; and an antibody containing a heavy chain variable region sequence comprising amino acid residues 20 to 140 of the amino acid sequence shown in SEQ ID NO: 24 and a light chain variable region sequence comprising amino acid residues 21 to 129 of the amino acid sequence shown in SEQ ID NO: 12.

(7) The antibody or an antigen-binding fragment thereof according to any one of (1) to (6), characterized in that:

the heavy chain sequence contains a variable region having CDRH1, CDRH2, and CDRH3, and the CDRH1 comprises the amino acid sequence shown in SEQ ID NO: 9, the CDRH2 comprises the amino acid sequence shown in SEQ ID NO: 10, and the CDRH3 comprises the amino acid sequence shown in SEQ ID NO: 11, and the light chain sequence contains a variable region having CDRL1, CDRL2, and CDRL3, and the CDRL1 comprises the amino acid sequence shown in SEQ ID NO: 5, the CDRL2 comprises the amino acid sequence shown in SEQ ID NO: 6, and the CDRL3 comprises the amino acid sequence shown in SEQ ID NO: 7.

(8) The antibody or an antigen-binding fragment thereof according to (7), characterized by containing a heavy chain variable region sequence comprising amino acid residues 20 to 140 of the amino acid sequence shown in SEQ ID NO: 8 and a light chain variable region sequence comprising amino acid residues 21 to 129 of the amino acid sequence shown in SEQ ID NO: 4.

(9) The antibody or an antigen-binding fragment thereof according to any one of (1) to (6), characterized in that:

the heavy chain sequence contains a variable region having CDRH1, CDRH2, and CDRH3, and the CDRH1 comprises the amino acid sequence shown in SEQ ID NO: 17, the CDRH2 comprises the amino acid sequence shown in SEQ ID NO: 18, and the CDRH3 comprises the amino acid sequence shown in SEQ ID NO: 19, and the light chain sequence contains a variable region having CDRL1, CDRL2, and CDRL3, and the CDRL1 comprises the amino acid sequence shown in SEQ ID NO: 13, the CDRL2 comprises the amino acid sequence shown in SEQ ID NO: 14, and the CDRL3 comprises the amino acid sequence shown in SEQ ID NO: 15.

(10) The antibody or an antigen-binding fragment thereof according to (9), characterized by containing a heavy chain variable region sequence comprising amino acid residues 20 to 144 of the amino acid sequence shown in SEQ ID NO: 16 and a light chain variable region sequence comprising amino acid residues 21 to 129 of the amino acid sequence shown in SEQ ID NO: 12.

(11) The antibody or an antigen-binding fragment of the antibody according to any one of (1) to (6), characterized in that:

the heavy chain sequence contains a variable region having CDRH1, CDRH2, and CDRH3, and the CDRH1 comprises the amino acid sequence shown in SEQ ID NO: 25, the CDRH2 comprises the amino acid sequence shown in SEQ ID NO: 26, and the CDRH3 comprises the amino acid sequence shown in SEQ ID NO: 27, and the light chain sequence contains a variable region having CDRL1, CDRL2, and CDRL3, and the CDRL1 comprises the amino acid sequence shown in SEQ ID NO: 13, the CDRL2 comprises the amino acid sequence shown in SEQ ID NO: 14, and the CDRL3 comprises the amino acid sequence shown in SEQ ID NO: 15.

(12) The antibody or an antigen-binding fragment thereof according to (11), characterized by containing a heavy chain variable region sequence comprising amino acid residues 20 to 140 of the amino acid sequence shown in SEQ ID NO: 24 and a light chain variable region sequence comprising amino acid residues 21 to 129 of the amino acid sequence shown in SEQ ID NO: 12.

(13) An antigen-binding fragment of the antibody according to any one of (1) to (12), characterized by being selected from the group consisting of Fab, F(ab')2, Fab' and Fv.

(14) The antibody according to any one of (1) to (12), characterized by being scFv.

(15) The antibody or an antigen-binding fragment thereof according to (1) to (12), characterized by being a chimeric antibody.

(16) The antibody or an antigen-binding fragment thereof according to (1) to (12), characterized by being a humanized antibody.

(17) The antibody according to any one of (1) to (16), wherein the heavy chain contains a constant region of a human immunoglobulin G1 heavy chain, and the light chain contains a constant region of a human immunoglobulin κ light chain.

(18) An antibody, or an antigen-binding fragment thereof, which has a binding activity to the LPS O11 antigen of *Pseudomonas aeruginosa* characterized in that the antibody contains:

(a) a heavy chain variable region sequence selected from the group consisting of the following amino acid sequences:

a1) an amino acid sequence comprising amino acid residues 20 to 144 of the amino acid sequence shown in SEQ ID NO: 57;

a2) an amino acid sequence comprising amino acid residues 20 to 144 of the amino acid sequence shown in SEQ ID NO: 59;

a3) an amino acid sequence comprising amino acid residues 20 to 144 of the amino acid sequence shown in SEQ ID NO: 61;

a4) an amino acid sequence comprising amino acid residues 20 to 144 of the amino acid sequence shown in SEQ ID NO: 63;

a5) an amino acid sequence comprising amino acid residues 20 to 144 of the amino acid sequence shown in SEQ ID NO: 65;

a6) an amino acid sequence having a homology of at least 95% with any one of the amino acid sequences selected from a1) to a5);

a7) an amino acid sequence having a homology of at least 99% with any one of the amino acid sequences selected from a1) to a5); and a8) an amino acid sequence including substitution, deletion, or addition of one to several amino acid residues in any one of the amino acid sequences selected from a1) to a5); and (b) a light chain variable region sequence selected from the group consisting of the following amino acid sequences:

b1) an amino acid sequence comprising amino acid residues 21 to 129 of the amino acid sequence shown in SEQ ID NO: 67;

b2) an amino acid sequence comprising amino acid residues 21 to 129 of the amino acid sequence shown in SEQ ID NO: 69;

b3) an amino acid sequence comprising amino acid residues 21 to 129 of the amino acid sequence shown in SEQ ID NO: 71;

b4) an amino acid sequence comprising amino acid residues 21 to 129 of the amino acid sequence shown in SEQ ID NO: 73;

b5) an amino acid sequence comprising amino acid residues 21 to 129 of the amino acid sequence shown in SEQ ID NO: 75;

b6) an amino acid sequence having a homology of at least 95% with any one of the amino acid sequences selected from b1) to b5);

b7) an amino acid sequence having a homology of at least 99% with any one of the amino acid sequences selected from b1) to b5); and b8) an amino acid sequence including substitution, deletion, or addition of one to several amino acid residues in any one of the amino acid sequences selected from b1) to b5).

(19) The antibody or an antigen-binding fragment thereof according to (18), characterized by containing a heavy chain variable region sequence comprising amino acid residues 20 to 144 of the amino acid sequence shown in SEQ ID NO: 59 and a light chain variable region sequence comprising amino acid residues 21 to 129 of the amino acid sequence shown in SEQ ID NO: 69.

(20) The antibody or an antigen-binding fragment thereof according to (18), characterized by containing a heavy chain variable region sequence comprising amino acid residues 20 to 144 of the amino acid sequence shown in SEQ ID NO: 61 and a light chain variable region sequence comprising amino acid residues 21 to 129 of the amino acid sequence shown in SEQ ID NO: 71.

(21) An antibody or an antigen-binding fragment thereof having a binding activity to the LPS O11 antigen of *Pseudomonas aeruginosa*, characterized by containing:

(a) a heavy chain variable region sequence selected from the group consisting of the following amino acid sequences:

a1) an amino acid sequence comprising amino acid residues 20 to 140 of the amino acid sequence shown in SEQ ID NO: 77;

a2) an amino acid sequence comprising amino acid residues 20 to 140 of the amino acid sequence shown in SEQ ID NO: 79;

a3) an amino acid sequence comprising amino acid residues 20 to 140 of the amino acid sequence shown in SEQ ID NO: 81;

a4) an amino acid sequence comprising amino acid residues 20 to 140 of the amino acid sequence shown in SEQ ID NO: 83;

a5) an amino acid sequence comprising amino acid residues 20 to 140 of the amino acid sequence shown in SEQ ID NO: 85;

a6) an amino acid sequence having a homology of at least 95% with any one of the amino acid sequences selected from a1) to a5);

a7) an amino acid sequence having a homology of at least 99% with any one of the amino acid sequences selected from a1) to a5); and a8) an amino acid sequence including substitution, deletion, or addition of one to several amino acid residues in any one of the amino acid sequences selected from a1) to a5); and (b) a light chain variable region sequence selected from the group consisting of the following amino acid sequences:

b1) an amino acid sequence comprising amino acid residues 21 to 129 of the amino acid sequence shown in SEQ ID NO: 67;

b2) an amino acid sequence comprising amino acid residues 21 to 129 of the amino acid sequence shown in SEQ ID NO: 69;

b3) an amino acid sequence comprising amino acid residues 21 to 129 of the amino acid sequence shown in SEQ ID NO: 71;

b4) an amino acid sequence comprising amino acid residues 21 to 129 of the amino acid sequence shown in SEQ ID NO: 73;

b5) an amino acid sequence comprising amino acid residues 21 to 129 of the amino acid sequence shown in SEQ ID NO: 75;

b6) an amino acid sequence having a homology of at least 95% with any one of the amino acid sequences selected from b1) to b5);

b7) an amino acid sequence having a homology of at least 99% with any one of the amino acid sequences selected from b1) to b5); and b8) an amino acid sequence including substitution, deletion, or addition of one to several amino acid residues in any one of the amino acid sequences selected from b1) to b5).

(22) The antibody or an antigen-binding fragment thereof according to (21), characterized by containing a heavy chain variable region sequence comprising amino acid residues 20 to 140 of the amino acid sequence shown in SEQ ID NO: 79 and a light chain variable region sequence comprising amino acid residues 21 to 129 of the amino acid sequence shown in SEQ ID NO: 69.

(23) The antibody or an antigen-binding fragment thereof according to (21), characterized by containing a heavy chain variable region sequence comprising amino acid residues 20 to 140 of the amino acid sequence shown in SEQ ID NO: 81 and a light chain variable region sequence comprising amino acid residues 21 to 129 of the amino acid sequence shown in SEQ ID NO: 71.

(24) The antibody according to any one of (18) to (23), comprising a heavy chain including deletion of one to several amino acids from the carboxyl terminus.

(25) A pharmaceutical composition comprising at least one of the antibody or the antigen-binding fragment thereof according to (1) to (24).

(26) The pharmaceutical composition according to (25), characterized by being a therapeutic and/or prophylactic agent for pseudomonal infection.

(27) A pharmaceutical composition for the treatment and/or prophylaxis of pseudomonal infection, characterized by comprising at least one of the antibody or antigen-binding fragment thereof according to any one of (1) to (24) and at least one selected from the group consisting of penicillin, cephem, carbapenem, monobactam, quinolone, aminoglycoside, polymyxin, rifampicin, and macrolide antimicrobial agents.

(28) The pharmaceutical composition according to (26) or (27), characterized in that the pseudomonal infection is a systemic infectious disease caused by a multidrug-resistant *Pseudomonas aeruginosa*.

(29) The pharmaceutical composition according to (26) or (27), characterized in that the pseudomonal infection is:

bloodstream infection, sepsis, meningitis, endocarditis, otitis media, sinusitis, pneumonia, lung abscess, empyema, chronic respiratory tract infection, peritonitis, post-operative infection, cholecystitis, cholangitis, eyelid tumor, dacryocystitis, conjunctivitis, corneal ulcer, corneal abscess, panophthalmitis, orbital infection, urinary tract infection, catheter infection, perianal abscess, secondary infection of burn wounds, decubitus infection, cystic fibrosis disease, lymphangitis, lymphadenitis, osteomyelitis, arthritis, tonsillitis, liver abscess, skin and soft tissue infections, intrauterine infection, uterine adnexitis, parametritis, perimandibular phlegmon, or jaw inflammation.

(30) The pharmaceutical composition according to (26) or (27), characterized in that the pseudomonal infection is pneumonia.

(31) A method for the treatment and/or prophylaxis of pseudomonal infection, characterized by administering at least one of the antibody, or the antigen-binding fragment thereof, according to (1) to (24), or the pharmaceutical composition according to (26) or (27).

(32) A method for the treatment and/or prophylaxis of pseudomonal infection, characterized by simultaneously or sequentially administering at least one of the antibodies or the antigen-binding fragment thereof according to any one of (1) to (24), or the pharmaceutical composition according to (26), and at least one selected from the group consisting of penicillin, cephem, carbapenem, monobactam, quinolone, aminoglycoside, polymyxin, rifampicin, and macrolide antimicrobial agents.

(33) The method for the treatment and/or prophylaxis of pseudomonal infection according to (31) or (32), characterized in that the pseudomonal infection is a systemic infectious disease caused by a multidrug-resistant *Pseudomonas aeruginosa*.

(34) The method for the treatment and/or prophylaxis of pseudomonal infection according to (33), characterized in that the pseudomonal infection is bloodstream infection, sepsis, meningitis, endocarditis, otitis media, sinusitis, pneumonia, lung abscess, empyema, chronic respiratory tract infection, peritonitis, post-operative infection, cholecystitis, cholangitis, eyelid tumor, dacryocystitis, conjunctivitis, corneal ulcer, corneal abscess, panophthalmitis, orbital infection, urinary tract infection, catheter infection, perianal abscess, secondary infection of burn wounds, decubitus infection, cystic fibrosis disease, lymphangitis, lymphadenitis, osteomyelitis, arthritis, tonsillitis, liver abscess, skin and soft tissue infections, intrauterine infection, uterine adnexitis, parametritis, perimandibular phlegmon, or jaw inflammation.

(35) The method for the treatment and/or prophylaxis of pseudomonal infection according to (33), characterized in that the pseudomonal infection is pneumonia.

(36) A diagnostic agent for pseudomonal infection, characterized by containing at least one of the antibodies or the antigen-binding fragments thereof according to (1) to (24).

(37) A detection kit for *Pseudomonas aeruginosa*, characterized by containing at least one of the antibodies or the antigen-binding fragments thereof according to (1) to (24).

(38) A polynucleotide encoding any one of the antibodies according to (1) to (24).

(39) The polynucleotide according to (38), characterized by containing:

(a) a polynucleotide selected from the group consisting of the following nucleotide sequences:

a1) a nucleotide sequence comprising nucleotides 58 to 432 of the nucleotide sequence shown in SEQ ID NO: 56;

a2) a nucleotide sequence comprising nucleotides 58 to 432 of the nucleotide sequence shown in SEQ ID NO: 58;

a3) a nucleotide sequence comprising nucleotides 58 to 432 of the nucleotide sequence shown in SEQ ID NO: 60;

a4) a nucleotide sequence comprising nucleotides 58 to 432 of the nucleotide sequence shown in SEQ ID NO: 62;

a5) a nucleotide sequence comprising nucleotides 58 to 432 of the nucleotide sequence shown in SEQ ID NO: 64;

a6) a nucleotide sequence having a homology of at least 95% with any one of the nucleotide sequences selected from a1) to a5);

a7) a nucleotide sequence having a homology of at least 99% with any one of the nucleotide sequences selected from a1) to a5);

a8) a nucleotide sequence of a polynucleotide which hybridizes to a polynucleotide comprising a nucleotide sequence complementary to any one of the nucleotide sequences selected from a1) to a5) under stringent conditions; and a9) a nucleotide sequence including substitution, deletion, or addition of one to several nucleotides in any one of the nucleotide sequences selected from a1) to a5); and (b) a polynucleotide selected from the group consisting of the following nucleotide sequences:

b1) a nucleotide sequence comprising nucleotides 61 to 387 of the nucleotide sequence shown in SEQ ID NO: 66;

b2) a nucleotide sequence comprising nucleotides 61 to 387 of the nucleotide sequence shown in SEQ ID NO: 68;

b3) a nucleotide sequence comprising nucleotides 61 to 387 of the nucleotide sequence shown in SEQ ID NO: 70;

b4) a nucleotide sequence comprising nucleotides 61 to 387 of the nucleotide sequence shown in SEQ ID NO: 72;

b5) a nucleotide sequence comprising nucleotides 61 to 387 of the nucleotide sequence shown in SEQ ID NO: 74;

b6) a nucleotide sequence having a homology of at least 95% with any one of the nucleotide sequences selected from b1) to b5);

b7) a nucleotide sequence having a homology of at least 99% with any one of the nucleotide sequences selected from b1) to b5);

b8) a nucleotide sequence of a polynucleotide which hybridizes to a polynucleotide comprising a nucleotide sequence complementary to any one of the nucleotide sequences selected from b1) to b5) under stringent conditions; and b9) a nucleotide sequence including substitution, deletion, or addition of one to several nucleotides in any one of the nucleotide sequences selected from b1) to b5).

(40) The polynucleotide according to (39), characterized by containing a polynucleotide comprising nucleotides 58 to 432 of the nucleotide sequence shown in SEQ ID NO: 58 and a polynucleotide comprising nucleotides 61 to 387 of the nucleotide sequence shown in SEQ ID NO: 68.

(41) The polynucleotide according to (39), characterized by containing a polynucleotide comprising nucleotides 58 to 432 of the nucleotide sequence shown in SEQ ID NO: 60 and a polynucleotide comprising nucleotides 61 to 387 of the nucleotide sequence shown in SEQ ID NO: 70.

(42) The polynucleotide according to (38), characterized by containing:

(a) a polynucleotide selected from the group consisting of the following nucleotide sequences:

a1) a nucleotide sequence comprising nucleotides 58 to 420 of the nucleotide sequence shown in SEQ ID NO: 76;

a2) a nucleotide sequence comprising nucleotides 58 to 420 of the nucleotide sequence shown in SEQ ID NO: 78;

a3) a nucleotide sequence comprising nucleotides 58 to 420 of the nucleotide sequence shown in SEQ ID NO: 80;

a4) a nucleotide sequence comprising nucleotides 58 to 420 of the nucleotide sequence shown in SEQ ID NO: 82;

a5) a nucleotide sequence comprising nucleotides 58 to 420 of the nucleotide sequence shown in SEQ ID NO: 84;

a6) a nucleotide sequence having a homology of at least 95% with any one of the nucleotide sequences selected from a1) to a5);

a7) a nucleotide sequence having a homology of at least 99% with any one of the nucleotide sequences selected from a1) to a5);

a8) a nucleotide sequence of a polynucleotide which hybridizes to a polynucleotide comprising a nucleotide sequence complementary to any one of the nucleotide sequences selected from a1) to a5) under stringent conditions; and a9) a nucleotide sequence including substitution, deletion, or addition of one to several nucleotides in any one of the nucleotide sequences selected from a1) to a5); and (b) a polynucleotide selected from the group consisting of the following nucleotide sequences:

b1) a nucleotide sequence comprising nucleotides 61 to 387 of the nucleotide sequence shown in SEQ ID NO: 66;

b2) a nucleotide sequence comprising nucleotides 61 to 387 of the nucleotide sequence shown in SEQ ID NO: 68;

b3) a nucleotide sequence comprising nucleotides 61 to 387 of the nucleotide sequence shown in SEQ ID NO: 70;

b4) a nucleotide sequence comprising nucleotides 61 to 387 of the nucleotide sequence shown in SEQ ID NO: 72;

b5) a nucleotide sequence comprising nucleotides 61 to 387 of the nucleotide sequence shown in SEQ ID NO: 74;

b6) a nucleotide sequence having a homology of at least 95% with any one of the nucleotide sequences selected from b1) to b5);

b7) a nucleotide sequence having a homology of at least 99% with any one of the nucleotide sequences selected from b1) to b5);

b8) a nucleotide sequence of a polynucleotide which hybridizes to a polynucleotide comprising a nucleotide sequence complementary to any one of the nucleotide sequences selected from b1) to b5) under stringent conditions; and b9) a nucleotide sequence including substitution, deletion, or addition of one to several nucleotides in any one of the nucleotide sequences selected from b1) to b5).

(43) The polynucleotide according to (42), characterized by containing a polynucleotide comprising nucleotides 58 to 420 of the nucleotide sequence shown in SEQ ID NO: 78 and a polynucleotide comprising nucleotides 61 to 387 of the nucleotide sequence shown in SEQ ID NO: 68.

(44) The polynucleotide according to (42), characterized by containing a polynucleotide comprising nucleotides 58 to 420 of the nucleotide sequence shown in SEQ ID NO: 80 and a polynucleotide comprising nucleotides 61 to 387 of the nucleotide sequence shown in SEQ ID NO: 70.

(45) A vector containing any one of the polynucleotides according to (38) to (44).

(46) A transformed host cell containing any one of the polynucleotides according to (38) to (44).

(47) A transformed host cell containing the vector according to (45).

(48) A method for producing the antibody according to any one of (1) to (24), containing the steps of culturing the host cell according to (46) or (47) and purifying the antibody from the resulting cultured product.

Advantageous Effects of the Invention

According to the present invention, it is possible to obtain a therapeutic and/or prophylactic agent for a pseudomonal infection that is a systemic infectious disease caused by *Pseudomonas aeruginosa* including a multidrug-resistant *Pseudomonas aeruginosa*.

BRIEF DESCRIPTION OF DRAWINGS

FIG. 1 shows the amino acid sequence of each CDR sequence of No.76 antibody.

FIG. 2 shows the amino acid sequence of each CDR sequence of #1G5 antibody.

FIG. 3 shows the amino acid sequence of each CDR sequence of #4C12 antibody.

FIG. 9 shows the nucleotide sequence and the amino acid sequence of h#1G5-H1.

FIG. 10 shows the nucleotide sequence and the amino acid sequence of h#1G5-H2.

FIG. 11 shows the nucleotide sequence and the amino acid sequence of h#1G5-H3.

FIG. 12 shows the nucleotide sequence and the amino acid sequence of h#1G5-H4.

FIG. 13 shows the nucleotide sequence and the amino acid sequence of h#1G5-H5.

FIG. 14 shows the nucleotide sequence and the amino acid sequence of h#1G5-L1.

FIG. 15 shows the nucleotide sequence and the amino acid sequence of h#1G5-L2.

FIG. 16 shows the nucleotide sequence and the amino acid sequence of h#1G5-L3.

FIG. 17 shows the nucleotide sequence and the amino acid sequence of h#1G5-L4.

FIG. 18 shows the nucleotide sequence and the amino acid sequence of h#1G5-L5.

FIG. 19 shows the nucleotide sequence and the amino acid sequence of h#4C13K-H1.

FIG. 20 shows the nucleotide sequence and the amino acid sequence of h#4C13K-H2.

FIG. 21 shows the nucleotide sequence and the amino acid sequence of h#4C13K-H3.

FIG. 22 shows the nucleotide sequence and the amino acid sequence of h#4C13K-H4.

FIG. 23 shows the nucleotide sequence and the amino acid sequence of h#4C13K-H5.

FIG. 24 shows the amino acid sequence of each CDR sequence of #4C13 antibody.

FIG. 28 is a graph showing the competitive test with No.76 mIgG2a.

DESCRIPTION OF EMBODIMENTS

1. Definition

Figure 4:
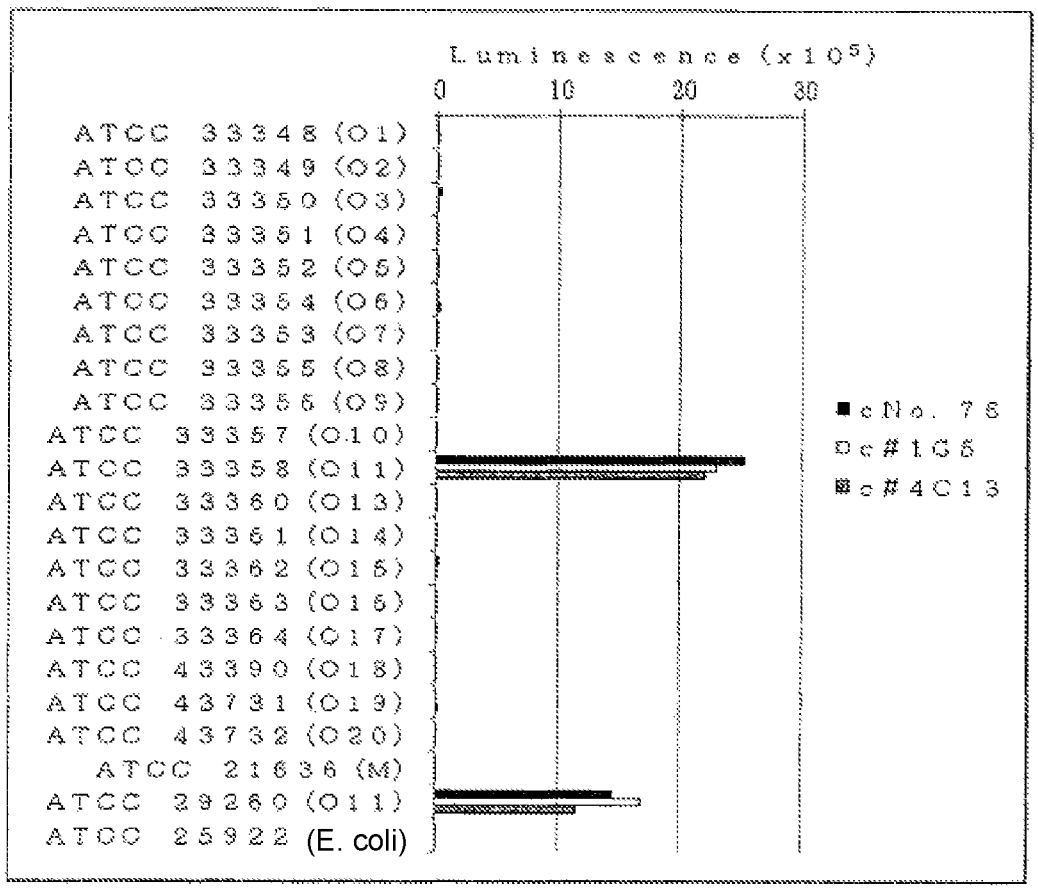
FIG. 4 is a graph showing the binding specificity to *Pseudomonas aeruginosa* O11 strains.

The term "gene" as used herein includes not only DNA, but also mRNA, cDNA, and cRNA.

The term "polynucleotide" as used herein is used with the same meaning as a "nucleic acid" and also includes DNA, RNA, probes, oligonucleotides, and primers.

The terms "polypeptide" and "protein" as used herein are used without distinction.

The term "RNA fraction" as used herein refers to a fraction containing RNA.

The term "cell" as used herein includes cells in an animal individual and also cultured cells.

The term "LPS" as used herein is used with the same meaning as a "lipopolysaccharide".

The term "serotype" as used herein refers to any known serotype of Pseudomonas aeruginosa.

The term "multidrug-resistant" as used herein means "resistant to all of the three series of carbapenems (imipenem or meropenem), quinolones (ciprofloxacin or levofloxacin), and aminoglycosides (tobramycin or amikacin)". The sensitivity of each drug was determined based on the breakpoints of Clinical and Laboratory Standards Institute (CLSI).

The term "O11 clinical isolate" as used herein means a positive strain by a commercially available immune serum for grouping Pseudomonas aeruginosa specific to the O11 antigen or by PCR using O11 antigen-specific primers.

The term "healthcare-associated infection" is also known as nosocomial infection or hospital-acquired infection, and means a newly acquired disease separate from an underlying disease in patients in a medical institution or in medical care at home, and an infection in health care workers affected in a medical institution or in medical care at home.

The term "antigen-binding fragment of an antibody" as used herein is also called as "functional fragment of an antibody" and refers to a partial fragment of an antibody having an antigen binding activity and includes Fab, F(ab')2, Fv, scFv, diabody, linear antibodies, polyspecific antibodies formed from antibody fragments, and the like. The term also encompasses Fab' which is a monovalent fragment in a variable region of an antibody obtained by treating F(ab')2 under reducing conditions. However, the term is not limited to these molecules as long as the fragment has a binding affinity for an antigen. Further, these antigen-binding fragments include not only a fragment obtained by treating a full-length molecule of an antibody protein with an appropriate enzyme, but also a protein produced in an appropriate host cell using a genetically modified antibody gene.

The term "epitope" as used herein refers to a partial structure of the LPS O11 antigen to which a specific anti-LPS O11 antibody binds. Since the O11 antigen is a repeating structure composed of three sugars (Microbiol. Mol. Biol. Rev. 63, 523-553 (1999)), it is possible to determine the epitope by synthesizing sugar chains of different lengths and examining the reactivity of the antibodies to such sugars. Further, the epitope which is a partial tertiary structure of the LPS O11 antigen that binds to a specific anti-LPS O11 antibody can be determined by specifying the structure of the LPS O11 antigen adjacent to the antibody by X-ray crystallography. If the second anti-LPS O11 antibody binds to the binding partial sugar chains of the first anti-LPS O11 antibody, the first antibody and the second antibody can be determined to have a common epitope. In addition, by confirming that the second anti-LPS O11 antibody cross-competes for binding to the LPS O11 antigen of the first anti-LPS O11 antibody (i.e., the second antibody interferes with the binding between the first antibody and the LPS O11 antigen), the first antibody and the second antibody can be determined to have a common epitope, even if specific sequence or structure of the epitope is not determined. Furthermore, if the first antibody and the second antibody bind to a common epitope and the first antibody has a special effect such as neutralizing activity to the antigen, the second antibody can be expected to also have the same activity.

It is known that each heavy and light chain of an antibody molecule has three complementarity determining regions (CDRs). The complementarity determining region is also called the hypervariable domain and is present in a variable region of each heavy and light chain of an antibody. Such a region is a site which has unusually high variability in its primary structure, and there are three separate CDRs in the primary structure of each heavy and light polypeptide chain. In this description, as for the complementarity determining regions of an antibody, the complementarity determining regions of the heavy chain are represented by CDRH1, CDRH2, and CDRH3 from the amino terminus of the amino acid sequence of the heavy chain, and the complementarity determining regions of the light chain are represented by CDRL1, CDRL2, and CDRL3 from the amino terminus of the amino acid sequence of the light chain. These regions are proximate to one another in the tertiary structure and determine the specificity for an antigen to which the antibody binds.

The phrase "hybridization is performed under stringent conditions" as used herein refers to hybridization that is performed under conditions under which identification can be achieved by performing hybridization at 68° C. in a commercially available hybridization solution, ExpressHyb Hybridization Solution (manufactured by Clontech, Inc.) or performing hybridization at 68° C. in the presence of 0.7 to 1.0 M NaCl using a filter having DNA immobilized thereon, followed by washing at 68° C. using 0.1 to 2-fold SSC solution (1-fold SSC solution is composed of 150 mM NaCl and 15 mM sodium citrate) or under conditions equivalent thereto.

As used herein, the term "several" in the description of "one to several" and "one or several" refers to from 2 to 10. Such term is preferably 10 or less, more preferably 5 or 6 or less, and furthermore preferably 2 or 3.

2. LPS O11

"LPS" to which an antibody of the present invention binds is a component of Gram-negative bacteria cell wall outer membrane and is a substance (glycolipid) composed of lipids and polysaccharides. A sugar chain portion is composed of a portion called a core polysaccharide (or core oligosaccharide) and a portion called O-antigen (O-side chain polysaccharides).

For different serotypes of *Pseudomonas aeruginosa*, there is typing by IATS (International Antigenic Typing System), and a grouping by the Serotyping Committee of *Pseudomonas Aeruginosa* (Japan *Pseudomonas Aeruginosa* Society, JPAS). Table 1 shows the correspondence relation of typing according to IATS and grouping by JPAS. Serotypes of *Pseudomonas aeruginosa* can be determined by using commercially available immune serums for grouping *Pseudomonas aeruginosa*.

TABLE 1

| IATS | JPAS |
|------|------|
| O1   | I    |
| O2   | B    |
| O3   | A    |
| O4   | F    |
| O5   | B    |
| O6   | G    |
| O7   | C    |
| O8   | C    |
| O9   | D    |
| O10  | H    |
| O11  | E    |
| O12  | L    |
| O13  | K    |
| O14  | K    |
| O15  | J    |
| O16  | B    |
| O17  | N    |
| O18  | —    |

TABLE 1-continued

| IATS | JPAS |
|------|------|
| O19  | —    |
| O20  | B    |

In recent years, the ratio of the strains having the O11 antigen (O11 strains) in multidrug-resistant *Pseudomonas aeruginosa* has been reported to be high. *Pseudomonas aeruginosa* of the LPS O11 serotype includes, for example, ATCC accession numbers 26290, 33358, etc.

3. Production of Anti-LPS O11 Antibody

An antibody against the LPS O11 antigen of *Pseudomonas aeruginosa* according to the present invention can be obtained, for example, by the method described in WO 2009/091048, WO 2011/027808, or WO 2012/133572. That is, a plasma cell and/or a plasmablast that specifically binds to a target antigen is selected by immunizing a non-human animal to the target antigen and collecting lymph fluid, lymphoid tissue, blood cell sample, or bone marrow derived cells from the non-human animal once immunization has been established. The antibody genes against the target antigen are collected from the plasma cells and/or plasmablasts obtained and the base sequence is identified, thereby to be able to obtain the antibody or a fragment of the antibody based on the base sequence of the identified gene. Moreover, by obtaining the plasma cells and/or plasmablasts similarly from blood of infected human patients, it is possible to obtain an antibody or antibody fragment. An antibody applicable to human disease can be obtained by testing the obtained antibody on the binding to the LPS O11 antigen. The monoclonal antibodies obtained in this way include No.76, #1G5, #4C12, #4C13, and #4C13K. The heavy chains of #4C12, #4C13, and #4C13K are identical with one another. #4C13 is an antibody wherein the amino acid No. 75 cysteine in the light chain of #4C12 is substituted by tyrosine, and #4C13K is an antibody wherein the light chain of #4C12 is substituted by the light chain of #1G5.

Further, a monoclonal antibody can be obtained by fusing antibody-producing cells which produce an antibody against an LPS O11 antigen with myeloma cells to establish a hybridoma according to a known method (for example, Kohler and Milstein, Nature, (1975) 256, pp. 495-497; Kennet, R. ed., Monoclonal Antibodies, pp. 365-367, Plenum Press, N.Y. (1980)). A specific example of such a method is described in WO 2009/48072 (published on Apr. 16, 2009) and WO 2010/117011 (published on Oct. 14, 2010). However, the method of obtaining monoclonal antibodies corresponds to a field which has been well established, and is not limited to the above specific example.

The antibody of the present invention includes not only the above-mentioned monoclonal antibody against the LPS O11 antigen but also a recombinant antibody obtained by artificial modification for the purpose of decreasing heterologous antigenicity to human such as a chimeric antibody, a humanized antibody and a human antibody. These antibodies can be produced using a known method.

An example of a chimeric antibody is an antibody in which antibody variable and constant regions are derived from different species, for example, a chimeric antibody in which a mouse- or rat-derived antibody variable region is joined to a human-derived constant region (see Proc. Natl. Acad. Sci. USA, 81, 6851-6855, (1984)). One example of a chimeric antibody derived from No.76 is an antibody containing a heavy chain having an amino acid sequence comprising amino acid residues 20 to 470 of SEQ ID NO: 33 in the Sequence Listing and a light chain having an amino acid sequence comprising amino acid residues 21 to 234 of SEQ ID NO: 31; one example of a chimeric antibody derived from #1G5 is an antibody containing a heavy chain having an amino acid sequence comprising amino acid residues 20 to 474 of SEQ ID NO: 37 in the Sequence Listing and a light chain having an amino acid sequence comprising amino acid residues 21 to 234 of SEQ ID NO: 35; and one example of a chimeric antibody derived from #4C13 is an antibody containing a heavy chain having an amino acid sequence comprising amino acid residues 20 to 470 of SEQ ID NO: 41 in the Sequence Listing and a light chain having an amino acid sequence comprising amino acid residues 21 to 234 of SEQ ID NO: 39.

An example of a humanized antibody is an antibody obtained by integrating only the CDRs into a human-derived antibody (see Nature (1986) 321, pp. 522-525), and an antibody obtained by grafting a part of the amino acid residues of the framework as well as the CDR sequence to a human antibody by a CDR-grafting method (WO 90/07861).

Humanized antibodies derived from the antibody No.76 are included in the antibodies of the present invention as long as the humanized antibodies carry all six CDR sequences of No.76 and have a binding activity to the LPS O11 antigen of *Pseudomonas aeruginosa*. In addition, the heavy chain variable region of No.76 antibody carries CDRH1 (NYWIN) comprising the amino acid sequence shown in SEQ ID NO: 9, CDRH2 (DIYPGTSTTNYNEKFKN) comprising the amino acid sequence shown in SEQ ID NO: 10, and CDRH3 (IYYDYDGYYFDY) comprising the amino acid sequence shown in SEQ ID NO: 11. Further, the light chain variable region of No.76 antibody carries CDRL1 (KASENVGTSVS) comprising the amino acid sequence shown in SEQ ID NO: 5, CDRL2 (GASNRYT) comprising the amino acid sequence shown in SEQ ID NO: 6, and CDRL3 (GQSYSYPYT) comprising the amino acid sequence shown in SEQ ID NO: 7. The amino acid sequences of these CDRs are also shown in FIG. 1.

Humanized antibodies derived from the #1G5 antibody are included in the antibodies of the present invention as long as the humanized antibodies carry all six CDR sequences of #1G5 and have a binding activity to the LPS O11 antigen of *Pseudomonas aeruginosa*. In addition, the heavy chain variable region of the #1G5 antibody carries CDRH1 (SYWIN) comprising the amino acid sequence shown in SEQ ID NO: 17, CDRH2 (NIYPGSSSINYNEKFKS) comprising the amino acid sequence shown in SEQ ID NO: 18, and CDRH3 (TIYNYGSSGYNYAMDY) comprising the amino acid sequence shown in SEQ ID NO: 19. Moreover, the light chain variable region of the #1G5 antibody carries CDRL1 (KASENVGNSVS) comprising the amino acid sequence shown in SEQ ID NO: 13, CDRL2 (GASNRYT) comprising the amino acid sequence shown in SEQ ID NO: 14, and CDRL3 (GQSYSYPYT) comprising the amino acid sequence shown in SEQ ID NO: 15. The amino acid sequences of these CDRs are also shown in FIG. 2.

Humanized antibodies derived from the #4C12 antibody are included in the antibodies of the present invention as long as the humanized antibodies carry all six CDR sequences of #4C12 and have a binding activity to the LPS O11 antigen of *Pseudomonas aeruginosa*. In addition, the heavy chain variable region of the #4C12 antibody carries CDRH1 (TYWIN) comprising the amino acid sequence shown in SEQ ID NO: 25, CDRH2 (NIYPGTRSSNYNEKFKN) comprising the amino acid sequence shown in SEQ ID NO: 26, and CDRH3 (VYYDHVGYYFDY) comprising the amino acid sequence shown in SEQ ID NO: 27. Moreover, the light chain variable region of the #4C12 antibody carries CDRL1 (KASENVGVSVS) comprising the amino acid sequence shown in SEQ ID NO: 21, CDRL2 (GASNRCT) comprising the amino acid sequence shown in SEQ ID NO: 22, and CDRL3 (GQSYSYPYT) comprising the amino acid sequence shown in SEQ ID NO: 23. The amino acid sequences of these CDRs are also shown in FIG. 3.

Humanized antibodies derived from the #4C13 antibody are included in the antibodies of the present invention as long as the humanized antibodies carry all six CDR sequences of #4C13 and have a binding activity to the LPS O11 antigen of *Pseudomonas aeruginosa*. In addition, the heavy chain variable region of the #4C13 antibody carries CDRH1 (TYWIN) comprising the amino acid sequence shown in SEQ ID NO: 86, CDRH2 (NIYPGTRSSNYNEKFKN) comprising the amino acid sequence shown in SEQ ID NO: 87, and CDRH3 (VYYDHVGYYFDY) comprising the amino acid sequence shown in SEQ ID NO: 88. Moreover, the light chain variable region of the #4C13 antibody carries CDRL1 (KASENVGVSVS) comprising the amino acid sequence shown in SEQ ID NO: 123, CDRL2 (GASNRYT) comprising the amino acid sequence shown in SEQ ID NO: 124, and CDRL3 (GQSYSYPYT) comprising the amino acid sequence shown in SEQ ID NO: 125. The amino acid sequences of these CDRs are also shown in FIG. 24.

Humanized antibodies derived from the #4C13K antibody are included in the antibodies of the present invention as long as the humanized antibodies carry all six CDR sequences of #4C13K and have a binding activity to the LPS O11 antigen of *Pseudomonas aeruginosa*. In addition, the heavy chain variable region of the #4C13K antibody carries CDRH1 (TYWIN) comprising the amino acid sequence shown in SEQ ID NO: 86, CDRH2 (NIYPGTRSSNYNEKFKN) comprising the amino acid sequence shown in SEQ ID NO: 87, and CDRH3 (VYYDHVGYYFDY) comprising the amino acid sequence shown in SEQ ID NO: 88. Moreover, the light chain variable region of the #4C13K antibody is completely common with that of the #1G5 antibody, and carries CDRL1 (KASENVGNSVS) comprising the amino acid sequence shown in SEQ ID NO: 13, CDRL2 (GASNRYT) comprising the amino acid sequence shown in SEQ ID NO: 14, and CDRL3 (GQSYSYPYT) comprising the amino acid sequence shown in SEQ ID NO: 15. The amino acid sequences of these CDRs are also shown in FIG. 24 and FIG. 2.

In addition, CDR-modified humanized antibodies obtained by substituting 1 to 3 amino acid residues in each CDR with other amino acid residues are also included in the antibodies of the present invention as long as such humanized antibodies have a binding activity to the LPS O11 antigen of *Pseudomonas aeruginosa*.

Examples of humanized antibodies derived from the #1G5 antibody include an arbitrary combination of a heavy chain containing a heavy chain variable region comprising an amino acid sequence comprising amino acid residues 20 to 144 of the amino acid sequence shown in SEQ ID NO: 57 in the Sequence Listing, an amino acid sequence comprising amino acid residues 20 to 144 of the amino acid sequence shown in SEQ ID NO: 59, an amino acid sequence comprising amino acid residues 20 to 144 of the amino acid sequence shown in SEQ ID NO: 61, an amino acid sequence comprising amino acid residues 20 to 144 of the amino acid sequence shown in SEQ ID NO: 63, or an amino acid sequence comprising amino acid residues 20 to 144 of the amino acid sequence shown in SEQ ID NO: 65 and a light chain containing a light chain variable region comprising an amino acid sequence comprising amino acid residues 21 to 129 of the amino acid sequence shown in SEQ ID NO: 67, an amino acid sequence comprising amino acid residues 21 to 129 of the amino acid sequence shown in SEQ ID NO: 69, an amino acid sequence comprising amino acid residues 21 to 129 of the amino acid sequence shown in SEQ ID NO: 71, an amino acid sequence comprising amino acid residues 21 to 129 of the amino acid sequence shown in SEQ ID NO: 73, or an amino acid sequence comprising amino acid residues 21 to 129 of the amino acid sequence shown in SEQ ID NO: 75.

A preferred combination includes an antibody comprising a heavy chain containing a heavy chain variable region comprising an amino acid sequence comprising amino acid residues 20 to 144 of the amino acid sequence shown in SEQ ID NO: 57 and a light chain containing a light chain variable region comprising an amino acid sequence comprising amino acid residues 21 to 129 of the amino acid sequence shown in SEQ ID NO: 67, an antibody comprising a heavy chain containing a heavy chain variable region comprising an amino acid sequence comprising amino acid residues 20 to 144 of the amino acid sequence shown in SEQ ID NO: 59 and a light chain containing a light chain variable region comprising an amino acid sequence comprising amino acid residues 21 to 129 of the amino acid sequence shown in SEQ ID NO: 69, an antibody comprising a heavy chain containing a heavy chain variable region comprising an amino acid sequence comprising amino acid residues 20 to 144 of the amino acid sequence shown in SEQ ID NO: 61 and a light chain containing a light chain variable region comprising an amino acid sequence comprising amino acid residues 21 to 129 of the amino acid sequence shown in SEQ ID NO: 71, an antibody comprising a heavy chain containing a heavy chain variable region comprising an amino acid sequence comprising amino acid residues 20 to 144 of the amino acid sequence shown in SEQ ID NO: 63 and a light chain containing a light chain variable region comprising an amino acid sequence comprising amino acid residues 21 to 129 of the amino acid sequence shown in SEQ ID NO: 73, or an antibody comprising a heavy chain containing a heavy chain variable region comprising an amino acid sequence comprising amino acid residues 20 to 144 of the amino acid sequence shown in SEQ ID NO: 65 and a light chain containing a light chain variable region comprising an amino acid sequence comprising amino acid residues 21 to 129 of the amino acid sequence shown in SEQ ID NO: 75.

A more preferred combination includes an antibody comprising a heavy chain containing a heavy chain variable region comprising an amino acid sequence comprising amino acid residues 20 to 144 of the amino acid sequence shown in SEQ ID NO: 59 and a light chain containing a light chain variable region comprising an amino acid sequence comprising amino acid residues 21 to 129 of the amino acid sequence shown in SEQ ID NO: 69, or an antibody comprising a heavy chain containing a heavy chain variable region comprising an amino acid sequence comprising amino acid residues 20 to 144 of the amino acid sequence shown in SEQ ID NO: 61 and a light chain containing a light chain variable region comprising an amino acid sequence comprising amino acid residues 21 to 129 of the amino acid sequence shown in SEQ ID NO: 71.

Examples of humanized antibodies derived from the #4C13K antibody include an arbitrary combination of a heavy chain containing a heavy chain variable region comprising an amino acid sequence comprising amino acid residues 20 to 140 of the amino acid sequence shown in SEQ ID NO: 77, an amino acid sequence comprising amino acid residues 20 to 140 of the amino acid sequence shown in SEQ ID NO: 79, an amino acid sequence comprising amino acid residues 20 to 140 of the amino acid sequence shown in SEQ ID NO: 81, an amino acid sequence comprising amino acid residues 20 to 140 of the amino acid sequence shown in SEQ ID NO: 83, or an amino acid sequence comprising amino acid residues 20 to 140 of the amino acid sequence shown in SEQ ID NO: 85 and a light chain containing a light chain variable region comprising an amino acid sequence comprising amino acid residues 21 to 129 of the amino acid sequence shown in SEQ ID NO: 67, an amino acid sequence comprising amino acid residues 21 to 129 of the amino acid sequence shown in SEQ ID NO: 69, an amino acid sequence comprising amino acid residues 21 to 129 of the amino acid sequence shown in SEQ ID NO: 71, an amino acid sequence comprising amino acid residues 21 to 129 of the amino acid sequence shown in SEQ ID NO: 73, or an amino acid sequence comprising amino acid residues 21 to 129 of the amino acid sequence shown in SEQ ID NO: 75.

A preferred combination includes an antibody comprising a heavy chain containing a heavy chain variable region comprising an amino acid sequence comprising amino acid residues 20 to 140 of the amino acid sequence shown in SEQ ID NO: 77 and a light chain containing a light chain variable region comprising an amino acid sequence comprising amino acid residues 21 to 129 of the amino acid sequence shown in SEQ ID NO: 67, an antibody comprising a heavy chain containing a heavy chain variable region comprising an amino acid sequence comprising amino acid residues 20 to 140 of the amino acid sequence shown in SEQ ID NO: 79 and a light chain containing a light chain variable region comprising an amino acid sequence comprising amino acid residues 21 to 129 of the amino acid sequence shown in SEQ ID NO: 69, an antibody comprising a heavy chain containing a heavy chain variable region comprising an amino acid sequence comprising amino acid residues 20 to 140 of the amino acid sequence shown in SEQ ID NO: 81 and a light chain containing a light chain variable region comprising an amino acid sequence comprising amino acid residues 21 to 129 of the amino acid sequence shown in SEQ ID NO: 71, an antibody comprising a heavy chain containing a heavy chain variable region comprising an amino acid sequence comprising amino acid residues 20 to 140 of the amino acid sequence shown in SEQ ID NO: 83 and a light chain containing a light chain variable region comprising an amino acid sequence comprising amino acid residues 21 to 129 of the amino acid sequence shown in SEQ ID NO: 73, or an antibody comprising a heavy chain containing a heavy chain variable region comprising an amino acid sequence comprising amino acid residues 20 to 140 of the amino acid sequence shown in SEQ ID NO: 85 and a light chain containing a light chain variable region comprising an amino acid sequence comprising amino acid residues 21 to 129 of the amino acid sequence shown in SEQ ID NO: 75.

A more preferred combination includes an antibody comprising a heavy chain containing a heavy chain variable region comprising an amino acid sequence comprising amino acid residues 20 to 140 of the amino acid sequence shown in SEQ ID NO: 79 and a light chain containing a light chain variable region comprising an amino acid sequence comprising amino acid residues 21 to 129 of the amino acid sequence shown in SEQ ID NO: 69, or an antibody comprising a heavy chain containing a heavy chain variable region comprising an amino acid sequence comprising amino acid residues 20 to 140 of the amino acid sequence shown in SEQ ID NO: 81 and a light chain containing a light chain variable region comprising an amino acid sequence comprising amino acid residues 21 to 129 of the amino acid sequence shown in SEQ ID NO: 71.

Further, the antibody of the present invention includes a human antibody. An anti-LPS O11 human antibody refers to a human antibody having only a gene sequence of an antibody derived from a human chromosome. An anti-LPS O11 human antibody can be obtained by a method using a human antibody-producing mouse having a human chromosome fragment containing heavy and light chain genes of a human antibody (see Tomizuka, K. et al., Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects vol. 10, pp. 69-73 (Kitagawa, Y., Matsuda, T. and Iijima, S. eds.), Kluwer Academic Publishers, 1999; Tomizuka, K. et al., Proc. Natl. Acad. Sci. USA (2000) 97, pp. 722-727, etc).

Such a human antibody-producing mouse can be created specifically as follows. A genetically modified animal in which endogenous immunoglobulin heavy and light chain gene loci have been disrupted, and instead, human immunoglobulin heavy and light chain gene loci have been introduced via a yeast artificial chromosome (YAC) vector or the like, is created by producing a knockout animal and a transgenic animal and mating these animals each other.

Further, according to a genetic engineering technique, by using cDNAs encoding such a heavy chain and a light chain of a human antibody, respectively, and preferably a vector containing the cDNAs, eukaryotic cells are transformed, and a transformant which produces a recombinant human monoclonal antibody is cultured, and thus, the antibody can also be obtained from the culture supernatant. Here, as the host, for example, eukaryotic cells, preferably mammalian cells such as CHO cells, lymphocytes or myeloma cells can be used.

In addition, a method of obtaining a phage display-derived human antibody screened from a human antibody library (see Wormstone, I. M. et al., Investigative Ophthalmology & Visual Science (2002) 43 (7), pp. 2301-2308; Carmen, S. et al., Briefings in Functional Genomics and Proteomics (2002), 1 (2), pp. 189-203; Siriwardena, D. et al., Ophthalmology (2002) 109 (3), pp. 427-431, etc.) is also known.

For example, a phage display method in which a variable region of a human antibody is expressed on the surface of a phage as a single-chain antibody (scFv) and a phage which binds to an antigen is selected (Nature Biotechnology (2005), 23 (9), pp. 1105-1116) can be used. By analyzing the gene of the phage selected based on the binding to an antigen, a DNA sequence encoding the variable region of a human antibody which binds to the antigen can be determined. If the DNA sequence of an scFv which binds to the antigen is determined, a human antibody can be obtained by preparing an expression vector having the sequence and introducing the vector into an appropriate host to express it (WO 92/01047, WO 92/20791, WO 93/06213, WO 93/11236, WO 93/19172, WO 95/01438, WO 95/15388, Annu. Rev. Immunol. (1994) 12, pp. 433-455, Nature Biotechnology (2005) 23(9), pp. 1105-1116).

The above antibody is evaluated on its binding activity to an antigen, opsonophagocytic killing activity, complement-dependent killing activity and/or agglutination activity, thereby to be able to select a suitable antibody. The binding activity to antigens can be evaluated by whole cell ELISA method shown in Example 3, which makes it possible to determine the range of serotypes of Pseudomonas aeruginosa to which the antibody exhibit a binding activity. The opsonophagocytic killing activity can be evaluated by the viable cell count measurement shown in Example 1 for percentage or amount of bacteria that are phagocytosed by phagocytic cells or by treatment of the bacteria with a fluorescent label, followed by quantification using a flow cytometry, etc. The complement-dependent killing activity can be evaluated by a method such as viable cell count measurement for the amount of bacteria to be sterilized by the complement and the antibody. Also, the agglutination activity can be evaluated as an agglutination titer per the amount of IgG by detecting agglutination ability of serially diluted antibody to bacteria. Further, antimicrobial activity against systemic infection and lung infection can be assessed by the method described in Example 4 and the like.

As one example of another index for use in the comparison of the properties of antibodies, the stability of antibodies can be exemplified. The differential scanning calorimetry (DSC) is a method capable of quickly and accurately measuring a thermal denaturation midpoint temperature (Tm) to be used as a favorable index of the relative conformational stability of proteins. By measuring the Tm values using DSC and comparing the values, the difference in thermal stability can be compared. It is known that the storage stability of antibodies shows some correlation with the thermal stability of antibodies (Lori Burton, et. al., Pharmaceutical Development and Technology (2007) 12, pp. 265-273), and a preferred antibody can be selected by using thermal stability as an index. Examples of other indices for selecting antibodies include the following factors: the yield in an appropriate host cell is high and the agglutinating property in an aqueous solution is low. For example, an antibody which shows the highest yield does not always show the highest thermal stability, and therefore, it is necessary to select an antibody most suitable for the administration to humans by making a comprehensive evaluation based on the above-described indices.

Further, a method in which the full-length heavy and light chain sequences of an antibody are connected using an appropriate linker to obtain a single-chain immunoglobulin is also known (Lee, H-S, et. al., Molecular Immunology (1999) 36, pp. 61-71; Shirrmann, T. et. al., mAbs (2010), 2 (1) pp. 1-4). By dimerizing such a single-chain immunoglobulin, the resulting dimer can have a structure and an activity similar to those of an antibody which is a tetramer itself. Further, the antibody of the present invention may be an antibody which has a single heavy chain variable region and does not have a light chain sequence. Such an antibody is called a single domain antibody (sdAb) or a nanobody, and in fact, such an antibody is observed in camels and llamas and has been reported to have an antigen-binding affinity (Muyldemans S. et. al., Protein Eng. (1994) 7 (9), 1129-35, Hamers-Casterman C. et. al., Nature (1993) 363 (6428), 446-8). The above-described antibodies can also be interpreted as a type of antigen-binding fragment of the antibodies of the present invention.

Further, by controlling the modification of sugar chain that is bound to the antibody of the present invention, it is possible to enhance an opsonophagocytic killing activity. The technique for controlling the sugar chain modification of antibodies is known from WO 99/54342, WO 2000/61739, WO 2002/31140, etc. However, such techniques are not limited thereto.

In the case where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody described in this specification and a gene encoding a light chain sequence thereof. When a host cell is transformed, it is possible to insert the heavy chain sequence gene and the light chain sequence gene into the same expression vector, and also into different expression vectors separately. In the case where eukaryotic cells are used as the host, animal cells, plant cells, and eukaryotic microorganisms can be used. As the animal cells, (1) mammalian cells, for example, dihydrofolate reductase-deficient strains (Urlaub, G. and Chasin, L. A., Proc. Natl. Acad. Sci. USA (1980) 77, pp. 4126-4220) of simian COS cells (Gluzman, Y., Cell, (1981) 23, pp. 175-182, ATCC CRL-1650), murine fibroblasts NIH3T3 (ATCC No. CRL-1658), and Chinese hamster ovarian cells (CHO cells; ATCC: CCL-61) can be exemplified. Further, in the case where prokaryotic cells are used, for example, *Escherichia coli* and *Bacillus subtilis* can be exemplified. By introducing a target antibody gene into these cells through transformation and culturing the thus transformed cells in vitro, the antibody can be obtained. In the above-described culture method, the yield may sometimes vary depending on the sequence of the antibody, and therefore, it is possible to select an antibody which is easily produced as a medicine by using the yield as an index among the antibodies having comparable binding activity.

There is no limitation on isotype of the antibody of the present invention, and examples thereof include IgG (IgG1, IgG2, IgG3, IgG4), IgM, IgA (IgA1, IgA2), IgD, and IgE, and preferred examples thereof include IgG and IgM, and further more preferred examples thereof include IgG1 and IgG3.

Further, the antibody of the present invention may be an antigen-binding fragment of the antibody having an antigen-binding site of the antibody or a modified fragment thereof. The fragment of the antibody can be obtained by treating the antibody with a protease such as papain or pepsin, or modifying the antibody gene according to a genetic engineering technique and expressing the modified gene in suitable cultured cells. Among these antibody fragments, a fragment having all or part of the functions of the full-length molecule of the antibody can be called an antigen-binding fragment of the antibody. The functions of the antibody generally include an antigen-binding activity, neutralizing the activity of an antigen, enhancing the activity of an antigen, an opsonophagocytic killing activity, and a complement-dependent killing activity. The function of the antigen-binding fragment of the antibody according to the present invention is to bind to the LPS O11 antigen of *Pseudomonas aeruginosa*, preferably the opsonophagocytic killing activity to the LPS O11 antigen of *Pseudomonas aeruginosa* strains.

Examples of the fragment of the antibody include Fab, F(ab')2, Fv, single-chain Fv (scFv) in which Fv molecules of the heavy chain and the light chain are connected via an appropriate linker, a diabody (diabodies), a linear antibody, and a polyspecific antibody composed of the antibody fragments. Further, Fab' which is a monovalent fragment in a variable region of an antibody obtained by treating F(ab')2 under reducing conditions is also included in the fragment of the antibody.

Further, the antibody of the present invention may be a polyspecific antibody with specificity for at least two different antigens. In general, such a molecule binds to two antigens (that is, bispecific antibody), however, the term "polyspecific antibody" as used herein includes an antibody having specificity to two or more (for example, three) antigens.

The polyspecific antibody of the present invention may be a full-length antibody or a fragment of such an antibody (for example, a F(ab')2 bispecific antibody). The bispecific antibody can be produced by connecting the heavy and light chains (HL pairs) of two types of antibodies, or can also be produced by fusing hybridomas which produce different monoclonal antibodies to prepare bispecific antibody-producing fused cells (Millstein et al., Nature (1983) 305, pp. 537-539).

The antibody of the present invention may be a single-chain antibody (also referred to as scFv). The single-chain antibody can be obtained by connecting the heavy chain variable region and the light chain variable region of the antibody via a polypeptide linker (Pluckthun, The Pharmacology of Monoclonal Antibodies, 113 (edited by Rosenberg and Moore), Springer Verlag, New York, pp. 269-315 (1994), Nature Biotechnology (2005), 23, pp. 1126-1136). Further, a BiscFv fragment produced by connecting two scFv molecules via a polypeptide linker can also be used as the bispecific antibody.

A method of producing a single-chain antibody is well known in this technical field (see, for example, U.S. Pat. Nos. 4,946,778, 5,260,203, 5,091,513, 5,455,030, etc). In this scFv, the heavy chain variable region and the light chain variable region are connected via a linker that does not form a conjugate, preferably via a polypeptide linker (Huston, J. S. et al., Proc. Natl. Acad. Sci. USA (1988), 85, pp. 5879-5883). In the scFv, the heavy chain variable region and the light chain variable region may be derived from the same antibody or different antibodies. As the polypeptide linker to be used for connecting the variable regions, any single-chain peptide composed of 12 to 19 residues is used, for example.

DNA encoding scFv can be obtained by performing amplification using a DNA encoding the entire amino acid sequence or a desired partial amino acid sequence of a DNA selected from a DNA encoding the heavy chain or the heavy chain variable region of the above-described antibody and a DNA encoding the light chain or the light chain variable region thereof as a template by a PCR method using a primer pair that defines both ends thereof, and further performing amplification by combining a DNA encoding a polypeptide linker portion and a primer pair that defines both ends thereof so as to connect the both ends to the heavy chain and the light chain, respectively.

Further, once DNA encoding a scFv is produced, an expression vector containing the same and a host transformed by the expression vector can be obtained according to common procedures. Further, by using the resulting host, scFv can be obtained according to a common procedure. An antibody fragment thereof can be produced in a host by obtaining a gene and expressing the gene in the same manner as described above.

The antibody of the present invention may be polymerized to increase its affinity for an antigen. The antibody to be polymerized may be one type of antibody or a plurality of antibodies which recognize a plurality of epitopes of the same antigen. A method of polymerization of the antibody includes binding of the IgG CH3 domain to two scFv molecules, binding to streptavidin, introduction of a helix-turn-helix motif, and the like.

The antibody of the present invention may be a polyclonal antibody which is a mixture of plural types of anti-LPS O11 antibodies having different amino acid sequences. One example of a polyclonal antibody includes a mixture of plural types of antibodies having different CDRs. Such polyclonal a antibodies can be obtained by culturing a mixture of cells which produce different antibodies and then purifying the antibodies from the resulting culture (see WO 2004/061104).

The antibody of the present invention may be an antibody having an identity of 80% to 99% as compared to the heavy and/or light chains of the antibodies described above. By combining sequences having a high homology to the heavy chain amino acid sequence and the light chain amino acid sequence, it is possible to select an antibody having an antigen-binding affinity, opsonophagocytic killing activity, and/or complement-dependent killing activity equivalent to those of each antibody. Such a homology is generally a homology of 80% or more, preferably a homology of 90% or more, more preferably a homology of 95% or more, most preferably a homology of 99% or more. Further, by combining an amino acid sequence wherein one to several amino acid residues are substituted, deleted or added in the heavy chain and/or light chain amino acid sequence, it is also possible to select an antibody having various activities equivalent to those of each of the above-described antibodies. The number of the amino acid residues to be substituted, deleted or added is generally 10 amino acid residues or less, preferably 5 to 6 amino acid residues or less, more preferably 2 or 3 amino acid residues or less, most preferably 1 amino acid residue.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue located at the carboxyl terminus is newly amidated (Analytical Biochemistry, 360:75-83 (2007)). However, such deletion and modification of the heavy chain sequence does not affect the antigen-binding affinity and the effector function (activation of a complement or opsonophagocytic killing activity, etc.) of the antibody. Therefore, in the present invention, an antibody subjected to such modification is also included, and a deletion variant in which one or two amino acids have been deleted at the carboxyl terminus of the heavy chain, and a variant obtained by amidation of the deletion variant (for example, a heavy chain in which the carboxyl terminal proline residue has been amidated), and the like can be exemplified. The type of deletion variant having a deletion at the carboxyl terminus of the heavy chain of the antibody according to the present invention is not limited to the above variants as long as the antigen-binding affinity and the effector function are conserved. The two heavy chains constituting the antibody according to the present invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the present invention and the culture conditions, however, a case where one amino acid residue at the carboxyl terminus has been deleted in both of the two heavy chains contained as main components in the antibody according to the present invention can be exemplified.

The homology between two amino acid sequences can be determined using default parameters of Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm can be used also through the Internet by accessing the site www.ncbi.nlm.nih.gov/blast. Incidentally, two types of percentage values of identity (or identities) and positivity (or positivities) are calculated by the Blast algorithm. The former is a value when amino acid residues match each other in two amino acid sequences for which a degree of homology is to be determined, and the latter is a value obtained by also considering amino acid residues having a similar chemical structure. In this specification, the value of the identity when amino acid residues match each other is used as the homology value.

As a modified antibody, an antibody bound to any of various types of molecules such as polyethylene glycol (PEG) can also be used.

Further, the antibody of the present invention may be in the form of a conjugate formed between any of these antibodies and another medicinal agent (immunoconjugate). Examples of such an antibody include one in which the antibody is conjugated to a radioactive material or a compound having a pharmacological action (Nature Biotechnology (2005) 23, pp. 1137-1146).

The obtained antibody can be purified to homogeneity. The separation and purification of the antibody can be performed by employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, adsorption chromatography, and the like.

Such chromatography can be performed by employing liquid chromatography such as HPLC, FPLC, and the like.

A column to be used in affinity chromatography includes a Protein A column and a Protein G column.

For example, a column using a Protein A column includes Hyper D, POROS, Sepharose F. F. (Pharmacia) and the like.

Further, by using a carrier having an antigen immobilized thereon, an antibody can also be purified utilizing the binding property of the antibody to the antigen.

4. Medicament Containing Anti-LPS O11 Antibody

Since the anti-LPS O11 antibody obtained by the method described in the above section "3. Production of anti-LPS O11 antibody" exhibits opsonophagocytic killing action (OPK) and/or complement dependent killing (CDK) action, it therefore can be used as a therapeutic and/or prophylactic agent for pseudomonal infection.

Examples of pseudomonal infection with which an anti-LPS O11 antibody is capable of treatment and/or prophylaxis include systemic infectious disease caused by pseudomonal infection, preferably caused by multidrug-resistant pseudomonal infection. The systemic pseudomonal infection caused by pseudomonal infection includes, for example, bloodstream infection, sepsis, meningitis, endocarditis, otitis media, sinusitis, pneumonia, lung abscess, empyema, chronic respiratory tract infection, peritonitis, post-operative infection, cholecystitis, cholangitis, eyelid tumor, dacryocystitis, conjunctivitis, corneal ulcer, corneal abscess, panophthalmitis, orbital infection, urinary tract infection, catheter infection, perianal abscess, secondary infection of burn wounds, decubitus infection, cystic fibrosis disease, lymphangitis, lymphadenitis, osteomyelitis, arthritis, tonsillitis, liver abscess, skin and soft tissue infections, intrauterine infection, uterine adnexitis, parametritis, perimandibular phlegmon, or jaw inflammation, preferably pneumonia, but is not limited thereto as long as such pseudomonal infection is a systemic infectious disease caused by pseudomonal infection.

Examples of anti-LPS O11 antibodies as a medicament for the above diseases include chimeric antibody or humanized antibody produced from #1G5 antibody or #4C13K antibody according to the method described in "3. Production of Anti-LPS O11 Antibody". Furthermore, chimeric antibodies, humanized antibodies, and human antibodies having the same epitope as the #1G5 antibody and/or #4C13K antibody can also be used as a medicament. It is possible to confirm that some anti-LPS O11 antibodies have the same epitope as the #1G5 antibody and/or #4C13K antibody by observing whether or not these antibodies commonly bind to specific sugar chain of the LPS O11 antigen. Also, if some anti-LPS O11 antibodies compete with the #1G5 antibody and/or #4C13K antibody in binding to the LPS O11 antigen, these antibodies can be determined to have common epitopes.

The in vitro antimicrobial activity of the anti-LPS O11 antibodies can be confirmed by measuring the opsonophagocytic killing activity or complement dependent killing activity against, for example, *Pseudomonas aeruginosa* ATCC 29260. The ATCC 29260 strain is one of the most famous O11 strains and was obtained from ATCC. This strain has been deposited at ATCC by P. V. Liuof University of Louisville (J. Infect. Dis, 128:506-513 (1973)). This strain is available from the Institute Pasteur as CIP 102967, or even from The National Institute of Public Health as CNCTC 5997.

The therapeutic or prophylactic effect of the anti-LPS O11 antibody on pseudomonal infection in vivo using experimental animals can be confirmed by intravenously administering the anti-LPS O11 antibody in a mouse or rat model of lung infection, systemic infection, thigh infection, or burn wound infection, and measuring the change of the viable cell count of the infected sites or the survival rate.

The thus obtained anti-LPS O11 antibody is useful as a medicament, in particular as a pharmaceutical composition for treatment or prophylaxis of pseudomonal infections such as blood stream infection, pneumonia, chronic respiratory tract infections, septicemia, peritonitis, skin soft tissue infection, secondary infections of burn wounds, or as an antibody for immunological diagnosis of such diseases.

The anti-LPS O11 antibody of the present invention is an antibody that recognizes the LPS of *Pseudomonas aeruginosa*, and binds to the O11 antigen, but does not bind to O1, O2, O3, O4, O5, O6, O7, O8, O9, O10, O13, O14, O15, O16, O17, O18, O19, O20 antigens and O-antigen-deficient strain.

The anti-LPS O11 antibody of the present invention has a coverage ratio for O11 clinical isolates, namely a ratio of the strains to which an antibody can bind being 85% or more, preferably 90% or more, more preferably 95% or more, and most preferably 100%.

Further, the anti-LPS O11 antibody of the present invention shows that the 50% minimum growth inhibitory concentration of opsonophagocytic killing activity against *Pseudomonas aeruginosa* identified by ATCC 29260 is 12 ng/mL or less, preferably 4.1 ng/mL or less, more preferably 1.4 ng/mL or less.

As one example, the anti-LPS O11 antibody can be administered alone or in combination with at least one other anti-infective agent for the treatment or prophylaxis of *Pseudomonas aeruginosa* infectious diseases. As one example, the anti-LPS O11 antibody can be administered in combination with a therapeutically effective amount of a therapeutic agent. Examples of such anti-infective agent that can be administered in combination with the anti-LPS O11 antibody include, but not limited to, penicillin, cephem, carbapenem, monobactam, quinolone, aminoglycoside, polymyxin, rifampicin, macrolide antimicrobial agents, etc.

The penicillin antimicrobial agent includes piperacillin, piperacillin/tazobactam, ticarcillin, ticarcillin/clavulanic acid, etc., preferably piperacillin or piperacillin/tazobactam.

The cephem antimicrobial agent includes cefotaxime, ceftizoxime, ceftriaxone, ceftazidime, cefepime, cefozopran, etc., preferably ceftazidime or cefepime.

The carbapenem antimicrobial agent includes imipenem, panipenem, meropenem, doripenem, etc., preferably meropenem or doripenem.

The monobactam antimicrobial agent includes aztreonam, carumonam, etc., preferably aztreonam.

The quinolone antimicrobial agent includes ciprofloxacin, levofloxacin, ofloxacin, moxifloxacin, gatifloxacin, sitafloxacin, etc., preferably ciprofloxacin or levofloxacin.

The aminoglycoside antimicrobial agent includes gentamicin, tobramycin, amikacin, arbekacin, etc., preferably tobramycin or amikacin.

The polymyxin antimicrobial agent includes polymyxin, colistin, etc.

The macrolide antimicrobial agent includes erythromycin, clarithromycin, azithromycin, etc., preferably azithromycin.

Depending on the state of pseudomonal infection or the intended degree of treatment and/or prophylaxis, two or three, or more types of therapeutic agents can be administered, and these other therapeutic agents can be administered simultaneously by encapsulating them in the same preparation. These other therapeutic agents and the anti-LPS O11 antibody can be administered simultaneously by encapsulating them in the same preparation. Also, the anti-LPS O11 antibody and these other therapeutic agents can be administered simultaneously by encapsulating them in separate preparations. Further, these other therapeutic agents and the anti-LPS O11 antibody can be separately administered one after another. In other words, after administration of these other therapeutic agents, a therapeutic agent containing an anti-LPS O11 antibody or an antigen-binding fragment thereof as an active ingredient may be administered, or after administration of a therapeutic agent containing an anti-LPS O11 antibody or an antigen-binding fragment thereof as an active ingredient, other therapeutic agent may be administered. In the case of administration in gene therapy, a gene of a proteinaceous therapeutic agent for infectious disease and a gene of the anti-LPS O11 antibody can be inserted downstream of the same promoter region or different promoter regions, and can be introduced into the same vector or different vectors.

By conjugating a therapeutic agent for infectious disease to the anti-LPS O11 antibody or a fragment thereof, a targeted drug conjugate as described in M. C. Garnet "Targeted drug conjugates: principles and progress", Advanced Drug Delivery Reviews, (2001) 53, 171-216 can be produced. For achieving this purpose, other than the antibody molecule, any antibody fragment can be applied as long as it does not completely lose the ability to recognize the LPS O11 antigen, and examples thereof include fragments such as Fab, F(ab')2, Fv, and the like. In the present invention, the antibody, fragment and the like can be used in the same manner. The conjugation mode between the anti-LPS O11 antibody or a fragment thereof and a therapeutic agent for infectious disease can be any of various forms described in M. C. Garnet "Targeted drug conjugates: principles and progress", Advanced Drug Delivery Reviews, (2001) 53, 171-216, G. T. Hermanson "Bioconjugate Techniques" Academic Press, California (1996), Putnam and J. Kopecek "Polymer Conjugates with Anticancer Activity" Advances in Polymer Science (1995) 122, 55-123 and the like. That is, a conjugate form in which the LPS O11 antibody and a therapeutic agent for infectious disease are conjugated to each other chemically and directly or via a spacer such as an oligopeptide, and a conjugate form via an appropriate drug carrier can be exemplified. Examples of a drug carrier include a liposome and a water-soluble polymer. More specific examples of a conjugate formed via such a drug carrier include a conjugate form in which the antibody and a therapeutic agent for infectious disease are incorporated in a liposome, and the liposome and the antibody are conjugated to each other, and a conjugate form in which a therapeutic agent for infectious disease is conjugated to a water-soluble polymer (a compound having a molecular weight of about 1000 to 100000) chemically and directly or via a spacer such as an oligopeptide and the antibody is conjugated to the water-soluble polymer. Conjugation of the antibody (or a fragment thereof) to a therapeutic agent for infectious disease or a drug carrier such as a liposome or a water-soluble polymer can be effected by a method well known to those skilled in the art such as the method described in G. T. Hermanson "Bioconjugate Techniques" Academic Press, California (1996), Putnam and J. Kopecek "Polymer Conjugates with Anticancer Activity" Advances in Polymer Science (1995) 122, 55-123 or the like. Incorporation of a therapeutic agent for infectious disease in a liposome can be effected by a method well known to those skilled in the art such as the method described in D. D. Lasic "Liposomes: From Physics to Applications" Elsevier Science Publishers B. V., Amsterdam (1993) or the like. Conjugation of a therapeutic agent for infectious disease to a water-soluble polymer can be effected by a method well known to those skilled in the art such as the method described in D. Putnam and J. Kopecek "Polymer Conjugates with Anticancer Activity" Advances in Polymer Science (1995) 122, 55-123 or the like. A conjugate between the antibody (or a fragment thereof) and a proteinaceous therapeutic agent for infectious disease (or a fragment thereof) can be produced by a method well known to those skilled in the art through genetic engineering other than the above-mentioned method.

The present invention also provides a pharmaceutical composition containing a therapeutically and/or prophylactically effective amount of the anti-LPS O11 antibody and a pharmaceutically acceptable diluent, carrier, solubilizing agent, emulsifier, preservative and/or adjuvant.

The present invention also provides a pharmaceutical composition containing a therapeutically and/or prophylactically effective amount of the anti-LPS O11 antibody, a therapeutically and/or prophylactically effective amount of at least one therapeutic agent for infectious disease, and a pharmaceutically acceptable diluent, carrier, solubilizing agent, emulsifier, preservative and/or adjuvant.

A substance to be used in a pharmaceutical formulation acceptable in a pharmaceutical composition according to the present invention is preferably non-toxic to a person to whom the pharmaceutical composition is to be administered, in terms of the dose and concentration.

The pharmaceutical composition of the present invention can contain a substance for pharmaceutical formulation which is capable of changing or maintaining the pH, osmotic pressure, viscosity, transparency, color, isotonicity, aseptic condition, stability, solubility, release rate, absorption rate, or permeability. Examples of the substance for pharmaceutical formulation include, but are not limited to, amino acids such as glycine, alanine, glutamine, asparagine, arginine and lysine; antimicrobial agents; antioxidants such as ascorbic acid, sodium sulfate and sodium hydrogen sulfite; buffers such as phosphate, citrate, borate buffers, bicarbonate and Tris-Hcl solutions; fillers such as mannitol and glycine; chelating agents such as ethylenediamine tetraacetate (EDTA); complexing agents such as caffeine, polyvinylpyrrolidine, β-cyclodextrin and hydroxypropyl-β-cyclodextrin; fillers such as glucose, mannose and dextrin; other carbohydrates such as monosaccharide and disaccharides; coloring agents; flavors; diluents; emulsifiers; hydrophilic polymers such as polyvinylpyrrolidine; preservatives such as low molecular weight polypeptides, salt forming counter ions, benzalkonium chloride, benzoate, salicylic acid, thimerosal, phenethyl alcohol, methylparaben, propylparaben, chlorhexidine, sorbic acid, and hydrogen peroxide; solvents such as glycerin, propylene glycol and polyethylene glycol; sugar alcohols such as mannitol and sorbitol; suspending agents; surfactants such as sorbitan ester, polysorbates including polysorbate 20 and polysorbate 80, triton, tromethamine, lecithin and cholesterol; stability enhancing agents such as sucrose and sorbitol; elasticity enhancing agents such as sodium chloride, potassium chloride and mannitol/sorbitol; transport agents; excipients; and/or pharmaceutical adjuvants. The addition amount of these substances for pharmaceutical formulation is preferably from 0.01 to 100 times, particularly preferably from 0.1 to 10 times the weight of the anti-LPS O11 antibody. Those skilled in the art can appropriately determine a preferred composition of the pharmaceutical composition in a pharmaceutical formulation depending on the disease to be treated, the route of administration to be applied, or the like.

The excipient or carrier in the pharmaceutical composition may be in the form of a liquid or a solid. An appropriate excipient or carrier may be injectable water, physiological saline, an artificial cerebral spinal fluid or other substance commonly used for parenteral administration. Further, neutral physiological saline or physiological saline containing serum albumin can also be used as a carrier. The pharmaceutical composition may contain a Tris buffer of pH 7.0 to 8.5, an acetate buffer of pH 4.0 to 5.5, or a citrate buffer of pH 3.0 to 6.2, which may be supplemented with sorbitol or another compound. Examples of the pharmaceutical composition of the present invention include a pharmaceutical composition containing the anti-LPS O11 antibody, and a pharmaceutical composition containing the anti-LPS O11 antibody and at least one therapeutic agent for infectious disease. The pharmaceutical composition of the present invention is prepared in the form of a lyophilized product or a liquid as a medicinal agent having a selected composition and a required purity. The pharmaceutical composition containing the anti-LPS O11 antibody and the pharmaceutical composition containing the anti-LPS O11 antibody and at least one therapeutic agent for infectious disease can also be formed into a lyophilized product using an appropriate excipient such as sucrose.

The pharmaceutical composition of the present invention can be prepared for parenteral administration or for gastrointestinal absorption via oral administration route. The composition and concentration of a pharmaceutical formulation can be determined depending on the administration method. To the extent that the affinity of the anti-LPS O11 antibody contained in the pharmaceutical composition of the present invention for the LPS O11 antigen is higher, that is, as the dissociation constant (Kd value) for the LPS O11 antigen is lower, the anti-LPS O11 antibody can exhibit its drug efficacy even at a lower dose for humans, and therefore, the dose of the pharmaceutical composition of the present invention for humans can also be determined based on this result. As for the dose, in the case where a human anti-LPS O11 antibody is administered to humans, the antibody may be administered at a dose of from about 0.1 to 100 mg/kg once per 1 to 180 days.

Examples of the dosage form of the pharmaceutical composition of the present invention are injections including infusions, suppositories, transnasal agents, sublingual agents and percutaneous absorption agents.

The antibody of the present invention binds to LPS which is exposed on the cell surface of Pseudomonas aeruginosa, and thus can also be used as a diagnostic agent for pseudomonal infection.

When the antibody of the present invention is formulated as a diagnostic agent, this diagnostic agent can be obtained in any dosage form by adopting any means suitable for its purpose. For example, ascites, a culture solution containing an antibody of interest, or a purified antibody is measured for the antibody titer and appropriately diluted with PBS (phosphate buffer containing a saline) or the like; thereafter, a preservative such as 0.1% sodium azide is added thereto. Alternatively, the antibody of the present invention adsorbed to latex or the like is determined for the antibody titer and appropriately diluted, and a preservative is added thereto for use. As the latex in this case, appropriate resin materials, for example, latex such as polystyrene, polyvinyl toluene, and polybutadiene, can be exemplified.

According to the present invention, a diagnostic method for pseudomonal infection using the antibody of the present invention is provided. The diagnostic method of the present invention can be carried out by collecting a biological sample such as sputum, lung lavage fluid, pus, tear, blood, or urine from mammals including a human at a risk of pseudomonal infection, subsequently bringing the collected sample into contact with the antibody of the present invention, and determining whether or not an antigen-antibody reaction occurs.

According to the present invention, a kit is provided for detecting the presence of Pseudomonas aeruginosa, the kit comprising at least the antibody of the present invention.

The antibody of the present invention may be labeled. This detection kit is capable of detecting the presence of Pseudomonas aeruginosa by detecting the antigen-antibody reaction.

Therefore, the detection kit of the present invention can further comprise various reagents for carrying out the antigen-antibody reaction, for example, a secondary antibody, a chromogenic reagent, a buffer, instructions, and/or an instrument, etc., which are used in an ELISA method or the like, if desired.

EXAMPLES

Hereinafter, the invention will be more specifically described with reference to Examples; however, the invention is not limited thereto. Note that the respective operations regarding gene manipulation in the following Examples were performed according to the methods described "Molecular Cloning" (written by Sambrook, J., Fritsch, E. F. and Maniatis, T., published by Cold Spring Harbor Laboratory Press in 1989), or in the case of using commercially available reagents or kits, performed according to the protocols attached thereto unless otherwise stated.

Example 1 Screening of Anti-LPS O11 Antibody

1)-1 Immunity

Pseudomonas aeruginosa ATCC 29260 cultured in Mueller Hinton Agar (MHA, Becton, Dickinson and Company) was suspended in saline, and ICR mice (Charles River) were immunized by administering the suspension to the gastrocnemius muscle 5 times every 10 to 11 days. The knee lymph nodes were harvested on day 6 after the final immunization, and the cells were individually separated by a cell strainer (Becton, Dickinson and Company), washed with RPMI 1640 (Invitrogen), suspended in Cell Banker (Juji Field Inc.), and stored at −80° C.

1)-2 Obtaining a Monoclonal Antibody

A monoclonal antibody was obtained according to the methods described in WO 2009/091048, WO 2011/027808, WO 2012/133572, BMC Biotechnology, 11, 39 (2011), and BMC Biotechnology 11, 75 (2011).

1)-2-1 Isolation of an Antibody-Producing Cell

The cells collected from the lymph nodes of the immunized mice were suspended with 0.5% BSA/2 mM EDTA/PBS, and allophycocyanin-labeled anti-mouse CD138 antibody (Becton, Dickinson and Company) was added thereto. The suspension was incubated at 4° C. for 15 minutes, and then the cells were washed in RPMI 1640, added with ER-Tracker Blue-White DPX (Invitrogen), and allowed to react for 5 minutes under light shielding conditions. The cells were suspended in PBS and the double positive cells were individually separated using a FACS Aria cell sorter (Becton, Dickinson and Company).

1)-2-2 Synthesis of cDNA

The cells individually separated by the cell sorter were dissolved in a cell lysate (50 mM Tris-HCl (pH 7.5), 250 mM LiCl, 5 mM EDTA (pH 8), 0.5% lithium dodecyl sulfate (LiDS), 2.5 mM dithiothreitol (DTT)) containing magnetic beads (Dynabeads mRNA DIRECT Kit, Invitrogen) bound to oligo dT25, so that mRNA was bound to magnetic beads. Then the magnetic beads were washed once with mRNA washing solution A (10 mM Tris-HCl (pH 7.5), 0.15 M LiCl, 1 mM EDTA, 0.1% LiDS, 0.1% Triton X-100) and cDNA synthesis solution (50 mM Tris-HCl (pH 8.3), 75 mM KCl, 3 mM $MgCl_2$, 5 mM DTT, 0.5 mM dNTP, 0.2% Triton X-100, and 48 units RNase inhibitor (Invitrogen)), respectively, and synthesis of cDNA was performed in a cDNA synthesis solution supplemented with 480 units SuperScript III Reverse Transcriptase (Invitrogen). The beads were washed with 3' tailing reaction solution (50 mM potassium phosphate, 4 mM $MgCl_2$, 0.5 mM dGTP, 0.2% Triton X-100, 48 units RNase inhibitor (Invitrogen)), and the 3' tailing reaction was carried out in a reaction solution to which 480 units Terminal Transferase, recombinant (Roche) was added.

1)-2-3 Amplification of Mouse Heavy and Light Chain Variable Region Gene Fragments After washing the magnetic beads in TE solution (10 mM Tris-HCl (pH 7.5), 1 mM EDTA, 0.1% Triton X-100), amplification of the mouse immunoglobulin heavy and light chain genes was carried out using the 5'-RACE PCR method. First, the magnetic beads were transferred to a PCR reaction solution (0.2 µM primer, 0.2 mM dNTP, 0.1 units PrimeSTAR HS DNA Polymerase (TAKARA)), and 35 cycles of reactions for 30 seconds at 94° C. and for 90 seconds at 68° C. were conducted (1st PCR). Then the 1st PCR products were diluted 10-fold, and the variable regions of mouse immunoglobulin heavy and light chain genes were separately amplified respectively (2nd PCR) using the diluted 1st PCR products as a template under the same conditions as in the 1st PCR. Each primer set is as follows.

```
1st PCR Primer Set
                                        (SEQ ID NO: 89)
5'-cggtaccgcgggcccgggatcccccccccccccdn-3'

(AP3dC-S)

(SEQ ID NO: 90)
5'-accytgcatttgaactccttgcc-3' (mIgγRT1 1111-AS)

(SEQ ID NO: 91)
5'-actgccatcaatcttccacttgaca-3' (mIgκ 1st 589-AS)

2nd PCR primer set (heavy chain)
                                        (SEQ ID NO: 92)
5'-cttcgaattctgcagtcgacggtaccgcgggcccggga-3'

(MCS-AP3-S)

(SEQ ID NO: 93)
5'-ctggacagggatccagagttcca-3' (mIgγ 3rd 656T-AS)

2nd PCR primer set (light chain)
                                        (SEQ ID NO: 92)
5'-cttcgaattctgcagtcgacggtaccgcgggcccggga-3'

MCS-AP3-S)

(SEQ ID NO: 94)
5'-actgaggcacctccagatgttaact-3' (mIgκ 3rd 525-AS)
```

1)-2-4 Preparation of Mouse IgG2a or Human IgG1 Constant Region Gene Joining Double-Stranded DNA Fragment and Mouse Light Chain Constant Region Gene Joining Double-Stranded DNA Fragment Mouse IgG2a or human IgG1 constant region gene joining double-stranded DNA fragment and mouse light chain constant region gene joining double-stranded DNA fragment were obtained by amplification by PCR reaction with each primer set using plasmids pJON mIgG2a, pJON mIgG2a-hIgG1, and pJON mIgκ shown in SEQ ID NOs: 1-3, respectively, as a template, followed by treatment with DpnI (Roche). Twenty-five cycles of PCR reaction using 0.4 ng/ml pJON as a template were run in a reaction solution containing 0.2 mM dNTP, 0.2 µM primer, and 20 units PrimeSTAR HS DNA Polymerase at 94° C. for 40 seconds, 65° C. for 40 seconds, and 72° C. for 30 seconds.

```
Primer set for pJON mIgG2a and pJON mIgG2a-hIgG1
                                        (SEQ ID NO: 95)
5'-gcctggtcaagggctatttccctgag-3' (mIgG joint

PCR-S)

(SEQ ID NO: 96)
5'-ggggggggggggggggatcccgg-3' (polyG-AS)

Primer set forpJON mIgκ
                                        (SEQ ID NO: 97)
5'-ctgtatccatcttcccaccatccagt-3' (mIgκ joint

PCR-S)

(SEQ ID NO: 96)
5'-ggggggggggggggggatcccgg-3' (polyG-AS)
```

1)-2-5 Preparation of Mouse or Human Chimeric Immunoglobulin Linearized Expression Vector 16 units of Terminal Transferase, recombinant (Roche), was added to the 2nd PCR product and the mixture was allowed to react at 37° C. for 30 minutes and then heated at 94° C. for 5 minutes to stop the enzymatic reaction. To the 3' end polynucleotide addition mouse heavy chain variable region gene solution prepared above were added mouse IgG2a or human IgG1 constant region gene joining double-stranded DNA fragment, 0.2 µM primer, and 0.2 mM dNTP. With use of 0.1 units of PrimeSTAR HS DNA polymerase, 5 cycles of reactions of 30 seconds at 94° C. and 4 minutes at 70° C. were carried out, followed by 30 cycles of reactions of 30 seconds at 94° C., 30 seconds at 60° C., and 1 minute at 72° C., thereby to prepare a mouse heavy chain or human chimeric heavy chain gene expression unit. Similarly, to a mouse light chain variable region gene solution were added mouse light chain constant region gene joining double-stranded DNA fragments and a reaction was conducted to prepare a mouse light chain gene expression unit. The primers used were as follows.

```
Primer set for joining
                                        (SEQ ID NO: 98)
5'-agagaaaccgtctatcagggcgatggc-3' (miniCMV f1-S)

(SEQ ID NO: 99)
5'-agagacccttttgacgttggagtccacg-3' (miniCMV f1-AS)
```

1)-2-6 Expression of Antibody Gene

The full length of mouse heavy chain or human chimeric heavy chain and mouse light chain gene expression unit amplified in the above experiments was genetically introduced into HEK 293T cells using Lipofectamine 2000 (Invitrogen) and the cells were cultured at 37° C. for 4 days under 5% $CO_2$ to obtain an antibody culture supernatant.

1)-3 Screening of Monoclonal Antibody

1)-3-1 Measurement of Antibody Concentration

Antibody concentration was measured using Mouse IgG2a ELISA Quantitation Set (Bethyl Laboratories) or Human IgG ELISA Quantitation Set (Bethyl Laboratories). This method was carried out in accordance with the accompanying manual. In other words, Affinity purified Goat anti-Mouse IgG2a Coating Antibody or Affinity purified Goat anti-Human IgG-Fc Coating Antibody was diluted 101-fold with 0.05 M carbonate-bicarbonate buffer (pH 9.6). The diluted solution of 100 µl was added to a well and immobilized at room temperature for 1 hour. After washing the well three times with 150 µl of Tris buffered saline (TBS; Tween 20-added TBS was TBST) supplemented with 0.05% Tween 20, 200 µl of 1% BSA/TBS was added to the well and blocking was carried out for 0.5 to 2 hours. Each antibody culture supernatant or purified antibody (if necessary, diluted in 1% BSA/TBST) was directly added in an amount of 100 µl to the well and allowed to react at room temperature for 1 hour. After washing the well three times with TBST, 50,000-fold diluted HRP Conjugated Goat anti-Mouse IgG2a Detection Antibody or 100,000-fold diluted HRP Conjugated Goat anti-Human IgG-Fc Detection Antibody was added in an amount of 100 µl/well, and allowed to react for 1 hour. The well was washed three times with TBST, and SuperSignal ELISA Pico Chemiluminescent Substrate (Thermo Fisher Scientific K.K.) was added thereto, and luminescence was measured with ARVO 1420 multilabel counter (Perkin Elmer) immediately after the addition. A calibration curve was obtained by using the standard attached to the kit, thereby to calculate the concentration of antibody.

1)-3-2 Measurement of Opsonophagocytic Killing Activity

As a buffer for measurement, 0.1% gelatin/1% FBS/Hank's balanced salt solution (opsonization buffer) was prepared. HL60 as effector cells were cultured in 10% FBS-containing RPMI 1640 (Invitrogen) supplemented with 0.8% N,N-dimethylformamide for 5 or 6 days to prepare neutrophil-like, differentiated HL60 in an opsonization buffer. As the target bacteria, *Pseudomonas aeruginosa* ATCC 29260 cultured on MHA was prepared by suspending it in the opsonization buffer. As a complement, Baby Rabbit Serum (Cederlane) was prepared by dissolving it with ice-cold distilled water. Bacterial suspension (final concentration of $2 \times 10^4$ cells/ml) was mixed with antibody culture supernatant or purified antibody, allowed to stand at 4° C. for 30 minutes, and the prepared neutrophil-like, differentiated HL60 cells (final concentration of $4 \times 10^6$ cells/ml) and a complement (final concentration 10%) were added thereto, followed by incubation with gentle agitation at 37° C. for 1 hour under 5% $CO_2$. After the incubation, each sample was spread on MHA, and colonies were counted on the next day. Compared with the control to which the antibody was not added, a sample that showed 50% growth inhibitory effect was determined to have an activity.

1)-3-3 Determination of CDR Sequence

Using the mouse heavy and light chain variable region gene product obtained in 1)-2-3 as a template, CDR sequence was confirmed with the following sequence primers. Sequence analysis was performed using a gene sequence analyzer of Applied Biosystems 3730xl DNA Analyzer (Life technologies). Based on the obtained sequences, CDR sequence was determined according to Abysis database (http://www.bioinf.org.uk/abs/#cdrid) by Andrew C. R. Martin et al.

```
Sequence primer (for heavy chain)
                                        (SEQ ID NO: 100)
5'-acaccgctggacagggatccagag-3' (mIgG sequence)

Sequence primer (for light chain)
                                        (SEQ ID NO: 101)
5'-gtagaagttgttcaagaagcacac-3' (mIgκ sequence)
```

1)-3-4 Selection of Monoclonal Antibodies

From the above screening, antibody culture supernatant samples No.76, #1G5, and #4C12 each having a strong opsonophagocytic killing activity and a unique CDR sequence were found. The No.76 is an antibody prepared by using pJON mIgG2a and pJON mIgκ, and the #1G5 and #4C12 are antibodies prepared by using pJON mIgG2a-hIgG1 and pJON mIgκ, respectively. The amino acid sequences of each heavy and light chain variable region and CDR are shown in SEQ ID NOs: 4 to 27. Although the light chain of #4C12 shown in SEQ ID NO: 20 in the Sequence Listing includes a cysteine residue at amino acid number 75, a light chain in which the cysteine residue at the position of 75 in #4C12 was replaced with tyrosine was named "#4C13". Also, a combination of the heavy chain of #4C12 and the light chain of #1G5 was named "#4C13K". The #4C13K was obtained by expressing the human chimeric heavy chain gene expression unit of #4C12 prepared in 1)-2-5 and the mouse light chain gene expression unit of #1G5, in HEK293T according to the method of 1)-2-6. The #1G5 and #4C13K were purified by Protein G (GE Healthcare), and were named as "c#1G5M" and "c#4C13KM", respectively. The antibody concentration was calculated according to the method of 1)-3-1.

Example 2

Preparation of Human Chimeric Anti-LPS O11 Antibody and Meiji 1640, Meiji 1656, Human IgG1 Type 1BO11 (1BO11 hIgG1), Mouse IgG2a Type No.76 (No.76 mIgG2a)

2)-1 Construction of Chimeric and Humanized Antibody Light Chain Expression Vector pCMA-LK An approximately 5.4 kb fragment obtained by digesting a plasmid pcDNA3.3-TOPO/LacZ and (INVITROGEN Corp.) with the restriction enzymes XbaI and PmeI and a DNA fragment comprising a DNA sequence encoding a human light chain secretory signal shown in SEQ ID NO: 28 and a human light chain constant region were ligated to each other by using In-Fusion Advantage PCR Cloning Kit (Clontech Inc.), to prepare pcDNA3.3/LK.

Using the pcDNA3.3/LK as a template, a PCR reaction was performed with the following primer set and the resulting approximately 3.8 kb fragment was phosphorylated and subjected to self-ligation, thereby to construct a chimeric and humanized antibody light chain expression vector pCMA-LK having a signal sequence, a cloning site, and a human light chain constant region downstream of the CMV promoter.

```
Primer set
                                        (SEQ ID NO: 102)
5'-tataccgtcgacctctagctagagcttggc-3' (3.3-F1)

(SEQ ID NO: 103)
5'-gctatggcagggcctgccgccccgacgttg-3' (3.3-R1)
```

2)-2 Construction of Chimeric and Humanized Antibody IgG1 Type Heavy Chain Expression Vector pCMA-G1

A DNA fragment obtained by removing the light chain secretory signal and the human light chain constant region by digestion of the pCMA-LK with XbaI and PmeI, and a DNA fragment comprising a DNA sequence encoding a human heavy chain signal sequence shown in SEQ ID NO: 29 and amino acids of a human IgG1 constant region were ligated to each other by using In-Fusion Advantage PCR Cloning Kit (Clontech Inc.), thereby to construct a chimeric and humanized antibody IgG1-type heavy chain expression vector pCMA-G1 having a signal sequence, a cloning site, and a human IgG1 heavy chain constant region downstream of the CMV promoter.

2)-3 Preparation of Human Chimeric Anti-LPS O11 Antibody

2)-3-1 Construction of Human Chimeric No.76 Light Chain Expression Vector

By using the cDNA containing the light chain variable region of No.76 obtained in Example 1)-2-3 as a template and also using KOD-Plus-(TOYOBO, Co., Ltd.) and the following primer set, a DNA fragment comprising the cDNA encoding the light chain variable region was amplified, and a chimeric and humanized antibody light chain expression vector (pCMA-LK) was inserted at the site cleaved with the restriction enzyme BsiWI using an In-Fusion HD PCR cloning kit (Clontech, Inc.), and thus, a human chimeric No.76 light chain expression vector was constructed. The thus obtained expression vector was named "pCMA-LK/No.76". The nucleotide sequence of the human chimeric No.76 light chain was shown in SEQ ID NO: 30 in the Sequence Listing, and the amino acid sequence thereof was shown in SEQ ID NO: 31.

```
Primer set for No. 76 light chain
                                        (SEQ ID NO: 104)
5'-atctccggcgcgtacggcaacattgtaatgacccaatctcccaaat
c-3' (76L-F)

(SEQ ID NO: 105)
5'-ggaggggcggccacagcccgttttatttccagcttggtcctccc-
3' (76L-R)
```

2)-3-2 Construction of Human Chimeric No.76 Heavy Chain Expression Vector

By using, as a template, the cDNA containing the heavy chain variable region of No.76 obtained in Example 1)-2-3 and also using KOD-Plus-(TOYOBO, Co., Ltd.) and the following primer set, a DNA fragment comprising the cDNA encoding the heavy chain variable region was amplified, and a chimeric and humanized antibody IgG1-type heavy chain expression vector (pCMA-G1) was inserted at the site cleaved with the restriction enzyme BlpI using an In-Fusion HD PCR cloning kit (Clontech, Inc.), and thus, a human chimeric No.76 heavy chain expression vector was constructed. The thus obtained expression vector was named "pCMA-G1/No.76". The nucleotide sequence of the human chimeric No.76 heavy chain was shown in SEQ ID NO: 32 in the Sequence Listing, and the amino acid sequence thereof was shown in SEQ ID NO: 33.

```
Primer set for human chimeric No. 76 heavy chain
                                       (SEQ ID NO: 106)
5'-ccagatgggtgctgagccaggtccaactgcagcagcctggtg ctgag-3' (76H-F)

(SEQ ID NO: 107)
5'-cttggtggaggctgagctgactgtgagagtggtgccttggcccc ag-3' (76H-R)
```

2)-3-3 Construction of Human Chimeric #1G5 Light Chain Expression Vector

A DNA fragment comprising a DNA sequence encoding a human chimeric #1G5 light chain shown in SEQ ID NO: 34 in the Sequence Listing was synthesized (GENEART Inc., Artificial Gene Synthesis Service). By using the synthesized DNA fragment as a template and also using KOD-Plus-(TOYOBO, Co., Ltd.) and the following primer set, a DNA fragment comprising a DNA sequence encoding the human chimeric #1G5 light chain was amplified, and a chimeric and humanized antibody light chain expression vector pCMA-LK was inserted at the site cleaved with the restriction enzymes XbaI and PmeI using an In-Fusion HD PCR cloning kit (Clontech, Inc.), and thus, a human chimeric #1G5 light chain expression vector was constructed. The thus obtained expression vector was named "pCMA-LK/1G5". The amino acid sequence of the human chimeric #1G5 light chain was shown in SEQ ID NO: 35 in the Sequence Listing.

```
Primer set for human chimeric #1G5 light chain
                                       (SEQ ID NO: 108)
5'-ccagcctccggactctagagccacc-3' (CM-inf-F)

(SEQ ID NO: 109)
5'-agttagcctcccccgtttaaactc-3' (CM-inf-R)
```

2)-3-4 Construction of Human Chimeric #1G5 Heavy Chain Expression Vector

A DNA fragment containing a DNA sequence encoding a human chimeric #1G5 heavy chain variable region represented by nucleotide numbers 36 to 449 of the human chimeric #1G5 heavy chain nucleotide sequence of SEQ ID NO: 36 in the Sequence Listing was synthesized (GENEART Inc., Artificial Gene Synthesis Service). By using the synthesized DNA fragment as a template and also using KOD-Plus-(TOYOBO, Co., Ltd.) and the following primer set, a DNA fragment comprising a DNA sequence encoding the human chimeric #1G5 heavy chain variable region was amplified, and a chimeric and humanized antibody IgG1-type heavy chain expression vector pCMA-G1 was inserted at the site cleaved with the restriction enzyme BlpI using an In-Fusion HD PCR cloning kit (Clontech, Inc.), and thus, a human chimeric #1G5 heavy chain expression vector was constructed. The thus obtained expression vector was named "pCMA-G1/1G5". The amino acid sequence of the human chimeric #1G5 heavy chain was shown in SEQ ID NO: 37 in the Sequence Listing.

```
Primer set for human chimeric #1G5 heavy chain
                                       (SEQ ID NO: 110)
5'-agctcccagatgggtgctgagc-3' (EG-Inf-F)

(SEQ ID NO: 111)
5'-gggcccttggtggaggctgagc-3' (EG1-Inf-R)
```

2)-3-5 Construction of Human Chimeric #4C13 Light Chain Expression Vector

A DNA fragment containing a DNA sequence encoding a human chimeric #4C13 light chain shown in SEQ ID NO: 38 in the Sequence Listing was synthesized (GENEART Inc., Artificial Gene Synthesis Service). By using the synthesized DNA fragment as a template and also using KOD-Plus-(TOYOBO, Co., Ltd.) and the following primer set, a DNA fragment comprising a DNA sequence encoding the human chimeric #4C13 light chain was amplified, and a chimeric and humanized antibody light chain expression vector pCMA-LK was inserted at the site cleaved with the restriction enzymes XbaI and PmeI using an In-Fusion HD PCR cloning kit (Clontech, Inc.), and thus, a human chimeric #4C13 light chain expression vector was constructed. The thus obtained expression vector was named "pCMA-LK/4C13". The amino acid sequence of the human chimeric #4C13 light chain was shown in SEQ ID NO: 39 in the Sequence Listing.

```
Primer set for human chimeric #4C13 light chain
                                       (SEQ ID NO: 108)
5'-ccagcctccggactctagagccacc-3' (CM-inf-F)

(SEQ ID NO: 109)
5'-agttagcctcccccgtttaaactc-3' (CM-inf-R)
```

2)-3-6 Construction of Human Chimeric #4C13 Heavy Chain Expression Vector

A DNA fragment containing a DNA sequence encoding a human chimeric #4C13 heavy chain variable region represented by nucleotide numbers 36 to 437 of the human chimeric #4C13 heavy chain nucleotide sequence of SEQ ID NO: 40 in the Sequence Listing was synthesized (GENEART Inc., Artificial Gene Synthesis Service). By using the synthesized DNA fragment as a template and also using KOD-Plus-(TOYOBO, Co., Ltd.) and the following primer set, a DNA fragment comprising a DNA sequence encoding the human chimeric #4C13 heavy chain variable region was amplified, and a chimeric and humanized antibody IgG1-type heavy chain expression vector pCMA-G1 was inserted at the site cleaved with the restriction enzyme BlpI using an In-FusionHD PCR cloning kit (Clontech, Inc.) to thereby construct a human chimeric #4C13 heavy chain expression vector. The thus obtained expression vector was named "pCMA-G1/4C13". The amino acid sequence of the human chimeric #4C13 heavy chain was shown in SEQ ID NO: 41 in the Sequence Listing.

```
Primer set for human chimeric #4C13 heavy chain
                                       (SEQ ID NO: 110)
5'-agctcccagatgggtgctgagc-3' (EG-Inf-F)

(SEQ ID NO: 111)
5'`gggcccttggtggaggctgagc-3' (EG1-Inf-R)
```

2)-3-7 Preparation of Human Chimeric Anti-LPS O11 Antibody

2)-3-7-1 Production of Human Chimeric Anti-LPS O11 Antibody

FreeStyle 293-F cells (Invitrogen Inc.) were passaged and cultured according to the manual.

FreeStyle 293-F cells (Invitrogen, Inc.) of $2 \times 10^9$ in logarithmic growth phase were seeded in 3 L of Fernbach Erlenmeyer Flask (CORNING Co.), diluted with FreeStyle 293 expression medium (INVITROGEN Corp.) to $1.0 \times 10^6$ cells/ml, and cultured with shaking at 37° C. for one hour at 90 rpm in an 8% $CO_2$ incubator. Polyethyleneimine (Polyscience, Inc., #24765) of 3.6 mg was dissolved in 20 ml of Opti-Pro SFM medium (INVITROGEN, Inc.), and then a light chain expression vector (0.8 mg) and a heavy chain expression vector (0.4 mg) prepared with use of PureLink HiPure Plasmid kit (Invitrogen Corp.) were suspended in 20 ml of Opti-Pro SFM (Invitrogen Corp). To the polyethyleneimine/Opti-Pro SFM mixed liquid (20 ml) was added 20 ml of the expression vector/Opti-Pro SFM mixed liquid, and the resulting liquid was gently agitated and allowed to stand for further 5 minutes. After that, the liquid was added to the FreeStyle 293-F cells. The shaking culture was performed at 90 rpm and at 37° C. for 7 days in an 8% $CO_2$ incubator, and the culture supernatant was filtered with Disposable Capsule Filter (ADVANTEC #CCS-045-E1H).

A human chimeric No.76 acquired by a combination of pCMA-LK/No.76 and pCMA-G1/No.76 was named "cNo.76"; a human chimeric #1G5 acquired by a combination of pCMA-LK/1G5 and pCMA-G1/1G5 was named "c#1G5"; and a human chimeric #4C13 acquired by a combination of pCMA-LK/4C13 and pCMA-G1/4C13 was named "c#4C13".

2)-3-7-2 Purification of Human Chimeric Anti-LPS O11 Antibody

The antibody from the culture supernatant obtained in 2)-3-7-1 was purified by one-step process of rProtein A affinity chromatography (at 4-6° C.). After purification by the rProtein A affinity chromatography, buffer replacement process was performed at 4-6° C. First, the culture supernatant was applied to a column filled with MabSelect SuRe (manufactured by GE Healthcare Bioscience Co.) equilibrated with PBS. After all of the culture liquid was placed in the column, the column was washed with two or more times the column volumes of PBS. Then the column was eluted with 2M arginine hydrochloride solution (pH 4.0) to collect fractions containing the antibody. The fractions were dialyzed (Thermo Scientific, Inc., Slide-A-Lyzer Dialysis Cassette) to replace the solution with HBSor (25 mM histidine/5% sorbitol, pH 6.0). The solution was concentrated with Centrifugal UF Filter Device VIVASPIN20 (fractionation molecular weight UF10K, Sartorius, Inc., at 4° C.) to adjust to 5 mg/ml or more of IgG concentration. Finally, the solution was filtered through a Minisart-Plus filter (Sartorius Inc.) and served as a purified sample.

2)-4 Preparation of Meiji 1640 and Meiji 1656, Human IgG1 Type 1BO11 (1BO11 hIgG1), Mouse IgG2a Type No.76 (No.76 mIgG2a)

2)-4-1 Preparation of Meiji 1640

The Meiji 1640 was prepared based on the amino acid sequences of the light chain and the heavy chain as described in WO 2011/102551.

2)-4-1-1 Construction of Meiji 1640 Light Chain Expression Vector

A DNA fragment containing a DNA sequence encoding a Meiji 1640 light chain variable region represented by nucleotide numbers 38 to 408 of the Meiji 1640 light chain nucleotide sequence of SEQ ID NO: 42 in the Sequence Listing was synthesized (GENEART Inc., Artificial Gene Synthesis Service). By using the synthesized DNA fragment as a template and also using KOD-Plus-(TOYOBO, Co., Ltd.) and the following primer set, a DNA fragment comprising a DNA sequence encoding the Meiji 1640 light chain variable region was amplified, and a chimeric and humanized antibody light chain expression vector pCMA-LK was inserted at the site cleaved with the restriction enzyme BsiWI using an In-Fusion HD PCR cloning kit (Clontech, Inc.) to thereby construct a Meiji 1640 light chain expression vector. The thus obtained expression vector was named "pCMA-LK/Meiji 1640". The amino acid sequence of the Meiji 1640 light chain was shown in SEQ ID NO: 43 in the Sequence Listing.

```
Primer set for Meiji 1640 light chain
                                (SEQ ID NO: 112)
5'-ctgtggatctccggcgcgtacggc-3'  (CM-LKF)

(SEQ ID NO: 113)
5'-ggaggggcggccaccgtacg-3'      (KCL-Inf-R)
```

2)-4-1-2 Construction of Meij 1640 Heavy Chain Expression Vector

A DNA fragment containing a DNA sequence encoding a Meiji 1640 heavy chain variable region represented by nucleotide numbers 36 to 458 of the Meiji 1640 heavy chain nucleotide sequence of SEQ ID NO: 44 in the Sequence Listing was synthesized (GENEART Inc., Artificial Gene Synthesis Service). By using the synthesized DNA fragment as a template and also using KOD-Plus-(TOYOBO, Co., Ltd.) and the following primer set, a DNA fragment comprising a DNA sequence encoding the Meiji 1640 heavy chain variable region was amplified, and a chimeric and humanized antibody IgG1 type heavy chain expression vector pCMA-G1 was inserted at the site cleaved with the restriction enzyme BlpI using an In-Fusion HD PCR cloning kit (Clontech, Inc.) to thereby construct a Meiji 1640 heavy chain expression vector. The thus obtained expression vector was named "pCMA-G1/Meiji 1640". The amino acid sequence of the Meiji 1640 heavy chain was shown in SEQ ID NO: 45 in the Sequence Listing.

```
Primer set for Meiji 1640 heavy chain
                                (SEQ ID NO: 110)
5'-agctcccagatgggtgctgagc-3'   (EG-Inf-F)

(SEQ ID NO: 111)
5'-gggcccttggtggaggctgagc-3'   (EG1-Inf-R)
```

2)-4-2 Preparation of Meiji 1656

The Meiji 1656 was prepared based on the amino acid sequences of the light chain and the heavy chain as described in WO 2011/102551.

2)-4-2-1 Construction of Meiji 1656 Light Chain Expression Vector

A DNA fragment containing a DNA sequence encoding a Meiji 1656 light chain variable region represented by nucleotide numbers 38 to 402 of the Meiji 1656 light chain nucleotide sequence of SEQ ID NO: 46 in the Sequence Listing was synthesized (GENEART Inc., Artificial Gene Synthesis Service). By using the synthesized DNA fragment as a template and also using KOD-Plus-(TOYOBO, Co., Ltd.) and the following primer set, a DNA fragment comprising a DNA sequence encoding the Meiji 1656 light chain variable region was amplified, and a chimeric and humanized antibody light chain expression vector pCMA-LK was inserted at the site cleaved with the restriction enzyme BsiWI using an In-Fusion HD PCR cloning kit (Clontech, Inc.) to thereby construct a Meiji 1640 light chain expression vector. The thus obtained expression vector was named "pCMA-LK/Meiji 1656". The amino acid sequence of the Meiji 1656 light chain was shown in SEQ ID NO: 47 in the Sequence Listing.

```
Primer set for Meiji 1656 light chain
                                        (SEQ ID NO: 112)
5'-ctgtggatctccggcgcgtacggc-3'  (CM-LKF)

(SEQ ID NO: 113)
5'-ggaggggggcggccaccgtacg-3'  (KCL-Inf-R)
```

2)-4-2-2 Construction of Meij 1656 Heavy Chain Expression Vector

A DNA fragment containing a DNA sequence encoding a Meiji 1656 heavy chain variable region represented by nucleotide numbers 36 to 467 of the Meiji 1656 heavy chain nucleotide sequence of SEQ ID NO: 48 in the Sequence Listing was synthesized (GENEART Inc., Artificial Gene Synthesis Service). By using the synthesized DNA fragment as a template and also using KOD-Plus-(TOYOBO, Co., Ltd.) and the following primer set, a DNA fragment comprising a DNA sequence encoding the Meiji 1656 heavy chain variable region was amplified, and a chimeric and humanized antibody IgG1 type heavy chain expression vector pCMA-G1 was inserted at the site cleaved with the restriction enzyme BlpI using an In-Fusion HD PCR cloning kit (Clontech, Inc.) to thereby construct a Meiji 1656 heavy chain expression vector. The thus obtained expression vector was named "pCMA-G1/Meiji 1656". The amino acid sequence of the Meiji 1656 heavy chain was shown in SEQ ID NO: 49 in the Sequence Listing.

```
Primer set for Meiji 1656 heavy chain
                                        (SEQ ID NO: 110)
5'-agctcccagatgggtgctgagc-3'  (EG-Inf-F)

(SEQ ID NO: 111)
5'-gggcccttggtggaggctgagc-3'  (EG1-Inf-R)
```

2)-4-3 Preparation of Human IgG1 Type 1BO11 (1BO11 hIgG1)

The 1BO11 hIgG1 was prepared based on the amino acid sequences of the light chain and the heavy chain as described in FIGS. 1 and 2 of WO 2006/084758.

2)-4-3-1 Construction of 1BO11 hIgG1 Light Chain Expression Vector

A DNA fragment encoding a mouse IgG2b type chimeric 1BO11 light chain shown in SEQ ID NO: 50 in the Sequence Listing was synthesized (MBL Co., Ltd., Artificial Gene Synthesis Service). By using the synthesized DNA fragment as a template and also using KOD-Plus-(TOYOBO, Co., Ltd.) and the following primer set, a DNA fragment comprising a cDNA encoding the light chain variable region was amplified, and a chimeric and humanized antibody light chain expression vector pCMA-LK was inserted at the site cleaved with the restriction enzyme BsiWI, with use of an In-Fusion HD PCR cloning kit (Clontech, Inc.) to thereby construct a 1BO11 hIgG1 light chain expression vector. The thus obtained expression vector was named "pCMA-LK/1BO11". The nucleotide sequence of the 1BO11 hIgG1 light chain was shown in SEQ ID NO: 51 in the Sequence Listing and the amino acid sequence of the 1BO11 hIgG1 light chain was shown in SEQ ID NO: 52.

```
Primer set for 1BO11 hIgG1 light chain
                                        (SEQ ID NO: 114)
5'-atctccggcgcgtacggcgacgtggtgatgacccagagccctct
gtcc-3'  (h1BO-LF)

(SEQ ID NO: 115)
5'-gggcggccaccgtacgcttgatctccaccttggtgcctccgccg-3'
(h1BO-LR)
```

2)-4-3-2 Construction of 1BO11 hIgG1 Heavy Chain Expression Vector

A DNA fragment encoding a mouse IgG2b type chimeric 1BO11 heavy chain shown in SEQ ID NO: 53 in the Sequence Listing was synthesized (MBL Co., Ltd., Artificial Gene Synthesis Service). By using the synthesized DNA fragment as a template and also using KOD-Plus-(TOYOBO, Co., Ltd.) and the following primer set, a DNA fragment comprising a cDNA encoding the heavy chain variable region was amplified, and a chimeric and humanized antibody IgG1 type heavy chain expression vector pCMA-G1 was inserted at the site cleaved with the restriction enzyme BlpI using an In-Fusion HD PCR cloning kit (Clontech, Inc.) to thereby construct a 1BO11 hIgG1 heavy chain expression vector. The thus obtained expression vector was named "pCMA-G1/1BO11". The nucleotide sequence of the 1BO11 hIgG1 heavy chain was shown in SEQ ID NO: 54 in the Sequence Listing, and the amino acid sequence of the 1BO11 hIgG1 heavy chain was shown in SEQ ID NO: 55.

```
Primer set for 1BO11 hIgG1 heavy chain
                                        (SEQ ID NO: 116)
5'-ccagatgggtgctgagcgaggagcaagtggtggagagcgg-3'
(h1BO-HF)

(SEQ ID NO: 117)
5'-cttggtggaggctgagctcacggtcaccatggtgccttgtc-3'
(h1BO-HR)
```

2)-4-4 Preparation of Mouse IgG2a Type No.76 (No.76 mIgG2a)

2)-4-4-1 Preparation of No.76 mIgG2a Light Chain Expression Vector

A DNA fragment containing a sequence encoding No.76 mIgG2a light chain shown in SEQ ID NO: 118 was synthesized (GENEART Inc., Strings DNA Fragments). The synthesized DNA was inserted at the site where the chimeric and humanized antibody light chain expression vector pCMA-LK was digested with the restriction enzymes XbaI and PmeI to remove the κ chain secretion signal and human κ chain constant region, using an In-Fusion HD PCR cloning kit (Clontech, Inc.) to thereby construct a No.76 mIgG2a light chain expression vector. The thus obtained expression vector was named "pCMA/No.76 mIgG2aL". The amino acid sequence of the No.76 mIgG2a light chain was shown in SEQ ID NO: 119.

2)-4-4-2 Preparation of No.76 mIgG2a Heavy Chain Expression Vector

A DNA fragment containing a sequence encoding No.76 mIgG2a heavy chain shown in SEQ ID NO: 120 was synthesized (GENEART Inc., Artificial Gene Synthesis Service). By using the synthesized DNA fragment as a template and also using KOD-Plus-(TOYOBO, Co., Ltd.) and the following primer set, a DNA fragment comprising a sequence encoding the No.76 mIgG2a heavy chain was amplified, and inserted at the site where the chimeric and humanized antibody light chain expression vector pCMA-LK was digested with the restriction enzymes XbaI and PmeI to remove the κ chain secretion signal and human κ chain constant region, with use of an In-Fusion HD PCR cloning kit (Clontech, Inc.) to thereby construct a No.76 mIgG2a heavy chain expression vector. The thus obtained expression vector was named "pCMA/No.76 mIgG2aH". The amino acid sequence of the No.76 mIgG2a heavy chain was shown in SEQ ID NO: 121.

```
Primer set for No. 76 mIgG2a heavy chain
                                    (SEQ ID NO: 108)
 5'-ccagcctccggactctagagccacc-3' (CM-inf-F)

(SEQ ID NO: 109)
 5'-agttagcctcccccgtttaaactc-3' (CM-inf-R)
```

2)-4-5 Production and Purification of Meiji 1640, Meiji 1656, 1BO11 hIgG1, and No.76 mIgG2a
2)-4-5-1 Production of Meiji 1640, Meiji 1656, 1BO11 hIgG1, and No.76 mIgG2a These antibodies were produced in the same manner as in Example 2)-3-7-1.

Meiji 1640 was obtained by a combination of the pCMA-LK/Meiji 1640 and the pCMA-G1/Meiji 1640; Meiji 1656 was obtained by a combination of the pCMA-LK/Meiji 1656 and the pCMA-G1/Meiji 1656; 1BO11 hIgG1 was obtained by a combination of the pCMA-LK/1BO11 and the pCMA-G1/1BO11; and the No.76 mIgG2a was obtained by a combination of the pCMA/No.76 mIgG2aL and the pCMA/No.76 mIgG2aH.

2)-4-5-2 Purification of Meiji 1640, Meiji 1656, 1BO11 hIgG1, and No.76 mIgG2a

These antibodies were purified from the culture supernatant obtained in 2)-4-5-1 in the same manner as in Example 2)-3-7-2.

Example 3 In Vitro Activity of Anti-LPS O11 Antibody

3)-1 Opsonophagocytic Killing Activity Against *Pseudomonas aeruginosa* ATCC 29260

Opsonophagocytic killing activity of each of cNo.76, c#1G5M, c#1G5, c#4C13KM, c#4C13, Meiji 1640, Meiji 1656, and 1BO11 hIgG1 against *Pseudomonas aeruginosa* ATCC 29260 was measured in accordance with the method of 1)-3-2. The opsonophagocytic killing activity was expressed in terms of 50% minimum growth inhibitory concentration. The results are shown in Table 2.

cytic killing activity of Meiji 1656, and 243-729 times the opsonophagocytic killing activity of 1BO11 hIgG1.

3)-2 Binding Specificity to *Pseudomonas aeruginosa* O11 Strains

The binding specificity of cNo.76, c#1G5, and c#4C13 to *Pseudomonas aeruginosa* carrying various O antigens was confirmed by the whole cell ELISA. The strains and O antigens used are shown in Table 3.

TABLE 3

| Strain No | O-antigen |
|---|---|
| ATCC 33348 | O1 |
| ATCC 33349 | O2 |
| ATCC 33350 | O3 |
| ATCC 33351 | O4 |
| ATCC 33352 | O5 |
| ATCC 33354 | O6 |
| ATCC 33353 | O7 |
| ATCC 33355 | O8 |
| ATCC 33356 | O9 |
| ATCC 33357 | O10 |
| ATCC 33358 | O11 |
| ATCC 33360 | O13 |
| ATCC 33361 | O14 |
| ATCC 33362 | O15 |
| ATCC 33363 | O16 |
| ATCC 33364 | O17 |
| ATCC 43390 | O18 |
| ATCC 43731 | O19 |
| ATCC 43732 | O20 |
| ATCC 21636 | M (untypable) |
| ATCC 29260 | O11 (positive control) |
| ATCC 25922 | *E. coli* (negative control) |

The bacteria cultured on MHA was suspended in saline to adjust to 0.5-0.6 of $OD_{600}$ and immobilized for one hour. After blocking with 5% skim milk (Becton, Dickinson and Company)/TBST for 2 hours, 0.1 μg/ml of cNo.76, c#1G5,

TABLE 2

| | Opsonophagocytic killing activity (ng/mL) | | | | | | | |
|---|---|---|---|---|---|---|---|---|
| Strain No. | cNo. 76 | c#1G5M | c#1G5 | c#4C13KM | c#4C13 | Meiji1640 | Meiji1656 | 1BO11 hIgG1 |
| ATCC 29260 | 4.1 | 1.4 | 4.1 | 1.4 | 4.1 | 110 | 37 | 1000 |

The cNo.76, c#1G5M, c#1G5, c#4C13KM, and c#4C13 exhibit almost the same level of opsonophagocytic killing activity, and they showed 27-81 times the opsonophagocytic killing activity of Meiji 1640, 9-27 times the opsonophagoand c#4C13 was added as the primary antibody to the suspension. The suspension was allowed to react for 1 hour, followed by reaction with Anti-Human IgG, HRP-Linked WholeAb Sheep (GE Healthcare) as the secondary antibody for 1 hour, after which SuperSignal ELISA Pico Chemiluminescent Substrate (Thermo Fisher Scientific K.K.) was added, and light emission was measured immediately after the addition with ARVO 1420 multi-label counter (Perkin Elmer). Between each step, two or three times washing with TBST were performed. *Pseudomonas aeruginosa* ATCC 29260 was used as a positive control, and *E. coli* ATCC 25922 was used as a negative control. The cNo.76, c#1G5, and c#4C13 showed a high binding activity to the O11 strains. On the other hand, since the cNo.76, c#1G5, and c#4C13 showed no binding activity to other O-antigen-carrying strains, they were found to specifically recognize the antigen O11 (FIG. 4).

3)-3 Binding Activity to *Pseudomonas aeruginosa* O11 Clinical Isolates

The binding activity of the antibodies to 31 clinical isolates of *Pseudomonas aeruginosa* O11 held by Daiichi Sankyo Co., Ltd. and to ATCC 29260 as a positive control was measured by the whole cell ELISA. The O-antigen of *Pseudomonas aeruginosa* was determined by mixing 20 μl of immune serum for serotyping *Pseudomonas aeruginosa* (Denka Seiken Co., Ltd.) and 20 μl of bacterial solution and observing the presence or absence of agglutination caused by the antigen-antibody reaction. The Whole cell ELISA was performed in the same manner as in 3)-2, and 0.1 μg/ml of cNo.76, c#1G5M, c#4C13KM, Meiji 1640, and Meiji 1656, and 6.4 μg/ml of 1BO11 hIgG1 were prepared as the primary antibody and allowed to react for 1 hour. Information of the bacterial strains used is shown in Table 4 and the measurement results are shown in Table 5.

TABLE 4

| Strain No. | Isolation year | Isolation country | Isolation part |
|---|---|---|---|
| 1 | 2010 | Japan | Respiratory tract |
| 2 | 2010 | Japan | Respiratory tract |
| 3 | 2010 | Japan | Respiratory tract |
| 4 | 2010 | Japan | Respiratory tract |
| 5 | 2010 | Japan | Respiratory tract |
| 6 | 2010 | Japan | Respiratory tract |
| 7 | 2010 | Japan | Respiratory tract |
| 8 | 2010 | Japan | Respiratory tract |
| 9 | 2010 | Japan | Urine |
| 10 | 2010 | Japan | Urine |
| 11 | 2009 | U.S. | Respiratory tract |
| 12 | 2009 | U.S. | Blood |
| 13 | 2009 | U.S. | Respiratory tract |
| 14 | 2009 | U.S. | Respiratory tract |
| 15 | 2009 | U.S. | Blood |
| 16 | 2009 | U.S. | Respiratory tract |
| 17 | 2009 | U.S. | Respiratory tract |
| 18 | 2009 | U.S. | Blood |
| 19 | 2009 | U.S. | Blood |
| 20 | 2009 | U.S. | Blood |
| 21 | 2009 | Germany | Blood |
| 22 | 2009 | Spain | Respiratory tract |
| 23 | 2009 | Spain | Respiratory tract |
| 24 | 2009 | France | Blood |
| 25 | 2009 | Italy | Respiratory tract |
| 26 | 2009 | Italy | Respiratory tract |
| 27 | 2009 | France | Respiratory tract |
| 28 | 2009 | Spain | Blood |
| 29 | 2010 | Sweden | Blood |
| 30 | 2003 | Spain | Respiratory tract |
| 31 | 2007 | Japan | Respiratory tract |

TABLE 5

| Strain No. | cNo. 76 | c#1G5M | c#4C13KM | Meiji1640 | Meiji1656 | 1BO11 hIgG1 |
|---|---|---|---|---|---|---|
| ATCC 29260 | + | + | + | + | + | + |
| 1 | + | + | + | + | + | + |
| 2 | + | + | + | + | + | + |
| 3 | + | + | + | + | + | − |
| 4 | + | + | + | + | + | + |
| 5 | + | + | + | + | + | + |
| 6 | + | + | + | + | + | + |
| 7 | + | + | + | + | + | + |
| 8 | + | + | + | + | + | + |
| 9 | + | + | + | − | − | − |
| 10 | + | + | + | + | + | + |
| 11 | + | + | + | − | − | − |
| 12 | + | + | + | − | − | − |
| 13 | + | + | + | + | + | + |
| 14 | + | + | + | + | + | + |
| 15 | + | + | + | − | + | − |
| 16 | + | + | + | + | + | + |
| 17 | + | + | + | + | + | + |
| 18 | + | + | + | − | − | − |
| 19 | + | + | + | − | + | − |
| 20 | + | + | + | − | + | − |
| 21 | + | + | + | + | + | + |
| 22 | + | + | + | + | + | + |
| 23 | + | + | + | + | + | + |
| 24 | + | + | + | + | + | + |
| 25 | + | + | + | + | + | + |
| 26 | + | + | + | + | + | + |
| 27 | + | + | + | + | + | + |
| 28 | + | + | + | − | − | − |
| 29 | + | + | + | − | − | − |
| 30 | + | + | + | + | + | + |
| 31 | + | + | + | + | + | + |

+: positive,
−: negative

When the binding activity of the antibody against *Pseudomonas aeruginosa* O11 clinical isolates is 4 or more times stronger than the binding activity against *E. coli*, such an antibody was judged to have a binding activity against *Pseudomonas aeruginosa* O11 clinical isolates. The cNo.76, c#1G5M, and c#4C13KM showed the binding activity against all strains, and Meiji 1640 showed the binding activity against only 22 strains, Meiji 1656 showed the binding activity against only 25 strains, and 1BO11 hIgG1 showed the binding activity against only 21 strains. The coverage ratios of cNo.76, c#1G5M, c#4C13KM, Meiji 1640, Meiji 1656, and 1BO11 hIgG1 for O11 clinical isolates are 100%, 100%, 100%, 71%, 81%, and 68%, respectively.

3)-4 Opsonophagocytic Killing Activity Against *Pseudomonas aeruginosa* O11 Clinical Isolates Opsonophagocytic killing activity against No. 9, No. 12, No. 18, No. 24, No. 26, and No. 31 strains among the O11 strains used in 3)-3 was measured. The method was carried out in the same manner as in 1)-3-2, and the minimum concentration at which the 50% minimum growth inhibitory concentration is observed was determined. The results are shown in Table 6.

TABLE 6

| | Opsonophagocytic killing activity (ng/mL) | | | | | |
|---|---|---|---|---|---|---|
| Strain No. | cNo. 76 | c#1G5/ c#1G5M | c#4C13/ c#4C13KM | Meiji 1640 | Meiji 1656 | 1BO11 hIgG1 |
| 9 | 4.1 | 4.1 | 1.4 | >3000 | >3000 | >27000 |
| 12 | 4.1 | 4.1 | 12 | >3000 | >3000 | >27000 |
| 18 | 4.1 | 1.4 | 1.4 | >3000 | >3000 | >27000 |
| 24 | 4.1 | 1.4 | 1.4 | 110 | 37 | 1000 |
| 26 | 4.1 | 1.4 | 1.4 | 110 | 37 | 1000 |
| 31 | 4.1 | 4.1 | 4.1 | 330 | 110 | 3000 |

The cNo.76, c#1G5 or c#1G5M, c#4C13 or c#4C13KM showed the activity against all the strains. On the other hand, Meiji 1640, Meiji 1656, and 1BO11 hIgG1 did not show opsonophagocytic killing activity against No. 9, 12, and 18 strains to which binding activity was not observed. These results revealed that the cNo.76, c#1G5 or c#1G5M, c#4C13 or c#4C13KM showed a higher coverage ratio against the O11 strains in vitro in comparison with the Meiji 1640, Meiji 1656, and 1BO11 hIgG1.

Example 4 In Vivo Activity of Anti-LPS O11 Antibody

4)-1 Therapeutic Efficacy on Mouse Model of Lung Infection by *Pseudomonas aeruginosa* ATCC 29260 (Intravenous Administration)

Figure 5:
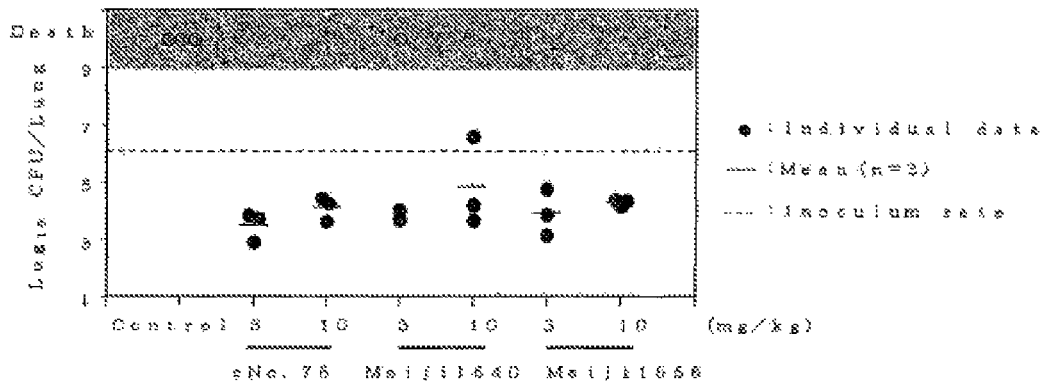
FIG. 5 is a graph showing the therapeutic efficacy (intravenous administration) on a mouse model of lung infection by *Pseudomonas aeruginosa* ATCC 29260.

*Pseudomonas aeruginosa* ATCC 29260 which had been cultured on MHA was prepared to $OD_{600}$=0.10, and 10-fold dilution series of $10^0$-$10^9$ were prepared with Mueller Hinton Broth (Becton, Dickinson and Company) and cultured overnight at 35° C. Using a bacterial suspension of $OD_{600}$=0.10 or the highest dilution of greater than $OD_{600}$=0.10 among the dilution series, the suspension was prepared to $OD_{600}$=0.10, diluted four-fold, and the diluted suspension was served as an inoculum. ICR mice (Charles River) were intranasally inoculated with the inoculum of 50 μl, and 3 or 10 mg/kg of cNo.76, Meiji 1640, and Meiji 1656 was intravenously administered 1 hour after the inoculation (n=3). After 24 hours of the inoculation, the viable cell count in lung was measured to determine the therapeutic efficacy. Compared with the control group without administration of the antibody, a good therapeutic efficacy was confirmed in the cNo.76 administration group, and such therapeutic efficacy was equivalent to or greater than the effect of each of Meiji 1640 and Meiji 1656 (FIG. 5).

4)-2 Therapeutic Efficacy on Mouse Model of Lung Infection by *Pseudomonas aeruginosa* Clinical Isolates 4)-2-1 Therapeutic Efficacy on Mouse Model of Lung Infection by *Pseudomonas aeruginosa* Clinical Isolate No. 12 (Mixed Administration of Bacteria and Antibody)

Figure 6:
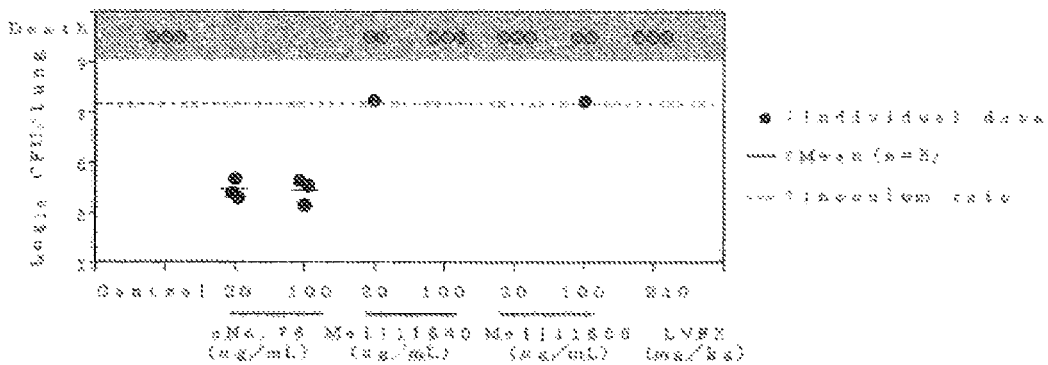
FIG. 6 is a graph showing the therapeutic efficacy (mixed administration of bacteria and antibodies) on a mouse model of lung infection by *Pseudomonas aeruginosa* clinical isolate No. 12.

*Pseudomonas aeruginosa* clinical isolate No. 12 cultured on MHA was suspended in saline and adjusted to $OD_{600}$=2.0 (10-fold diluted suspension was adjusted to prepare a bacterial suspension of $OD_{600}$=0.2). The cNo.76, Meiji 1640, or Meiji 1656 of 20 μg/ml or 100 μg/ml were mixed in a ratio of 1:9 so that the binding between bacteria and antibodies surely occurs, and ICR mice (Charles River) (n=3) were intranasally inoculated with 50 μl of the mixture. At 24 hours after the inoculation, the viable cell count in the lung was measured to determine the therapeutic effect. In addition, the therapeutic efficacy of levofloxacin (LVFX) as a control was also examined (the minimum inhibitory concentration (MIC) of LVFX against No. 12 strain was >128 μg/ml). In other words, the bacterial suspension and saline were mixed in a ratio of 1:9, and 50 μl of the mixture was inoculated into mice and LVFX of 240 mg/kg was subcutaneously administered to the inoculated mice immediately after the inoculation. Compared with the control group without administration of the antibody, a good therapeutic efficacy was confirmed in the cNo.76 administration group, but was not observed in the Meiji 1640, Meiji 1656, or LVFX administration group (FIG. 6).

4)-2-2 Therapeutic Efficacy on Mouse Model of Lung Infection by *Pseudomonas aeruginosa* Clinical Isolate No. 31 (Mixed Administration of Bacteria and Antibody)

Figure 7:
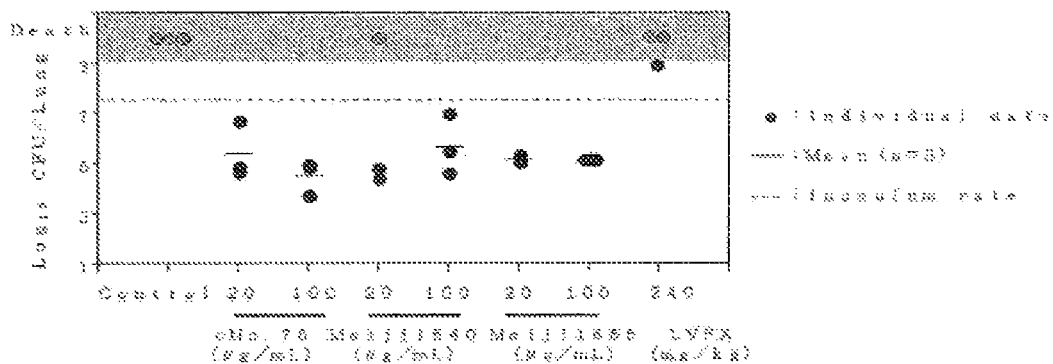
FIG. 7 is a graph showing the therapeutic efficacy (mixed administration of bacteria and antibodies) on a mouse model of lung infection by Pseudomonas aeruginosa clinical isolate No. 31.

*Pseudomonas aeruginosa* clinical isolate No. 31 cultured on MHA was suspended in saline and adjusted to $OD_{600}$=5.0 (10-fold diluted suspension is adjusted to prepare a bacterial suspension of $OD_{600}$=0.5). The bacterial suspension and cNo.76, Meiji 1640, or Meiji 1656 of 20 μg/ml or 100 μg/ml were mixed in a ratio of 1:9 so that the binding between bacteria and antibodies surely occurs, and ICR mice (Charles River) (n=3) were intranasally inoculated with 50 μl of the mixture. At 24 hours after the inoculation, the viable cell count in the lung was measured to determine the therapeutic efficacy. In addition, the therapeutic efficacy of LVFX as a control was also examined (the MIC of LVFX against strain No. 31 was 32 μg/ml). In other words, the bacterial suspension and saline were mixed in a ratio of 1:9, and 50 μl of the mixture was inoculated into mice and LVFX of 240 mg/kg was subcutaneously administered to the inoculated mice immediately after the inoculation. Compared with the control group without administration of the antibody, a good therapeutic efficacy was confirmed in the cNo.76, Meiji 1640, and Meiji 1656 administration groups, but was not observed in the LVFX administration group (FIG. 7).

4)-2-3 Therapeutic Efficacy on Mouse Model of Lung Infection by *Pseudomonas aeruginosa* clinical isolate No. 12 (Intravenous Administration)

Figure 8:
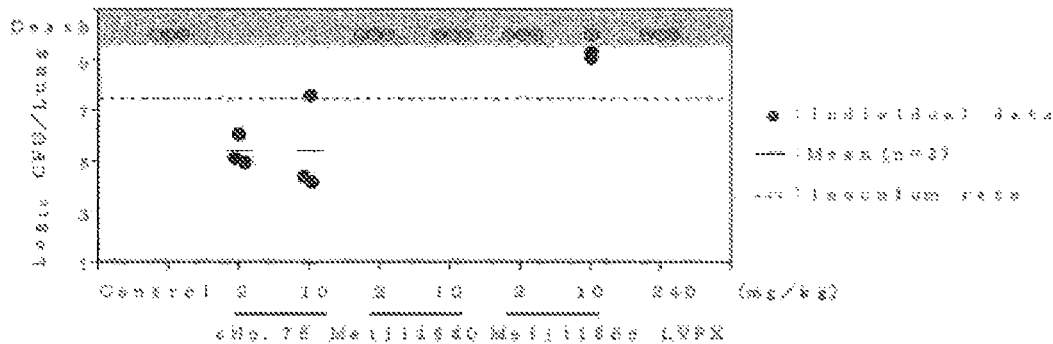
FIG. 8 is a graph showing the therapeutic efficacy (intravenous administration) on a mouse model of lung infection by Pseudomonas aeruginosa clinical isolate No. 12.

*Pseudomonas aeruginosa* clinical isolate No. 12 which had been cultured on MHA was suspended in saline to adjust it to $OD_{600}$=0.20 and this was served as an inoculum. ICR mice (Charles River) (n=3) were intranasally inoculated with the inoculum (50 μl), and 2 mg/kg or 10 mg/kg of cNo.76, Meiji 1640, or Meiji 1656 was intravenously administered immediately after the inoculation. At 24 hours after the inoculation, the viable cell count in the lung was measured to determine the therapeutic effect. In addition, the therapeutic efficacy of LVFX as a control was also examined by subcutaneous administration at a dose of 240 mg/kg. The cNo.76 showed a good therapeutic efficacy even in the intravenous administration, but therapeutic efficacy was not observed in the Meiji 1640, Meiji 1656, or LVFX administration group (FIG. 8). It was suggested that the cNo.76 is effective even against multidrug-resistant *Pseudomonas aeruginosa* against which existing drugs such as LVFX were not effective. In addition, a characteristic high coverage ratio in vitro shown in Example 3 of the cNo.76 was also demonstrated in vivo.

Example 5 Designing of Humanized #1G5 and #4C13K

5)-1 Designing of Humanized Version of #1G5
5)-1-1 Molecular Modeling of #1G5 Variable Region The molecular modeling of the #1G5 variable regions was performed according to a method generally known as homology modeling (Methods in Enzymology, 203, 121-153, (1991)). The primary sequences (three-dimensional structures derived from the X-ray crystal structures are available) of the variable regions of human immunoglobulin registered in Protein Data Bank (Nuc. Acid Res. 35, D301-D303 (2007)) were compared with the #1G5 variable regions determined above. As a result, 1UYW was selected as a sequence having the highest sequence homology with the #1G5 light chain variable region among the antibodies which similarly have a deletion in the framework. Further, 3GI9 was selected as a sequence having the highest sequence homology with the #1G5 heavy chain variable region. The three-dimensional structure of a framework region was prepared based on a "framework model" by combining the coordinates of 1UYW corresponding to the #1G5 light chain with the coordinates of 3GI9 corresponding to the #1G5 heavy chain. Then, representative conformations for each CDR are incorporated into the framework model.

Finally, in order to obtain a possible molecular model of the #1G5 variable region in terms of energy, an energy calculation was performed for excluding disadvantageous interatomic contact. The above procedure was carried out using commercially available protein conformational analysis program Discovery Studio (Accelrys, Inc).

5)-1-2 Designing of Amino Acid Sequence of Humanized #1G5

A humanized #1G5 antibody was constructed according to the method generally known as CDR grafting (Proc. Natl. Acad. Sci. USA 86, 10029-10033 (1989)). An acceptor antibody was selected based on the amino acid homology within the framework region. The sequence of the framework region of #1G5 was compared with all human framework sequences in the Kabat Database (Nuc. Acid Res. 29, 205-206 (2001)) of antibody amino acid sequences. As a result, an HuMc3 antibody was selected as an acceptor based on a sequence homology of 75% in the framework region. The amino acid residues in the framework region of HuMc3 were aligned with the amino acid residues of #1G5, and the positions where different amino acids were used were identified. The positions of these residues were analyzed using the three-dimensional model of #1G5 constructed above. Then, donor residues to be grafted onto the acceptor were selected according to the criteria provided by Queen et al. (Proc. Natl. Acad. Sci. USA 86, 10029-10033 (1989)). By transferring some selected donor residues to the acceptor antibody, humanized #1G5 sequences were constructed as described in the following Example.

5)-2 Humanization of #1G5 Heavy Chain
5)-2-1 h#1G5-H1 Type Heavy Chain:

A humanized #1G5 heavy chain designed by substituting amino acid number 24 (glutamine) with valine, amino acid number 26 (proline) with serine, amino acid number 30 (leucine) with valine, amino acid number 31 (valine) with lysine, amino acid number 39 (leucine) with valine, amino acid number 57 (lysine) with arginine, amino acid number 59 (arginine) with alanine, amino acid number 67 (isoleucine) with methionine, amino acid number 86 (lysine) with arginine, amino acid number 87 (alanine) with valine, amino acid number 89 (leucine) with isoleucine, amino acid number 91 (valine) with alanine, amino acid number 95 (serine) with threonine, amino acid number 101 (glutamine) with glutamic acid, amino acid number 106 (threonine) with arginine, amino acid number 108 (aspartic acid) with glutamic acid, amino acid number 110 (serine) with threonine, amino acid number 116 (serine) with alanine, amino acid number 139 (serine) with leucine, and amino acid number 141 (isoleucine) with threonine of the #1G5 heavy chain shown in SEQ ID NO: 37 in the Sequence Listing was named "h#1G5-H1 type heavy chain".

The amino acid sequence of the h#1G5-H1 type heavy chain is set forth in SEQ ID NO: 57 in the Sequence Listing. A sequence comprising amino acid residues 1 to 19 of the amino acid sequence of SEQ ID NO: 57, a sequence comprising amino acid residues 20 to 144 of the amino acid sequence of SEQ ID NO: 57, and a sequence comprising amino acid residues 145 to 474 of the amino acid sequence of SEQ ID NO: 57 correspond to the signal sequence, the heavy chain variable region, and the heavy chain constant region, respectively. The nucleotide sequence encoding the amino acid sequence of SEQ ID NO: 57 is set forth in SEQ ID NO: 56 in the Sequence Listing. A sequence comprising nucleotides 1 to 57 of the nucleotide sequence of SEQ ID NO: 56, a sequence comprising nucleotides 58 to 432 of the nucleotide sequence of SEQ ID NO: 56, and a sequence comprising nucleotides 433 to 1422 of the nucleotide sequence of SEQ ID NO: 56 encode the signal sequence, the heavy chain variable region sequence, and the heavy chain constant region sequence, respectively. The nucleotide sequence of SEQ ID NO: 56 and the amino acid sequence of SEQ ID NO: 57 are also described in FIG. 9.

5)-2-2 h#1G5-H2 Type Heavy Chain:

A humanized #1G5 heavy chain designed by substituting amino acid number 24 (glutamine) with valine, amino acid number 26 (proline) with serine, amino acid number 30 (leucine) with valine, amino acid number 31 (valine) with lysine, amino acid number 39 (leucine) with valine, amino acid number 57 (lysine) with arginine, amino acid number 59 (arginine) with alanine, amino acid number 67 (isoleucine) with methionine, amino acid number 86 (lysine) with arginine, amino acid number 87 (alanine) with valine, amino acid number 95 (serine) with threonine, amino acid number 101 (glutamine) with glutamic acid, amino acid number 106 (threonine) with arginine, amino acid number 108 (aspartic acid) with glutamic acid, amino acid number 110 (serine) with threonine, amino acid number 139 (serine) with leucine, and amino acid number 141 (isoleucine) with threonine of the #1G5 heavy chain shown in SEQ ID NO: 37 in the Sequence Listing was named "h#1G5-H2 type heavy chain".

The amino acid sequence of the h#1G5-H2 type heavy chain is set forth in SEQ ID NO: 59 in the Sequence Listing. A sequence comprising amino acid residues 1 to 19 of the amino acid sequence of SEQ ID NO: 59, a sequence comprising amino acid residues 20 to 144 of the amino acid sequence of SEQ ID NO: 59, and a sequence comprising amino acid residues 145 to 474 of the amino acid sequence of SEQ ID NO: 59 correspond to the signal sequence, the heavy chain variable region, and the heavy chain constant region, respectively. The nucleotide sequence encoding the amino acid sequence of SEQ ID NO: 59 is set forth in SEQ ID NO: 58 in the Sequence Listing. A sequence comprising nucleotides 1 to 57 of the nucleotide sequence of SEQ ID NO: 58, a sequence comprising nucleotides 58 to 432 of the nucleotide sequence of SEQ ID NO: 58, and a sequence comprising nucleotides 433 to 1422 of the nucleotide sequence of SEQ ID NO: 58 encode the signal sequence, the heavy chain variable region sequence, and the heavy chain constant region sequence, respectively. The nucleotide sequence of SEQ ID NO: 58 and the amino acid sequence of SEQ ID NO: 59 are also described in FIG. 10.

5)-2-3 h#1G5-H3 Type Heavy Chain:

A humanized #1G5 heavy chain designed by substituting amino acid number 30 (leucine) with valine, amino acid number 31 (valine) with lysine, amino acid number 39 (leucine) with valine, amino acid number 57 (lysine) with arginine, amino acid number 59 (arginine) with alanine, amino acid number 67 (isoleucine) with methionine, amino acid number 86 (lysine) with arginine, amino acid number 95 (serine) with threonine, amino acid number 101 (glutamine) with glutamic acid, amino acid number 108 (aspartic acid) with glutamic acid, amino acid number 110 (serine) with threonine, amino acid number 139 (serine) with leucine, and amino acid number 141 (isoleucine) with threonine of the #1G5 heavy chain shown in SEQ ID NO: 37 in the Sequence Listing was named "h#1G5-H3 type heavy chain".

The amino acid sequence of the h#1G5-H3 type heavy chain is set forth in SEQ ID NO: 61 in the Sequence Listing. A sequence comprising amino acid residues 1 to 19 of the amino acid sequence of SEQ ID NO: 61, a sequence comprising amino acid residues 20 to 144 of the amino acid sequence of SEQ ID NO: 61, and a sequence comprising amino acid residues 145 to 474 of the amino acid sequence of SEQ ID NO: 61 correspond to the signal sequence, the heavy chain variable region, and the heavy chain constant region, respectively. The nucleotide sequence encoding the amino acid sequence of SEQ ID NO: 61 is set forth in SEQ ID NO: 60 in the Sequence Listing. A sequence comprising nucleotides 1 to 57 of the nucleotide sequence of SEQ ID NO: 60, a sequence comprising nucleotides 58 to 432 of the nucleotide sequence of SEQ ID NO: 60, and a sequence comprising nucleotides 433 to 1422 of the nucleotide sequence of SEQ ID NO: 60 encode the signal sequence, the heavy chain variable region sequence, and the heavy chain constant region sequence, respectively. The nucleotide sequence of SEQ ID NO: 60 and the amino acid sequence of SEQ ID NO: 61 are also described in FIG. 11.

5)-2-4 h#1G5-H4 Type Heavy Chain

A humanized #1G5 heavy chain designed by substituting amino acid number 31 (valine) with lysine, amino acid number 39 (leucine) with valine, amino acid number 57 (lysine) with arginine, amino acid number 59 (arginine) with alanine, amino acid number 139 (serine) with leucine, and amino acid number 141 (isoleucine) with threonine of the #1G5 heavy chain shown in SEQ ID NO: 37 in the Sequence Listing was named "h#1G5-H4 type heavy chain".

The amino acid sequence of the h#1G5-H4 type heavy chain is set forth in SEQ ID NO: 63 in the Sequence Listing. A sequence comprising amino acid residues 1 to 19 of the amino acid sequence of SEQ ID NO: 63, a sequence comprising amino acid residues 20 to 144 of the amino acid sequence of SEQ ID NO: 63, and a sequence comprising amino acid residues 145 to 474 of the amino acid sequence of SEQ ID NO: 63 correspond to the signal sequence, the heavy chain variable region, and the heavy chain constant region, respectively. The nucleotide sequence encoding the amino acid sequence of SEQ ID NO: 63 is set forth in SEQ ID NO: 62 in the Sequence Listing. A sequence comprising nucleotides 1 to 57 of the nucleotide sequence of SEQ ID NO: 62, a sequence comprising nucleotides 58 to 432 of the nucleotide sequence of SEQ ID NO: 62, and a sequence comprising nucleotides 433 to 1422 of the nucleotide sequence of SEQ ID NO: 62 encode the signal sequence, the heavy chain variable region sequence, and the heavy chain constant region sequence, respectively. The nucleotide sequence of SEQ ID NO: 62 and the amino acid sequence of SEQ ID NO: 63 are also described in FIG. 12.

5)-2-5 h#1G5-H5 Type Heavy Chain

A humanized #1G5 heavy chain designed by substituting amino acid number 31 (valine) with lysine, and amino acid number 39 (leucine) with valine of the #1G5 heavy chain shown in SEQ ID NO: 37 in the Sequence Listing was named "h#1G5-H5 type heavy chain".

The amino acid sequence of the h#1G5-H5 type heavy chain is set forth in SEQ ID NO: 65 in the Sequence Listing. A sequence comprising amino acid residues 1 to 19 of the amino acid sequence of SEQ ID NO: 65, a sequence comprising amino acid residues 20 to 144 of the amino acid sequence of SEQ ID NO: 65, and a sequence comprising amino acid residues 145 to 474 of the amino acid sequence of SEQ ID NO: 65 correspond to the signal sequence, the heavy chain variable region, and the heavy chain constant region, respectively. The nucleotide sequence encoding the amino acid sequence of SEQ ID NO: 65 is set forth in SEQ ID NO: 64 in the Sequence Listing. A sequence comprising nucleotides 1 to 57 of the nucleotide sequence of SEQ ID NO: 64, a sequence comprising nucleotides 58 to 432 of the nucleotide sequence of SEQ ID NO: 64, and a sequence comprising nucleotides 433 to 1422 of the nucleotide sequence of SEQ ID NO: 64 encode the signal sequence, the heavy chain variable region sequence, and the heavy chain constant region sequence, respectively. The nucleotide sequence of SEQ ID NO: 64 and the amino acid sequence of SEQ ID NO: 65 are also described in FIG. 13.

5)-3 Humanization of #1G5 Light Chain

5)-3-1 h#1G5-L1 Type Light Chain

A humanized #1G5 light chain designed by substituting amino acid number 21 (asparagine) with aspartic acid, amino acid number 29 (lysine) with aspartic acid, amino acid number 31 (methionine) with leucine, amino acid number 32 (serine) with alanine, amino acid number 33 (methionine) with valine, amino acid number 35 (valine) with leucine, amino acid number 39 (valine) with alanine, amino acid number 41 (leucine) with isoleucine, amino acid number 42 (serine) with asparagine, amino acid number 60 (alanine) with proline, amino acid number 61 (glutamic acid) with glycine, amino acid number 63 (serine) with proline, amino acid number 66 (proline) with leucine, amino acid number 83 (threonine) with serine, amino acid number 88 (alanine) with glycine, amino acid number 98 (valine) with leucine, amino acid number 103 (leucine) with valine, amino acid number 105 (aspartic acid) with valine, amino acid number 107 (histidine) with tyrosine, amino acid number 120 (glycine) with glutamine, amino acid number 124 (leucine) with valine, and amino acid number 129 (alanine) with threonine of the #1G5 light chain shown in SEQ ID NO: 35 in the Sequence Listing was named "h#1G5-L1 type light chain".

The amino acid sequence of the h#1G5-L1 type light chain is set forth in SEQ ID NO: 67 in the Sequence Listing. A sequence comprising amino acid residues 1 to 20 of the amino acid sequence of SEQ ID NO: 67, a sequence comprising amino acid residues 21 to 129 of the amino acid sequence of SEQ ID NO: 67, and a sequence comprising amino acid residues 130 to 234 of the amino acid sequence of SEQ ID NO: 67 correspond to the signal sequence, the light chain variable region, and the light chain constant region, respectively. The nucleotide sequence encoding the amino acid sequence of SEQ ID NO: 67 is set forth in SEQ ID NO: 66 in the Sequence Listing. A sequence comprising nucleotides 1 to 60 of the nucleotide sequence of SEQ ID NO: 66, a sequence comprising nucleotides 61 to 387 of the nucleotide sequence of SEQ ID NO: 66, and a sequence comprising nucleotides 388 to 702 of the nucleotide sequence of SEQ ID NO: 66 encode the signal sequence, the light chain variable region sequence, and the light chain constant region sequence, respectively. The nucleotide sequence of SEQ ID NO: 66 and the amino acid sequence of SEQ ID NO: 67 are also described in FIG. 14.

5)-3-2 h#1G5-L2 Type Light Chain:

A humanized #1G5 light chain designed by substituting amino acid number 29 (lysine) with aspartic acid, amino acid number 31 (methionine) with leucine, amino acid number 32 (serine) with alanine, amino acid number 33 (methionine) with valine, amino acid number 35 (valine) with leucine, amino acid number 39 (valine) with alanine, amino acid number 41 (leucine) with isoleucine, amino acid number 60 (alanine) with proline, amino acid number 61 (glutamic acid) with glycine, amino acid number 83 (threonine) with serine, amino acid number 98 (valine) with leucine, amino acid number 103 (leucine) with valine, amino acid number 105 (aspartic acid) with valine, amino acid number 124 (leucine) with valine, and amino acid number 129 (alanine) with threonine of the #1G5 light chain shown in SEQ ID NO: 35 in the Sequence Listing was named "h#1G5-L2 type light chain".

The amino acid sequence of the h#1G5-L2 type light chain is set forth in SEQ ID NO: 69 in the Sequence Listing. A sequence comprising amino acid residues 1 to 20 of the amino acid sequence of SEQ ID NO: 69, a sequence comprising amino acid residues 21 to 129 of the amino acid sequence of SEQ ID NO: 69, and a sequence comprising amino acid residues 130 to 234 of the amino acid sequence of SEQ ID NO: 69 correspond to the signal sequence, the light chain variable region, and the light chain constant region, respectively. The nucleotide sequence encoding the amino acid sequence of SEQ ID NO: 69 is set forth in SEQ ID NO: 68 in the Sequence Listing. A sequence comprising nucleotides 1 to 60 of the nucleotide sequence of SEQ ID NO: 68, a sequence comprising nucleotides 61 to 387 of the nucleotide sequence of SEQ ID NO: 68, and a sequence comprising nucleotides 388 to 702 of the nucleotide sequence of SEQ ID NO: 68 encode the signal sequence, the light chain variable region sequence, and the light chain constant region sequence, respectively. The nucleotide sequence of SEQ ID NO: 68 and the amino acid sequence of SEQ ID NO: 69 are also described in FIG. 15.

5)-3-3 h#1G5-L3 Type Light Chain

A humanized #1G5 light chain designed by substituting amino acid number 29 (lysine) with aspartic acid, amino acid number 31 (methionine) with leucine, amino acid number 32 (serine) with alanine, amino acid number 33 (methionine) with valine, amino acid number 35 (valine) with leucine, amino acid number 39 (valine) with alanine, amino acid number 41 (leucine) with isoleucine, amino acid number 60 (alanine) with proline, amino acid number 61 (glutamic acid) with glycine, amino acid number 83 (threonine) with serine, amino acid number 98 (valine) with leucine, amino acid number 103 (leucine) with valine, amino acid number 124 (leucine) with valine, and amino acid number 129 (alanine) with threonine of the #1G5 light chain shown in SEQ ID NO: 35 in the Sequence Listing was named "h#1G5-L3 type light chain".

The amino acid sequence of the h#1G5-L3 type light chain is set forth in SEQ ID NO: 71 in the Sequence Listing. A sequence comprising amino acid residues 1 to 20 of the amino acid sequence of SEQ ID NO: 71, a sequence comprising amino acid residues 21 to 129 of the amino acid sequence of SEQ ID NO: 71, and a sequence comprising amino acid residues 130 to 234 of the amino acid sequence of SEQ ID NO: 71 correspond to the signal sequence, the light chain variable region, and the light chain constant region, respectively. The nucleotide sequence encoding the amino acid sequence of SEQ ID NO: 71 is set forth in SEQ ID NO: 70 in the Sequence Listing. A sequence comprising nucleotides 1 to 60 of the nucleotide sequence of SEQ ID NO: 70, a sequence comprising nucleotides 61 to 387 of the nucleotide sequence of SEQ ID NO: 70, and a sequence comprising nucleotides 388 to 702 of the nucleotide sequence of SEQ ID NO: 70 encode the signal sequence, the light chain variable region sequence, and the light chain constant region sequence, respectively. The nucleotide sequence of SEQ ID NO: 70 and the amino acid sequence of SEQ ID NO: 71 are also described in FIG. 16.

5)-3-4 h#1G5-L4 Type Light Chain

A humanized h#1G5 light chain designed by substituting amino acid number 29 (lysine) with aspartic acid, amino acid number 39 (valine) with alanine, amino acid number 98 (valine) with leucine, and amino acid number 129 (alanine) with threonine of the #1G5 light chain shown in SEQ ID NO: 35 in the Sequence Listing was named "h#1G5-L4 type light chain".

The amino acid sequence of the h#1G5-L4 type light chain is set forth in SEQ ID NO: 73 in the Sequence Listing. A sequence comprising amino acid residues 1 to 20 of the amino acid sequence of SEQ ID NO: 73, a sequence comprising amino acid residues 21 to 129 of the amino acid sequence of SEQ ID NO: 73, and a sequence comprising amino acid residues 130 to 234 of the amino acid sequence of SEQ ID NO: 73 correspond to the signal sequence, the light chain variable region, and the light chain constant region, respectively. The nucleotide sequence encoding the amino acid sequence of SEQ ID NO: 73 is set forth in SEQ ID NO: 72 in the Sequence Listing. A sequence comprising nucleotides 1 to 60 of the nucleotide sequence of SEQ ID NO: 72, a sequence comprising nucleotides 61 to 387 of the nucleotide sequence of SEQ ID NO: 72, and a sequence comprising nucleotides 388 to 702 of the nucleotide sequence of SEQ ID NO: 72 encode the signal sequence, the light chain variable region sequence, and the light chain constant region sequence, respectively. The nucleotide sequence of SEQ ID NO: 72 and the amino acid sequence of SEQ ID NO: 73 are also described in FIG. 17.

5)-3-5 h#1G5-L5 Type Light Chain

A humanized #1G5 light chain designed by substituting amino acid number 29 (lysine) with aspartic acid, amino acid number 98 (valine) with leucine, and amino acid number 129 (alanine) with threonine of the #1G5 light chain shown in SEQ ID NO: 35 in the Sequence Listing was named "h#1G5-L5 type light chain".

The amino acid sequence of the h#1G5-L5 type light chain is set forth in SEQ ID NO: 75 in the Sequence Listing.

A sequence comprising amino acid residues 1 to 20 of the amino acid sequence of SEQ ID NO: 75, a sequence comprising amino acid residues 21 to 129 of the amino acid sequence of SEQ ID NO: 75, and a sequence comprising amino acid residues 130 to 234 of the amino acid sequence of SEQ ID NO: 75 correspond to the signal sequence, the light chain variable region, and the light chain constant region, respectively. The nucleotide sequence encoding the amino acid sequence of SEQ ID NO: 75 is set forth in SEQ ID NO: 74 in the Sequence Listing. A sequence comprising nucleotides 1 to 60 of the nucleotide sequence of SEQ ID NO: 74, a sequence comprising nucleotides 61 to 387 of the nucleotide sequence of SEQ ID NO: 74, and a sequence comprising nucleotides 388 to 702 of the nucleotide sequence of SEQ ID NO: 74 encode the signal sequence, the light chain variable region sequence, and the light chain constant region sequence, respectively. The nucleotide sequence of SEQ ID NO: 74 and the amino acid sequence of SEQ ID NO: 75 are also described in FIG. 18.

5)-4 Designing of Humanized Version of #4C13K

5)-4-1 Molecular Modeling of #4C13K Variable Region

The molecular modeling of the #4C13K variable regions was performed according to a method generally known as homology modeling (Methods in Enzymology, 203, 121-153, (1991)). The primary sequences (three-dimensional structures derived from the X-ray crystal structures are available) of the variable regions of human immunoglobulin registered in Protein Data Bank (Nuc. Acid Res. 35, D301-D303 (2007)) were compared with the #4C13K variable regions determined above. As a result, 1UYW was selected as a sequence having the highest sequence homology with the #4C13K light chain variable region among the antibodies which similarly have a deletion in the framework. Further, 1CIC was selected as a sequence having the highest sequence homology with the #4C13K heavy chain variable region. The three-dimensional structure of a framework region was prepared based on a "framework model" by combining the coordinates of 1UYW corresponding to the #4C13K light chain with the coordinates of 1CIC corresponding to the #4C13K heavy chain. Then, representative conformations for each CDR were incorporated into the framework model.

Finally, in order to obtain a possible molecular model of the #4C13K variable region in terms of energy, an energy calculation was performed for excluding disadvantageous interatomic contact. The above procedure was carried out using commercially available protein conformational analysis program Discovery Studio (Accelrys, Inc).

5)-4-2 Designing of Amino Acid Sequence of Humanized #4C13K

A humanized #4C13K antibody was constructed according to a method generally known as CDR grafting (Proc. Natl. Acad. Sci. USA 86, 10029-10033 (1989)). An acceptor antibody was selected based on the amino acid homology within the framework region. The sequence of the framework region of #4C13K was compared with all human framework sequences in the Kabat Database (Nuc. Acid Res. 29, 205-206 (2001)) of antibody amino acid sequences. As a result, an HuMc3 antibody was selected as an acceptor based on a sequence homology of 73% in the framework region. The amino acid residues in the framework region of HuMc3 were aligned with the amino acid residues of #4C13K, and the positions where different amino acids were used were identified. The positions of these residues were analyzed using the three-dimensional model of #4C13K constructed above. Then, donor residues to be grafted onto the acceptor were selected according to the criteria provided by Queen et al. (Proc. Natl. Acad. Sci. USA 86, 10029-10033 (1989)). By transferring some selected donor residues to the acceptor antibody, humanized #4C13K sequences were constructed as described in the following Example. The light chain of the humanized #4C13K sequence was completely common with the light chain of the humanized #1G5 sequence.

5)-5 Humanization of #4C13K Heavy Chain

5)-5-1 h#4C13K-H1 Type Heavy Chain

A humanized #4C13K heavy chain designed by substituting amino acid number 24 (glutamine) with valine, amino acid number 26 (proline) with serine, amino acid number 30 (leucine) with valine, amino acid number 31 (valine) with lysine, amino acid number 39 (leucine) with valine, amino acid number 56 (methionine) with valine, amino acid number 57 (glutamine) with arginine, amino acid number 59 (arginine) with alanine, amino acid number 67 (isoleucine) with methionine, amino acid number 86 (lysine) with arginine, amino acid number 87 (alanine) with valine, amino acid number 89 (leucine) with isoleucine, amino acid number 91 (valine) with alanine, amino acid number 95 (serine) with threonine, amino acid number 101 (glutamine) with glutamic acid, amino acid number 103 (asparagine) with serine, amino acid number 106 (threonine) with arginine, amino acid number 108 (aspartic acid) with glutamic acid, amino acid number 110 (serine) with threonine, amino acid number 116 (threonine) with alanine, amino acid number 135 (threonine) with leucine, and amino acid number 136 (leucine) with valine of the #4C13K heavy chain shown in SEQ ID NO: 41 in the Sequence Listing was named "h#4C13K-H1 type heavy chain".

The amino acid sequence of the h#4C13K-H1 type heavy chain is set forth in SEQ ID NO: 77 in the Sequence Listing. A sequence comprising amino acid residues 1 to 19 of the amino acid sequence of SEQ ID NO: 77, a sequence comprising amino acid residues 20 to 140 of the amino acid sequence of SEQ ID NO: 77, and a sequence comprising amino acid residues 141 to 470 of the amino acid sequence of SEQ ID NO: 77 correspond to the signal sequence, the heavy chain variable region, and the heavy chain constant region, respectively. The nucleotide sequence encoding the amino acid sequence of SEQ ID NO: 77 is set forth in SEQ ID NO: 76 in the Sequence Listing. A sequence comprising nucleotides 1 to 57 of the nucleotide sequence of SEQ ID NO: 76, a sequence comprising nucleotides 58 to 420 of the nucleotide sequence of SEQ ID NO: 76, and a sequence comprising nucleotides 421 to 1410 of the nucleotide sequence of SEQ ID NO: 76 encode the signal sequence, the heavy chain variable region sequence, and the heavy chain constant region sequence, respectively. The nucleotide sequence of SEQ ID NO: 76 and the amino acid sequence of SEQ ID NO: 77 are also described in FIG. 19.

5)-5-2 h#4C13K-H2 Type Heavy Chain

A humanized #4C13K heavy chain designed by substituting amino acid number 24 (glutamine) with valine, amino acid number 26 (proline) with serine, amino acid number 30 (leucine) with valine, amino acid number 31 (valine) with lysine, amino acid number 39 (leucine) with valine, amino acid number 56 (methionine) with valine, amino acid number 57 (glutamine) with arginine, amino acid number 59 (arginine) with alanine, amino acid number 67 (isoleucine) with methionine, amino acid number 86 (lysine) with arginine, amino acid number 87 (alanine) with valine, amino acid number 95 (serine) with threonine, amino acid number 101 (glutamine) with glutamic acid, amino acid number 103 (asparagine) with serine, amino acid number 106 (threonine) with arginine, amino acid number 108 (aspartic acid) with glutamic acid, amino acid number 110 (serine) with threonine, amino acid number 135 (threonine) with leucine, and amino acid number 136 (leucine) with valine of the #4C13K heavy chain shown in SEQ ID NO: 41 in the Sequence Listing was named "h#4C13K-H2 type heavy chain".

The amino acid sequence of the h#4C13K-H2 type heavy chain is set forth in SEQ ID NO: 79 in the Sequence Listing. A sequence comprising amino acid residues 1 to 19 of the amino acid sequence of SEQ ID NO: 79, a sequence comprising amino acid residues 20 to 140 of the amino acid sequence of SEQ ID NO: 79, and a sequence comprising amino acid residues 141 to 470 of the amino acid sequence of SEQ ID NO: 79 correspond to the signal sequence, the heavy chain variable region, and the heavy chain constant region, respectively. The nucleotide sequence encoding the amino acid sequence of SEQ ID NO: 79 is set forth in SEQ ID NO: 78 in the Sequence Listing. A sequence comprising nucleotides 1 to 57 of the nucleotide sequence of SEQ ID NO: 78, a sequence comprising nucleotides 58 to 420 of the nucleotide sequence of SEQ ID NO: 78, and a sequence comprising nucleotides 421 to 1410 of the nucleotide sequence of SEQ ID NO: 78 encode the signal sequence, the heavy chain variable region sequence, and the heavy chain constant region sequence, respectively. The nucleotide sequence of SEQ ID NO: 78 and the amino acid sequence of SEQ ID NO: 79 are also described in FIG. 20.

5)-5-3 h#4C13K-H3 Type Heavy Chain

A humanized #4C13K heavy chain designed by substituting amino acid number 30 (leucine) with valine, amino acid number 31 (valine) with lysine, amino acid number 39 (leucine) with valine, amino acid number 67 (isoleucine) with methionine, amino acid number 86 (lysine) with arginine, amino acid number 95 (serine) with threonine, amino acid number 101 (glutamine) with glutamic acid, amino acid number 103 (asparagine) with serine, amino acid number 108 (aspartic acid) with glutamic acid, amino acid number 110 (serine) with threonine, amino acid number 135 (threonine) with leucine, and amino acid number 136 (leucine) with valine of the #4C13K heavy chain shown in SEQ ID NO: 41 in the Sequence Listing was named "h#4C13K-H3 type heavy chain".

The amino acid sequence of the h#4C13K-H3 type heavy chain is set forth in SEQ ID NO: 81 in the Sequence Listing. A sequence comprising amino acid residues 1 to 19 of the amino acid sequence of SEQ ID NO: 81, a sequence comprising amino acid residues 20 to 140 of the amino acid sequence of SEQ ID NO: 81, and a sequence comprising amino acid residues 141 to 470 of the amino acid sequence of SEQ ID NO: 81 correspond to the signal sequence, the heavy chain variable region, and the heavy chain constant region, respectively. The nucleotide sequence encoding the amino acid sequence of SEQ ID NO: 81 is set forth in SEQ ID NO: 80 in the Sequence Listing. A sequence comprising nucleotides 1 to 57 of the nucleotide sequence of SEQ ID NO: 80, a sequence comprising nucleotides 58 to 420 of the nucleotide sequence of SEQ ID NO: 80, and a sequence comprising nucleotides 421 to 1410 of the nucleotide sequence of SEQ ID NO: 80 encode the signal sequence, the heavy chain variable region sequence, and the heavy chain constant region sequence, respectively. The nucleotide sequence of SEQ ID NO: 80 and the amino acid sequence of SEQ ID NO: 81 are also described in FIG. 21.

5)-5-4 h#4C13K-H4 Type Heavy Chain

A humanized #4C13K heavy chain designed by substituting amino acid number 31 (valine) with lysine, amino acid number 39 (leucine) with valine, amino acid number 101 (glutamine) with glutamic acid, amino acid number 103 (asparagine) with serine, amino acid number 135 (threonine) with leucine, and amino acid number 136 (leucine) with valine of the #4C13K heavy chain shown in SEQ ID NO: 41 in the Sequence Listing was named "h#4C13K-H4 type heavy chain".

The amino acid sequence of the h#4C13K-H4 type heavy chain is set forth in SEQ ID NO: 83 in the Sequence Listing. A sequence comprising amino acid residues 1 to 19 of the amino acid sequence of SEQ ID NO: 83, a sequence comprising amino acid residues 20 to 140 of the amino acid sequence of SEQ ID NO: 83, and a sequence comprising amino acid residues 141 to 470 of the amino acid sequence of SEQ ID NO: 83 correspond to the signal sequence, the heavy chain variable region, and the heavy chain constant region, respectively. The nucleotide sequence encoding the amino acid sequence of SEQ ID NO: 83 is set forth in SEQ ID NO: 82 in the Sequence Listing. A sequence comprising nucleotides 1 to 57 of the nucleotide sequence of SEQ ID NO: 82, a sequence comprising nucleotides 58 to 420 of the nucleotide sequence of SEQ ID NO: 82, and a sequence comprising nucleotides 421 to 1410 of the nucleotide sequence of SEQ ID NO: 82 encode the signal sequence, the heavy chain variable region sequence, and the heavy chain constant region sequence, respectively. The nucleotide sequence of SEQ ID NO: 82 and the amino acid sequence of SEQ ID NO: 83 are also described in FIG. 22.

5)-5-5 h#4C13K-H5 Type Heavy Chain

A humanized #4C13K heavy chain designed by substituting amino acid number 31 (valine) with lysine, amino acid number 39 (leucine) with valine, amino acid number 135 (threonine) with leucine, and amino acid number 136 (leucine) with valine of the #4C13K heavy chain shown in SEQ ID NO: 41 in the Sequence Listing was named "h#4C13K-H5 type heavy chain".

The amino acid sequence of the h#4C13K-H5 type heavy chain is set forth in SEQ ID NO: 85 in the Sequence Listing. A sequence comprising amino acid residues 1 to 19 of the amino acid sequence of SEQ ID NO: 85, a sequence comprising amino acid residues 20 to 140 of the amino acid sequence of SEQ ID NO: 85, and a sequence comprising amino acid residues 141 to 470 of the amino acid sequence of SEQ ID NO: 85 correspond to the signal sequence, the heavy chain variable region, and the heavy chain constant region, respectively. The nucleotide sequence encoding the amino acid sequence of SEQ ID NO: 85 is set forth in SEQ ID NO: 84 in the Sequence Listing. A sequence comprising nucleotides 1 to 57 of the nucleotide sequence of SEQ ID NO: 84, a sequence comprising nucleotides 58 to 420 of the nucleotide sequence of SEQ ID NO: 84, and a sequence comprising nucleotides 421 to 1410 of the nucleotide sequence of SEQ ID NO: 84 encode the signal sequence, the heavy chain variable region sequence, and the heavy chain constant region sequence, respectively. The nucleotide sequence of SEQ ID NO: 84 and the amino acid sequence of SEQ ID NO: 85 are also described in FIG. 23.

Example 6 Preparation of Humanized Antibodies #1G5 and #4C13K

6)-1 Construction of Humanized #1G5 Antibody Light Chain Expression Vector

6)-1-1 Construction of h#1G5-L2 Type Light Chain Expression Vector

A DNA fragment containing a sequence encoding the h#1G5-L2 type light chain variable region shown in nucleotide numbers 38 to 402 of the nucleotide sequence of the h#1G5-L2 type light chain shown in ID SEQ NO: 68 was synthesized (GENEART Inc., Artificial Gene Synthesis Service). By using the synthesized DNA fragment as a template and also using KOD-Plus-(TOYOBO, Co., Ltd.) and the following primer set, a DNA fragment comprising a DNA sequence encoding the h#1G5-L2 type light chain variable region was amplified, and a chimeric and humanized antibody light chain expression vector pCMA-LK was inserted at the site cleaved with the restriction enzyme BsiWI using an In-Fusion HD PCR cloning kit (Clontech, Inc.), and thus, a human chimeric h#1G5-L2 type light chain expression vector was constructed. The obtained expression vector was named "pCMA-LK/h#1G5-L2".

```
Primer set for humanized antibody light chain
                                    (SEQ ID NO: 112)
5'-ctgtggatctccggcgcgtacggc-3' (CM-LKF)

(SEQ ID NO: 113)
5'-ggaggggcggccaccgtacg-3' (KCL-Inf-R)
```

6)-1-2 Construction of h#1G5-L3 Type Light Chain Expression Vector

A DNA fragment containing a sequence encoding the h#1G5-L3 type light chain variable region shown in nucleotide numbers 38 to 402 of the nucleotide sequence of the #1G5-L3 type light chain shown in ID SEQ NO: 70 was synthesized (GENEART Inc., Artificial Gene Synthesis Service). A h#1G5-L3 type light chain expression vector was constructed in the same manner as in Example 6)-1-1. The obtained expression vector was named "pCMA-LK/h#1G5-L3".

6)-2 Construction of Humanized Antibody #1G5 Heavy Chain Expression Vector

6)-2-1 Construction of h#1G5-H2 Type Heavy Chain Expression Vector

A DNA fragment containing a sequence encoding the h#1G5-H2 type heavy chain variable region shown in nucleotide numbers 36 to 432 of the nucleotide sequence of the h#1G5-H2 type heavy chain shown in ID SEQ NO: 58 was synthesized (GENEART Inc., Artificial Gene Synthesis Service). By using the synthesized DNA fragment as a template and also using KOD-Plus-(TOYOBO, Co., Ltd.) and the following primer set, a DNA fragment comprising a DNA sequence encoding the h#1G5-H2 type heavy chain variable region was amplified, and a chimeric and humanized antibody IgG1 type heavy chain expression vector pCMA-G1 was inserted at the site cleaved with the restriction enzyme BlpI using an In-Fusion HD PCR cloning kit (Clontech, Inc.), and thus, a h#1G5-H2 type heavy chain expression vector was constructed. The obtained expression vector was named "pCMA-G1/h#1G5-H2".

```
Primer set for humanized antibody heavy chain
                                    (SEQ ID NO: 110)
5'-agctcccagatgggtgctgagc-3' (EG-Inf-F)

(SEQ ID NO: 122)
5'-cttggtggaggctgagctcacggtcacgagggtgccctggcc-3'
(H-R)
```

6)-2-2 Construction of h#1G5-H3 Type Heavy Chain Expression Vector

A DNA fragment containing a sequence encoding the h#1G5-H3 type heavy chain variable region as shown in the nucleotide numbers 36 to 432 of the nucleotide sequence of the #1G5-H3 type heavy chain shown in ID SEQ NO: 60 was synthesized (GENEART Inc., Artificial Gene Synthesis Service). A h#1G5-H3 type heavy chain expression vector was constructed in the same manner as in Example 6)-2-1. The obtained expression vector was named "pCMA-G1/h#1G5-H3".

6)-3 Construction of Humanized Antibody #4C13K Heavy Chain Expression Vector

6)-3-1 Construction of h#4C13K-H2 Type Heavy Chain Expression Vector

A DNA fragment containing a sequence encoding the h#4C13K-H2 type heavy chain variable region as shown in nucleotide numbers 36 to 420 of the nucleotide sequence of the h#4C13K-H2 type heavy chain shown in ID SEQ NO: 78 was synthesized (GENEART Inc., Artificial Gene Synthesis Service). A h#4C13K-H2 type heavy chain expression vector was constructed in the same manner as in Example 6)-2-1. The obtained expression vector was named "pCMA-G1/h#4C13K-H2".

6)-3-2 Construction of h#4C13K-H3 Type Heavy Chain Expression Vector

A DNA fragment containing a sequence encoding the h#4C13K-H3 type heavy chain variable region shown in nucleotide numbers 36 to 420 of the nucleotide sequence of the #4C13K-H3 type heavy chain shown in ID SEQ NO: 80 was synthesized (GENEART Inc., Artificial Gene Synthesis Service). A #4C13K-H3 type heavy chain expression vector was constructed in the same manner as in Example 6)-2-1. The obtained expression vector was named "pCMA-G1/#4C13K-H3".

Example 7 Preparation of Humanized Antibodies of #1G5 and #4C13K

7)-1 Production of Humanized Antibodies of #1G5 and #4C13K

These humanized antibodies were produced in the same manner as in Example 2)-3-7-1.

In the present specification, it is to be noted that, for example, an antibody having a h#1G5-H1 heavy chain and a h#1G5-L1 is referred to as "h#1G5-H1/L1" or "h#1G5-H1/L1 antibody", and an antibody having a h#4C13K-H1 heavy chain and h#1G5-L1 is referred to as "h#4C13K-H1/L1" or "h#4C13K-H1/L1 antibody".

The h#1G5-H2/L2 was obtained by the combination of pCMA-G1/h#1G5-H2 and pCMA-LK/h#1G5-L2; the h#1G5-H3/L3 was obtained by the combination of pCMA-G1/h#1G5-H3 and pCMA-LK/h#1G5-L3; the h#4C13K-H2/L2 was obtained by the combination of pCMA-G1/h#4C13K-H2 and pCMA-LK/h#1G5-L2; the h#4C13K-H3/L3 was obtained by the combination of pCMA-G1/h#4C13K-H3 and pCMA-LK/h#1G5-L3.

7)-2 Construction of Humanized Antibodies of #1G5 and #4C13K

The culture supernatant obtained in the above 7)-1 was purified in the same manner as in Example 2)-3-7-2.

Example 8

Measurement of In Vitro Activity of Humanized Antibodies of #1G5 and #4C13K

8)-1 Opsonophagocytic Killing Activity Against *Pseudomonas aeruginosa* ATCC 29260

In accordance with the method of 1)-3-2, the opsonophagocytic killing activities of h#1G5-H2/L2, h#1G5-H3/L3, h#4C13K-H2/L2, and h#4C13k-H3/L3 against ATCC 29260 were measured, and then compared to those of c#1G5 and c#4C13. The opsonophagocytic killing activity was expressed in terms of 50% minimum growth inhibitory concentration. The results are shown in Table 7.

TABLE 7

| | Opsonophagocytic killing activity (ng/mL) | | | | | |
|---|---|---|---|---|---|---|
| Strain No. | c#1G5 | c#4C13 | h#1G5-H2/L2 | h#1G5-H3/L3 | h#4C13K-H2/L2 | h#4C13K-H3/L3 |
| ATCC 29260 | 4.1 | 4.1 | 4.1 | 4.1 | 4.1 | 4.1 |

The four humanized antibodies showed activities equivalent to those of c#1G5 and c#4C13.

8)-2 Binding Specificity to *Pseudomonas aeruginosa* O11 Strains

Figure 25:
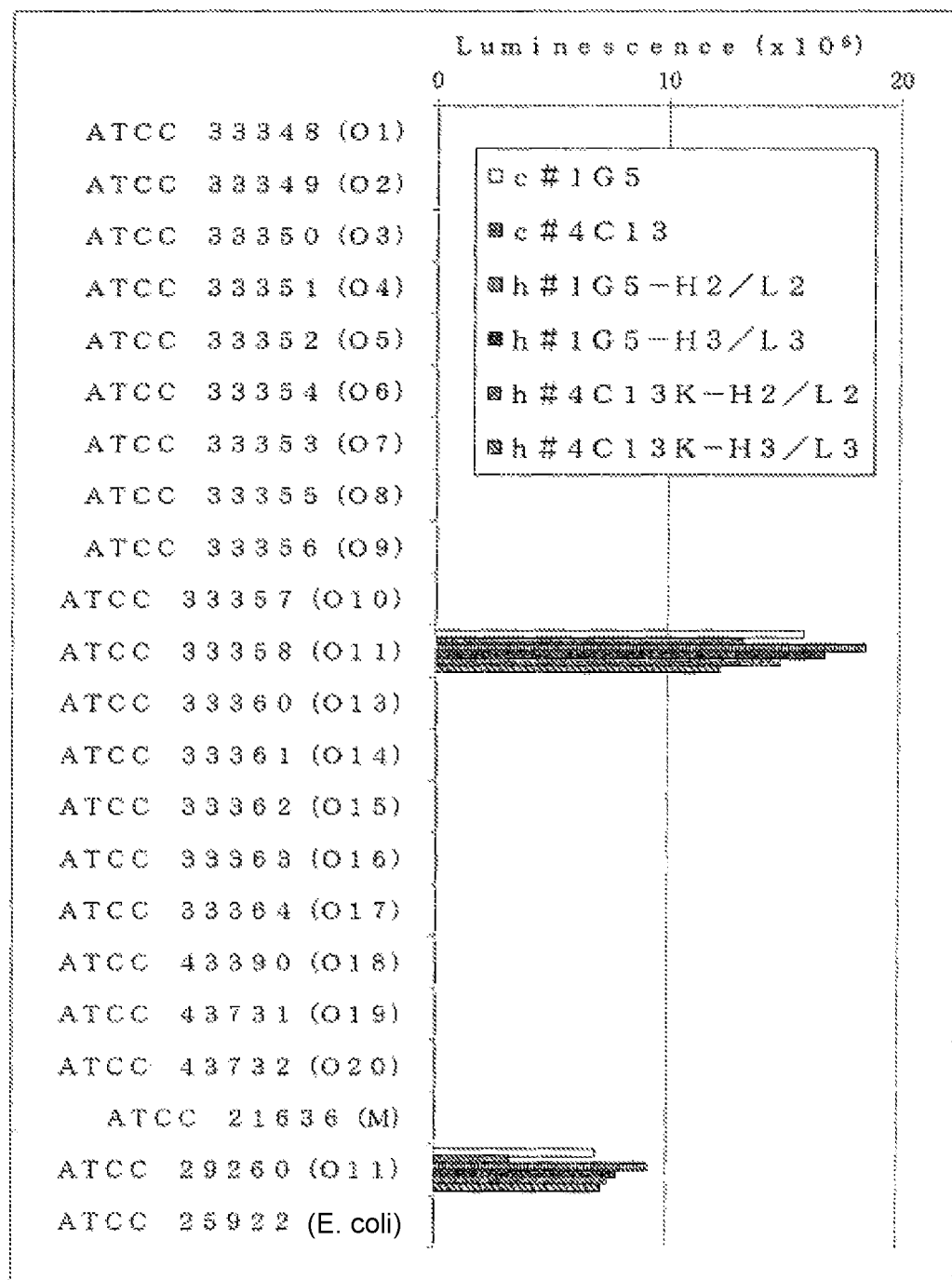
FIG. 25 is a graph showing the binding specificity to Pseudomonas aeruginosa O11 strains.

The binding specificities of h#1G5-H2/L2, h#1G5-H3/L3, h#4C13K-H2/L2, and h#4C13K-H3/L3 to *Pseudomonas aeruginosa* carrying various O antigens were confirmed according to the method of 3)-2. The four humanized antibodies showed high specific activities only to the O11 strains as with c#1G5 and c#4C13 (FIG. 25).

8)-3 Binding Activity Against *Pseudomonas aeruginosa* O11 Clinical Isolates

Figure 26:
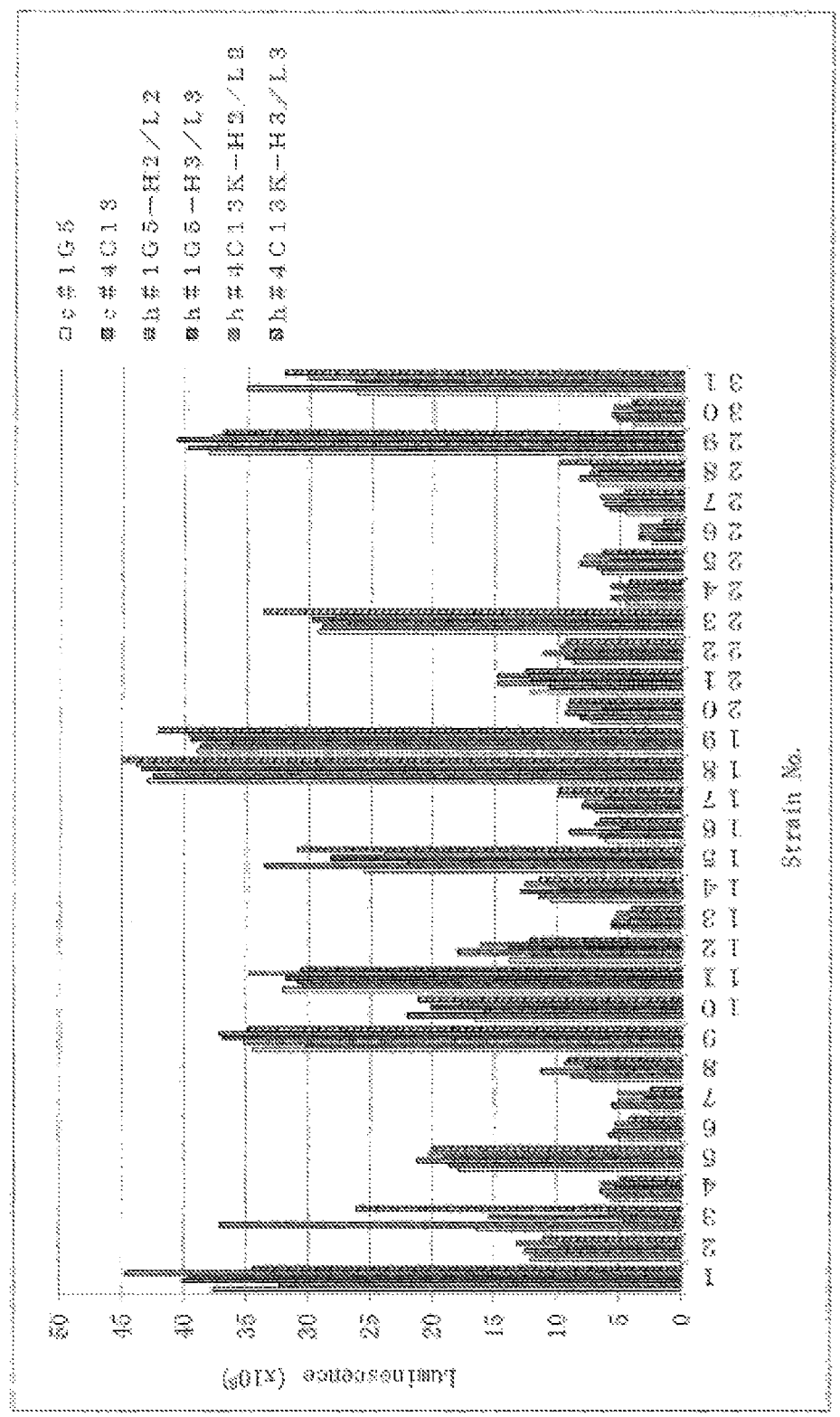
FIG. 26 is a graph showing the binding activity to clinical isolates of Pseudomonas aeruginosa O11.

The binding activities of h#1G5-H2/L2, h#1G5-H3/L3, h#4C13K-H2/L2, and h#4C13K-H3/L3 to 31 *Pseudomonas aeruginosa* O11 clinical isolates held by Daiichi Sankyo Co., Ltd. were evaluated according to the method of 3)-3. The four humanized antibodies showed binding activities to all of the O11 clinical isolates as with c#1G5 and c#4C13 (FIG. 26).

Figure 27:
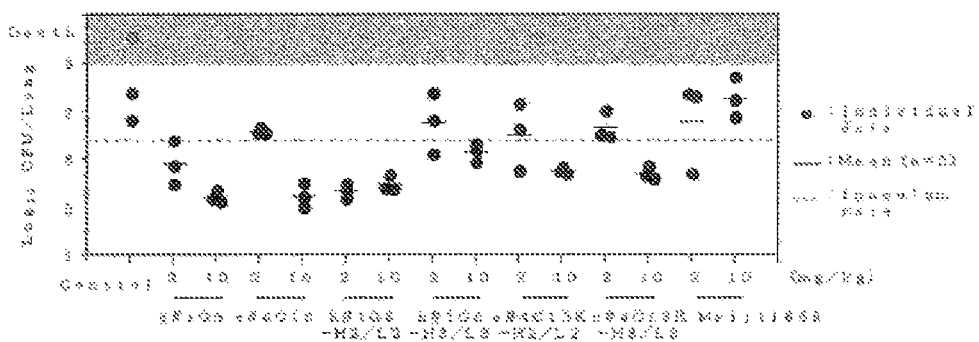
FIG. 27 is a graph showing the therapeutic efficacy (intravenous administration) on a mouse model of lung infection by Pseudomonas aeruginosa ATCC 29260.

Example 9 Evaluation of In Vivo Activity of Humanized Antibodies of #1G5 and #4C13K The in vivo activities of c#1G5, c#4C13, h#1G5-H2/L2, h#1G5-H3/L3, h#4C13K-H2/L2, and h#4C13K-H3/L3 against ATCC 29260 were evaluated according to the method of 4)-1. In comparison with the control group to which the antibody was not administered, all of c#1G5, c#4C13, and the four humanized antibodies showed therapeutic efficacies, and such efficacies were greater than the efficacy of Meiji 1656 (FIG. 27).

Example 10 Competition Assay

Figure 28:
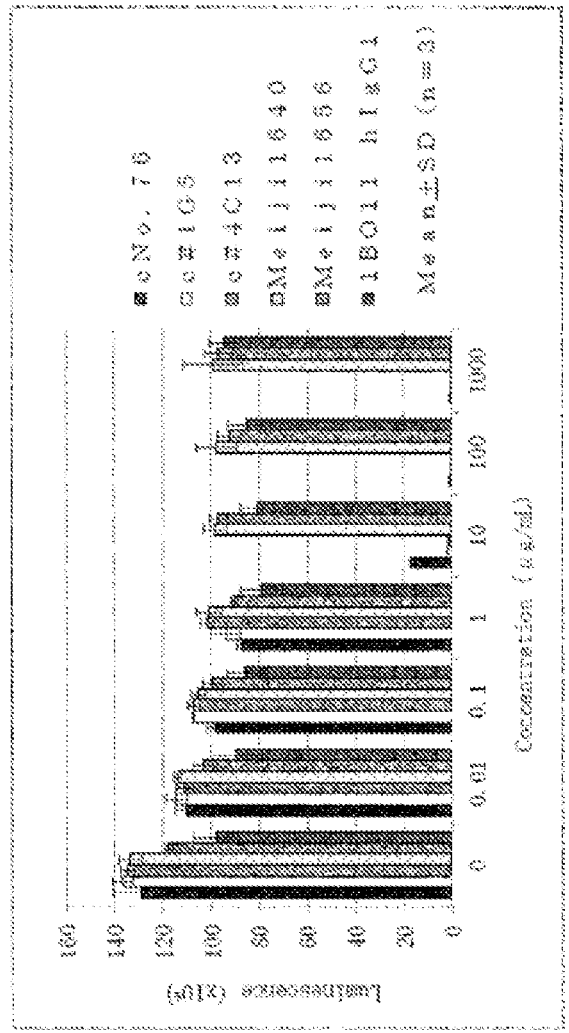

A competition assay between No.76 mIgG2a and cNO.76, c#1G5, c#4C13, Meiji 1640, Meiji 1656, or 1BO11 hIgG1 was performed with *Pseudomonas aeruginosa* ATCC 29260 using a binding activity in the whole cell ELISA as an index. According to the method of 3)-2, No.76 mIgG2a (final concentration of 0.01 μg/ml) and any one of cNO.76, c#1G5, c#4C13, Meiji 1640, Meiji 1656, and 1BO11 hIgG1 (final concentration of 0.01, 0.1, 1, 10, 100, 1,000 μg/ml) were respectively added as a primary antibody, and Goat anti-Mouse IgG2a HRP conjugated (Bethyl Laboratories, Inc.) was used as a secondary antibody. The No.76 mIgG2a competed with cNO.76, c#1G4, and c#4C13, but did not compete with the Meiji 1640, Meiji 1656, and 1BO11 hIgG1. From this, it was revealed that the epitope of the cNO.76, c#1G5, and c#4C13 was different from the epitope of the Meiji 1640, Meiji 1656, and 1BO11 hIgG1 (FIG. 28).

INDUSTRIAL APPLICABILITY

Since the chimeric or humanized anti-LPS O11 antibody of the present invention has an opsonophagocytic killing action and/or complement dependent killing action, a pharmaceutical composition containing the anti-LPS O11 antibody can be a therapeutic agent or a prophylactic agent for pseudomonal infection.

Sequence Listing Free Text

SEQ ID NO: 1: Nucleotide sequence of pJON mIgG2a
SEQ ID NO: 2: Nucleotide sequence of pJON mIgG2a-hIgG1
SEQ ID NO: 3: Nucleotide sequence of pJON mIgκ
SEQ ID NO: 4: Amino acid sequence of No.76 light chain variable region
SEQ ID NO: 5: Amino acid sequence of No.76 light chain CDR1
SEQ ID NO: 6: Amino acid sequence of No.76 light chain CDR2
SEQ ID NO: 7: Amino acid sequence of No.76 light chain CDR3
SEQ ID NO: 8: Amino acid sequence of No.76 heavy chain variable region
SEQ ID NO: 9: Amino acid sequence of No.76 heavy chain CDR1
SEQ ID NO: 10: Amino acid sequence of No.76 heavy chain CDR2
SEQ ID NO: 11: Amino acid sequence of No.76 heavy chain CDR3
SEQ ID NO: 12: Amino acid sequence of #1G5 light chain variable region
SEQ ID NO: 13: Amino acid sequence of #1G5 light chain CDR1
SEQ ID NO: 14: Amino acid sequence of #1G5 light chain CDR2
SEQ ID NO: 15: Amino acid sequence of #1G5 light chain CDR3
SEQ ID NO: 16: Amino acid sequence of #1G5 heavy chain variable region
SEQ ID NO: 17: Amino acid sequence of #1G5 heavy chain CDR1
SEQ ID NO: 18: Amino acid sequence of #1G5 heavy chain CDR2
SEQ ID NO: 19: Amino acid sequence of #1G5 heavy chain CDR3
SEQ ID NO: 20: Amino acid sequence of #4C12 light chain variable region
SEQ ID NO: 21: Amino acid sequence of #4C12 light chain CDR1
SEQ ID NO: 22: Amino acid sequence of #4C12 light chain CDR2
SEQ ID NO: 23: Amino acid sequence of #4C12 light chain CDR3
SEQ ID NO: 24: Amino acid sequence of #4C12 heavy chain variable region
SEQ ID NO: 25: Amino acid sequence of #4C12 heavy chain CDR1
SEQ ID NO: 26: Amino acid sequence of #4C12 heavy chain CDR2
SEQ ID NO: 27: Amino acid sequence of #4C12 heavy chain CDR3
SEQ ID NO: 28: DNA fragment comprising a DNA sequence encoding the amino acids of the human light chain secretion signal and the human light chain constant region
SEQ ID NO: 29: DNA fragment comprising a DNA sequence encoding the amino acids of the human heavy chain signal sequence and the human IgG1 constant region
SEQ ID NO: 30: Nucleotide sequence of human chimeric No.76 light chain
SEQ ID NO: 31: Amino acid sequence of human chimeric No.76 light chain SEQ ID NO: 32: Nucleotide sequence of human chimeric No.76 heavy chain
SEQ ID NO: 33: Amino acid sequence of human chimeric No.76 heavy chain
SEQ ID NO: 34: Nucleotide sequence of DNA fragment comprising DNA sequence encoding human chimeric #1G5 light chain.
SEQ ID NO: 35: Amino acid sequence of human chimeric #1G5 light chain
SEQ ID NO: 36: Nucleotide sequence of human chimeric #1G5 heavy chain
SEQ ID NO: 37: Amino acid sequence of human chimeric #1G5 heavy chain
SEQ ID NO: 38: Nucleotide sequence of DNA fragment comprising DNA sequence encoding human chimeric #4C13 light chain.
SEQ ID NO: 39: Amino acid sequence of human chimeric #4C13 light chain
SEQ ID NO: 40: Nucleotide sequence of human chimeric #4C13 heavy chain
SEQ ID NO: 41: Amino acid sequence of human chimeric #4C13 heavy chain
SEQ ID NO: 42: Nucleotide sequence of Meiji 1640 light chain
SEQ ID NO: 43: Amino acid sequence of Meiji 1640 light chain
SEQ ID NO: 44: Nucleotide sequence of Meiji 1640 heavy chain
SEQ ID NO: 45: Amino acid sequence of Meiji 1640 heavy chain
SEQ ID NO: 46: Nucleotide sequence of Meiji 1656 light chain
SEQ ID NO: 47: Amino acid sequence of Meiji 1656 light chain
SEQ ID NO: 48: Nucleotide sequence of Meiji 1656 heavy chain
SEQ ID NO: 49: Amino acid sequence of Meiji 1656 heavy chain
SEQ ID NO: 50: Nucleotide sequence of DNA fragment encoding mouse IgG2b type chimeric 1BO11 light chain
SEQ ID NO: 51: Nucleotide sequence of human IgG1 type 1BO11 light chain
SEQ ID NO: 52: Amino acid sequence of human IgG1 type 1BO11 light chain
SEQ ID NO: 53: Nucleotide sequence of DNA fragment encoding mouse IgG2b type chimeric 1BO11 heavy chain
SEQ ID NO: 54: Nucleotide sequence of human IgG1 type 1BO11 heavy chain
SEQ ID NO: 55: Amino acid sequence of human IgG1 type 1BO11 heavy chain
SEQ ID NO: 56: Nucleotide sequence of h#1G5-H1
SEQ ID NO: 57: Amino acid sequence of h#1G5-H1
SEQ ID NO: 58: Nucleotide sequence of h#1G5-H2
SEQ ID NO: 59: Amino acid sequence of h#1G5-H2
SEQ ID NO: 60: Nucleotide sequence of h#1G5-H3
SEQ ID NO: 61: Amino acid sequence of h#1G5-H3
SEQ ID NO: 62: Nucleotide sequence of h#1G5-H4
SEQ ID NO: 63: Amino acid sequence of h#1G5-H4
SEQ ID NO: 64: Nucleotide sequence of h#1G5-H5
SEQ ID NO: 65: Amino acid sequence of h#1G5-H5
SEQ ID NO: 66: Nucleotide sequence of h#1G5-L1
SEQ ID NO: 67: Amino acid sequence of h#1G5-L1
SEQ ID NO: 68: Nucleotide sequence of h#1G5-L2
SEQ ID NO: 69: Amino acid sequence of h#1G5-L2
SEQ ID NO: 70: Nucleotide sequence of h#1G5-L3
SEQ ID NO: 71: Amino acid sequence of h#1G5-L3
SEQ ID NO: 72: Nucleotide sequence of h#1G5-L4
SEQ ID NO: 73: Amino acid sequence of h#1G5-L4
SEQ ID NO: 74: Nucleotide sequence of h#1G5-L5
SEQ ID NO: 75: Amino acid sequence of h#1G5-L5
SEQ ID NO: 76: Nucleotide sequence of h#4C13K-H1
SEQ ID NO: 77: Amino acid sequence of h#4C13K-H1
SEQ ID NO: 78: Nucleotide sequence of h#4C13K-H2
SEQ ID NO: 79: Amino acid sequence of h#4C13K-H2
SEQ ID NO: 80: Nucleotide sequence of h#4C13K-H3
SEQ ID NO: 81: Amino acid sequence of h#4C13K-H3
SEQ ID NO: 82: Nucleotide sequence of h#4C13K-H4
SEQ ID NO: 83: Amino acid sequence of h#4C13K-H4
SEQ ID NO: 84: Nucleotide sequence of h#4C13K-H5
SEQ ID NO: 85: Amino acid sequence of h#4C13K-H5
SEQ ID NO: 86: Amino acid sequence of #4C13 heavy chain CDR1
SEQ ID NO: 87: Amino acid sequence of #4C13 heavy chain CDR2
SEQ ID NO: 88: Amino acid sequence of #4C13 heavy chain CDR3
SEQ ID NO: 89: AP3DC-S
SEQ ID NO: 90: mIgγRT1 1111-AS
SEQ ID NO: 91: mIgκ 1st 589-AS
SEQ ID NO: 92: MCS-AP3-S
SEQ ID NO: 93: mIgγ 3rd 656T-AS
SEQ ID NO: 94: mIgκ 3rd 525-AS
SEQ ID NO: 95: mIgG joint PCR-S
SEQ ID NO: 96: polyG-AS
SEQ ID NO: 97: mIgκ joint PCR-S
SEQ ID NO: 98: miniCMV f1-S
SEQ ID NO: 99: miniCMV f1-AS
SEQ ID NO: 100: mIgG sequence
SEQ ID NO: 101: mIgκ sequence
SEQ ID NO: 102: 3.3-F1
SEQ ID NO: 103: 3.3-R1
SEQ ID NO: 104: 76L-F
SEQ ID NO: 105: 76L-R
SEQ ID NO: 106: 76H-F
SEQ ID NO: 107: 76H-R
SEQ ID NO: 108: CM-inf-F
SEQ ID NO: 109: CM-inf-R
SEQ ID NO: 110: EG-inf-F
SEQ ID NO: 111: EG1-inf-R
SEQ ID NO: 112: CM-LKF
SEQ ID NO: 113: KCL-inf-R
SEQ ID NO: 114: h1BO-LF
SEQ ID NO: 115: h1BO-LR
SEQ ID NO: 116: h1BO-HF
SEQ ID NO: 117: h1BO-HR
SEQ ID NO: 118: Nucleotide sequence comprising a DNA fragment comprising a sequence encoding No.76 mIgG2a light chain
SEQ ID NO: 119: Amino acid sequence of No.76 mIgG2a light chain
SEQ ID NO: 120: Nucleotide sequence comprising a DNA fragment comprising a sequence encoding No.76 mIgG2a heavy chain
SEQ ID NO: 121: Amino acid sequence of No.76 mIgG2a heavy chain
SEQ ID NO: 122: H-R
SEQ ID NO: 123: Amino acid sequence of #4C13 light chain CDR1
SEQ ID NO: 124: Amino acid sequence of #4C13 light chain CDR2
SEQ ID NO: 125: Amino acid sequence of #4C13 light chain CDR3

The invention claimed is:

1. An antibody, or an antigen-binding fragment thereof, that recognizes LPS of *Pseudomonas aeruginosa*, and binds to O11 antigen, the antibody or antigen-binding fragment thereof comprising a heavy chain sequence and a light chain sequence,
wherein the heavy chain sequence comprises a variable region having a CDRH1, a CDRH2, and a CDRH3, the CDRH1 comprising the amino acid of SEQ ID NO: 25, the CDRH2 comprising the amino acid sequence of SEQ ID NO: 26, and the CDRH3 comprising the amino acid sequence of SEQ ID NO: 27; or the CDRH1 comprising the amino acid of SEQ ID NO: 17, the CDRH2 comprising the amino acid sequence of SEQ ID NO: 18, and the CDRH3 comprising the amino acid sequence of SEQ ID NO: 19; and
wherein the light chain sequence comprises a variable region having a CDRL1, a CDRL2, and a CDRL3, the CDRL1 comprising the amino acid of SEQ ID NO: 13, the CDRL2 comprising the amino acid sequence of SEQ ID NO: 14, and the CDRL3 comprising the amino acid sequence of SEQ ID NO: 15.

2. The antibody or an antigen-binding fragment thereof according claim 1,
wherein the CDRH1 comprises the amino acid sequence of SEQ ID NO: 17, the CDRH2 comprises the amino acid sequence of SEQ ID NO: 18, and the CDRH3 comprises the amino acid sequence of SEQ ID NO: 19.

3. The antibody or an antigen-binding fragment thereof according to claim 2, characterized by containing a heavy chain variable region sequence comprising amino acid residues 20 to 144 of the amino acid sequence shown in SEQ ID NO: 16 and a light chain variable region sequence comprising amino acid residues 21 to 129 of the amino acid sequence shown in SEQ ID NO: 12.

4. The antibody or an antigen-binding fragment thereof according to claim 1,
wherein the CDRH1 comprises the amino acid sequence of SEQ ID NO: 25, the CDRH2 comprises the amino acid sequence of SEQ ID NO: 26, and the CDRH3 comprises the amino acid sequence of SEQ ID NO: 27.

5. The antibody or an antigen-binding fragment thereof according to claim 4, characterized by containing a heavy chain variable region sequence comprising amino acid residues 20 to 140 of the amino acid sequence shown in SEQ ID NO: 24 and a light chain variable region sequence comprising amino acid residues 21 to 129 of the amino acid sequence shown in SEQ ID NO: 12.

6. An antigen-binding fragment of the antibody according to claim 1, characterized by being selected from the group consisting of Fab, F(ab')2, Fab' and Fv.

7. The antibody according to claim 1, characterized by being scFv.

8. The antibody or an antigen-binding fragment thereof according to claim 1, characterized by being a chimeric antibody.

9. The antibody or an antigen-binding fragment thereof according to claim 1, characterized by being a humanized antibody.

10. The antibody or an antigen-binding fragment thereof according to claim 1, characterized by containing a heavy chain variable region sequence comprising amino acid residues 20 to 144 of the amino acid sequence shown in SEQ ID NO: 57 and a light chain variable region sequence comprising amino acid residues 21 to 129 of the amino acid sequence shown in SEQ ID NO: 67.

11. A polynucleotide encoding the antibody or the antigen-binding fragment thereof according to claim 1.

12. A vector containing the polynucleotide according to claim 11.

13. A transformed host cell containing the polynucleotide according to claim 11.

14. A transformed host cell containing the vector according to claim 12.

15. A method for producing an antibody or antigen-binding fragment thereof, comprising culturing a transformed host cell comprising a polynucleotide encoding any one of the antibodies according to claim 1 and purifying the antibody from the resulting culture.

16. A conjugate comprising the antibody or the antigen-binding fragment thereof according to claim 1, and another medicinal agent.

* * * * *